US007429667B2

(12) United States Patent
Abdellaoui et al.

(10) Patent No.: US 7,429,667 B2
(45) Date of Patent: Sep. 30, 2008

(54) PHENYLAMINO ISOTHIAZOLE CARBOXAMIDINES AS MEK INHIBITORS

(75) Inventors: Hassan Abdellaoui, Aliso Viejo, CA (US); Robert Tam, Irvine, CA (US); Huanming Chen, Irvine, CA (US); Varaprasad Chamakura, Irvine, CA (US); Dinesh Barawkar, Foothill Ranch, CA (US); Andreas Maderna, Los Angeles, CA (US); Zhi Hong, Irvine, CA (US); Stanley Lang, Laguna Niguel, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 296 days.

(21) Appl. No.: 11/337,243

(22) Filed: Jan. 20, 2006

(65) Prior Publication Data

US 2006/0194802 A1 Aug. 31, 2006

Related U.S. Application Data

(60) Provisional application No. 60/691,698, filed on Jun. 16, 2005, provisional application No. 60/688,628, filed on Jun. 7, 2005, provisional application No. 60/688,006, filed on Jun. 6, 2005, provisional application No. 60/688,005, filed on Jun. 6, 2005, provisional application No. 60/685,194, filed on May 26, 2005, provisional application No. 60/685,131, filed on May 26, 2005, provisional application No. 60/675,397, filed on Apr. 27, 2005, provisional application No. 60/653,340, filed on Feb. 16, 2005, provisional application No. 60/645,425, filed on Jan. 20, 2005.

(51) Int. Cl.
| | | |
|---|---|---|
| C07D 275/03 | (2006.01) | |
| C07D 413/12 | (2006.01) | |
| C07D 239/36 | (2006.01) | |
| C07D 217/06 | (2006.01) | |
| C07D 401/12 | (2006.01) | |
| C07D 401/14 | (2006.01) | |
| C07D 417/12 | (2006.01) | |

(52) U.S. Cl. .................. 548/213; 544/145; 544/298; 544/367; 546/145; 546/171; 546/209; 546/256; 546/271.1

(58) Field of Classification Search ............... 548/213; 544/145, 298, 367; 546/145, 171, 209, 256, 546/271.1
See application file for complete search history.

(56) References Cited

U.S. PATENT DOCUMENTS

| | | | |
|---|---|---|---|
| 5,596,008 A | 1/1997 | Lee et al. | |
| 5,861,510 A | 1/1999 | Piscopio et al. | |
| 5,863,949 A | 1/1999 | Robinson et al. | |
| 6,235,764 B1 | 5/2001 | Larson et al. | |
| 6,495,582 B1 | 12/2002 | Hale et al. | |
| 6,511,993 B1 | 1/2003 | Dack et al. | |
| 6,548,526 B2 | 4/2003 | Larson et al. | |
| 6,649,640 B2 | 11/2003 | Hale et al. | |
| 6,989,451 B2 * | 1/2006 | Zhang et al. ............. | 548/206 |
| 2003/0149015 A1 | 8/2003 | Barrett et al. | |
| 2004/0029898 A1 | 2/2004 | Boyle et al. | |
| 2004/0039037 A1 | 2/2004 | Zhang et al. | |
| 2004/0152691 A1 | 8/2004 | Lippa et al. | |
| 2005/0143438 A1 | 6/2005 | Wallace et al. | |
| 2007/0238710 A1 | 10/2007 | Yan et al. | |
| 2007/0244164 A1 | 10/2007 | Yan et al. | |
| 2008/0058340 A1 | 3/2008 | Maderna et al. | |

FOREIGN PATENT DOCUMENTS

| | | |
|---|---|---|
| EP | 0 239 362 | 9/1987 |
| EP | 0 606 046 | 7/1994 |
| EP | 0 780 386 | 6/1997 |
| EP | 0 818 442 | 1/1998 |
| EP | 0 931 788 | 8/1999 |
| EP | 1 004 578 | 5/2000 |
| EP | 1 181 017 | 2/2002 |
| WO | WO 90/05719 | 5/1990 |
| WO | WO 96/27583 | 9/1996 |
| WO | WO 96/33172 | 10/1996 |
| WO | WO 98/03516 | 1/1998 |
| WO | WO 98/07697 | 2/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 99/07675 | 2/1999 |
| WO | WO 99/29667 | 6/1999 |
| WO | WO 99/52889 | 10/1999 |
| WO | WO 99/52910 | 10/1999 |
| WO | WO 03/043985 | 5/2003 |

OTHER PUBLICATIONS

Berge et al., "Pharmaceutical salts," J. Pharm. Sci. 66(1): 1-19, 1977.
Buchwald et al., "Long-term, continuous intravenous heparin administration by an implantable infusion pump in ambulatory patients with recurrent venous thrombosis," Surgery 88(4): 507-16, 1980.
Bundgaard, H. Chapter 5: Design and application of prodrugs. A Textbook of Drug Design and Development. Krosgaard-Larsen, et al., eds., pp. 113-91, 1991.
Bundgaard, H., "Means to enhance penetration: Prodrugs as a means to improve the delivery of peptide drugs," Advanced Drug Delivery Reviews 8: 1-38, 1992.

(Continued)

Primary Examiner—Rebecca L Anderson
Assistant Examiner—Jason M Nolan
(74) Attorney, Agent, or Firm—Wilson Sonsini Goodrich & Rosati

(57) ABSTRACT

The invention concerns compounds which inhibit MEK and which have activity as anti-neoplastic agents. These compounds include N-substituted-3-hydroxy-5-arylamino-isothiazole-4-carboxamidines. Also included are the tautomeric isothiazol-3(2H)-ones.

13 Claims, No Drawings

OTHER PUBLICATIONS

Fedorak et al., "A novel colon-specific steroid prodrug enhances sodium chloride absorption in rat colitis," Am J Physiol 269(2 Pt 1): G210-8, 1995.

Fleisher et al., "Improved oral drug delivery: solubility limitations overcome by the use of prodrugs," Advanced Drug Delivery Reviews 19(2): 115-30, 1996.

Furniss et al., ed., Vogel's Textbook of Practical Organic Chemistry, 5th Ed. Suppl. (Longman Scientific and Technical Ltd, Essex, UK) pp. 809-16, 1991.

Gennaro, A., ed., Remington's Pharmaceutical Sciences, 18th Edition (Mack Publishing Company, Easton PA), pp. 62 and 1686, 1990.

Gennaro, A., ed. Remington's Pharmaceutical Sciences, 21st Edition (Mack Publishing Company, Easton PA), p. 958, 2005.

Goodman et al., eds. Goodman and Gilman's: The Pharmacological Basis of Therapeutics, 9th Edition (McGraw-Hill, New York), p. 11, 1996.

Goodson, J. Dental applications. Medical Applications of Controlled Release, vol. 2, Applications and Evaluations. Langer, et al., eds. (CRC Press, Boca Raton, FL) pp. 115-38, 1984.

Heller, A., "Electrical wiring of redox enzymes," Acc Chem Res 23(5): 128-34, 1990.

Hochhaus et al. A selective HPLC/RIA for dexamethasone and its prodrug dexamethasone-21-sulphobenzoate sodium in biological fluids. Biomed Chromatogr. 1992; 6(6): 283-286, 1992.

Langer, R., "New methods of drug delivery," Science 249(1976): 1527-33, 1990.

Larsen, et al., "Prodrug forms for the sulfonamide group. I. Evaluation of N-acyl derivative, N-sulfonylamidines, N-sulfonylsulfilimines and sulfonylureas as possible prodrug derivatives," Int J Pharmaceutics 37(1-2): 87-95, 1987.

Larsen et al., "Prodrug forms for the sulfonamide group, II. Water-soluble amino acid derivatives of N-methylsulfonamides as possible prodrugs," Int J Pharmaceutics 47(1-3): 103-10, 1988.

McLeod et al., "A glucocorticoid prodrug facilitates normal mucosal function in rat colitis without adrenal suppression," Gastroenterology 106(2): 405-13, 1994.

Robinson et al., "Discovery of the hemifumarate and (alpha-L-alanyloxy)methyl ether as prodrugs of an antirheumatic oxindole: prodrugs for the enolic OH group," J Med Chem 39(1): 10-18, 1996.

Saudek et al., "A preliminary trial of the programmable implantable medication system for insulin delivery," N Engl J Med 321(9): 574-9, 1989.

Saulnier et al., "An efficient method for the synthesis of guanidino prodrugs," Bioorganic & Medicinal Chemistry Letters 4(16): 1985-90, 1994.

Sefton, M., "Implantable pumbs," Crit Rev Biomed Eng 14(3): 201-40, 1987.

Sinkula et al., "Rationale for design of biologically reversible drug derivatives: prodrugs," J Pharm Sci 64(2): 181-210, 1975.

Treat et al., "Liposome encapsulated doxorubicin: Preliminary results of phase I and phase II trials," Liposomes in the Therapy of Infectious Diseases and Cancer. Lopez-Bernstein, et al., eds. (Alan R. Liss, New York) pp. 353-65, 1989.

Varaprasad et al., "Discovery of 3-hydroxy-4-carboxyalkylamindino-5-arylamino-isothiazoles as potent MEK1 inhibitors," Bioorg Med Chem Let 16(15):3975-3980, 2006.

Widder et al., ed., Methods in Enzymology (Academic Press, New York) vol. 112, pp. 309-396, 1985.

Vernier et al., "Inhibitors of MEK," U.S. Appl. No. 12/016,897 filed Jan. 18, 2008.

* cited by examiner

PHENYLAMINO ISOTHIAZOLE CARBOXAMIDINES AS MEK INHIBITORS

CROSS REFERENCE TO RELATED APPLICATIONS

This application claims the benefit of U.S. Provisional Application No. 60/645,425, filed Jan. 20, 2005; U.S. Provisional Application No. 60/653,340, filed Feb. 16, 2005; U.S. Provisional Application No. 60/675,395, filed Apr. 27, 2005; U.S. Provisional Application No. 60/685,131, filed May 26, 2005; U.S. Provisional Application No. 60/685,194, filed May 26, 2005; U.S. Provisional Application No. 60/688,005, filed Jun. 6, 2005; U.S. Provisional Application No. 60/688,006, filed Jun. 6, 2005; U.S. Provisional Application No. 60/688,628, filed Jun. 7, 2005; and U.S. Provisional Application No. 60/691,698, filed Jun. 16, 2005. All of these applications are hereby incorporated herein by reference.

FIELD OF THE INVENTION

The invention concerns compounds which inhibit MEK and which have activity as anti-neoplastic agents. These compounds include N-substituted-3-hydroxy-5-aryl-isothiazole-4-carboxamidines. Also included are the tautomeric isothiazol-3(2H)-ones.

BACKGROUND OF THE INVENTION

Oncogenes—genes that contribute to the production of cancers—are generally mutated forms of certain normal cellular genes ("proto-oncogenes"). Oncogenes often encode abnormal versions of signal pathway components, such as receptor tyrosine kinases, serine-threonine kinases, or downstream signaling molecules. The central downstream signaling molecules are the Ras proteins, which are anchored on the inner surfaces of cytoplasmic membranes, and which hydrolyze bound guanosine triphosphate (GTP) to guanosine diphosphate (GDP). When activated by a growth factor, growth factor receptors initiate a chain of reactions that leads to the activation of guanine nucleotide exchange activity on Ras. Ras alternates between an active "on" state with a bound GTP (hereafter "Ras.GTP") and an inactive "off" state with a bound GDP. The active "on" state, Ras.GTP, binds to and activates proteins that control the growth and differentiation of cells.

For example, in the "mitogen-activated protein kinase (MAP kinase) cascade," Ras.GTP leads to the activation of a cascade of serine/threonine kinases. One of several groups of kinases known to require a Ras.GTP for their own activation is the Raf family. The Raf proteins activate "MEK1" and "MEK2," abbreviations for mitogen-activated ERK-activating kinases (where ERK is extracellular signal-regulated protein kinase, another designation for MAPK). MEK1 and MEK2 are dual-function serine/threonine and tyrosine protein kinases and are also known as MAP kinase kinases. Thus, Ras.GTP activates Raf, which activates MEK1 and MEK2, which activate MAP kinase (MAPK). Activation of MAP kinase by mitogens appears to be essential for proliferation, and constitutive activation of this kinase is sufficient to induce cellular transformation. Blockade of downstream Ras signaling, as by use of a dominant negative Raf-1 protein, can completely inhibit mitogenesis, whether induced from cell surface receptors or from oncogenic Ras mutants.

The interaction of Raf and Ras is a key regulatory step in the control of cell proliferation. To date, no substrates of MEK other than MAPK have been identified; however, recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

Once activated, Raf and other kinases phosphorylate MEK on two neighboring serine residues, $S^{218}$ and $S^{222}$ in the case of MEK-1. These phosphorylations are required for activation of MEK as a kinase. In turn, MEK phosphorylates MAP kinase on two residues separated by a single amino acid: a tyrosine, $Y^{185}$, and a threonine, $T^{183}$. MEK appears to associate strongly with MAP kinase prior to phosphorylating it, suggesting that phosphorylation of MAP kinase by MEK may require a prior strong interaction between the two proteins. Two factors—MEK's unusual specificity and its requirement for a strong interaction with MAP kinase prior to phosphorylation—suggest that MEK's mechanism of action may differ sufficiently from the mechanisms of other protein kinases as to allow for selective inhibitors of MEK. Possibly, such inhibitors would operate through allosteric mechanisms rather than through the more usual mechanism involving blockage of an ATP binding site.

MEK1 and MEK2 are, therefore, validated and accepted targets for anti-proliferative therapies, even when the oncogenic mutation does not affect MEK structure or expression. See, e.g., U.S. Patent Publications 2003/0149015 by Barrett et al. and 2004/0029898 by Boyle et al.

An N-unsubstituted, 3-hydroxy-5-phenyoxyphenyl-isothiazole-4-carboxyamidine having anti MEK activity was described in a patent publication commonly assigned with the present application. US 2004/0039037 (Feb. 26, 2004). No analogs or derivatives of the compound were described. A group of 3-phenyloxy-5-alkylureido-isothiazole-4-carboxamide kinase inhibitors having anti-proliferative activity was reported in U.S. Pat. No. 6,548,526 and No. 6,235,764. These compounds were not noted to be MEK inhibitors; they inhibited a tyrosine kinase activity associated with the vascular endothelial growth factor receptor (VEGF).

A second group of isothiazole-4-carboxamides with anti-proliferative activity via blockage of Trk tyrosine kinase—not a VEGF-associated kinase—was described in U.S. Patent Publication 2004/0152691. The compounds are 3-arylsulfanyl-5-heteroarylamino-isothiazoles.

Isoxazole inhibitors of MEK-activated kinase (ERK or MAPK) were described in U.S. Pat. No. 6,649,640 and No. 6,495,582. Rather than 3-hydroxy-4-carboxamides or 3-hydroxy-4-carboxamidines, the compounds disclosed in these patents are 3-unsubstituted or 3-amino substituted-4-aryl isoxazoles.

BRIEF DESCRIPTION OF THE INVENTION

In general, this invention provides a compound of formula I

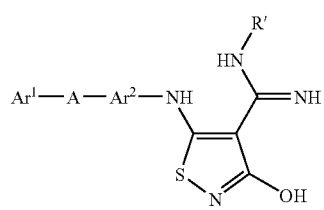

where $Ar^1$ is phenyl, pyridyl, pyrimidyl, pyridazinyl, or triazinyl, in which all ring carbon atoms are optionally substituted with substituents $R_1$, $R_2$, and $R_3$, where $R_1$, $R_2$, and $R_3$ are selected independently from hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_3$-$C_6$ cycloalkyl; $C_5$-$C_6$ cycloalkenyl, $C_5$-$C_6$ cycloalkadienyl, O—$C_1$-$C_6$ alkyl, O—$C_2$-$C_6$ alkenyl, $C_1$-$C_6$ alkyl-C(=O)—, $C_1$-$C_6$ alkenyl-C(=O)—, $C_1$-$C_6$ alkyl-O—C(=O)—, $C_1$-$C_6$ alkenyl-O—C(=O)—, $C_1$-$C_6$ alkyl-C(=O)—O—, $C_1$-$C_6$ alkenyl-C(=O)—O—, isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl, $CH_3SO_2$—, $NH_2SO_2$—, $CH_3NHSO_2$—, $CH_3SO_2NH$—, $R_7R_8N$—, $R_8R_9NCH_2$—, $R_7C(=O)NH$, —$S(O)_2NR_7R_8$, or $R_7R_8NC$ (=O), wherein $R_7$-$R_9$ are, independently, H, $C_1$-$C_4$ alkyl, phenyl, or $C_2$-$C_6$ alkenyl; $R_{10}$—C≡C—, wherein $R_{10}$ is H, $C_1$-$C_6$ alkyl, $C_2$-$C_6$ alkenyl, $C_3$-$C_6$ cycloalkyl, $C_5$-$C_6$ cycloalkenyl, $(CH_3)_2NCH_2$—, phenyl or $(CH_3)_2NCH_2CH_2$—; $R_4$ is H, $C_1$-$C_3$ alkyl, or $C_1$-$C_3$ alkenyl, said alkyl and said alkenyl groups optionally substituted with, independently, 1, 2, or 3 halogen atoms, O—$C_{1-2}$ alkyl, $C_1$-$C_3$ alkenyl, and $N(H)C_{1-2}$ alkyl; $R_5$ is H or $C_1$-$C_3$ alkyl; and in which all alkyl, cycloalkyl, alkenyl, cycloalkenyl, aryl, and heteroaryl groups in $R_1$-$R_{10}$ are optionally substituted with one, two, or three groups selected from F, Cl, Br, I, OH, CN, $C_1$-$C_4$ alkyl, $C_1$-$C_4$ alkoxyl, and $C_2$-$C_4$ alkenyl; or any of the pairs $R_1$ and $R_2$, $R_7$ and $R_8$, or $R_8$ and $R_9$ are attached to adjacent carbons and, together with the ring atoms to which they are attached, form an additional, fused, five- or six-membered ring, optionally containing one or two heteroatoms selected from O, N, and S, which ring may be aromatic or aliphatic; wherein all alkyl, alkenyl, and cycloalkyl groups and all rings are optionally substituted with 1-3 halogen atoms, and all rings are also optionally substituted with 1-3 $C_1$-$C_3$ alkyl groups or trifluoromethyl groups;

A is O, S, $CH_2$, $N_2$, C(O), NHC(O), $C(O)CH_2$, or $CH_2C(O)$;

or $Ar^1$-A is

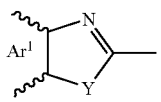

where the five-membered ring is fused to $Ar^1$ and Y is NH, S, or O, or $Ar^1$-A is

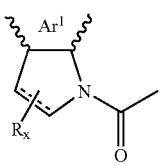

where the dotted line represents an optional double bond, the five-membered ring is fused to $Ar^1$, and $R_x$ is selected from substituents listed above for $R_3$;

or $Ar^1$-A is

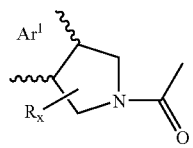

where the five-membered ring is fused to $Ar^1$, and $R_x$ is selected from substituents listed above for $R_3$;

$Ar^2$ is phenyl, pyridyl, pyrimidyl, pyridazinyl, or triazinyl, where ring carbon atoms are optionally substituted with substituents $R_4$-$R_6$, where $R_4$ is defined as for $R_1$-$R_3$ above; $R_5$ and $R_6$ are, independently, H, F, Cl, Br, $CH_3$, or $CF_3$; and in which all alkyl, cycloalkyl, alkenyl, cycloalkenyl, aryl, and heteroaryl groups in $R_1$-$R_9$ are optionally substituted with one, two, or three groups selected from F, Cl, Br, I, OH, CN, $C_1$-$C_4$ alkyl, $C_1$-$C_4$ alkoxyl, and $C_2$-$C_4$ alkenyl; which are selected independently from H, F, Cl, Br, $CH_3$, or $CF_3$;

or $Ar^2$—NH— is

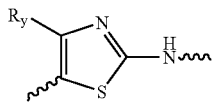

where $R_y$ is selected from substituents listed above for $R_3$;

and R' is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or R' is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or R' is —$CH(CH_2OH)CH_2D$, where D is selected from imidazolyl, indolyl, carboxamido, phenyl, cyclohexyl, —$CH_2SCH_3$, and adamantin-1-yl.

In one generic embodiment, this invention provides a compound of formula I where $Ar^1$ and $Ar^2$ are both 6-membered rings.

In another generic embodiment, this invention provides a compound of formula I in which A is S, $CH_2$, $N_2$, CO, $C(O)CH_2$, or NHC(O).

In another generic embodiment, this invention provides a compound of formula I, in which A is O, C(O), or $CH_2C(O)$.

In another generic embodiment, this invention provides a compound of formula I where R' is OH; O—$C_1$-$C_6$ alkyl;

$C_1$-$C_6$ alkyl, said $C_1$-$C_6$ alkyl groups optionally substituted with one to three groups selected independently from hydroxy, halogen, $C_1$-$C_3$ alkoxy, and phenyl, said phenyl group or groups optionally substituted with one to three groups selected independently from hydroxy, halogen, and methyl.

In another generic embodiment, this invention provides a compound of formula I where R' is —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl.

In another generic embodiment, this invention provides a compound of formula I where R' is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

In still another generic embodiment, this invention provides a compound of formula I where R' is $CH(CH_2OH)CH_2D$, where D is selected from imidazolyl, indolyl, carboxamido, phenyl, cyclohexyl, —$CH_2SCH_3$, and adamantin-1-yl.

In one subgeneric embodiment, this invention provides a compound of formula II

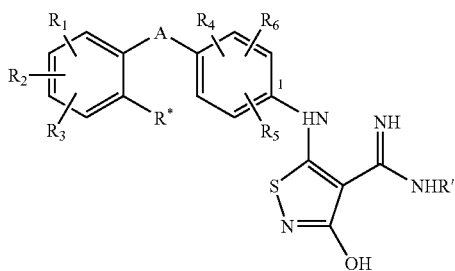

II in which A is —O—, —$CH_2$—, —$N_2$—, —$CH_2C(O)$—, $C(O)CH_2$, —S—, or —$C(O)$—;

$R_1$, $R_2$, and $R_3$ are, independently, hydrogen; halogen; hydroxy; nitro; cyano; $C_1$-$C_4$ alkyl, optionally substituted with one to three fluorine atoms; $CH_3O$; 2-methoxy ethenyl; $(CH_3)_2N$; $CH_3OC(O)$; $CH_3CH_2OC(O)$; $NR_7R_8$, —$C(O)NR_7R_8$; or —$S(O)_2NR_7R_8$, where $R_7$ and $R_8$ are, independently, H, $CH_3$, or $CH_3CH_2$; or $R_1$ and $R_2$ are attached to adjacent carbons and, together with the ring atoms to which they are attached, form an additional, fused, five- or six-membered ring, optionally containing one heteroatom, which ring may be aromatic or aliphatic;

$R_4$-$R_6$ are, independently, H, F, Cl, Br, $CH_3$, or $CF_3$;

R* is H, except when $R_1$ and $R_2$ are both F; when $R_1$ and $R_2$ are both F, R* is either H or Cl;

R' is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or R' is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds;

or R' is —$CH(CH_2OH)CH_2D$, where D is selected from imidazolyl, indolyl, carboxamido, phenyl, cyclohexyl, —$CH_2SCH_3$, and adamantin-1-yl.

In another subgeneric embodiment, this invention provides a compound of formula II in which A is O.

In a more specific embodiment, this invention provides a compound of formula II in which A is O and R' is —$CH(CH_2OH)CH_2D$, where D is selected from imidazolyl, indolyl, carboxamido, phenyl, cyclohexyl, —$CH_2SCH_3$, and adamantin-1-yl.

In another embodiment, this invention provides a compound of formula II in which A is O and R' is $(CH_2)_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

In another embodiment, this invention provides a compound of formula II in which A is O and R' is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; —$CH_2B$ or —$CH_2CH_2B$, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl.

In another subgeneric embodiment, this invention provides a compound of formula II in which A is —O—, $R_1$ is 2-C(O) G, where G is selected from:

—OJ, where J is isopropyl, cyclopropyl, cyclopentyl, dimethylamino, or methoxyethyl; and —NHJ' where J' is methyl, ethyl, isopropyl, cyclopropyl, dimethylaminomethyl, or 3-methyl-2-yl-butanoic acid methyl ester and —$N(CH_3)_2$; or N-methyl piperazinyl;

$R_2$ and $R_3$ are H; and $R_4$ is isopropyl or 1-hydroxy-isopropyl.

In another embodiment, this invention provides a compound of formula II in which A is O; R' is —$CH(CH_2OH)CH_2D$, where D is selected from imidazolyl, indolyl, carboxamido, phenyl, cyclohexyl, —$CH_2SCH_3$, and adamantin-1-yl; $R_1$ is H; $R_2$ is 2-Cl, 2-Me, 2-$CF_3$, 3-F, 3-Me, 3-$N(CH_3)_2$; 3-C(O)OEt, 3-C(O)OMe, 4-Cl, or 4-OH, and $R_3$ is hydrogen; halogen; hydroxy; nitro; cyano; $C_1$-$C_4$ alkyl, optionally substituted with one to three fluorine atoms; $CH_3O$; 2-methoxy ethenyl; $(CH_3)_2N$; $CH_3OC(O)$; $CH_3CH_2OC(O)$; $NR_7R_8$; —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is O; R' is —CH(CH$_2$OH)CH$_2$D, where D is selected from imidazolyl, indolyl, carboxamido, phenyl, cyclohexyl, —CH$_2$SCH$_3$, and adamantin-1-yl; $R_1$ is 2-Me, 2-F, or 2-Cl; $R_2$ is 3-Me, 3-F, 3-Cl, 5-Me, 5-F, 5-Cl or 3-CF$_3$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is O; R' is —CH(CH$_2$OH)CH$_2$D, where D is selected from imidazolyl, indolyl, carboxamido, phenyl, cyclohexyl, —CH$_2$SCH$_3$, and adamantin-1-yl; $R_1$ is 5-Cl; $R_2$ is —C(O)$NR_7R_8$, or —S(O)$_2NR_7R_8$, and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is O and R' is (CH$_2$)$_n$-G; $R_1$ is H; $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is O and R' is (CH$_2$)$_n$-G, where n is 1 or 2 and G is a five- or six-membered ring or a 9- to 14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds; $R_1$ is 2-Me, 2-F, or 2-Cl; $R_2$ is 3-Me, 3-F, 3-Cl, 5-Me, 5-F, 5-Cl or 3-CF$_3$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is O, R' is (CH$_2$)$_n$-G; $R_1$ is 5-Cl; $R_2$ is —C(O)$NR_7R_8$, or —S(O)$_2NR_7R_8$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is —O—, R' is OH; O—$C_1$-$C_6$ alkyl; or $C_1$-$C_6$ alkyl, said $C_1$-$C_6$ alkyl groups optionally substituted with one to three groups selected independently from hydroxy, halogen, $C_1$-$C_3$ alkoxy, and phenyl; $R_1$ is H; $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is —O—, R' is OH; O—$C_1$-$C_6$ alkyl; or $C_1$-$C_6$ alkyl, said $C_1$-$C_6$ alkyl groups optionally substituted with one to three groups selected independently from hydroxy, halogen, $C_1$-$C_3$ alkoxy, and phenyl; $R_1$ is 2-Me, 2-F, or 2-Cl; $R_2$ is 3-Me, 3-F, 3-Cl, 5-Me, 5-F, 5-Cl or 3-CF$_3$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II in which A is —O—, R' is OH; O—$C_1$-$C_6$ alkyl; or $C_1$-$C_6$ alkyl, said $C_1$-$C_6$ alkyl groups optionally substituted with one to three groups selected independently from hydroxy, halogen, $C_1$-$C_3$ alkoxy, and phenyl; $R_1$ is 5-Cl; $R_2$ is —C(O)$NR_7R_8$, or —S(O)$_2NR_7R_8$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and R are, independently, H, $CH_3$, or $CH_3CH_2$.

In another embodiment, this invention provides a compound of formula II in which A is —O—, R' is —CH$_2$B or —CH$_2$CH$_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is H; $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II II in which A is —O—, R' is —CH$_2$B or —CH$_2$CH$_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is 2-Me, 2-F, or 2-Cl; $R_2$ is 3-Me, 3-F, 3-Cl, 5-Me, 5-F, 5-Cl or 3-CF$_3$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; $(CH_3)_2N$; $CH_3OC(O)$; $CH_3CH_2OC(O)$; $NR_7R_8$, —C(O)$NR_7R_8$; or —S(O)$_2NR_7R_8$, where $R_7$ and $R_8$ are, independently, H, $CH_3$, or $CH_3CH_2$.

In another embodiment, this invention provides a compound of formula II II in which A is —O—, R' is —CH$_2$B or —CH$_2$CH$_2$B, where B is selected from $C_{3-7}$ cycloalkyl, $C_7$-$C_9$ bicycloalkyl, pyridyl, piperazinyl, piperidinyl, N-morpholyl, tetrahydrofuryl, and naphthyl; $C_3$-$C_7$ cycloalkyl; $C_7$-$C_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is 5-Cl; $R_2$ is —C(O)$NR_7R_8$, or —S(O)$_2NR_7R_8$; and $R_3$ is hydrogen; halogen; hydroxy; nitro; cyano; $C_1$-$C_4$ alkyl, optionally substituted with one to three fluorine atoms; CH$_3$O; 2-methoxy ethenyl; (CH$_3$)$_2$N; CH$_3$OC(O); CH$_3$CH$_2$OC(O); NR$_7$R$_8$, —C(O)NR$_7$R$_8$; or —S(O)$_2$NR$_7$R$_8$, where R$_7$ and R$_8$ are, independently, H, CH$_3$, or CH$_3$CH$_2$.

In another embodiment, this invention provides a compound of formula III

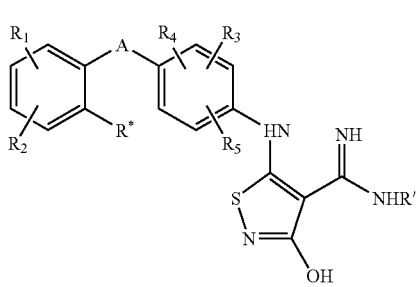

wherein A is —O—, —CH$_2$—, —N$_2$—, —CH$_2$C(O)—, —C(O)CH$_2$—, —S—, or —C(O)—; and substituents R$^1$-R' are as defined for formula I.

In another embodiment, this invention provides a compound of formula III in which A is —O—.

In another embodiment, this invention provides a compound of formula III in which A is C(O), —CH$_2$—, or C(O)CH$_2$.

In another embodiment, this invention provides a compound of formula III in which A is —O—, and R' is C$_1$-C$_6$ alkyl or C$_{3-6}$ cycloalkyl, all such C$_1$-C$_6$ alkyl and C$_{3-6}$ cycloalkyl optionally substituted with one to three OH groups.

In another embodiment, this invention provides a compound of formula III in which A is —O—; and R' is —CH$_2$B or —CH$_2$CH$_2$B, where B is selected from C$_{3-6}$ cycloalkyl, phenyl, pyridyl, piperazin-1-yl, piperidin-1-yl, N-morpholyl, tetrahydrofuryl, and naphthyl.

In another embodiment, this invention provides a compound of formula III in which A is —O—; and R' is 2-propyl, 1-hydroxy-2-propyl, 2-hydroxyethyl, 3-hydroxypropyl, or 2,3-dihydroxypropyl.

In another embodiment, this invention provides a compound of formula III in which A is —O—; R' is C$_1$-C$_6$ alkyl or C$_{3-6}$ cycloalkyl, all such C$_1$-C$_6$ alkyl and C$_{3-6}$ cycloalkyl optionally substituted with one to three OH groups; and R$_4$ is H, CH$_3$, or CF$_3$.

In another embodiment, this invention provides a compound of formula III in which A is —O—; R' is —CH$_2$B or —CH$_2$CH$_2$B, where B is selected from C$_{3-6}$ cycloalkyl, phenyl, pyridyl, piperazin-1-yl, piperidin-1-yl, N-morpholyl, tetrahydrofuryl, and naphthyl; and R$_4$ is H, CH$_3$, or CF$_3$.

In another embodiment, this invention provides a compound of formula III in which A is —O—; R' is 2-propyl, 1-hydroxy-2-propyl, 2-hydroxyethyl, 3-hydroxypropyl, or 2,3-dihydroxypropyl; and R$_4$ is H, CH$_3$, or CF$_3$.

In another embodiment, this invention provides a compound of formula III in which A is —O—; R' is C$_1$-C$_6$ alkyl or C$_{3-6}$ cycloalkyl, all such C$_1$-C$_6$ alkyl and C$_{3-6}$ cycloalkyl optionally substituted with one to three OH groups; and R$_4$ is F, Cl, or Br.

In another embodiment, this invention provides a compound of formula III in which A is —O; R' is —CH$_2$B or —CH$_2$CH$_2$B, where B is selected from C$_{3-6}$ cycloalkyl, phenyl, pyridyl, piperazin-1-yl, piperidin-1-yl, N-morpholyl, tetrahydrofuryl, and naphthyl; and R$_4$ is F, Cl, or Br.

In another embodiment, this invention provides a compound of formula III in which A is —O—; R' is 2-propyl, 1-hydroxy-2-propyl, 2-hydroxyethyl, 3-hydroxypropyl, or 2,3-dihydroxypropyl; and R$_4$ is F, Cl, or Br.

In another embodiment, this invention provides a compound of formula III in which A is —O—; R' is C$_1$-C$_6$ alkyl or C$_{3-6}$ cycloalkyl, all such C$_1$-C$_6$ alkyl and C$_{3-6}$ cycloalkyl optionally substituted with one to three OH groups; R$_4$ is H, CH$_3$, or CF$_3$; and R$_5$ is F.

In another embodiment, this invention provides a compound of formula III in which A is —O—; R' is —CH$_2$B or —CH$_2$CH$_2$B, where B is selected from C$_{3-6}$ cycloalkyl, phenyl, pyridyl, piperazin-1-yl, piperidin-1-yl, N-morpholyl, tetrahydrofuryl, and naphthyl; 4 is H, CH$_3$, or CF$_3$; and R$_5$ is F.

In another embodiment, this invention provides a compound of formula III in which A is —O—; R' is 2-propyl, 1-hydroxy-2-propyl, 2-hydroxyethyl, 3-hydroxypropyl, or 2,3-dihydroxypropyl; R$_4$ is H, CH$_3$, or CF$_3$; and R$_5$ is F.

In another embodiment, this invention provides a compound of formula III in which A is —O—; R' is C$_1$-C$_6$ alkyl or C$_{3-6}$ cycloalkyl, all such C$_1$-C$_6$ alkyl and C$_{3-6}$ cycloalkyl optionally substituted with one to three OH groups; R$_4$ is F, Cl, or Br; and R$_5$ is F.

In another embodiment, this invention provides a compound of formula III in which A is —O—; R' is —CH$_2$B or —CH$_2$CH$_2$B, where B is selected from C$_{3-6}$ cycloalkyl, phenyl, pyridyl, piperazin-1-yl, piperidin-1-yl, N-morpholyl, tetrahydrofuryl, and naphthyl; R$_4$ is F, Cl, or Br; and R$_5$ is F.

x14 In another embodiment, this invention provides a compound of formula III in which A is —O—; R' is 2-propyl, 1-hydroxy-2-propyl, 2-hydroxyethyl, 3-hydroxypropyl, or 2,3-dihydroxypropyl; R$_4$ is F, Cl, or Br; and R$_5$ is F.

x14 sub: In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is H, and R$_2$ is selected from 2-Cl, 2-Me, 2-CF$_3$, 3-F, 3-Me, 3-N(CH$_3$)$_2$; 3-C(O)OEt, 3-C(O)OMe, 4-Cl, and 4-OH.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is H, and R$_2$ is 2-Cl, 2-Me, 2-CF$_3$, 3-F, 3-Me, 3-N(CH$_3$)$_2$, 3-C(O)OEt, 3-C(O)OMe, 4-Cl, or 4-OH.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is 2-Me, 2-F, or 2-Cl; and R$_2$ is 3-Me, 3-F, 3-Cl, 5-Me, 5-F, 5-Cl or 3-CF$_3$.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is 5-Cl; and R$_2$ is —C(O)NR$_7$R$_8$, or —S(O)$_2$NR$_7$R$_8$.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is 2-Me, 2-F, or 2-C$_1$ and R$_2$ is 4-F, 4-Cl, 4-1,4-CF$_3$.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, R$_1$ is 3-Me or 3-F and R$_2$ is 5-F, 5-Me or 5-CF$_3$.

In another embodiment, this invention provides a compound of formula III in which A is —O—, R' is 2-propyl, 1-hydroxy-2-propyl, 2-hydroxyethyl, 3-hydroxypropyl, or 2,3-dihydroxypropyl, $R_{1,2}$ are 2-Cl and 5-Cl, $R_{4,5}$ are 2-F and 5-F, and $R_6$ is H.

In another embodiment, this invention provides a compound of formula III in which A is O; R' is —CH(CH$_2$OH) CH$_2$D, where D is selected from imidazolyl, indolyl, carboxamido, phenyl, cyclohexyl, —CH$_2$SCH$_3$, and adamantin-1-yl; $R_1$ is 2-Me, 2-F, or 2-Cl; and $R_2$ is 3-Me, 3-F, 3-Cl, 5-Me, 5-F, 5-Cl or 3-CF$_3$.

In another embodiment, this invention provides a compound of formula III in which A is O; R' is —CH(CH$_2$OH) CH$_2$D, where D is selected from imidazolyl, indolyl, carboxamido, phenyl, cyclohexyl, —CH$_2$SCH$_3$, and adamantin-1-yl; $R_1$ is 5-Cl; and $R_2$ is —C(O)NR$_7$R$_8$, or —S(O)$_2$NR$_7$R$_8$, In another embodiment, this invention provides a compound of formula III in which A is O; R' is (CH$_2$)$_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and C$_1$-C$_4$ alkyl, wherein said C$_1$-C$_4$ alkyl group is optionally substituted with one to three halogen atoms; and wherein each ring optionally contains one or more double bonds; $R_1$ is H; and $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH.

In another embodiment, this invention provides a compound of formula III in which A is O and R' is (CH$_2$)$_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and C$_1$-C$_4$ alkyl, wherein said C$_1$-C$_4$ alkyl group is optionally substituted with one to three halogen atoms; and wherein each ring optionally contains one or more double bonds; $R_1$ is 2-Me, 2-F, or 2-Cl; and $R_2$ is 3-Me, 3-F, 3-Cl, 5-Me, 5-F, 5-Cl or 3-CF$_3$.

In another embodiment, this invention provides a compound of formula III in which A is O, R' is (CH$_2$)$_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and C$_1$-C$_4$ alkyl, wherein said C$_1$-C$_4$ alkyl group is optionally substituted with one to three halogen atoms; and wherein each ring optionally contains one or more double bonds; $R_1$ is 5-Cl; and $R_2$ is —C(O)NR$_7$R$_8$, or —S(O)$_2$ NR$_7$R$_8$, In another embodiment, this invention provides a compound of formula III in which A is —O—, R' is OH; O—C$_1$-C$_6$ alkyl; or C$_1$-C$_6$ alkyl, said C$_1$-C$_6$ alkyl groups optionally substituted with one to three groups selected independently from hydroxy, halogen, C$_1$-C$_3$ alkoxy, and phenyl; $R_1$ is H and $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH.

In another embodiment, this invention provides a compound of formula III in which A is —O—, R' is OH; O—C$_1$-C$_6$ alkyl; or C$_1$-C$_6$ alkyl, said C$_1$-C$_6$ alkyl groups optionally substituted with one to three groups selected independently from hydroxy, halogen, C$_1$-C$_3$ alkoxy, and phenyl; $R_1$ is 2-Me, 2-F, or 2-Cl; and $R_2$ is 3-Me, 3-F, 3-Cl, 5-Me, 5-F, 5-Cl or 3-CF$_3$.

In another embodiment, this invention provides a compound of formula III in which A is —O—, R' is OH; O—C$_1$-C$_6$ alkyl; or C$_1$-C$_6$ alkyl, said C$_1$-C$_6$ alkyl groups optionally substituted with one to three groups selected independently from hydroxy, halogen, C$_1$-C$_3$ alkoxy, and phenyl; $R_1$ is 5-Cl; and $R_2$ is —C(O)NR$_7$R$_8$, or —S(O)$_2$NR$_7$R$_8$.

In another embodiment, this invention provides a compound of formula III in which A is —O—, R' is —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is H; and $R_2$ is 2-Cl, 2-Me, 2-CF$_3$, 3-F, 3-Me, 3-N(CH$_3$)$_2$; 3-C(O)OEt, 3-C(O)OMe, 4-Cl, or 4-OH.

In another embodiment, this invention provides a compound of formula III in which A is —O—, R' is —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is 2-Me, 2-F, or 2-Cl; and $R_2$ is 3-Me, 3-F, 3-Cl, 5-Me, 5-F, 5-Cl or 3-CF$_3$.

In another embodiment, this invention provides a compound of formula III in which A is —O—, R' is —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl; $R_1$ is 5-Cl; and $R_2$ is —C(O)NR$_7$R$_8$, or —S(O)$_2$NR$_7$R$_8$ In another embodiment, this invention provides a compound of formula IV

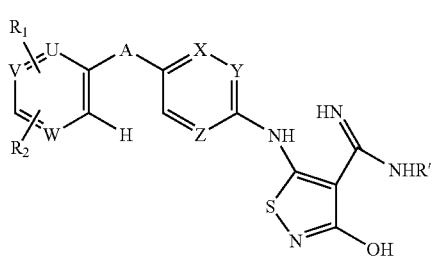

wherein U, V, W, X, Y, and Z are, independently CH or N, provided that U, V, W, X, Y, and Z are not all CH; A is —O—, —CH$_2$—, —N$_2$—, —NHC(O)—, —CH$_2$C(O)—, —C(O)CH$_2$—, —S—, or —C(O)—; $R_1$ and $R_2$ are, independently, hydrogen; halogen; hydroxy; cyano; CH$_3$, optionally substituted with 1-3 fluorine atoms; CH$_3$O; (CH$_3$)$_2$N; CH$_3$OC(O); 2-methoxy ethenyl; and CH$_3$CH$_2$OC(O); and R' is OH; OC$_1$-C$_6$ alkyl; C$_1$-C$_6$ alkyl, optionally substituted with one to three groups selected independently from hydroxy, halogen, C$_1$-C$_3$ alkoxy, and phenyl; —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl.

In a more specific embodiment, this invention provides a compound of formula IV, in which A is —O—, —CH₂—, —NHC(O)—, —S—, or —C(O)—.

In another embodiment, this invention provides a compound of formula V

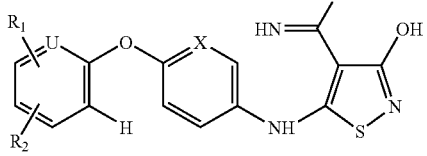

V wherein U and X are, independently CH or N, provided that U and X are not both CH; R₁ and R₂ are, independently, hydrogen; halogen; hydroxy; cyano; CH₃, optionally substituted with 1-3 fluorine atoms; CH₃O; (CH₃)₂N; CH₃OC(O); 2-methoxy ethenyl; and CH₃CH₂OC(O); and R' is selected from C₁-C₆ alkyl, optionally substituted with 1-3 hydroxyl groups; cyclopropyl; —CH₂B; and —CH₂CH₂B, where B is selected from C₃₋₆ cycloalkyl, phenyl, pyridyl, piperzin-1-yl, piperidin-1-yl, N-morpholyl, tetrahydrofuryl, and naphthyl.

In still another embodiment, this invention provides a compound of formula VI

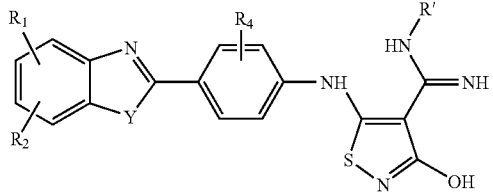

VI where Y is —NH—, —S— or —O—, and R₁—R' are defined as for formula II.

In a more specific embodiment, this invention provides a compound of formula VIa, where Y is —NH—, —S— or —O—,

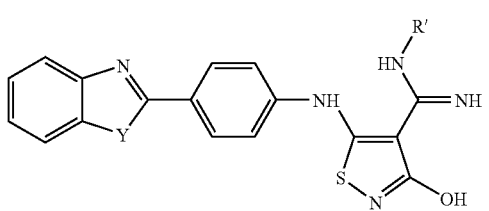

VIa

In a more specific embodiment, this invention provides a compound of formula VIa where Y is —S— or —O—, and R' is selected from 1-hydroxy-isopropyl, 2-hydroxy-n-propyl, 2-hydroxy-ethyl, and 2,3,-dihydroxy-n-propyl.

In another generic embodiment, this invention provides a compound of formula VII

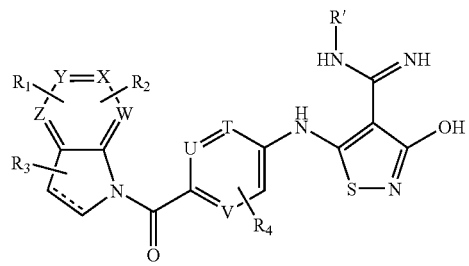

VII where the dashed bond represents an optional double bond, and where symbols T-Z represent N, CH, or CR₁, ₂, or ₄, provided that at most two of W, X, Y, and Z and at most 2 of T, U, and V are N; where R₁-R₄ are defined as for formula I; and where R' is OH; O—C₁-C₆ alkyl; C₁-C₆ alkyl, said C₁-C₆ alkyl groups optionally substituted with one to three groups selected independently from hydroxy, halogen, C₁-C₃ alkoxy, and phenyl; or R' is —(CH₂)ₙ—B where n is 1 or 2 and B is defined as above.

In one subgeneric embodiment, this invention provides a compound of formula VIIa,

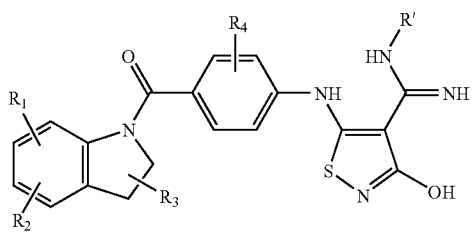

VIIa where R₁-R₄ and R' are defined as for formula I.

In a more specific embodiment, this invention provides a compound of formula VIIa where R₁ is defined as in formula II, R₃ and R₄ are both H and R' is —(CH₂)ₙ—B, where n is 1 or 2 and B is defined as above.

In another more specific embodiment, this invention provides a compound of formula VIIa where R₃ and R₄ are both H and R' is C₁-C₆ alkyl or O—C₁-C₆ alkyl, both optionally substituted as described above.

In another more specific embodiment, this invention provides a compound of formula VIIa, where R₂-R₄ are H and R' is C₁-C₆ alkyl, optionally substituted with halogen, C₁-C₃ alkoxy, or hydroxy.

In another more specific embodiment, this invention provides a compound of formula VIIa, where R₂—R are H and R' is —(CH₂)ₙ—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl, 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In another subgeneric embodiment, this invention provides a compound of formula VIIA in which R₁ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; R₂, R₃, and R₄ are H, R' is —(CH$_2$)$_n$—B, where n is 1, and B is pyridyl, piperazinyl, piperazinonyl, piperidinyl, piperidinonyl, morpholyl, furyl, tetrahydrofuryl, pyrimidyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a still more specific embodiment, this invention contemplates the compound of formula VIIA in which R$_1$ is 2-fluoro, -chloro, -bromo, -methyl, -trifluoromethyl, -methoxy, or -hydroxy; R$_2$, R$_3$, and R$_4$ are H; and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In a another more specific embodiment, this invention contemplates the compound of formula VIIA in which R$_1$ is 3-fluoro, -chloro, -bromo, -methyl, -trifluoromethyl, -methoxy, or -hydroxy; R$_2$, R$_3$, and R$_4$ are H; and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In a another more specific embodiment, this invention contemplates the compound of formula VIIA in which R$_1$ is 4-fluoro, -chloro, -bromo, -methyl, -trifluoromethyl, -methoxy, or -hydroxy; R$_2$, R$_3$, and R$_4$ are H; and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In a another more specific embodiment, this invention contemplates the compound of formula VIIA in which R$_1$ is 5-fluoro, -chloro, -bromo, -methyl, -trifluoromethyl, -methoxy, or -hydroxy; R$_2$, R$_3$, and R$_4$ are H; and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In another subgeneric embodiment, this invention provides a compound of formula VIIA-1, where R$_1$—R' are defined as for formula A.

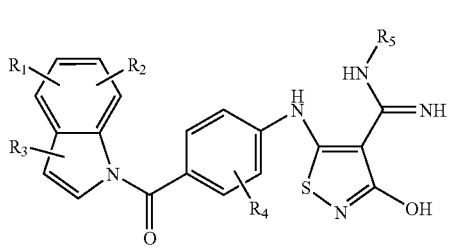

VIIA-1

In a more specific embodiment, this invention provides a compound of formula VIIA-1 where R$_1$-R$_4$ are H and R' is isopropyl, 2-butyl, 2-(2-furyl)ethyl, 2-hydroxyethyl, 2,3-dihydroxy-1-propyl, or 3,4-dihydroxy-2-butyl.

In another generic embodiment, this invention provides a compound of formula VII, in which at least one of T, U, V, W, X, Y, and Z is N.

In another generic embodiment, this invention provides a compound of formula VII, in which at least one of W, X, Y, and Z is N.

In another generic embodiment, this invention provides a compound of formula VII, in which at least one of T, U, and V is N.

In another generic embodiment, this invention provides a compound of formula VII, in which two of W, X, Y, and Z are N.

In another generic embodiment, this invention provides a compound of formula VII, in which one of T, U, and V and one of W, X, Y, and Z are N.

In another generic embodiment, this invention provides a compound of formula VIIB

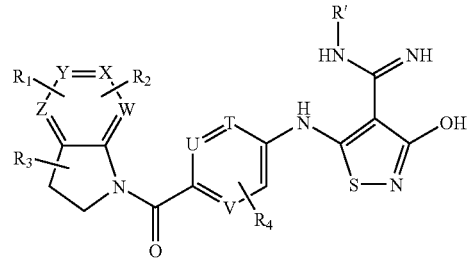

where substituents are defined as for formula II.

In a subgeneric embodiment, this invention provides a compound of formula VIIB-1

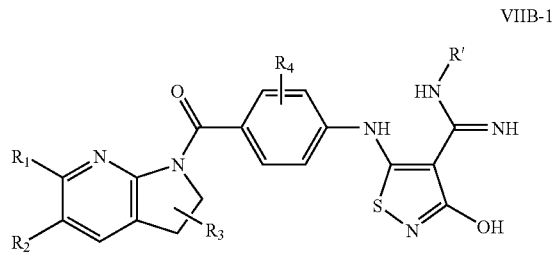

VIIB-1

In a more specific embodiment, this invention provides a compound of formula VIIB-1, where R$_1$-R$_4$ are, independently, H, C$_1$-C$_3$ alkyl, or halogen, and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In another more specific embodiment, this invention provides a compound of formula VIIB-1, where R$_1$-R$_4$ are H and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIB-1 where one of R$_1$ and R$_2$ is H and the other is amino, methyl amino, dimethylamino, dimethylaminomethyl, or acetylamino, R$_3$-R$_4$ are H, and R' is C$_1$-C$_6$ alkyl, optionally substituted with halogen, C$_1$-C$_3$ alkoxy, or hydroxy.

In another more specific embodiment, this invention provides a compound of formula VIIB-1, where one of R$_1$ and R$_2$ is H and the other is nitro, cyano, methylcarbamoyl, dimethylcarbamoyl, or aminosulfonyl, R$_3$-R$_4$ are H and R' is C$_1$-C$_6$ alkyl, optionally substituted with halogen, C$_1$-C$_3$ alkoxy, or hydroxy.

In another more specific embodiment, this invention provides a compound of formula VIIB-1, where R$_1$ and R$_2$ are fused cyclohexyl or fused cyclopentyl, R$_3$ and R$_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIB-1, where R$_1$ and R$_2$ are benzo, R$_3$ and R$_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIB-1, wherein $R_1$ and $R_2$ are halogen, $R_3$ and $R_4$ are H, and R' is isopropyl, 2-(2-furyl) ethyl, 2-hydroxyethyl, 2,3-dihydroxy-1-propyl, or 3,4-dihydroxy-2-butyl.

In a more specific embodiment, this invention provides a compound of formula VIIB-1, where $R_1$-$R_3$ are H, $R_4$ is 2-halo, 2-cyano, 2-hydroxy, or 2-methoxy, and R' is —(CH$_2$)$_n$—B, where n is 1, and B is pyridyl, piperazinyl, piperazinonyl, piperidinyl, piperidinonyl, morpholyl, furyl, tetrahydrofuryl, or pyrimidyl.

In another more specific embodiment, this invention provides a compound of formula VIIB-1, where $R_1$ is halo, $R_2$-$R_4$ are H and R' is —(CH$_2$)$_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, the invention contemplates a compound of formula VIIB-1, where $R_1$ is bromo, $R_2$-$R_4$ are H and R' is isopropyl, 2-hydroxyethyl, 1-hydroxy-2-propyl, or 2,3-dihydroxy-1-propyl.

In a subgeneric embodiment, this invention provides a compound of formula VIIB-2

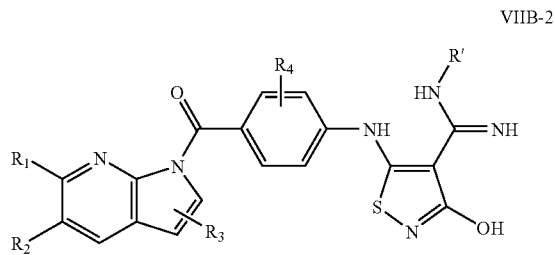

VIIB-2

In a more specific embodiment, this invention provides a compound of formula VIIB-2, where $R_1$-$R_4$ are, independently, H, $C_1$-$C_3$ alkyl, or halogen, and R' is —(CH$_2$)$_n$—B, where n is 1 or 2, and B is pyridyl, piperazinyl, piperazinonyl, piperidinyl, piperidinonyl, morpholyl, furyl, tetrahydrofuryl, or pyrimidyl.

In another more specific embodiment, this invention provides a compound of formula VIIB-2, wherein $R_1$ and $R_2$ are halogen, $R_3$ and $R_4$ are H, and R' is isopropyl, 2-(2-furyl) ethyl, 2-hydroxyethyl, 2,3-dihydroxy-1-propyl, or 3,4-dihydroxy-2-butyl.

In a still more specific embodiment, the invention contemplates a compound of formula VIIB-2, where $R_1$ is bromo, $R_2$-$R_4$ are H and R' is 2-cyclopropyl ethyl, 2-hydroxyethyl, 1-hydroxy-2-propyl, or 2,3-dihydroxy-1-propyl.

In another more specific embodiment, the invention contemplates a compound of formula VIIB-2, where $R_1$ and $R_2$ are fused (2,3) pyrido, $R_4$ is 2-chloroethyl, and R' is 2-cyclopropyl ethyl, 2-hydroxyethyl, or 2-cyclopenylethyl.

In another more specific embodiment, the invention contemplates a compound of formula VIIB-2, where $R_1$ and $R_2$ are fused (2,3) pyrrolo, fused (2,3) furyl, or fused (4,5) imidazolo, $R_4$ is H, and R' is 2-hydroxyethyl, or isopropyl.

Additional embodiments of generic structures with one or more of T-Z=nitrogen are shown below, together with a contemplated compound for each generic structure. These contemplated compounds indicate the range of contemplated substituents.

| Generic Structure | Example |
|---|---|
| VIIB-3 | VIIB-3a |
| VIIB-4 | VIIB-4a |

-continued
| Generic Structure | Example |
|---|---|
| 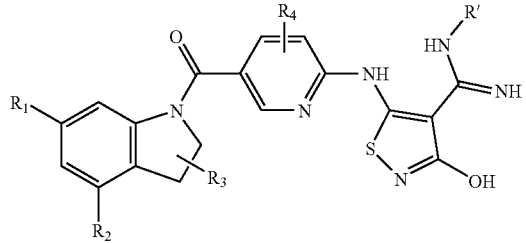 VIIB-9 | 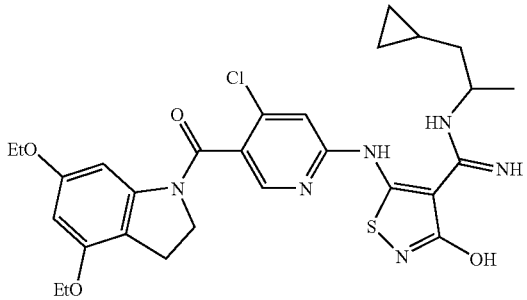 VIIB-9a |
| 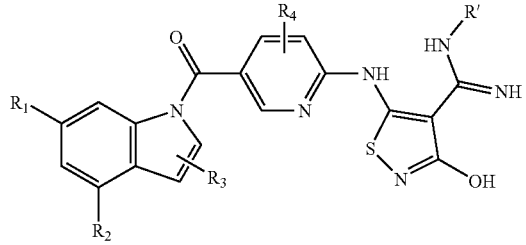 VIIB-10 | 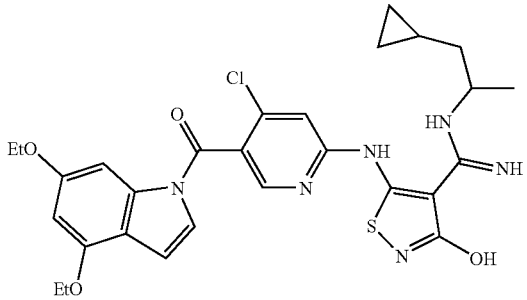 VIIB-10a |
| 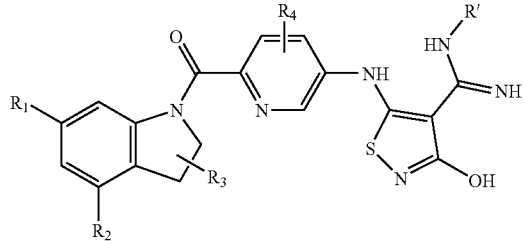 VIIB-11 | 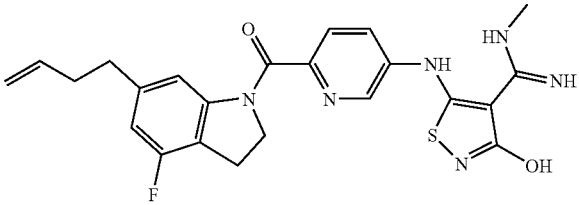 VIIB-11a |
| 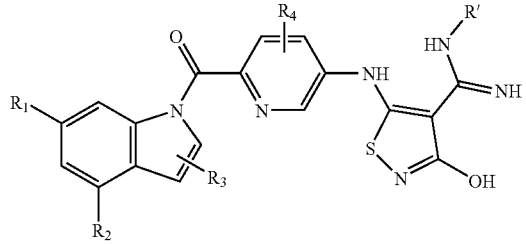 VIIB-12 | 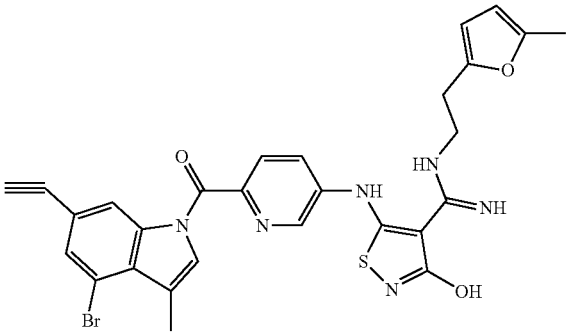 VIIB-12a |
| 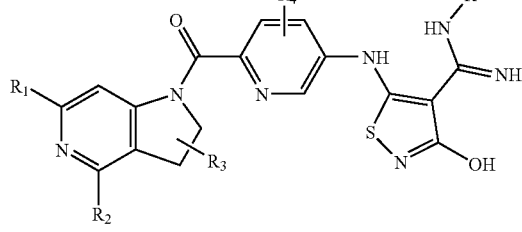 VIIB-13 | 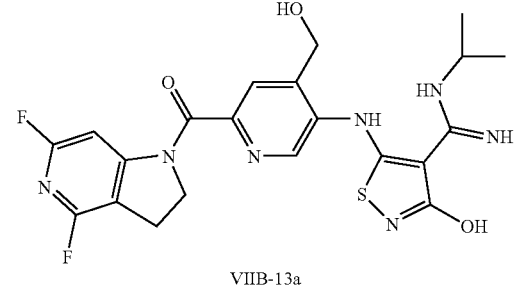 VIIB-13a |

-continued
| Generic Structure | Example |
|---|---|
| 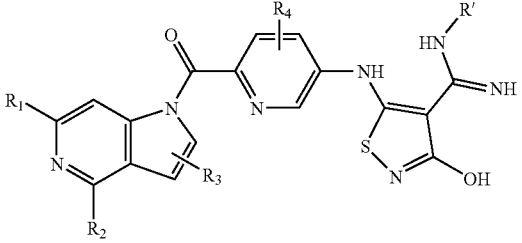  VIIB-14 | 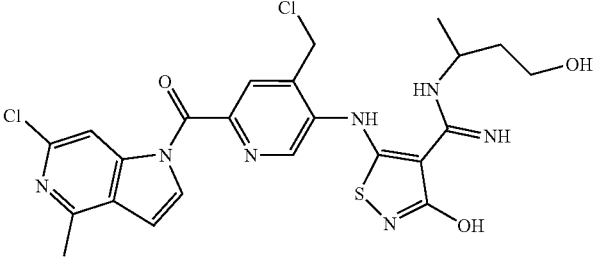  VIIB-14a |
| 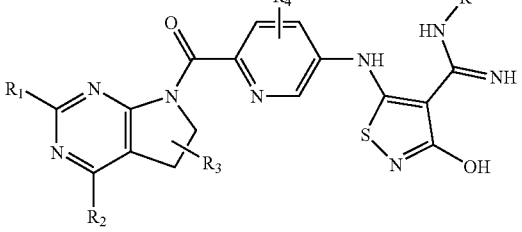  VIIB-15 | 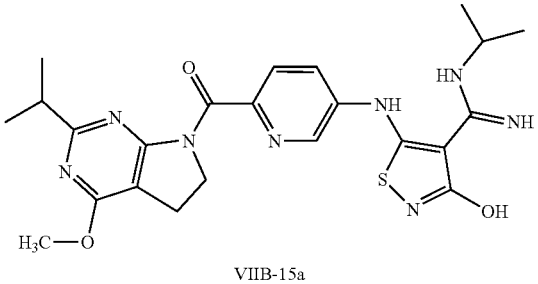  VIIB-15a |
| 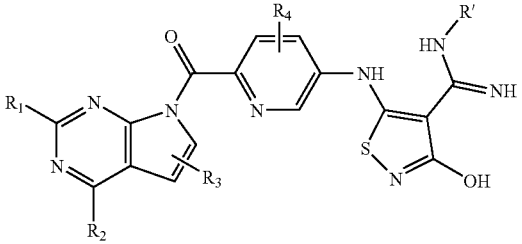  VIIB-16 | 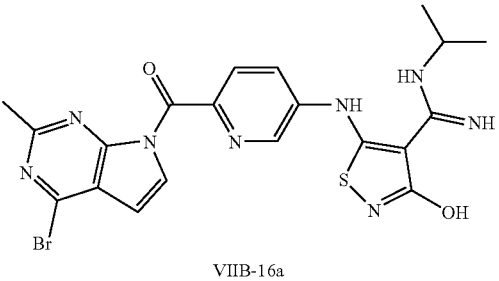  VIIB-16a |
| 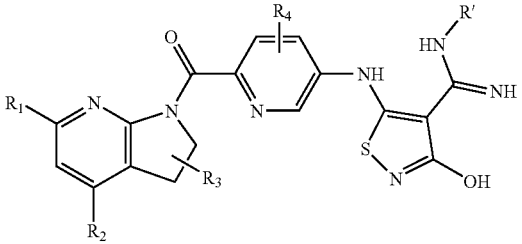  VIIB-17 | 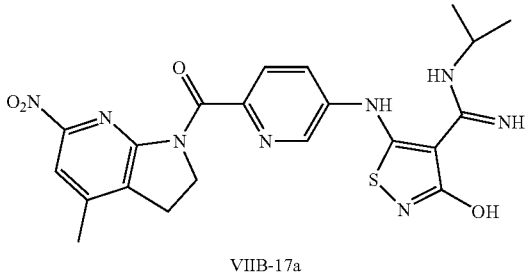  VIIB-17a |
| 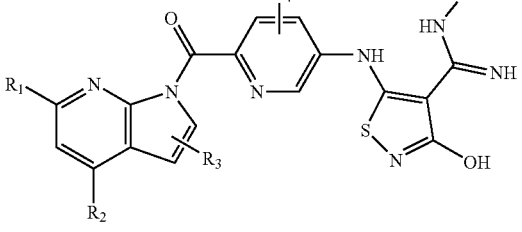  VIIB-18 | 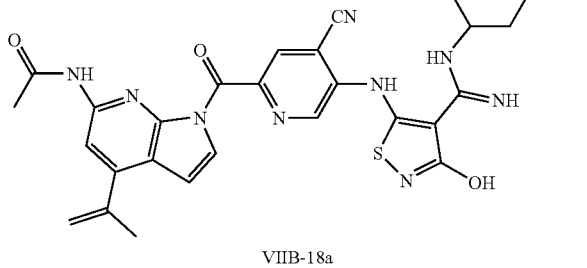  VIIB-18a |

-continued
| Generic Structure | Example |
|---|---|
| 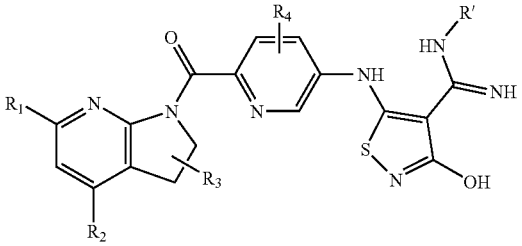 VIIB-19 | 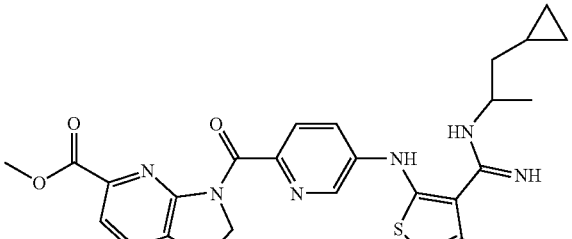 VIIB-19a |
| 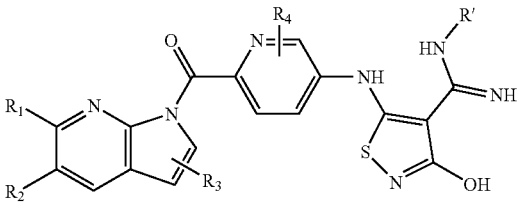 VIIB-20 | 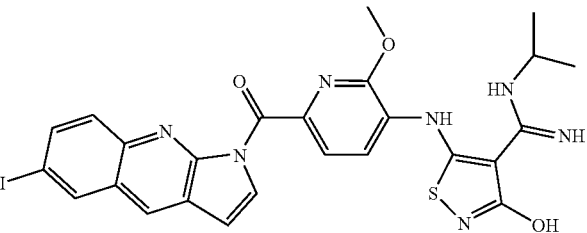 VIIB-20a |
| 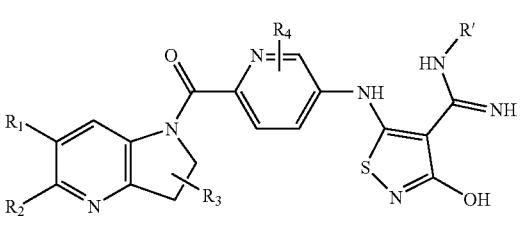 VIIB-21 | 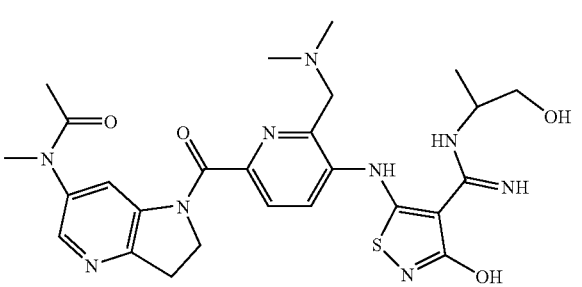 VIIB-21a |
| 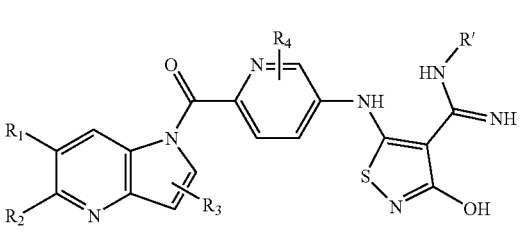 VIIB-22 | 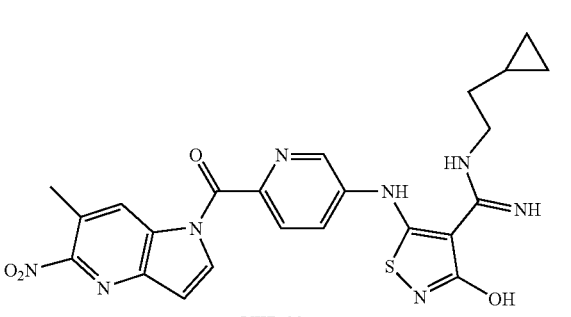 VIIB-22a |
| 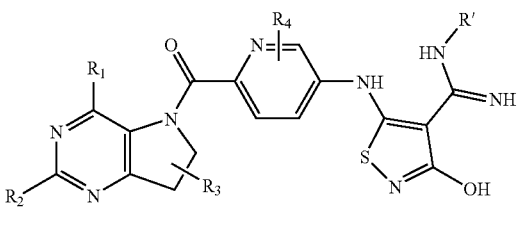 VIIB-23 | 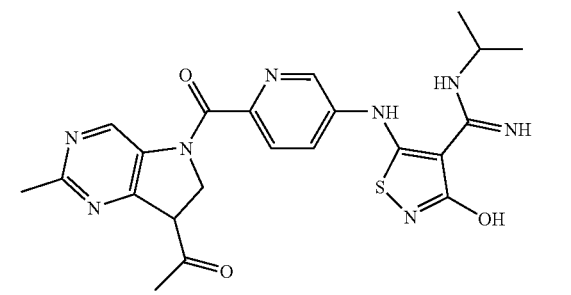 VIIB-23a |

-continued
| Generic Structure | Example |
|---|---|
| 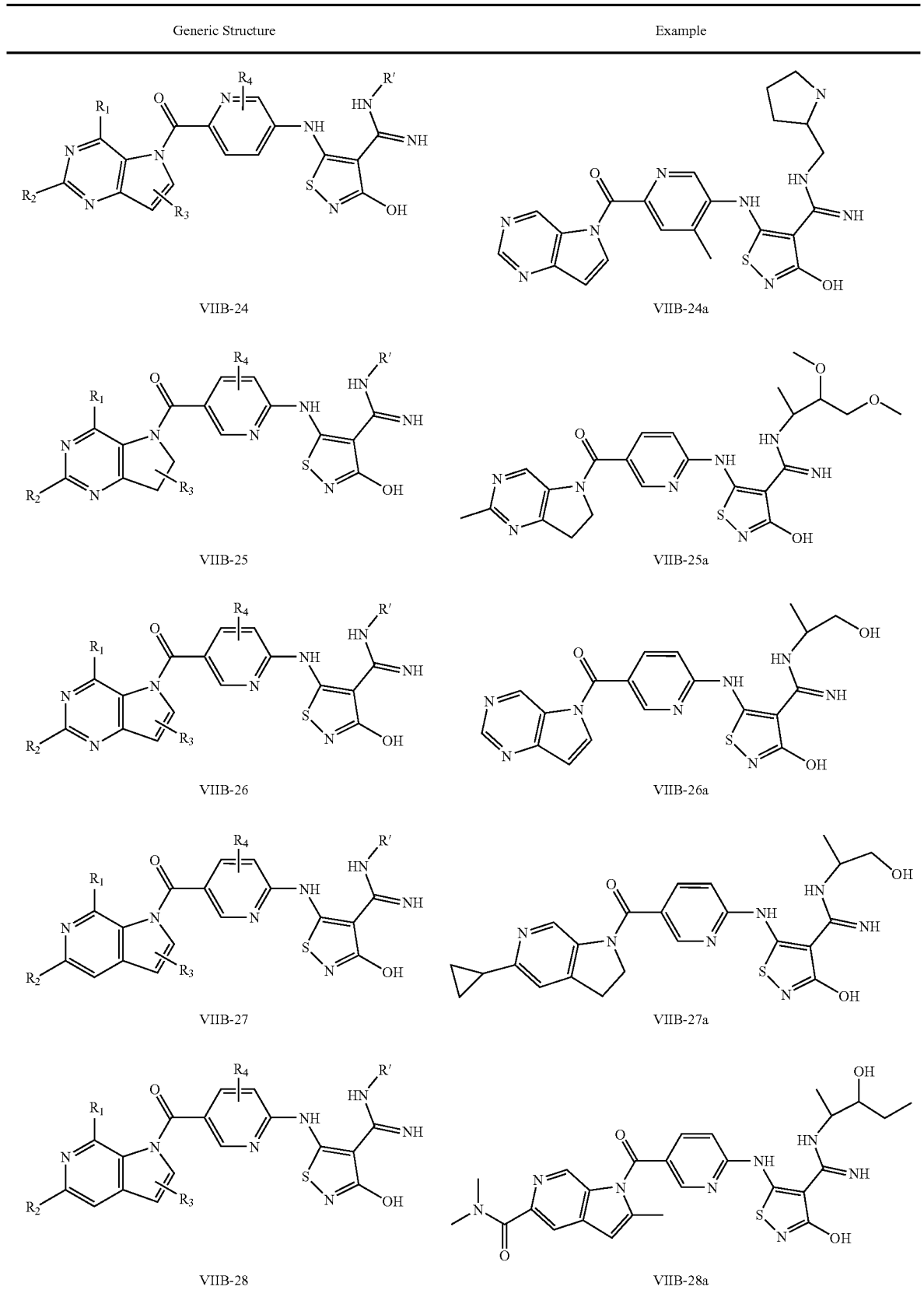 | |
VIIB-24
VIIB-24a
VIIB-25
VIIB-25a
VIIB-26
VIIB-26a
VIIB-27
VIIB-27a
VIIB-28
VIIB-28a -continued
| Generic Structure | Example |
|---|---|
| 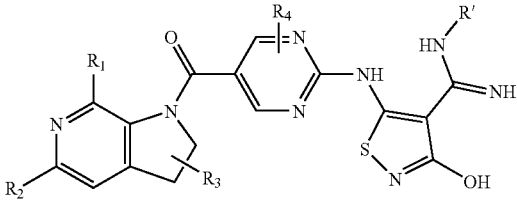<br>VIIB-29 | 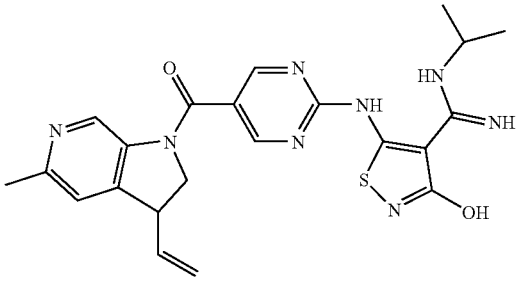<br>VIIB-29a |
| 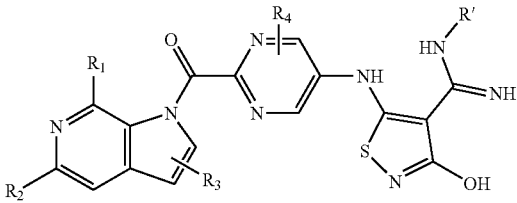<br>VIIB-30 | 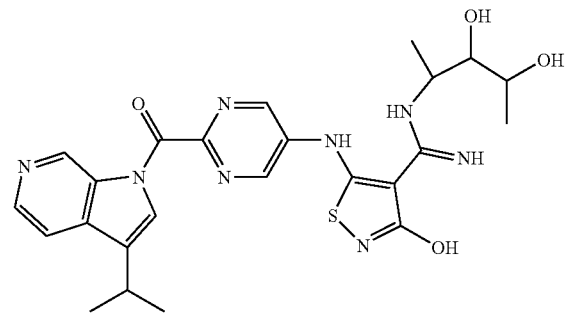<br>VIIB-30a |
| 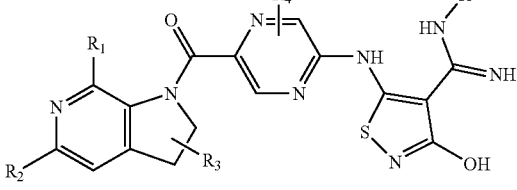<br>VIIB-31 | 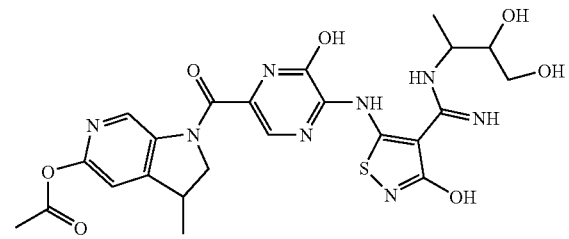<br>VIIB-31a |
| 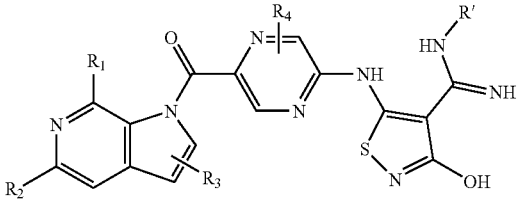<br>VIIB-32 | 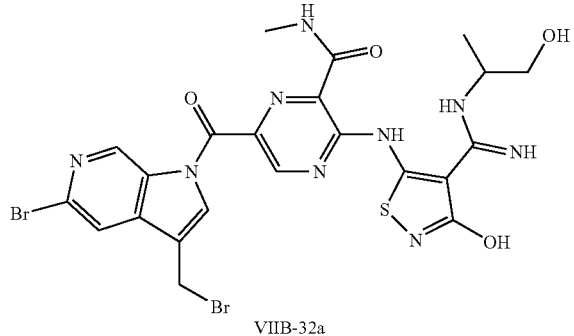<br>VIIB-32a |
| 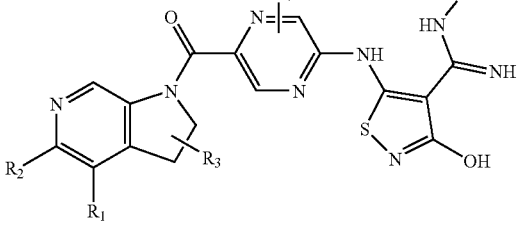<br>VIIB-33 | 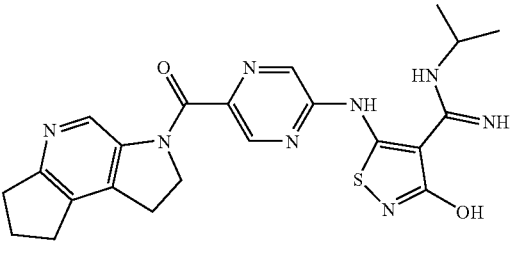<br>VIIB-33a |

-continued

| Generic Structure | Example |
|---|---|
| 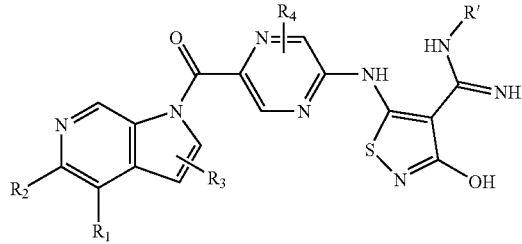<br>VIIB-34 | 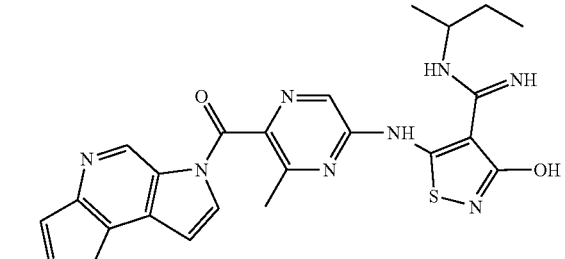<br>VIIB-34a |
| 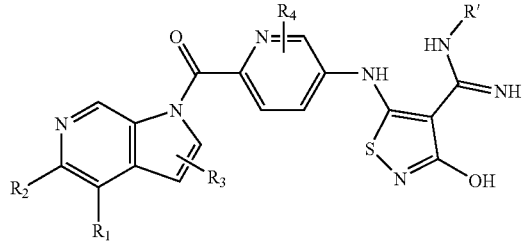<br>VIIB-35 | 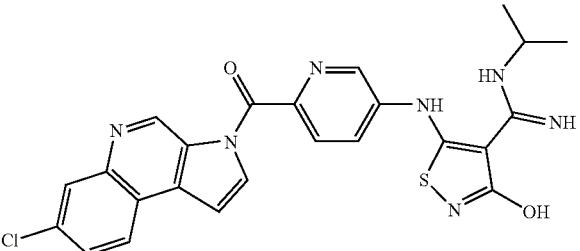<br>VIIB-35a |
| 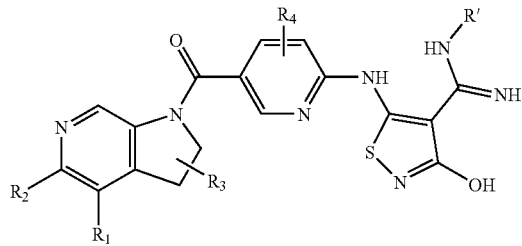<br>VIIB-36 | 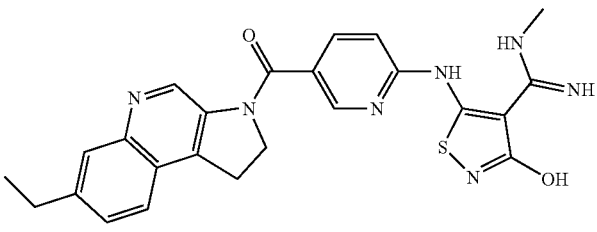<br>VIIB-36a |
| 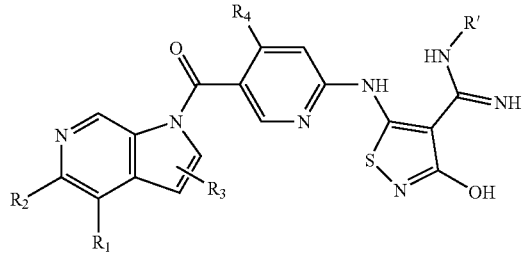<br>VIIB-37 | 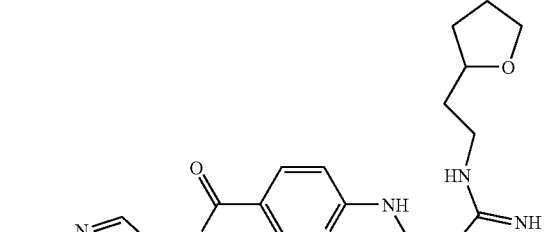<br>VIIB-37a |

In additional embodiments, the invention provides compounds according to any of formulas VIIB-3 to VIIB-37, wherein $R_1$-$R_4$ are all independently methyl, methoxy, ethyl, vinyl, ethynyl, halo, or H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, cyclopentyl, cyclopenten-3-yl, cyclopentadien-4-yl, cyclohexyl, or cyclohexen-2-yl.

In additional more specific embodiments, the invention provides compounds according to any of formulas VIIB-3 to VIIB-37, wherein $R_1$-$R_4$ are all independently halo, halomethyl, or H, and R' is —$(CH_2)_n$—B, where n is 1 or 2, and B is phenyl, pyridyl, piperazinyl, piperazinonyl, piperidinyl, piperidinonyl, morpholyl, furyl, tetrahydrofuryl, or pyrimidyl.

In additional more specific embodiments, the invention provides compounds according to any of formulas VIIB-3 to VIIB-37, wherein $R_1$-$R_4$ are all independently halo, halomethyl, or H, and R' is —$(CH_2)_n$—B, where n is 1 or 2, and B is quinolyl, thiazolidinonyl, isothiazolidinonyl, or oxindolyl.

In additional more specific embodiments, the invention contemplates compounds according to any of formulas VIIB-3 to VIIB-37, where $R_1$ is bromo, $R_2$-$R_4$ are H, and R' is isopropyl, 2-hydroxyethyl, 1-hydroxy-2-propyl, 2,3-dihydroxy-1-propyl, or 3,4-dihydroxy-2-butyl.

In additional more specific embodiments, the invention contemplates compounds according to any of formulas VIIB-3 to VIIB-37, where $R_1$-$R_4$ are H and R' is isopropyl or 2,3-dihydroxy-1-propyl.

In additional more specific embodiments, the invention contemplates compounds according to any of formulas VIIB-3 to VIIB-37, where $R_1$ is propyn-3-yl, $R_2$-$R_4$ are H and R' is isopropyl or 2,3-dihydroxy-1-propyl.

In additional more specific embodiments, the invention contemplates compounds according to any of formulas VIIB-3 to VIIB-37, where $R_1$ is nitro or cyano, $R_2$-$R_4$ are H and R' is 2-hydroxyethyl or 2-hydroxypropyl.

In additional more specific embodiments, the invention contemplates compounds according to any of formulas VIIB-3 to VIIB-37, where $R_2$ is dimethylamino or dimethylaminomethyl, $R_1$, $R_3$, and $R_4$ are H and R' is isobutyl or 3-cyclopentyl-propyl.

In still more specific embodiments, the invention contemplates compounds according to any of formulas VIIB-3 to VIIB-37, where $R_1$-$R_3$ are H, $R_4$ is chloro, and R' is isopropyl or 2,3-dihydroxy-1-propyl.

In still more specific embodiments, the invention contemplates compounds according to any of formulas VIIB-3 to VIIB-37, where $R_2$ is bromo, $R_1$, $R_3$, and $R_4$ are H, and R' is isopropyl or 2,3-dihydroxy-1-propyl.

Additional contemplated compounds for generic embodiments of formula VII are shown in the tables below.

| Cpd | Structure |
|---|---|
| 1. | (structure) |
| 2. | (structure) |
| 3. | (structure) |
| 4. | (structure) |
| 5. | (structure) |

-continued
| Cpd | Structure |
|---|---|
| 6. | 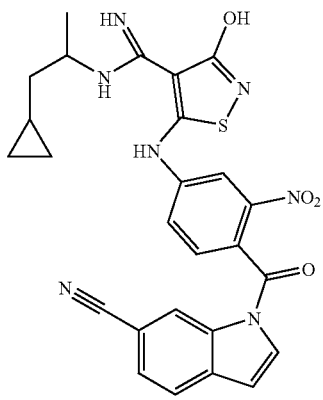 |
| 7. | 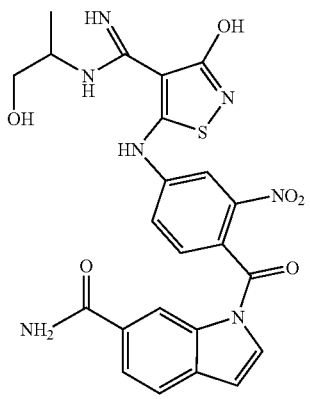 |
| 8. | 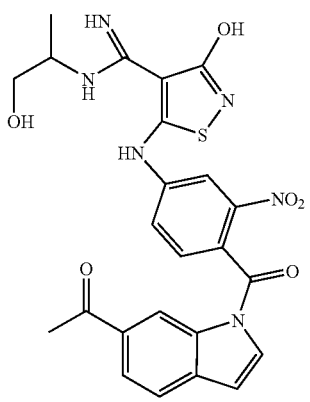 |
-continued
| Cpd | Structure |
|---|---|
| 9. | 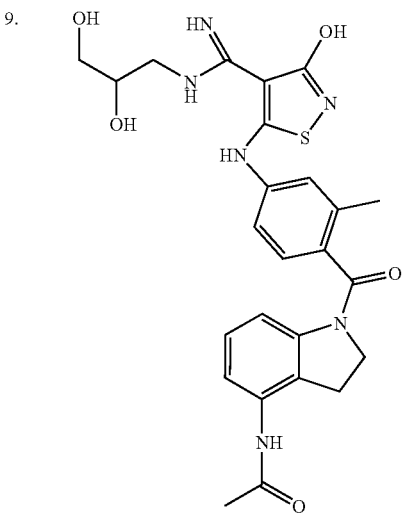 |
| 10. | 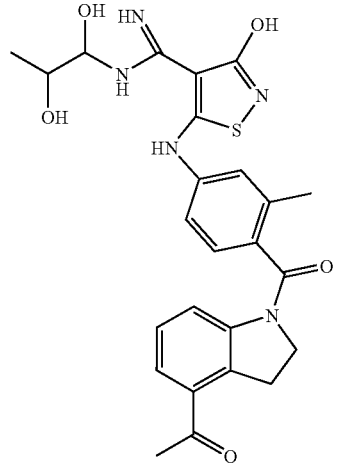 |
| 11. | 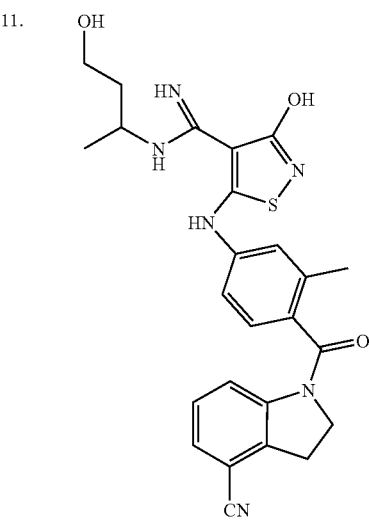 |

-continued

| Cpd | Structure |
|---|---|
| 12. | (structure with cyclopropyl, isothiazole, phenyl-methyl, indoline-NO₂) |
| 13. | (structure with hydroxymethyl-methyl amidine, isothiazole, methylphenyl, indoline-Br) |
| 14. | (structure with hydroxymethyl-methyl amidine, isothiazole, methylphenyl, indoline-Br) |

-continued

| Cpd | Structure |
|---|---|
| 15. | (structure with methylamino amidine, isothiazole, methylphenyl, indoline-SO₂CH₃) |
| 16. | (structure with dihydroxyethyl amidine, isothiazole, methylphenyl, indoline-SO₂NH₂) |
| 17. | (structure with hydroxymethyl-methyl amidine, isothiazole, methylphenyl, indoline-N(CH₃)₂) |

-continued
| Cpd | Structure |
|---|---|
| 18. | 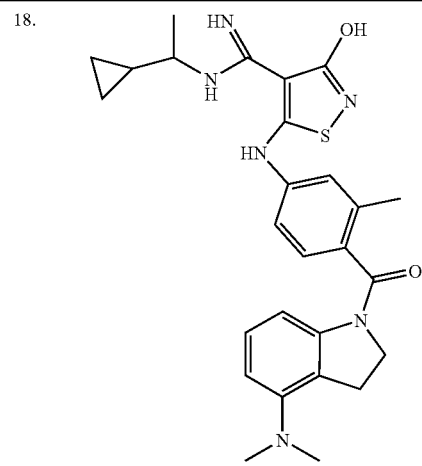 |
| 19. | 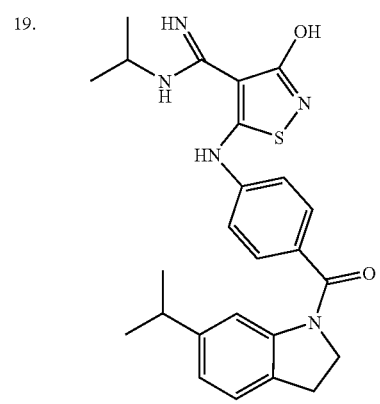 |
| 20. | 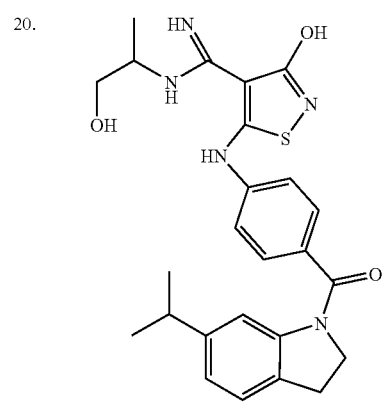 |
-continued
| Cpd | Structure |
|---|---|
| 21. | 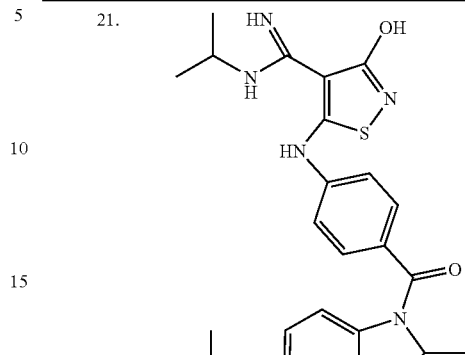 |
| 22. | 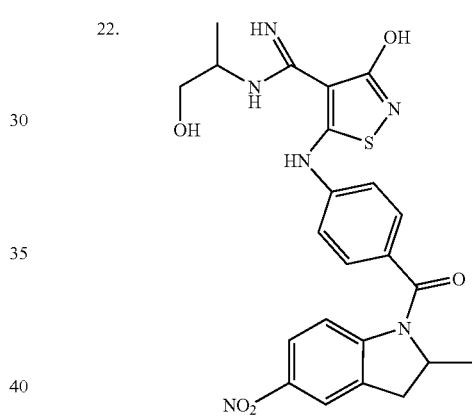 |
| 23. | 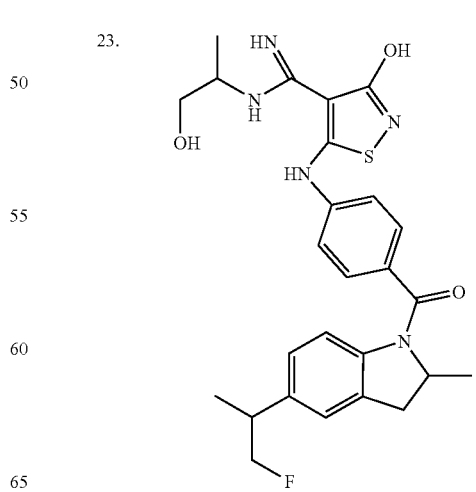 |

-continued
| Cpd | Structure |
|---|---|
| 24. | 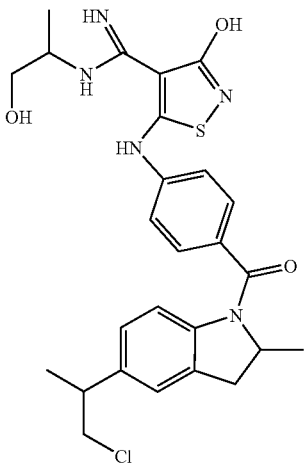 |
| 25. | 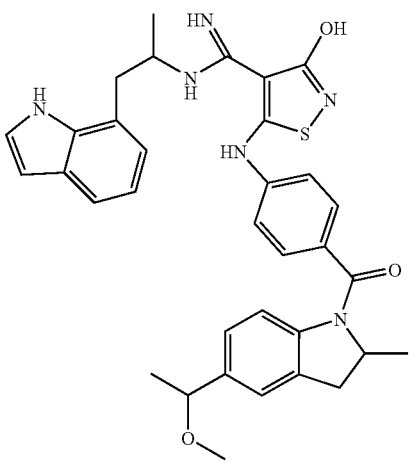 |
| 26. | 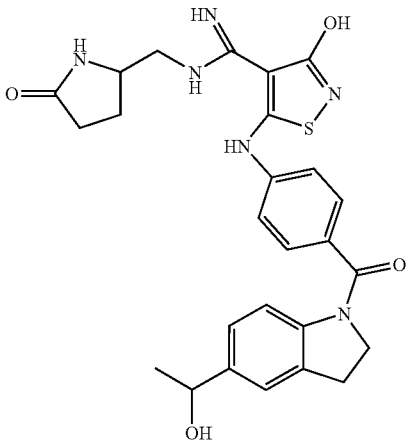 |
-continued
| Cpd | Structure |
|---|---|
| 27. | 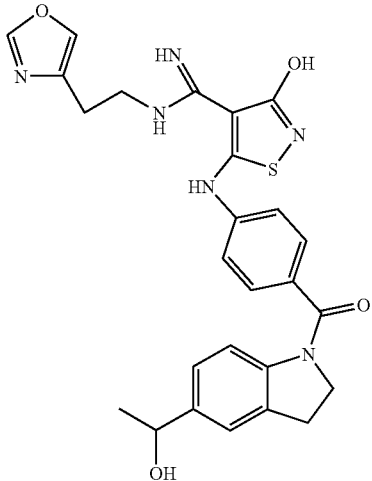 |
| 28. | 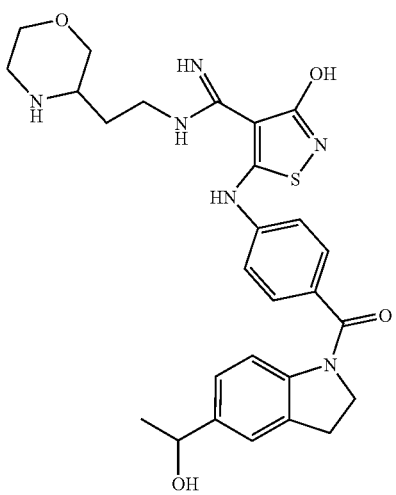 |
In another generic embodiment, this invention provides a compound of formula VIII below,
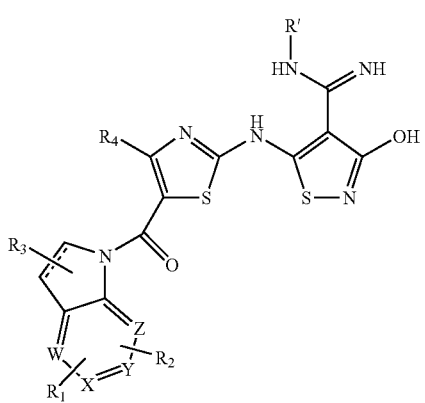
VIII where the dashed bond represents an optional double bond, where symbols W-Z represent N, CH, or $CR_{1 \text{ or } 2}$, and where $R_1$-R' are, defined as for formula VII.

In one subgeneric embodiment, this invention provides a compound of formula VIIIA below,

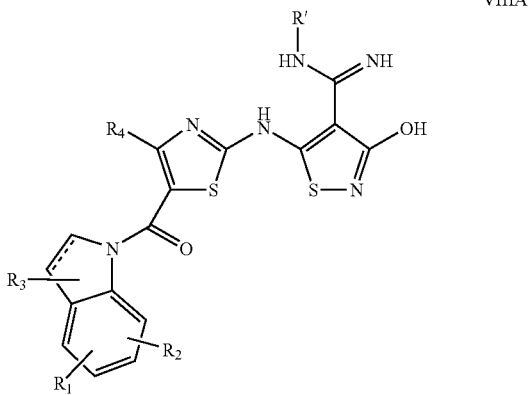

VIIIA where the dashed bond represents an optional double bond, and where all substituents are defined as for formula VIII.

In another generic embodiment, this invention provides a compound of formula VIIIB,

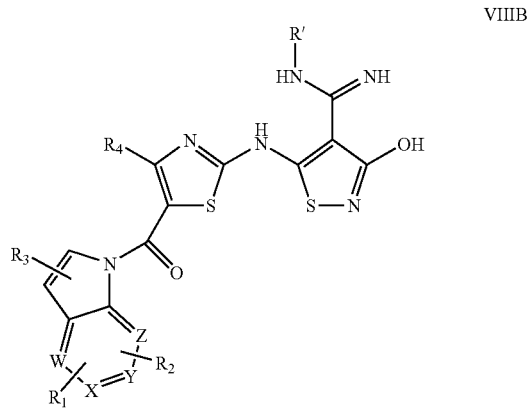

VIIIB where the dashed bond represents an optional double bond, where all substituents are defined as for formula VIII, and where symbols W-Z represent N, CH, or $CR_{1 \text{ or } 2}$, provided that at least one of W-Z is N.

In one subgeneric embodiment, this invention provides a compound of formula VIIIA-1,

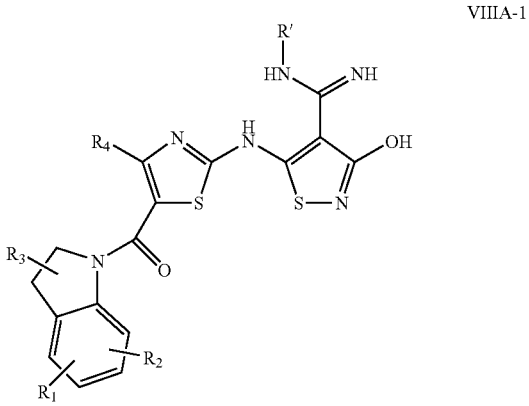

VIIIA-1 where all substituents are defined as for formula VIII.

In a more specific embodiment, this invention provides a compound of formula VIIIA-1, where $R_1$ and $R_2$ are as described above for formula VIII; $R_3$ and $R_4$ are both H; and R' is —$(CH_2)_n$—B, where n is 1 or 2 and B is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

In another more specific embodiment, this invention provides a compound of formula VIIIA-1, where $R_1$ and $R_2$ are as described above; $R_3$ and $R_4$ are both H; and R' is $C_1$-$C_6$ alkyl or O—$C_1$-$C_6$ alkyl, both optionally substituted as described above.

In another more specific embodiment, this invention provides a compound of formula VIIIA-1, where $R_1$ and $R_2$ are as described above; $R_3$ and $R_4$ are both H and R' is $C_1$-$C_6$ alkyl or O—$C_1$-$C_6$ alkyl, both optionally substituted as described above.

In a still more specific embodiment, this invention provides a compound of formula VIIIA-1, where $R_1$-$R_4$ are H and R' is $C_1$-$C_6$ alkyl or O—$C_1$-$C_6$ alkyl, both optionally substituted as described above.

In another more specific embodiment, this invention provides a compound of formula VIIIA-1, in which $R_1$ and $R_2$ are halogen; $R_3$ and $R_4$ are H; and R' is methyl, ethyl, isopropyl, or sec-butyl.

In another more specific embodiment, this invention provides a compound of formula VIIIA-1, in which $R_1$ is halogen; $R_2$-$R_4$ are H; and R' is methyl, ethyl, isopropyl, or sec-butyl.

In another more specific embodiment, this invention provides a compound of formula VIIIA-1, in which $R_1$ and $R_2$ are halogen; $R_3$ and $R_4$ are H; and R' is 1,2-chloropropan-3-yl or 1-hydroxy-butan-3-yl.

In another more specific embodiment, this invention provides a compound of formula VIIIA-1, in which $R_1$ is bromo; $R_2$-$R_4$ are H; and R' is isopropyl.

In another more specific embodiment, this invention provides a compound of formula VIIIA-1, in which $R_1$ and $R_2$ are halogen; $R_3$ and $R_4$ are H; and R' is 1,2-dihydroxy-propan-3-yl, 2-hydroxyethyl, 1,2-dihydroxybutan-4-yl, or 4-hydroxybutyl.

In another more specific embodiment, this invention provides a compound of formula VIIIA-1, in which $R_1$ and $R_2$ are halogen; $R_3$ and $R_4$ are $C_1$-$C_6$ alkyl; and R' is 1,2-dihydroxybutan-3-yl or 4-methoxybutyl.

In another more specific embodiment, this invention provides a compound of formula VIIIA-1, in which $R_1$ and $R_2$ are 5-chloro and 6-chloro; $R_3$ and $R_4$ are H; and R' is 3-hydroxypropyl.

In another more specific embodiment, this invention provides a compound of formula VIIIA-1, in which $R_1$ and $R_2$ are H; $R_3$ is 2-hydroxy; $R_4$ is H; and R' is 3-hydroxypropyl.

In another more specific embodiment, this invention provides a compound of formula VIIIA-1, in which $R_1$ and $R_2$ are 5-chloro and 6-chloro; $R_3$ is 2-hydroxy; $R_4$ is H; and R' is 3-hydroxypropyl.

In another more specific embodiment, this invention provides a compound of formula VIIIA-1, in which $R_1$ and $R_2$ are, independently, H or halogen; $R_3$ is H, 2-OH, or 2-methyl; $R_4$ is H or methyl; and R' is 1,2-chloropropan-3-yl.

In another more specific embodiment, this invention provides a compound of formula VIIIA-1, in which $R_1$ and $R_2$ are halogen; $R_3$ and $R_4$ are, independently H, OH, or methyl; and R' is 1-hydroxy-butan-3-yl, 1,2-dihydroxy-propan-3-yl, or 2-hydroxyethyl In another more specific embodiment, this invention provides a compound of formula VIIIA-1, in which $R_1$ is halo; $R_2$-$R_4$ are, independently H, OH, or methyl; and R' is isopropyl.

In another more specific embodiment, this invention provides a compound of formula VIIIA-1, in which $R_1$ and $R_2$ are, independently, H or halogen; $R_3$ and $R_4$ are, independently, H, OH, or methyl; and R' is 4-hydroxybutyl or 1,2-dihydroxybutan-4-yl In another more specific embodiment, this invention provides a compound of formula VIIIA-1, in which $R_1$ and $R_2$ are, independently, H or halogen; $R_3$ and $R_4$ are, independently, H, OH, or methyl; and R' is 1,2-dihydroxybutan-3-yl.

In another more specific embodiment, this invention provides a compound of formula VIIIA-1, in which $R_1$ and $R_2$ are, independently, H, $C_1$-$C_6$ alkyl, $C_1$-$C_6$ alkenyl, $C_1$-$C_6$ cycloalkyl, or halogen; $R_3$ and $R_4$ are, independently, H, OH, or $C_1$-$C_6$ alkyl; and R' is 1,2-dihydroxybutan-3-yl.

In another more specific embodiment, this invention provides a compound of formula VIIIA-1, in which $R_1$ and $R_2$ are, independently, H, $C_1$-$C_6$ alkyl, or halogen; $R_3$ and $R_4$ are, independently, H, OH or methyl; and R' is 4-methoxybutyl, 3-hydroxypropyl or 2-hydroxypropyl.

In another more specific embodiment, this invention provides a compound of formula VIIIA-1, where $R_1$ and $R_2$ are fused cyclohexyl or fused cyclopentyl; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIIA-1, where $R_1$ and $R_2$ are benzo; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 4 and 5, are fused (4,5)-imidazolo; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 5 and 6, are fused (2,3)-furyl, (2,3)-pyridyl, or fused cyclopentyl; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 5 and 6, are fused cyclopentyl; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 6 and 7, are fused cyclopentyl, $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 5 and 6, are benzo; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 6 and 7, are benzo; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula VIIIA-1, where $R_1$ and $R_2$, at positions 4 and 5, are benzo, said benzo group bearing fluoro at each ortho position; $R_3$ and $R_4$ are, independently, H, OH, or methyl; and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIIA-1, where $R_2$-$R_4$ are H and R' is $C_1$-$C_6$ alkyl, optionally substituted with halogen, $C_1$-$C_3$ alkoxy, or hydroxy.

In a still more specific embodiment, this invention provides a compound of formula VIIIA-1, where $R_1$-$R_4$ are H and R' is $C_1$-$C_4$ alkyl, optionally substituted with one or two hydroxy groups.

In another still more specific embodiment, this invention provides a compound of formula VIIIA-1, where $R_1$, $R_2$, and $R_4$ are H; $R_3$ is methyl or OH; and R' is $C_1$-$C_4$ alkyl, optionally substituted with one or two hydroxy groups.

In another more specific embodiment, this invention provides a compound of formula VIIIA-1, where $R_1$ and $R_2$ are H; $R_3$ is H, methyl, or OH; $R_4$ is H, OH, or $C_1$-$C_4$ alkyl, optionally substituted with halogen or hydroxy; and R' is $C_1$-$C_4$ alkyl, optionally substituted with one or two hydroxy groups.

In another more specific embodiment, this invention provides a compound of formula VIIIA-1, where $R_1$ and $R_2$ are H; $R_3$ is H, methyl, or OH; $R_4$ is methyl, optionally substituted with halogen or hydroxy; and R' is $C_1$-$C_4$ alkyl, optionally substituted with one or two hydroxy groups.

In another more specific embodiment, this invention provides a compound of formula VIIIA-1, where $R_1$ and $R_2$ are H; $R_3$ is H, methyl, or OH; $R_4$ is $C_1$-$C_4$ alkyl, optionally substituted with halogen or hydroxy; and R' is —$(CH_2)_n$—B, where n is 1 or 2, and B is isothiazolyl, isoxazolyl, oxazolyl, oxazolinyl, oxazolidinyl, oxazolidinonyl, thiazolyl, thienyl, furyl, pyrrolyl, pyrrolinyl, pyrrolidinyl, pyrrolidinonyl, thiazolinyl, thiazolidinyl, thiazolidinonyl, isothiazolinyl, isothiazolidinyl, imidazolinyl, imidazolyl, pyridyl, or phenyl.

In another more specific embodiment, this invention provides a compound of formula VIIIA-1, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula VIIIA-1, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In a still more specific embodiment, this invention provides a compound of formula VIIIA-1, in which $R_1$ and $R_2$ are both halogen, $R_3$ is 2-methyl, and $R_4$ is H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula VIIIA-1, in which $R_1$ and $R_2$ are both H, $R_3$ is 3-methyl, $R_4$ is 2-chloro, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula VIIIA-1, in which $R_1$ and $R_2$ are both H, $R_3$ is 3-methyl, $R_4$ is 2-(2-chloroethyl), and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula VIIIA-1, in which $R_1$ is 4-$CF_3$, $R_3$ is 2-hydroxymethyl, $R_2$ and $R_4$ are H, and R' is —$(CH_2)_n$—B, where n is 1 or 2, and B is isothiazolyl, isoxazolyl, oxazolyl, oxazolinyl, oxazolidinyl, oxazolidinonyl, thiazolyl, thienyl, furyl, pyrrolyl, pyrrolinyl, pyrrolidinyl, pyrrolidinonyl, thiazolinyl, thiazolidinyl, thiazolidinonyl, isothiazolinyl, isothiazolidinyl, imidazolinyl, imidazolyl, pyridyl, or phenyl.

In a still more specific embodiment, this invention provides a compound of formula VIIIA-1, in which $R_1$ and $R_2$ are both H, $R_3$ is 3-methyl, $R_4$ is 2-chloro, and R' is —$(CH_2)_n$—B, where n is 1 or 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula VIIIA-1, in which one or both of $R_1$ and $R_2$ are $CF_3$, $R_3$ and $R_4$ are H, and R' is —$(CH_2)_n$—B, where n is 1 or 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula VIIIA-1, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a still more specific embodiment, this invention contemplates the compound of formula VIIIA-1, in which $R_1$ is 6-chloro, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 5-chloro, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 4-chloro, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 7-chloro, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 7-bromo, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 4-bromo, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-1, in which $R_1$ is 5-bromo, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates a compound of formula VIIIA-1, in which $R_1$ is 5-$CF_3$, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, oxazolidinonyl, thiazolyl, thienyl, furyl, pyrrolyl, pyrrolinyl, pyrrolidinyl, thiazolinyl, thiazolidinyl, thiazolidinonyl, isothiazolinyl, isothiazolidinyl, imidazolinyl, imidazolyl, pyridyl, phenyl.

In another more specific embodiment, this invention provides a compound of formula VIIIA-1, in which $R_1$ and $R_2$, in positions 4 and 6, are both halogen, $R_3$ is 2-chloromethyl, and $R_4$ is H, and R' is —$(CH_2)_n$—B, where n is 1 or 2, and B is 2-pyridyl, 3-pyridyl, 4-pyridyl, 2-piperidyl, 3-piperidyl, or 4-piperidyl.

In another more specific embodiment, this invention provides a compound of formula VIIIA-1, in which $R_1$ and $R_2$, in positions 4 and 6, are both halogen, $R_3$ is 3-fluoromethyl, and $R_4$ is H, and R' is —$(CH_2)_n$—B, where n is 1 or 2, and B is 2-pyrimidyl, 4-pyrimidyl, 2-morpholyl, or 3-morpholyl.

In another more specific embodiment, this invention provides a compound of formula VIIIA-1, in which $R_1$ and $R_2$, in positions 4 and 6, are both halogen, $R_3$ is 3-fluoromethyl, and $R_4$ is H, and R' is —$(CH_2)_n$—B, where n is 2, and B is 4-bromo-2-pyrimidyl, 2-chloro-4-pyrimidyl, 2-morpholyl, or 3-morpholyl.

In a still more specific embodiment, this invention provides a compound of formula VIIIA-1, in which $R_1$ is 3-cyano, $R_2$-$R_4$ are H, and R' is —$(CH_2)_n$—B, where n is 1 or 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula VIIIA-1, in which $R_1$ is 3-hydroxy, 5-dimethylamino, 4-methoxy, 5-(2-methoxyethyl), or 6-methoxymethyl $R_2$-$R_4$ are H, and R' is —$(CH_2)_n$—B, where n is 1 or 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula VIIIA-1, in which $R_1$ is 4-ethoxy, 4-cyano, 4-$CH_2F$, 7-acetoxy, 7-acetyl, 6-methyloxycarbonyl, 6-dimethylaminocarbonyl, 4-dimethylamino, 5-dimethylaminocarbonyl, 5-methyloxycarbonyl, 4-acetyl, 4-acetoxy, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another embodiment, this invention provides a compound of formula VIIIA-2

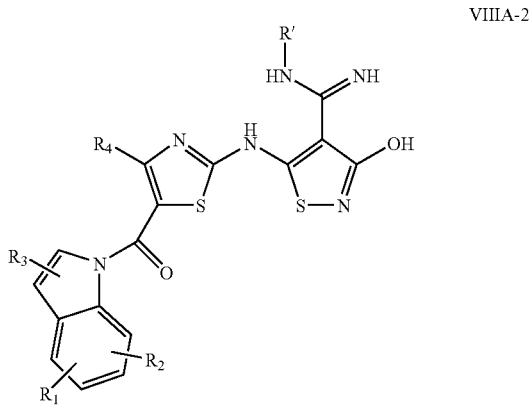

VIIIA-2

In a more specific embodiment, this invention provides a compound of formula A-2, where $R_3$ and $R_4$ are both H and R' is —$(CH_2)_n$—B.

In another subgeneric embodiment, this invention provides a compound of formula VIIIA-2, where R' is $C_1$-$C_6$ alkyl or O—$C_1$-$C_6$ alkyl, both optionally substituted as described above.

In another subgeneric embodiment, this invention provides a compound of formula VIIIA-2, where $R_3$ and $R_4$ are both H and R' is $C_1$-$C_6$ alkyl or O—$C_1$-$C_6$ alkyl, both optionally substituted as described above.

In a more specific embodiment, this invention provides a compound of formula VIIIA-2, where $R_2$-$R_4$ are H and R' is $C_1$-$C_6$ alkyl, optionally substituted with halogen, $C_1$-$C_3$ alkoxy, or hydroxy.

In another still more specific embodiment, this invention provides a compound of formula A-1, where $R_1$, $R_2$, and $R_4$ are H; $R_3$ is H, methyl or OH; and R' is $C_1$-$C_4$ alkyl, optionally substituted with one or two hydroxy groups.

In another more specific embodiment, this invention provides a compound of formula A-1, where $R_1$ and $R_2$ are H; $R_3$ is H, methyl, or OH; $R_4$ is $C_1$-$C_4$ alkyl, optionally substituted with halogen or hydroxy; and R' is $C_1$-$C_4$ alkyl, optionally substituted with one or two hydroxy groups.

In another more specific embodiment, this invention provides a compound of formula VIIIA-2, where $R_1$, in position 5, is dimethylamino, dimethylaminomethyl, or acetylamino, $R_3$, in position 3, is methoxy or methoxymethyl, $R_2$ and $R_4$ are H, and R' is $C_1$-$C_6$ alkyl, optionally substituted with halogen, $C_1$-$C_3$ alkoxy, or hydroxy.

In another more specific embodiment, this invention provides a compound of formula VIIIA-2, where $R_1$, in position 4, is dimethylamino, dimethylaminomethyl, or acetylamino, $R_2$, in position 6, is bromomethyl, $R_3$ and $R_4$ are H, and R' is mono-hydroxy $C_1$-$C_4$ alkyl.

In another more specific embodiment, this invention provides a compound of formula VIIIA-2, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula VIIIA-2, in which $R_1$ and $R_2$ are both halogen, $R_3$ is 2-methyl, and $R_4$ is H, and R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula VIIIA-2, in which $R_1$ and $R_2$, in positions 4 and 6, are both halogen, $R_3$ is 2-chloromethyl, and $R_4$ is H, and R' is —$(CH_2)_n$—B, where n is 1, and B is 2-pyridyl, 3-pyridyl, 4-pyridyl, 2-piperidyl, 3-piperidyl, or 4-piperidyl.

In another more specific embodiment, this invention provides a compound of formula VIIIA-2, in which $R_1$ and $R_2$, in positions 4 and 6, are both halogen, $R_3$ is 3-fluoromethyl, and $R_4$ is H, and R' is —$(CH_2)_n$—B, where n is 1, and B is 2-pyrimidyl, 4-pyrimidyl, 2-morpholyl, or 3-morpholyl.

In a more specific embodiment, this invention contemplates a compound of formula VIIIA-2, where $R_1$-$R_4$ are H and R' is 2-(2-furyl)ethyl, 2-hydroxyethyl, or 2,3-dihydroxy-1-propyl.

In another more specific embodiment, this invention contemplates a compound of formula VIIIA-2 in which $R_1$ and $R_2$ together, at positions 5 and 6, are benzo or fused cyclopentyl, $R_3$ and $R_4$ are H, and R' is isopropyl.

In another more specific embodiment, this invention contemplates a compound of formula VIIIA-2 in which $R_1$ and $R_2$ together, at positions 6 and 7, are fused 2,3-pyrido or pyrrolo, $R_3$ and $R_4$ are H, and R' is isopropyl.

In another more specific embodiment, this invention contemplates a compound of formula VIIIA-2 in which $R_1$ and $R_2$ together, at positions 4 and 5, are fused (2,3)-furyl, $R_3$ and $R_4$ are H, and R' is 1,2-dihydroxy-propan-3-yl.

In another more specific embodiment, this invention contemplates a compound of formula VIIIA-2 in which $R_1$ and $R_2$ together, at positions 6 and 7, are fused (2,3)thienyl, $R_3$ and $R_4$ are H, and R' is 2-hydroxyethyl.

In a still more specific embodiment, this invention provides a compound of formula VIIIA-2 in which $R_1$ and $R_2$ are both H, $R_3$ is 4-methyl or 5-methyl, $R_4$ is 7-chloro, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula VIIIA-2 in which $R_1$ is 4-$CF_3$, $R_3$ is 6-hydroxymethyl, $R_2$ and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula VIIIA-2 in which $R_1$ and $R_2$ are both H, $R_3$ is 3-methyl, $R_4$ is 2-chloro, and R' is —$(CH_2)_n$—B, where n is 1 or 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates the compound of formula VIIIA-2 in which $R_1$ is 5-chloro, 6-chloro, or 7-chloro, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-2 in which $R_1$ is 3-bromo, 4-bromo, or 5-bromo, $R_2$, $R_3$, and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula VIIIA-2 in which $R_1$ is 6-chloro, $R_2$ is 7-chloro, $R_3$ and $R_4$ are H, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula VIIIA-2 in which one or both of $R_1$ and $R_2$ are $CF_3$, $R_3$ and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula VIIIA-2 in which $R_1$ is 4-$CF_3$, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula VIIIA-2 in which $R_1$ is 4-cyano, 4-hydroxy, 4-methoxy, 5-hydroxy, or 4-methoxymethyl, $R_2$-$R_4$ are H, and R' is —$(CH_2)_n$—B, where n is 1 or 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula VIIIA-2 in which $R_1$ is 4-dimethylamino, 7-acetyl, 7-dimethylamino, 7-dimethylaminocarbonyl, or 7-methyloxycarbonyl, $R_2$, $R_3$, and $R_4$ are H, and R' is —$(CH_2)_n$—B, where n is 1 or 2, and B is isothiazol-4-yl, isoxazol-3-yl, oxazol-2-yl, 2-oxazolin-2-yl, oxazolidin-4-yl, thiazol-2-yl, thien-2-yl, fur-2-yl, pyrrol-3-yl, pyrrolin-4-yl, pyrrolidin-3-yl, thiazolin-4-yl, thiazolidin-4-yl, imidazol-2-yl, 2-pyridyl, 4-pyridyl, m-tolyl, or phenyl.

In a still more specific embodiment, this invention contemplates a compound of formula VIIIA-2 in which $R_1$ is 6-acetoxy, or 7-acetoxy, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula VIIIA-2 in which $R_1$ is 7-acetyl, or 7-acetoxy, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula VIIIA-2 in which $R_1$ is 3-$CH_2F$, $R_2$, $R_3$, and $R_4$ are H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

The following are subgeneric embodiments, as well as more specific embodiments and prophetic examples, which contain one or more of W-Z=nitrogen.

In one subgeneric embodiment, this invention provides a compound of formula VIIIB-1,

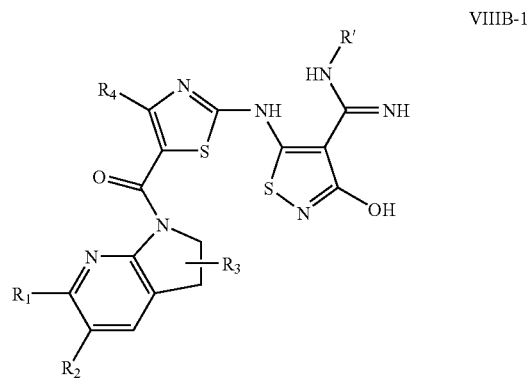

VIIIB-1 where all substituents are defined as for formula VIIIA.

In a more specific embodiment, this invention provides a compound of formula VIIIB-1, where $R_1$-$R_4$ are, independently, H, $C_1$-$C_3$ alkyl, OH, or halogen; and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula VIIIB-1, where $R_1$-$R_4$ are, independently, H, $C_1$-$C_3$ alkyl, OH, or halogen; and R' is $C_1$-$C_4$ alkyl, optionally substituted with one or two hydroxy groups.

In a still more specific embodiment, this invention provides a compound of formula VIIIB-1, where $R_1$-$R_4$ are H and R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In a specific contemplated example, this invention provides a compound of formula VIIIB-1, where $R_1$-$R_4$ are H and R' is 1-hydroxy-2-propyl, 2,3-dihydroxy-1-propyl, or isopropyl.

In a specific contemplated example, this invention provides a compound of formula VIIIB-1, where $R_1$ and $R_2$ are H; $R_3$ is 2-methyl or 2-hydroxy; $R_4$ is H or methyl; and R' is isopropyl.

In another specific contemplated example, this invention provides a compound of formula VIIIB-1, where $R_1$ and $R_2$ are H; $R_3$ is 2-methyl or 2-hydroxy; $R_4$ is H or methyl; and R' is 2,3-dihydroxy-1-propyl or 1-hydroxy-2-propyl.

In another specific contemplated example, this invention provides a compound of formula VIIIB-1, where $R_1$ is $C_1$-$C_4$ alkyl, $C_1$-$C_4$ alkenyl, $C_1$-$C_4$ alkynyl, halomethyl, or halogen; $R_2$-$R_4$ are H; and R' is 3,4-dihydroxy-2-butyl.

In another specific contemplated example, this invention provides a compound of formula VIIIB-1, where $R_1$ is $C_1$-$C_4$ alkyl, $C_1$-$C_4$ alkenyl, $C_1$-$C_4$ alkynyl, halomethyl, or halogen; $R_2$— is H; $R_3$ is 2-OH; $R_4$ is methyl or H; and R' is 3,4-dihydroxy-2-butyl.

In another specific contemplated example, this invention provides a compound of formula VIIIB-1, where $R_1$-$R_4$ are H and R' is 3,4-dihydroxy-2-butyl.

In another more specific embodiment, this invention contemplates a compound of formula VIIIB-1, where $R_1$-$R_4$ are H and R' is ethoxy, isopropoxy, or O—$CH(CH_3)CH_2CH_3$.

In another specific contemplated example, this invention provides a compound of formula VIIIB-1, where $R_1$-$R_4$ are H and R' is ethoxy.

In another more specific embodiment, this invention contemplates a compound of formula VIIIB-1, where $R_1$-$R_4$ are H and R' is 2-chloroethyl, 2-bromoethyl, or 1,2-dichloro-3-propyl.

In another more specific embodiment, this invention provides a compound of formula VIIIB-1 where one of $R_1$ and $R_2$ is H and the other is amino, methyl amino, dimethylamino, dimethylaminomethyl, or acetylamino, $R_3$-$R_4$ are H, and R' is $C_1$-$C_6$ alkyl, optionally substituted with halogen, $C_1$-$C_3$ alkoxy, or hydroxy.

In another more specific embodiment, this invention provides a compound of formula VIIIB-1, where one of $R_1$ and $R_2$ is H and the other is nitro, cyano, methylcarbamoyl, dimethylcarbamoyl, or aminosulfonyl, $R_3$-$R_4$ are H and R' is $C_1$-$C_6$ alkyl, optionally substituted with halogen, $C_1$-$C_3$ alkoxy, or hydroxy.

In another more specific embodiment, this invention provides a compound of formula VIIIB-1, where $R_1$ and $R_2$ are fused cyclohexyl or fused cyclopentyl, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIIB-1, where $R_1$ and $R_2$ are benzo, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula VIIIB-1, wherein $R_1$ and $R_2$ are halogen, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In a more specific embodiment, this invention provides a compound of formula VIIIB-1, where $R_1$-$R_3$ are H, $R_4$ is 2-halo, 2-cyano, 2-hydroxy, or 2-methoxy, and R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula VIIIB-1, where $R_1$ is halo, $R_2$-$R_4$ are H and R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, the invention contemplates a compound of formula VIIIB-1, where $R_1$ is bromo, $R_2$-$R_4$ are H and R' is isopropyl, 2-hydroxyethyl, 1-hydroxy-2-propyl, or 2,3-dihydroxy-1-propyl.

In another embodiment, this invention provides a compound of formula VIIIB-2,

VIIIB-2

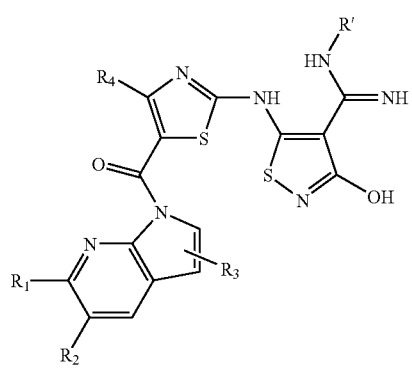

where substituents are defined as for formula I.

In a more specific embodiment, this invention provides a compound of formula VIIIB-2, where $R_1$-$R_4$ are, independently, H or halogen, and R' is isopropyl, 2-(2-furyl)ethyl, 2-hydroxyethyl, 2-methoxyethyl, 1-hydroxy-2-propyl, 1,2-dihydroxy-3-propyl, or 3,4-dihydroxy-2-butyl.

In another more specific embodiment, this invention provides a compound of formula VIIIB-2, where one of $R_1$ and $R_2$ is H and the other is amino, methyl amino, dimethylamino, dimethylaminomethyl, or acetylamino, $R_3$-$R_4$ are H, and R' is $C_1$-$C_6$ alkyl, optionally substituted with halogen, $C_1$-$C_3$ alkoxy, or hydroxy.

In another more specific embodiment, this invention provides a compound of formula VIIIB-2, where one of $R_1$ and $R_2$ is H and the other is nitro, cyano, methylcarbamoyl, dimethylcarbamoyl, or aminosulfonyl, $R_3$-$R_4$ are H and R' is $C_1$-$C_6$ alkyl, optionally substituted with halogen, $C_1$-$C_3$ alkoxy, or hydroxy.

Additional subgeneric embodiments of compounds of formula I with one or more of W-Z=nitrogen are shown below.

VIIIB-3

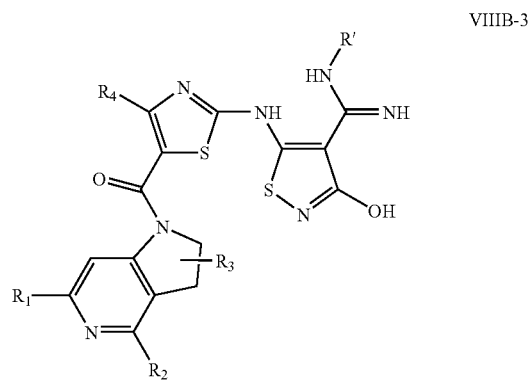

VIIIB-4

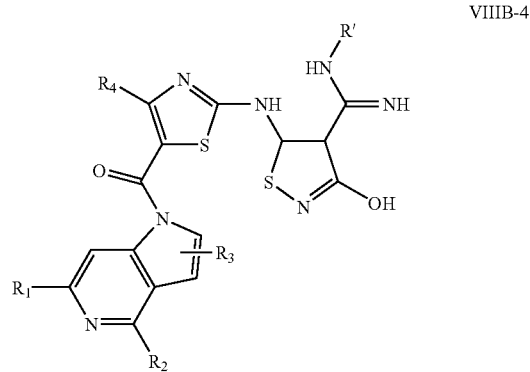

VIIIB-5

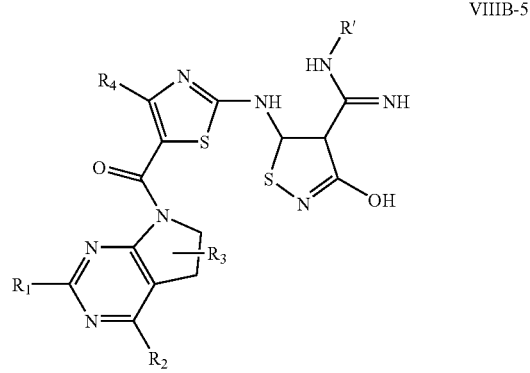

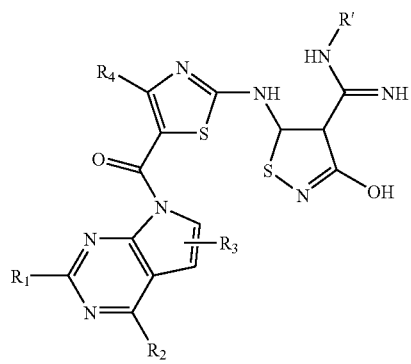
VIIIB-6
VIIIB-7
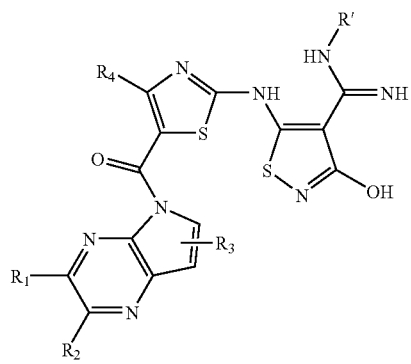
VIIIB-10
VIIIB-11
VIIIB-8
VIIIB-12
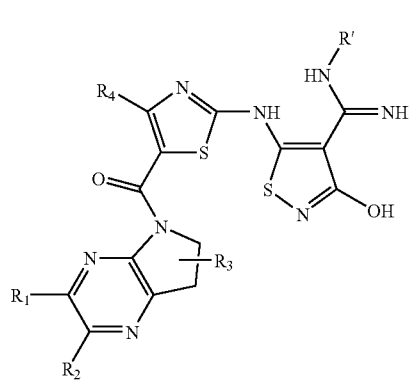
VIIIB-9
VIIIB-13

-continued

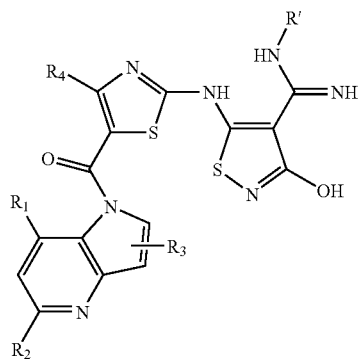
VIIIB-14

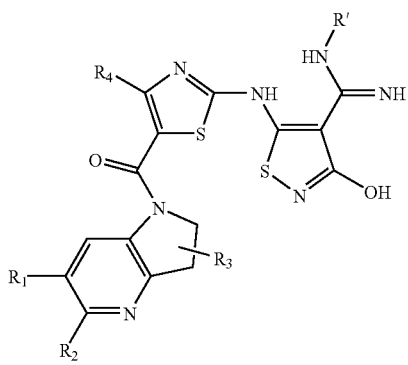
VIIIB-15

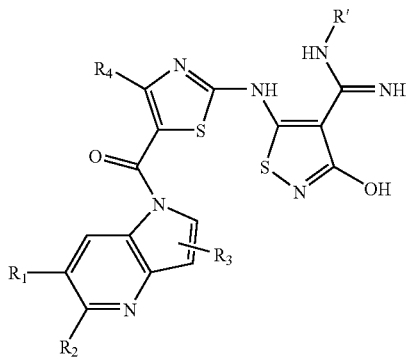
VIIIB-16

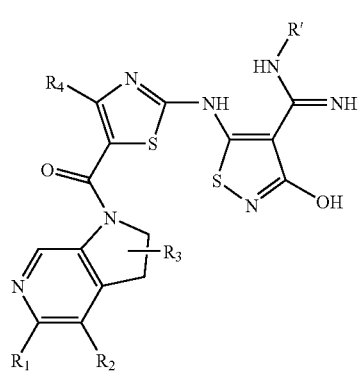
VIIIB-17

-continued

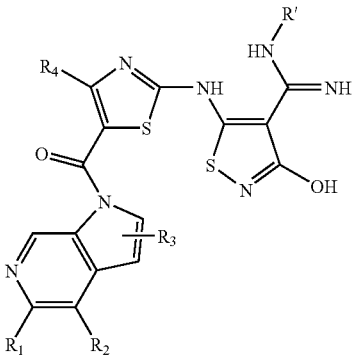
VIIIB-18

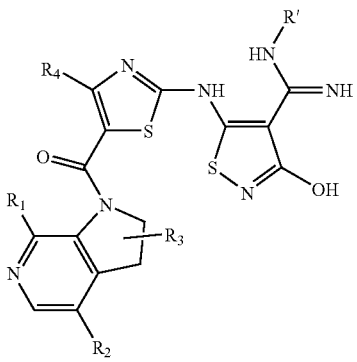
VIIIB-19

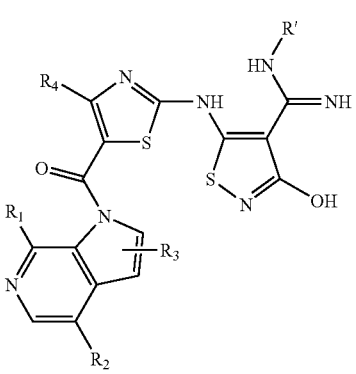
VIIIB-20

In more specific embodiments, the invention provides compounds according to any of formulas VIIIB-3 to VIIIB-20, wherein $R_1$-$R_4$ are all independently methyl, methoxy, ethyl, vinyl, ethynyl, halo, OH, or H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, cyclopentyl, cyclopenten-3-yl, cyclopentadien-4-yl; cyclohexyl, or cyclohexen-2-yl.

In additional more specific embodiments, the invention provides compounds according to any of formulas VIIIB-1 to VIIIB-20, wherein $R_1$-$R_4$ are all independently halo, halomethyl, OH, or H, and R' is —$(CH_2)_n$—B, where n is 1 or 2, and B is phenyl, pyridyl, piperazinyl, piperazinonyl, piperidinyl, piperidinonyl, morpholyl, furyl, tetrahydrofuryl, or pyrimidinyl.

In additional more specific embodiments, the invention contemplates compounds according to any of formulas VIIIB-1 to VIIIB-20, where $R_1$ is bromo; $R_2$-$R_4$ are all H; and R' is isopropyl, 2-hydroxyethyl, 1-hydroxy-2-propyl, 2,3-dihydroxy-1-propyl, or 3,4-dihydroxy-2-butyl.

In still more specific embodiments, the invention contemplates compounds according to any of formulas VIIIB-1 to VIIIB-20, where $R_1$-$R_4$ are, independently, H, OH, $C_1$-$C_4$ alkyl, $C_1$-$C_4$ alkenyl, $C_1$-$C_4$ alkynyl, halo, halomethyl, nitro, or cyano; and R' is isopropyl or 2,3-dihydroxy-1-propyl.

In still more specific embodiments, the invention contemplates compounds according to any of formulas VIIIB-1 to VIIIB-20, where $R_1$-$R_4$ are all H and R' is isopropyl or 2,3-dihydroxy-1-propyl.

In still more specific embodiments, the invention contemplates compounds according to any of formulas VIIIB-1 to VIIIB-20, where $R_1$-$R_4$ are H; $R_3$ and $R_4$ are, independently, H, methyl, or OH; and R' is isopropyl or 2,3-dihydroxy-1-propyl.

In still more specific embodiments, the invention contemplates compounds according to any of formulas VIIIB-1 to VIIIB-20, where $R_1$ is acetyl, acetoxy, acetamido, methylcarbamoyl, methylsulfonyl, methyloxycarbonyl, ethyloxycarbonyl, or cyclopropylethynyl; $R_2$-$R_4$ are all H; and R' is isopropyl or 2,3-dihydroxy-1-propyl.

In still more specific embodiments, the invention contemplates compounds according to any of formulas VIIIB-1 to VIIIB-20, where $R_1$ is acetyl, acetoxy, acetamido, methylcarbamoyl, methylsulfonyl, methyloxycarbonyl, ethyloxycarbonyl, or cyclopropylethynyl; $R_2$ is H; $R_3$ is 2-OH or 2-methyl; $R_4$ is H, OH, or methyl; and R' is isopropyl or 2,3-dihydroxy-1-propyl.

In still more specific embodiments, the invention contemplates compounds according to any of formulas VIIIB-1 to VIIIB-20, where $R_1$-$R_3$ are all H; $R_4$ is chloro; and R' is isopropyl or 2,3-dihydroxy-1-propyl.

In still more specific embodiments, the invention contemplates compounds according to any of formulas VIIIB-1 to VIIIB-20, where $R_2$ is bromo; $R_1$, $R_3$, and $R_4$ are all H; and R' is isopropyl or 2,3-dihydroxy-1-propyl.

A number of prophetic examples of compounds according to formulas VIIIB-1 to VIIIB-20 are shown below.

EXAMPLE OF VIIIB-3

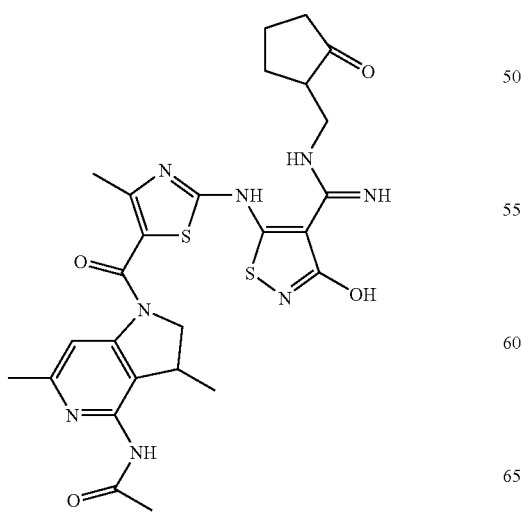

EXAMPLE OF VIIIB-4

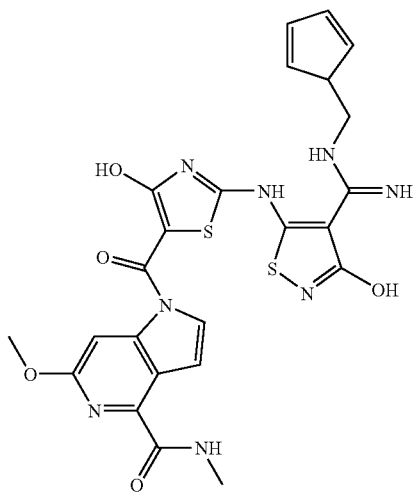

EXAMPLE OF VIIIB-5

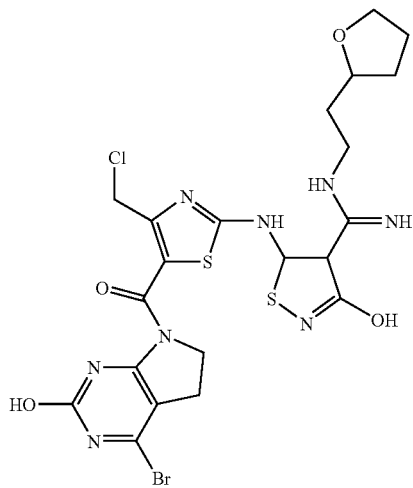

EXAMPLE OF VIIIB-6

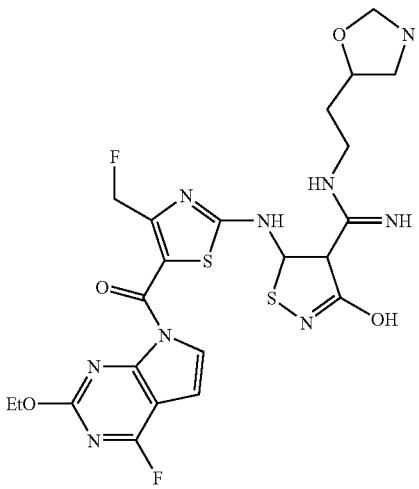

EXAMPLE OF VIIIB-7
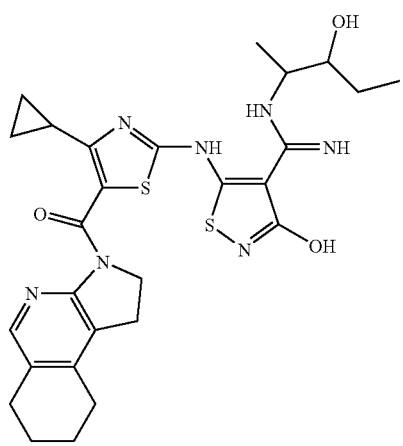
EXAMPLE OF VIIIB-8
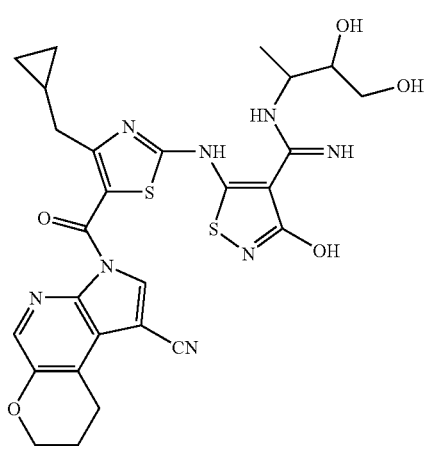
EXAMPLE OF VIIIB-9
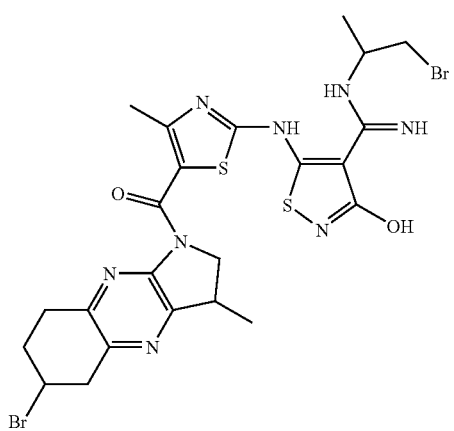
EXAMPLE OF VIIIB-10
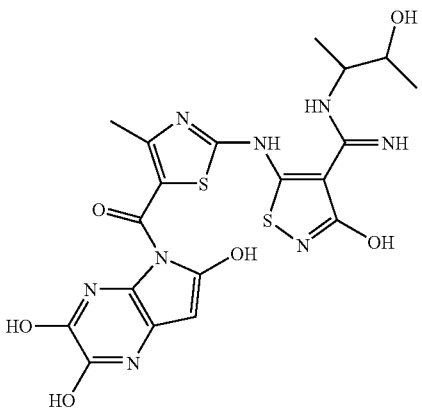
EXAMPLE OF VIIIB-11
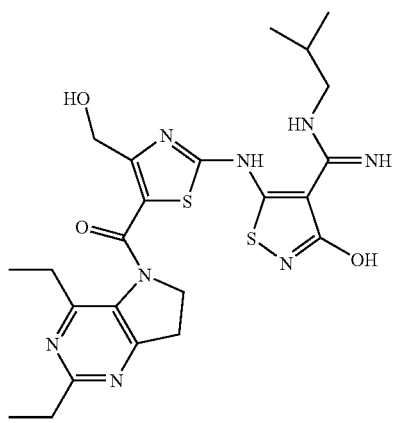
EXAMPLE OF VIIIB-12
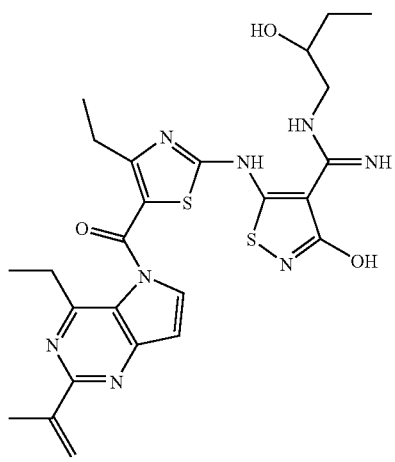

EXAMPLE OF VIIIB-13
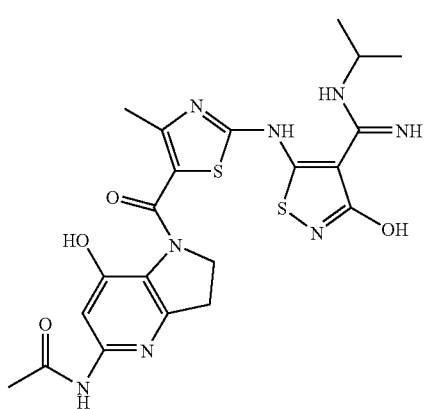
EXAMPLE OF VIIIB-14
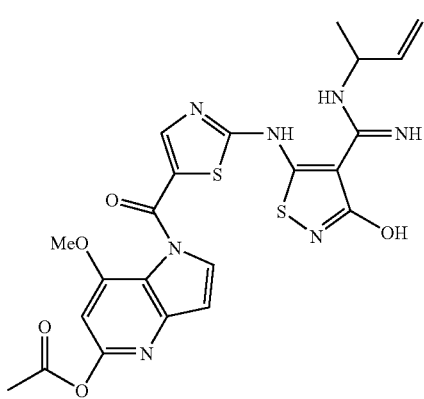
EXAMPLE OF VIIIB-15
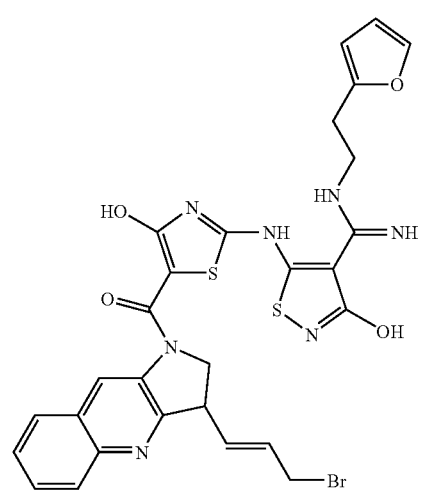
EXAMPLE OF VIIIB-16
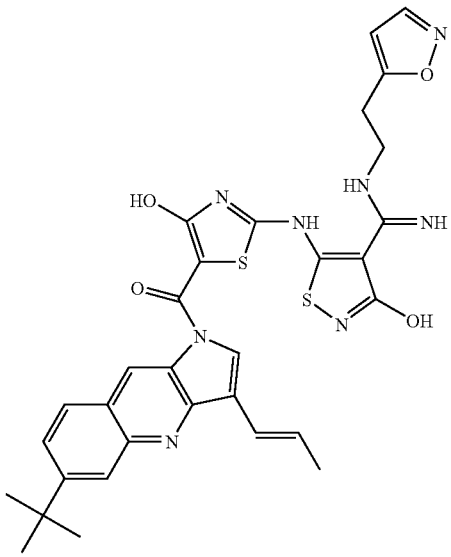
EXAMPLE OF VIIIB-17
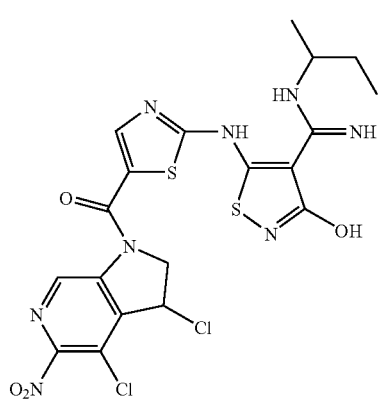
EXAMPLE OF VIIIB-18
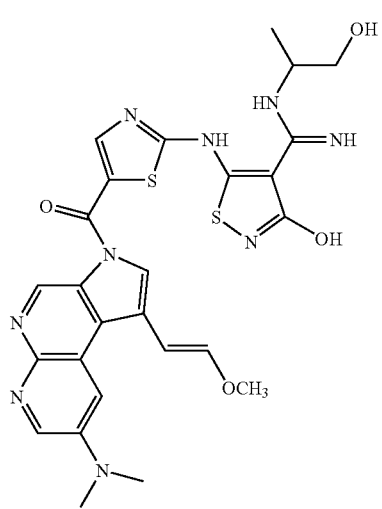

EXAMPLE OF VIIIB-19
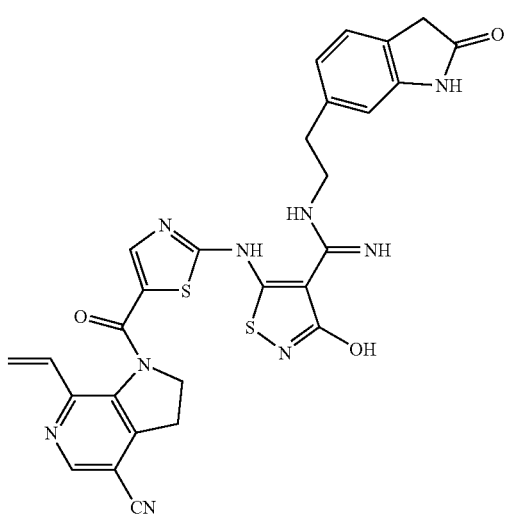
EXAMPLE OF VIIIB-20
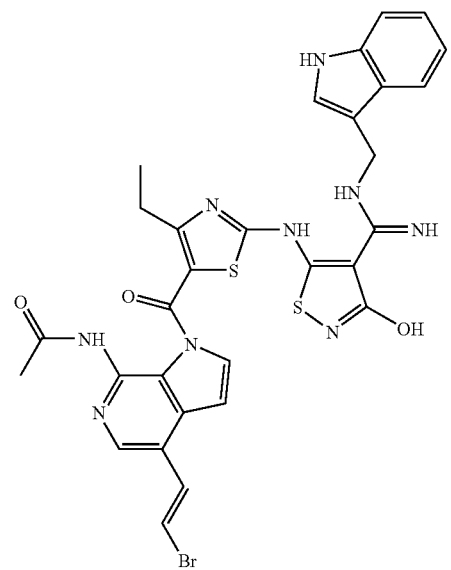
Still more prophetic examples of compounds of this invention are shown below:
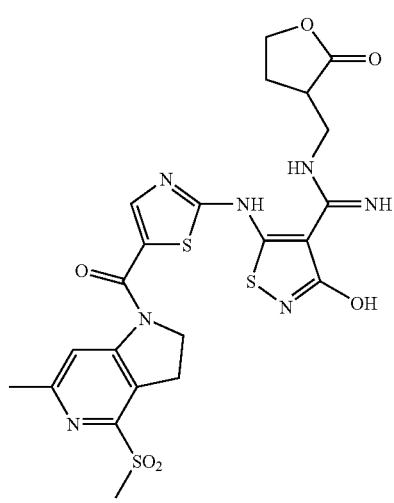
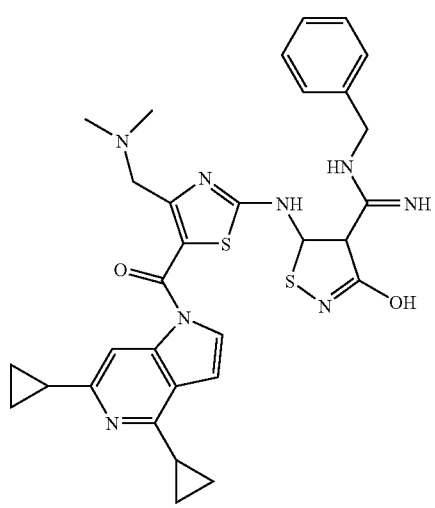
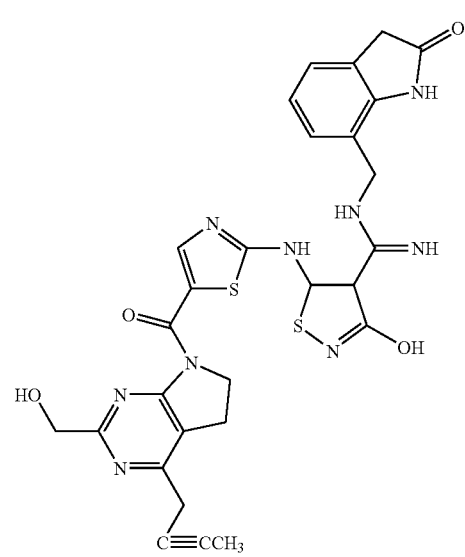
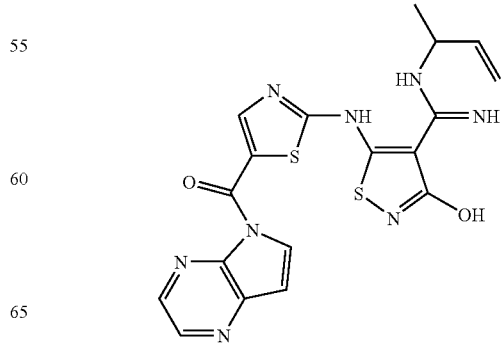

-continued
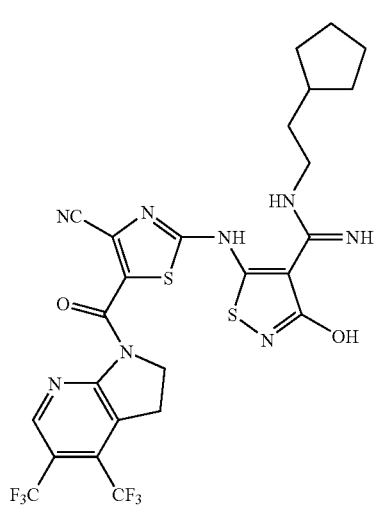
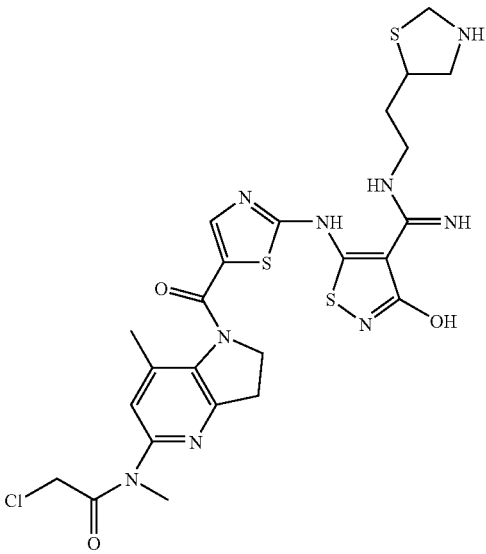
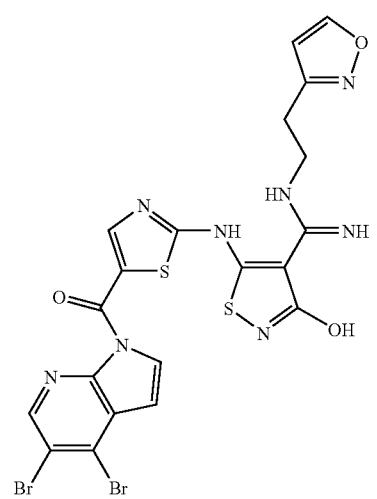
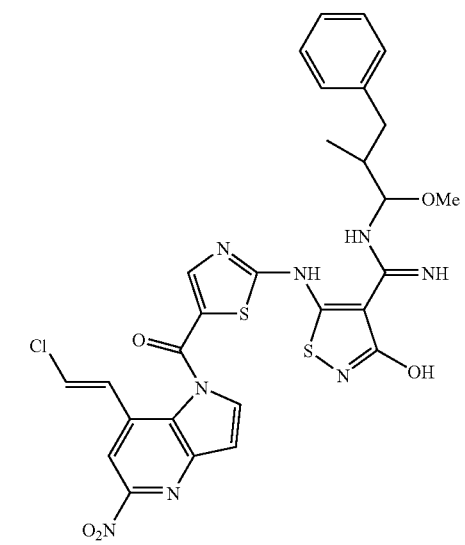
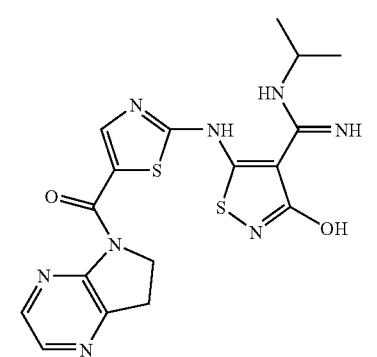
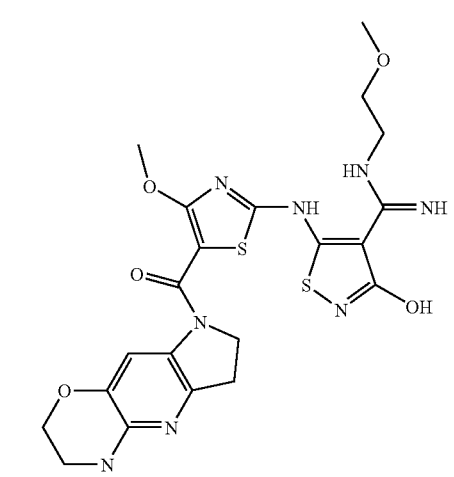

69
-continued
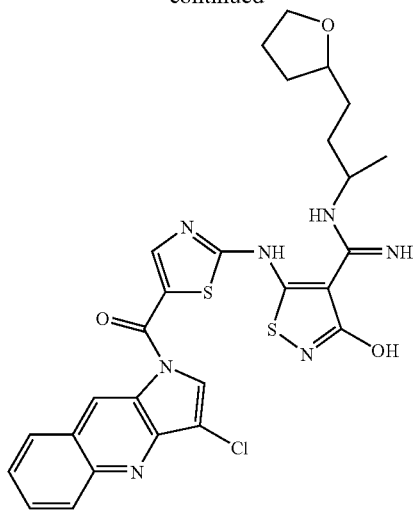
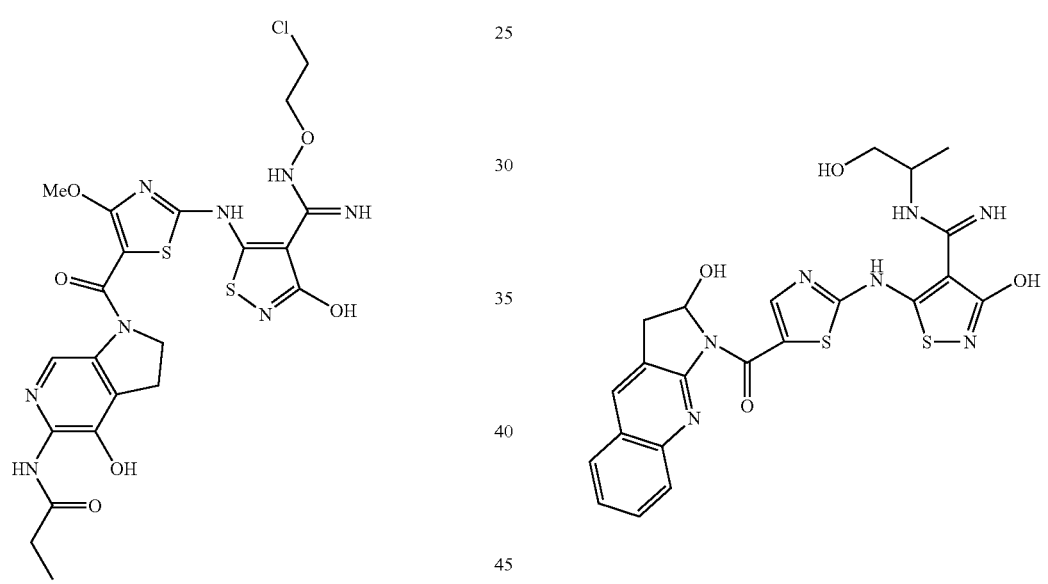
70
-continued
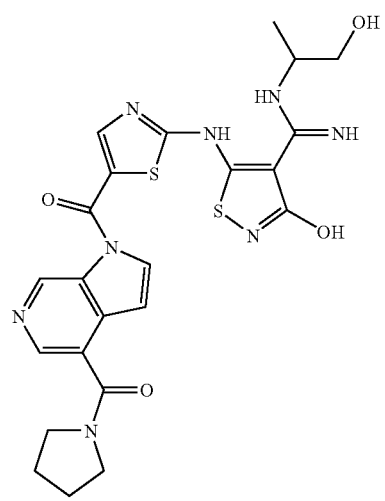
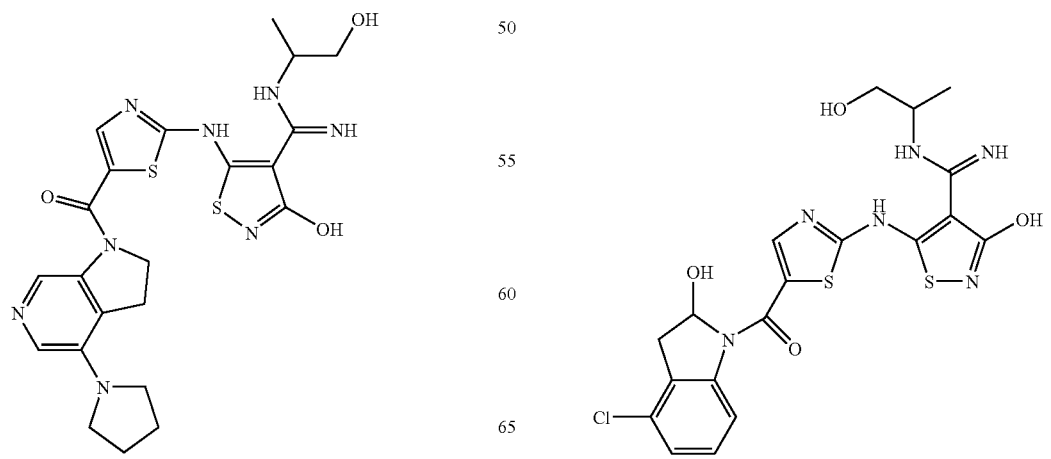

-continued
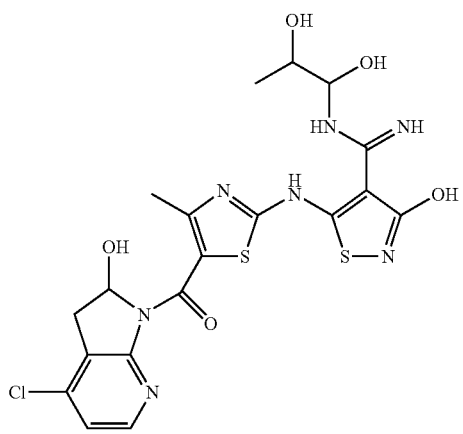
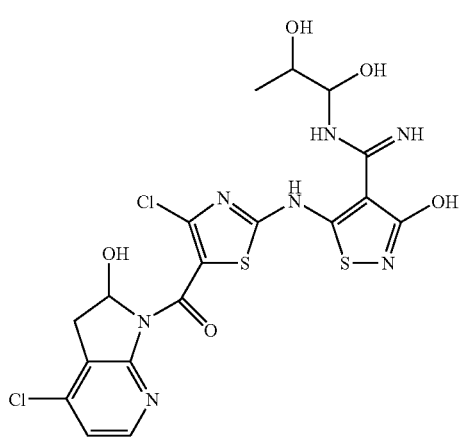
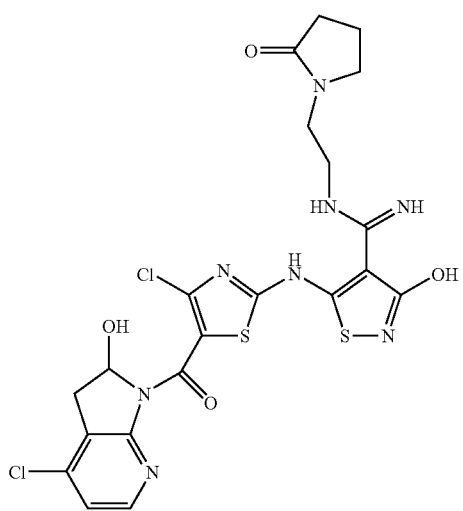
-continued
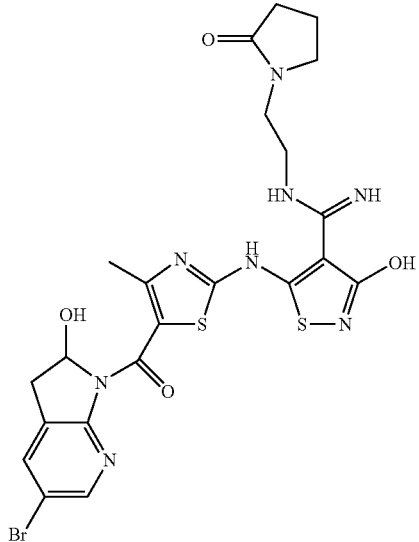
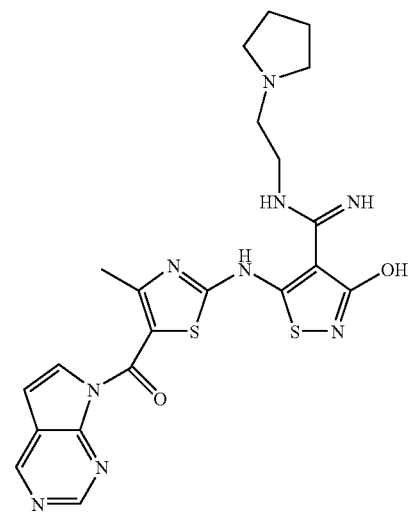
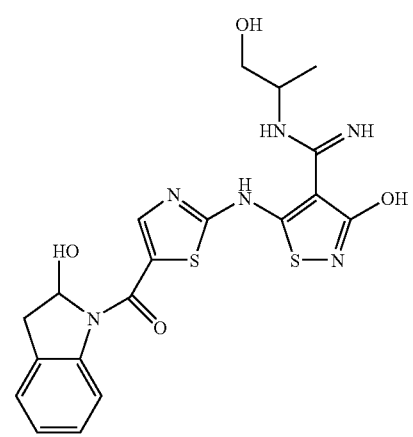

73
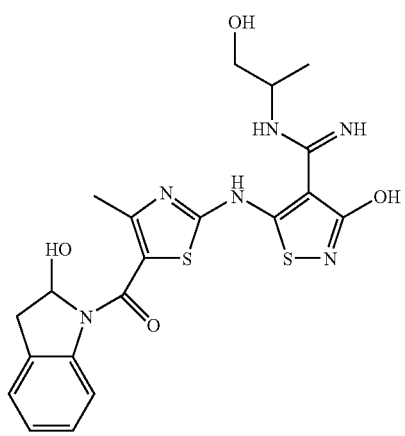
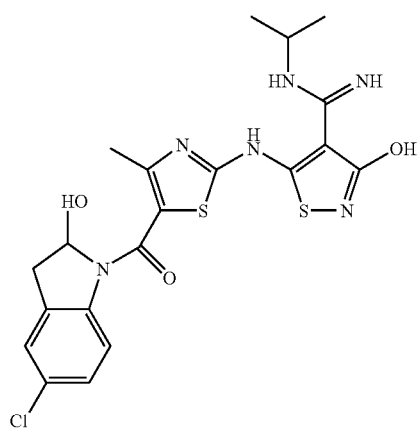
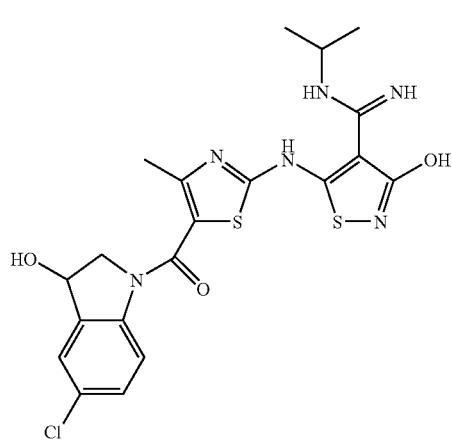
74
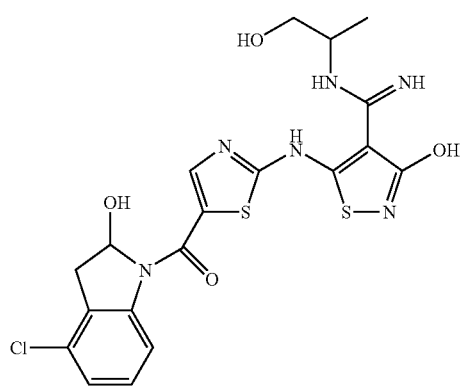
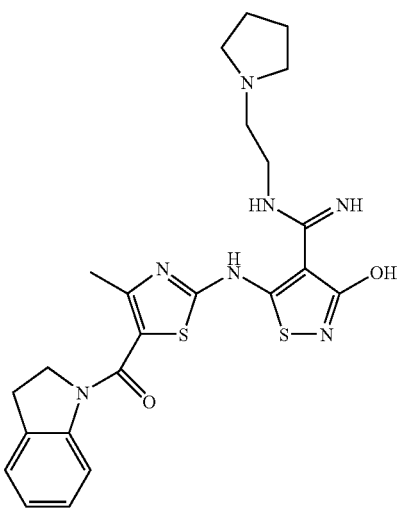
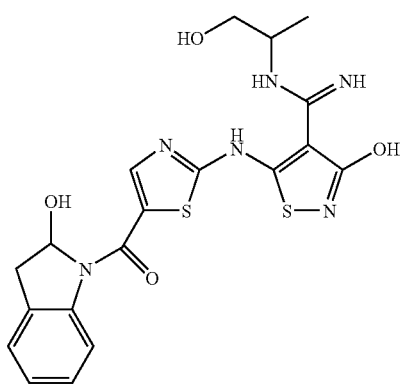

75
-continued
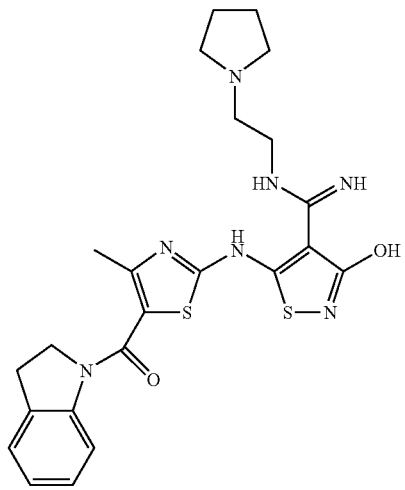
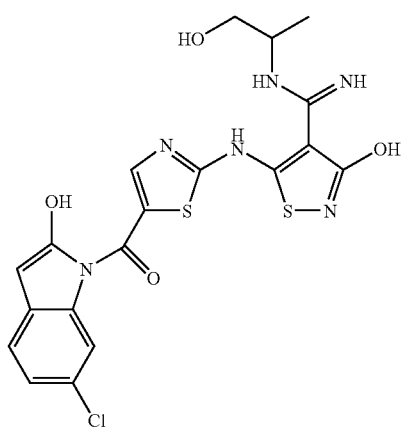
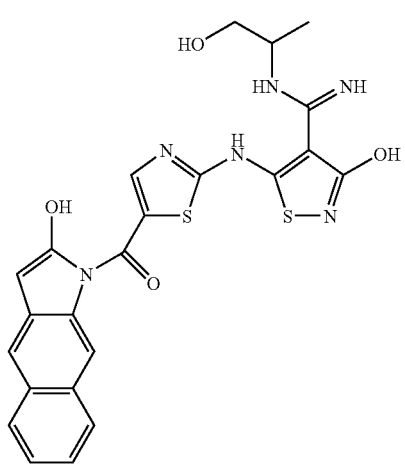
76
-continued
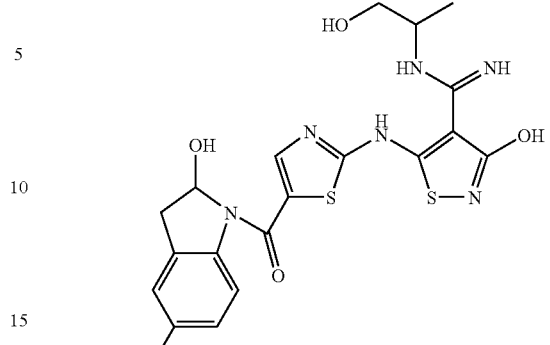
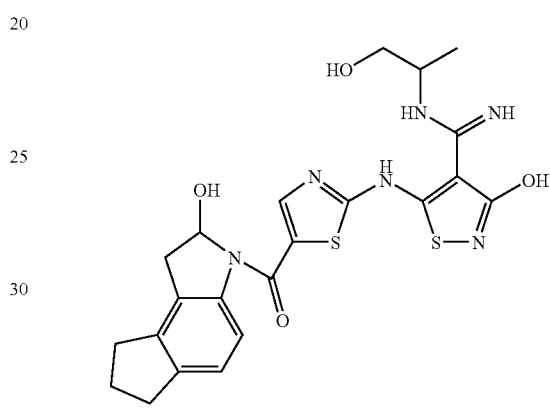
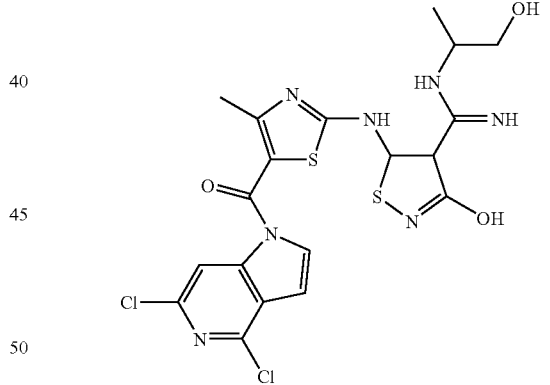
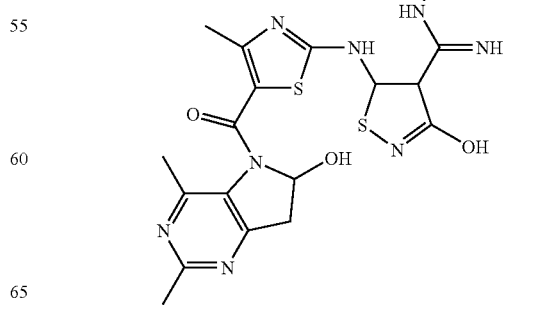

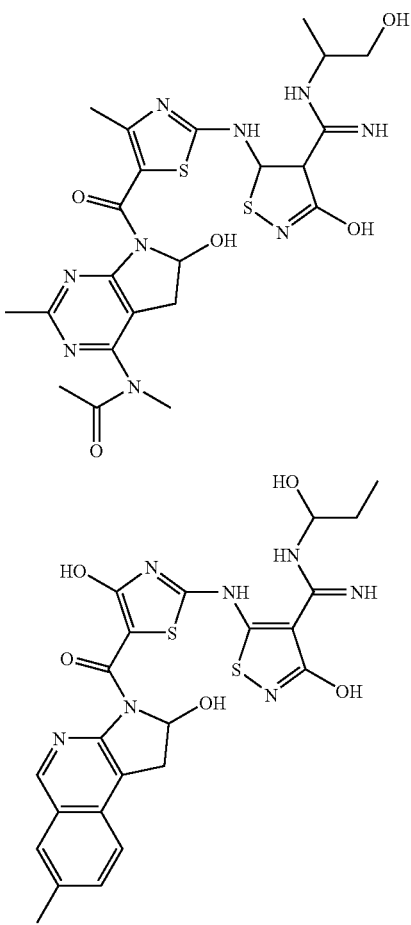

In another generic embodiment, this invention provides a compound of formula IX,

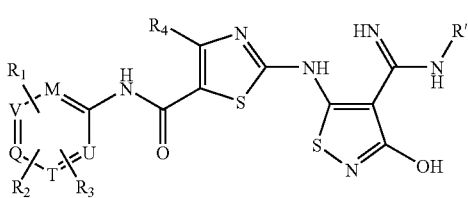

where M, Q, T, U, and V represent N, CH, or $CR_{1, 2, or 3}$, provided that no two nitrogen atoms are adjacent, where $R_1$-$R_4$ are, defined as for formula I.

In one subgeneric embodiment, this invention provides a compound of formula A below, where all substituents are as defined for formula I above.

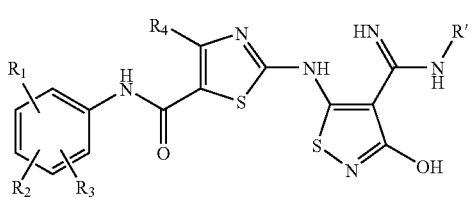

In another embodiment, this invention provides a compound of formula IXB,

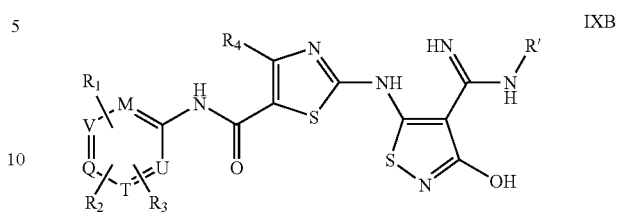

where M, Q, T, U, and V represent N, CH, or $CR_{1, 2, or 3}$, provided that at least one of M, Q, T, U, and V is N, and further provided that no two nitrogen atoms are adjacent, and where $R_1$-$R_4$ are as defined as above.

In one more specific embodiment, this invention provides a compound of formula IXA, where $R_1$-$R_4$ are defined as for formula IX, and R' is —$(CH_2)_n$-G, where n is 1 or 2; and G is isothiazolyl, isoxazolyl, isoxazolindinonyl, oxazolyl, oxazolinyl, oxazolidinyl, oxazolidinonyl, thiazolyl, thienyl, furyl, pyrrolyl, pyrrolinyl, pyrrolidinyl, thiazolinyl, thiazolidinyl, thiazolidinonyl, isothiazolinyl, isothiazolidinyl, isothiazolidinonyl, imidazolinyl, imidazolyl, pyridyl, tolyl, or phenyl, wherein all rings are optionally substituted as described above.

In another more specific embodiment, this invention provides a compound of formula IXA, where $R_1$ and $R_2$ are as defined for formula IX; $R_3$ and $R_4$ are both H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula IXA, where R is 2-chloro, $R_2$ is 6-methyl, and $R_3$—R' are as defined for formula IXA.

In another more specific embodiment, this invention provides a compound of formula IXA, where $R_1$-$R_4$ are defined as for formula I, and R' is —$(CH_2)_n$-G, where n is 1 or 2; and G is naphthyl, quinolyl, isoquinolyl, indanyl, or benzimidazolyl, wherein all rings are optionally substituted as described above in the definition of G for formula I.

In another more specific embodiment, this invention provides a compound of formula IXA, where $R_1$-$R_4$ are defined as for formula I, and R' is —$(CH_2)_n$-G, where n is 1 or 2; and G is cyclopentyl, cyclohexyl, tetrahydrofuryl, tetrahydrothienyl, piperidyl, piperazinyl, or morpholyl, wherein all rings are optionally substituted as with methyl or halo.

In another more specific embodiment, this invention provides a compound of formula IXA, where $R_1$-$R_4$ are defined as for formula I, and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, 2-pyrrolidon-1-yl, or 2-pyrrolidon-6-yl.

In a still more specific embodiment, this invention provides a compound of formula IXA, where $R_1$-$R_3$ are as defined for formula I, $R_4$ is H or methyl, and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl.

In a still more specific and more preferred embodiment, this invention provides a compound of formula IXA, where $R_1$ and $R_2$, in positions 2 and 6, are alkyl or halo, $R_3$ is H, $R_4$ is H or methyl, and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl.

In another more specific embodiment, this invention provides a compound of formula IXA, where $R_1$-$R_4$ are defined as for formula II, and R' is $C_1$-$C_6$ alkyl, optionally substituted with one or two or hydroxyl groups.

In a still more specific embodiment, this invention provides a compound of formula IXA, where $R_1$-$R_3$ are as defined for formula II, $R_4$ is H or methyl, and R' is $C_1$-$C_6$ alkyl, optionally substituted with one or two or hydroxyl groups.

In a still more specific and more preferred embodiment, this invention provides a compound of formula IXA, where $R_1$ and $R_2$, in positions 2 and 6, are alkyl or halo, $R_3$ is alkyl, haloalkyl, cycloalkyl, alkenyl, or alkynyl, $R_4$ is H or methyl, and R' is $C_1$-$C_6$ alkyl, optionally substituted with one or two or hydroxyl groups.

In a still more specific and more preferred embodiment, this invention provides a compound of formula IXA, where $R_1$ and $R_2$, in positions 2 and 6, are alkyl or halo, $R_3$ is H, $R_4$ is H or methyl, and R' is $C_1$-$C_6$ alkyl, optionally substituted with one or two or hydroxyl groups.

In a still more specific embodiment, this invention provides a compound of formula IXA, where $R_1$ and $R_2$ are, independently, H, halo, or $C_1$-$C_3$ alkyl; $R_3$ and $R_4$ are both H; and R' is $C_1$-$C_6$ alkyl, optionally substituted with one or two or hydroxyl groups.

In a preferred and more specific embodiment, this invention provides a compound of formula IXA, in which $R_1$ is 2-halo or 2-methyl; $R_2$ is 6-methyl; $R_3$ and $R_4$ are, independently, H, $C_1$-$C_3$ alkyl, or halo; and R' is isopropyl or mono- or di-hydroxy $C_1$-$C_4$ alkyl.

In another more preferred specific embodiment, this invention provides a compound of formula IXA, in which $R_1$ is 2-chloro; $R_2$ is 6-methyl; $R_3$ and $R_4$ are, independently, H, $C_1$-$C_3$ alkyl, vinyl, cyclopropyl, or halo; and R' is isopropyl or mono- or di-hydroxy $C_1$-$C_4$ alkyl.

In another more preferred specific embodiment, this invention provides a compound of formula IXA, in which $R_1$ is 2-methyl; $R_2$ and $R_3$ are H; $R_4$ is methyl; and R' is isopropyl or mono- or di-hydroxy $C_1$-$C_4$ alkyl.

In another more preferred specific embodiment, this invention provides a compound of formula IXA, in which $R_1$-$R_4$ are H; and R' is isopropyl or mono- or di-hydroxy $C_1$-$C_4$ alkyl.

In another more preferred subgeneric embodiment, this invention provides a compound of formula IXA, in which $R_1$ is 2-chloro; $R_2$ is 6-methyl; $R_3$ and $R_4$ are, independently, H, $C_1$-$C_3$ alkyl, $C_1$-$C_3$ alkoxy, $C_1$-$C_3$ alkenyl, $C_1$-$C_3$ alkenoxy, hydroxy, or halo; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a more specific embodiment, this invention provides a compound of formula IXA, in which $R_1$ is 2-chloro; $R_2$ is 6-methyl; $R_3$ and $R_4$ are, independently, H, methyl, methoxy, vinyl, 2-methoxyethene, hydroxy, or chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula IXA, where $R_1$ is $C_2$-$C_6$ alkenyl, $C_2$-$C_6$ alkynyl, or $C_1$-$C_6$ cycloalkyl; $R_2$ and $R_3$ are H; $R_4$ is H or methyl; and R' is $C_1$-$C_6$ alkyl, optionally substituted with one or two or hydroxyl groups.

In a still more specific embodiment, this invention provides a compound of formula IXA, where $R_1$ is 2-methylpropenyl, 1-propynyl, or cyclopropyl; $R_2$ and $R_3$ are H; $R_4$ is H or methyl; and R' is $C_1$-$C_6$ alkyl, optionally substituted with one or two or hydroxyl groups.

In another more specific embodiment, this invention provides a compound of formula IXA, where $R_1$ is amino, methyl amino, dimethylamino, dimethylaminomethyl, or acetamido; $R_2$-$R_4$ are H and R' is $C_1$-$C_6$ alkyl, optionally substituted with one or two or hydroxyl groups.

In another more specific embodiment, this invention provides a compound of formula IXA, where $R_1$ is nitro, cyano, methylcarbamoyl, dimethylcarbamoyl, or aminosulfonyl; $R_2$-$R_4$ are H and R' is $C_1$-$C_6$ alkyl, optionally substituted with one or two or hydroxyl groups.

In another more specific embodiment, this invention provides a compound of formula IXA, where $R_1$ is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl; $R_2$-$R_4$ are H; and R' is $C_1$-$C_6$ alkyl, optionally substituted with one or two or hydroxyl groups.

In a still more specific embodiment, this invention provides a compound of formula IXA, in which $R_1$ is 2-methyl; $R_2$ and $R_3$ are both halogen; $R_4$ is H; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidyl, or R' is $C_1$-$C_6$ alkyl, optionally substituted with one or two or hydroxyl groups.

In a still more specific embodiment, this invention provides a compound of formula IXA, in which $R_1$ and $R_2$ are both chloro; $R_3$ is H; $R_4$ is methyl; R' is —$(CH_2)_n$-G, where n is 1, and G is piperazinyl, piperazinonyl, piperidinyl, piperidinonyl, morpholyl, furyl, or tetrahydro furyl, or R' is $C_1$-$C_6$ alkyl, optionally substituted with one or two or hydroxyl groups.

In a still more specific embodiment, this invention provides a compound of formula IXA, in which $R_1$ is 3-methyl; $R_2$ and $R_3$ are both H; $R_4$ is 2-chloroethyl; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention provides a compound of formula IXA, in which $R_1$ is 2-hydroxymethyl; $R_3$ is 4-$CF_3$; $R_2$ and $R_4$ are H; and R' is —$(CH_2)_n$-G, where n is 1 or 2; and G is 4-imidazolyl, 4-morpholyl, 4-(2, 6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention provides a compound of formula IXA, in which $R_1$ 3-methyl; $R_2$ is 5-chloro; $R_3$ and $R_4$ are both H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another specific embodiment, this invention provides a compound of formula IXA, in which one or both of $R_1$ and $R_2$ are $CF_3$; $R_3$ and $R_4$ are H; and R' is —$(CH_2)_n$-G, where n is 1, and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another subgeneric embodiment, this invention provides a compound of formula IXA, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl; $R_2$, $R_3$, and $R_4$ are H; and R' is —$(CH_2)_n$-G, where n is 1 or 2; and G is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, or naphthyl, or R' is $C_1$-$C_6$ alkyl, optionally substituted with one or two or hydroxyl groups.

In a still more specific embodiment, this invention contemplates the compound of formula IXA, in which $R_1$ is 3-chloro; $R_2$, $R_3$, and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ is 2-chloro; $R_2$ is 6-methyl; $R_3$; and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ is 4-chloro; $R_2$, $R_3$, and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ and $R_2$ are 2- and 6-chloro; $R_2$, $R_3$, and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ is 2-bromo; $R_2$; $R_3$; and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is 3-bromo; $R_2$; $R_3$; and $R_4$ are H; and R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is 4-bromo; $R_2$, $R_3$, and $R_4$ are H; and R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is 2-, 3-, or 4-bromo; $R_2$, $R_3$, and $R_4$ are H; and R' is —$(CH_2)_n$-G, where n is 1, and G is R' is $C_1$-$C_6$ alkyl, optionally substituted with one or two or hydroxyl groups.

In another specific embodiment, this invention contemplates the compound of formula IXA, in which $R_1$ is 4-bromo; $R_2$ is 2-methyl; $R_3$ is 3-methyl; $R_4$ is H, methyl, or halo; and R' is $C_1$-$C_6$ alkyl, optionally substituted with one or two or hydroxyl groups.

In another specific embodiment, this invention contemplates the compound of formula IXA, in which $R_1$ is 2-bromo; $R_2$ is 6-methyl; $R_3$ is 3-methyl; $R_4$ is H, methyl, or halo; and R' is $C_1$-$C_6$ alkyl, optionally substituted with one or two or hydroxyl groups.

In another specific embodiment, this invention contemplates the compound of formula IXA, in which $R_1$ is 3-bromo; $R_2$ is 6-methyl; $R_3$ is H; $R_4$ is H, methyl, or halo; and R' is $C_1$-$C_4$ alkyl, optionally substituted with one or two or hydroxyl groups.

In a still more specific embodiment, this invention contemplates the compound of formula IXA, in which $R_1$ is 2-chloro; $R_2$ is 4-chloro; $R_3$ and $R_4$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates the compound of formula IXA, in which $R_1$ is 2-methyl; $R_2$ is 6-methyl; $R_3$ and $R_4$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention provides a compound of formula IXA, in which one or both of $R_1$ and $R_2$ are $CF_3$; $R_3$ and $R_4$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention contemplates a compound of formula IXA, in which $R_1$ is 2-$CF_3$; $R_2$; $R_3$; and $R_4$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula IXA, in which $R_1$ and $R_2$, in positions 2 and 6, are, independently, methyl or halogen; $R_3$ is 2-chloromethyl, $R_4$ is H; and R' is —$(CH_2)_n$-G, where n is 1 or 2; and G is 2-pyridyl, 3-pyridyl, 4-pyridyl, 2-piperidyl, 3-piperidyl, or 4-piperidyl or R' is isopropyl or mono- or di-hydroxy $C_1$-$C_4$ alkyl.

In another more specific embodiment, this invention provides a compound of formula IXA, in which $R_1$ and $R_2$, in positions 2 and 6, are, independently, methyl or halogen; $R_3$ is 3-fluoromethyl; and $R_4$ is H; R' is —$(CH_2)_n$-G, where n is 1 or 2; and G is 2-pyrimidyl, 4-pyrimidyl, 2-morpholyl, or 3-morpholyl or R' is isopropyl or mono- or di-hydroxy $C_1$-$C_4$ alkyl.

In another more specific embodiment, this invention provides a compound of formula IXA, in which $R_1$ and $R_2$, in positions 2 and 6, are, independently, methyl or halogen; $R_3$ is 3-methyl; and $R_4$ is H; R' is —$(CH_2)_n$-G, where n is 1 or 2; and G is 2-pyridyl, 3-pyridyl, 4-pyridyl, 2-piperidyl, 3-piperidyl, or 4-piperidyl.

In another more specific embodiment, this invention provides a compound of formula IXA, in which $R_1$ and $R_2$, in positions 2 and 6, are, independently, methyl or halogen; $R_3$ is 3-fluoromethyl; and $R_4$ is H; R' is —$(CH_2)_n$-G, where n is 1 or 2; and G is 4-bromo-2-pyrimidyl, 2-chloro-4-pyrimidyl, 2-morpholyl, or 3-morpholyl.

In a still more specific embodiment, this invention provides a compound of formula IXA, in which $R_1$ is 3-cyano; $R_2$ is H or 6-methyl; $R_3$ and $R_4$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula IXA, in which $R_1$ is 3-hydroxy; $R_2$ is H or 6-methyl; $R_3$ and $R_4$ are, independently, H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula IXA, in which $R_1$ is 4-hydroxy; $R_2$ is H or 2-methyl; $R_3$ and $R_4$ are, independently, H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula IXA, in which $R_1$ is 2-, 3-, or 4-methoxy; $R_2$ is H or 2-methyl; $R_3$ and $R_4$ are, independently, H, hydroxy, or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula IXA, in which $R_1$ is 2-, 3-, or 4-methoxy; $R_2$ is H or 6-methyl; $R_3$ and $R_4$ are, independently, H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In another more specific embodiment, this invention provides a compound of formula IXA, in which $R_1$ is 2-, 3-, or 4-ethoxymethyl; $R_2$ is H or 6-methyl; $R_3$ and $R_4$ are, independently, H, hydroxy, or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula IXA, in which $R_1$ is 2-, 3-, or 4-methoxymethyl; $R_2$ is H or 6-methyl; $R_3$ and $R_4$ are, independently, H, hydroxy, methoxy, halo, or methyl; and R' is $C_1$-$C_6$ alkyl, optionally substituted with one or two or hydroxyl groups.

In another more specific embodiment, this invention provides a compound of formula IX, in which $R_1$ is 3-(2-methoxyethyl); $R_2$ is H, 2-methyl, or 6-methyl; $R_3$ and $R_4$ are, independently, H, hydroxy, methoxy, or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In a still more specific embodiment, this invention provides a compound of formula IXA, in which $R_1$ is 4-(2-methoxyethyl); $R_2$ is H, 2-methyl, or 6-methyl; $R_3$ and $R_4$ are, independently, H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-dimethylamino; $R_2$ is H or 6-methyl; $R_3$ and $R_4$ are, independently, H, methyl, or hydroxy; and R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-dimethylamino; $R_2$ is H or 6-methyl; $R_3$ is 3-methyl; $R_4$ is methyl, halo, or H; and R' is $C_1$-$C_6$ alkyl, optionally substituted with one or two or hydroxyl groups.

In another more specific embodiment, this invention contemplates a compound of formula IXA, in which $R_1$ is 2-, 3-, or 4-dimethylaminocarbonyl; $R_2$ is H or 6-methyl; $R_3$ is H or methyl; $R_4$ is H; and R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-methyloxycarbonyl; $R_2$ is H or 6-methyl; $R_3$ is H or methyl, $R_4$ is H; and R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-acetyl; $R_2$ is H or 6-methyl, $R_3$ is H, chloro, or methyl; $R_4$ is H or 5-methyl; and R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-acetoxy; $R_2$ is H or 6-methyl; $R_3$ is H or methyl; $R_4$ is H, methyl, or chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates a compound of formula IXA, in which $R_1$ is 2-, 3-, or 4-dimethylamino; $R_2$ is H or 6-methyl; $R_3$ is H or methyl; $R_4$ is H, methyl, hydroxy, methoxy, or chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates a compound of formula IXA, in which $R_1$ is 2-, 3- or 4-dimethylaminocarbonyl; $R_2$ is H or 6-methyl; $R_3$ is H or 3-methyl; $R_4$ is H, methyl, or chloro; and R' is $C_1$-$C_6$ alkyl, optionally substituted with one or two or hydroxyl groups.

In another more specific embodiment, this invention contemplates a compound of formula IXA, in which $R_1$ is 2-, 3-, or 4-methyloxycarbonyl; $R_2$ is H or 6-methyl; $R_3$ is H or methyl; $R_4$ is H, methyl, hydroxy, methoxy, or chloro; and R' is $C_1$-$C_6$ alkyl, optionally substituted with one or two or hydroxyl groups.

In another more specific embodiment, this invention contemplates a compound of formula IXA, in which $R_1$ is 2-, 3- or 4-chloroacetyl; $R_2$ is H or 6-methyl; $R_3$ is H or methyl; $R_4$ is H, methyl, hydroxy, methoxy, or chloro; and R' is $C_1$-$C_6$ alkyl, optionally substituted with one or two or hydroxyl groups.

In another more specific embodiment, this invention contemplates a compound of formula IXA, in which $R_1$ is 2-, 3- or 4-acetoxy; $R_2$ is H or 6-methyl; $R_3$ is H or methyl; $R_4$ is H, hydroxy, methoxy, or chloro; and R' is $C_1$-$C_6$ alkyl, optionally substituted with one or two or hydroxyl groups.

In another more specific embodiment, this invention contemplates a compound of formula IXA, in which $R_1$ is 2-, 3- or 4-fluoromethyl; $R_2$ is H or 6-methyl; $R_3$ is H or methyl; $R_4$ is H or 5-chloro; and R' is $C_1$-$C_6$ alkyl, optionally substituted with one or two or hydroxyl groups.

In another more specific embodiment, this invention provides a compound of formula IXA, in which $R_1$ is 4-cyano; $R_2$ is H or 6-methyl; $R_3$ is H or methyl; $R_4$ is H, methyl, hydroxy, methoxy, halomethyl, or chloro; and R' is $C_1$-$C_6$ alkyl, optionally substituted with one or two or hydroxyl groups, or R' is $-(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula IXA, in which $R_1$ is 2-, 3- or 4-ethoxy; $R_2$ is H or 6-methyl; $R_3$ is H or methyl; $R_4$ is H, methyl, hydroxy, methoxy, vinyl, halomethyl, or chloro; and R' is $-(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula IXA, in which $R_1$ is 2-, 3-, or 4-vinyl; $R_2$ is H or 6-methyl; $R_3$ is H or methyl; $R_4$ is H, methyl, or chloro; and R' is $-(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula IXA, in which $R_1$ is 2-, 3-, or 4-chloromethoxy; $R_2$ is H or 6-methyl; $R_3$ is H or methyl; $R_4$ is H, methyl, hydroxy, methoxy, or chloro; and R' is $C_1$-$C_6$ alkyl, optionally substituted with one or two or hydroxyl groups.

In another more specific embodiment, this invention provides a compound of formula IXA, in which $R_1$ is 4-methoxy; $R_2$-$R_4$ are H; R' is $-(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula IXA, in which $R_1$ is 2-methyl; $R_2$ is 4-methylsulfonyl; $R_3$ and $R_4$ are, independently, H, hydroxy, halomethyl, or methyl; and R' is $-(CH_2)_n$-G, where n is 1, and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another more specific embodiment, this invention provides a compound of formula IXA, in which $R_1$ is 2-, 3-, or 4-methoxy; $R_2$ is H or 6-methyl; $R_3$ is H or methyl; $R_4$ is H, methyl, or chloro; and R' is $-(CH_2)_n$-G, where n is 1, and G is cyclopentyl, cyclopenten-3-yl, cyclopentadien-4-yl; cyclohexyl, or cyclohexen-2-yl.

In another more specific embodiment, this invention provides a compound of formula IXA, in which $R_1$ is 2-, 3-, or 4-bromo; $R_2$ is H or 6-methyl; $R_3$ is H or methyl; $R_4$ is H, methyl, or chloro; and R' is $-(CH_2)_n$-G, where n is 1, and G is cyclopentyl, cyclopenten-3-yl, cyclopentadien-4-yl; cyclohexyl, or cyclohexen-2-yl.

In another more specific embodiment, this invention provides a compound of formula IXA, in which $R_1$ is 2-chloro; $R_2$ is 3-, 4-, 5-, or 6-cyclopropyl, $R_3$ and $R_4$ are, independently, H, halo, or methyl; and R' is $C_1$-$C_6$ alkyl, optionally substituted with one or two or hydroxyl groups.

In another more specific embodiment, this invention provides a compound of formula IXA, in which $R_1$ is 3-cyclopropyl; $R_2$-$R_4$ are H; and R' is $C_1$-$C_6$ alkyl, optionally substituted with one or two or hydroxyl groups.

In another more specific embodiment, this invention provides a compound of formula IXA, in which $R_1$ is 3-cyclopropyl; $R_2$ is 2-, 4-, 5-, or 6-chloro; $R_3$ and $R_4$ are H; and R' is $C_1$-$C_6$ alkyl, optionally substituted with one or two or hydroxyl groups.

In another more specific embodiment, this invention provides a compound of formula IXA, in which $R_1$ is 2-chloro; $R_2$ is trans-4-(2-methylcyclopropyl); $R_3$ and $R_4$ are H; R' is $-(CH_2)_n$-G, where n is 1, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula IXA, in which $R_1$ is 4-cyclopropyl; $R_2$ is 2- or 3-chloro; $R_3$ and $R_4$ are, independently, H, halo, or $C_1$-$C_3$ alkyl; and R' is $C_1$-$C_6$ alkyl, optionally substituted with one or two or hydroxyl groups.

In another more specific embodiment, this invention provides a compound of formula IXA, in which $R_1$ is 4-isopropyl; $R_2$ is 2-chloro; $R_3$ is 2- or 3-chloro; $R_4$ is methyl, hydroxy, methoxy, or halo; and R' is $-(CH_2)_n$-G, where n is 1, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In another more specific embodiment, this invention provides a compound of formula IXA, in which $R_1$ and $R_2$ are both halogen; $R_3$ is 3-methyl; $R_4$ is H; and R' is $C_1$-$C_6$ alkyl, optionally substituted with one or two or hydroxyl groups.

In another more specific embodiment, this invention provides a compound of formula IXA, in which $R_1$ and $R_2$ are both H; $R_3$ is 3-chloro; $R_4$ is methyl, hydroxy, methoxy, or halo; and R' is $-(CH_2)_n$-G, where n is 2, and G is pyridyl, piperazinyl, piperazinonyl, piperidinyl, piperidinonyl, morpholyl, furyl, tetrahydrofuryl, or pyrimidinyl or R' is $C_1$-$C_6$ alkyl, optionally substituted with one or two or hydroxyl groups or R' is $C_1$-$C_6$ alkyl, optionally substituted with one or two or hydroxyl groups.

In another more specific embodiment, this invention provides a compound of formula IXA, in which $R_1$ and $R_2$ are both H; $R_3$ is 2-(2-chloroethyl); $R_4$ is methyl, hydroxy, methoxy, or halo; R' is $-(CH_2)_n$-G, where n is 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In another more specific embodiment, this invention provides a compound of formula IXA, in which $R_1$ is 2-hydroxymethyl; $R_2$ is 4-$CF_3$; $R_3$ and $R_4$ are H; R' is —$(CH_2)_n$-G, where n is 2, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula IXA, in which $R_1$ is 3-chloro; $R_2$ and $R_3$ are both H; $R_4$ is methyl; and R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In another more specific embodiment, this invention provides a compound of formula IXA, in which one or both of $R_1$ and $R_2$ are $CF_3$; $R_3$ and $R_4$ are H; R' is —$(CH_2)_n$-G, where n is 1 or 2; and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a more specific embodiment, this invention contemplates the compound of formula IXA, in which $R_1$ is 4-chloro; $R_2$ is 3-chloro; $R_3$ and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ is 2-, 3-, or 4-fluoro; $R_2$, $R_3$, and $R_4$ are H; and R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is fluoro; $R_2$ is methyl; $R_3$ and $R_4$ are H; R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula IXA, in which $R_1$ is 6-chloro; $R_2$, $R_3$, and $R_4$ are H; R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is 2-bromo, 3-bromo, or 4-bromo; $R_2$ is methyl; $R_3$; and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula IXA, in which $R_1$ is 2-(2-chloroethyl); $R_2$ is 6-chloro; $R_3$ and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl or R' is $C_1$-$C_6$ alkyl, optionally substituted with one or two or hydroxyl groups.

In a still more specific embodiment, this invention contemplates the compound of formula IXA, in which $R_1$ is 4-(3-chloropropyl); $R_2$ is 2-bromomethyl; $R_3$ and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates a compound of formula IXA, in which $R_1$ is 2-$CF_3$; $R_2$, $R_3$, and $R_4$ are H; R' is —$(CH_2)_n$-G, where n is 1 or 2, and G is isothiazol-4-yl, isoxazol-4-yl, oxazol-2-yl, 2-oxazolin-4-yl, oxazolidin-5-yl, or thiazol-2-yl, or R' is $C_1$-$C_6$ alkyl, optionally substituted with one or two hydroxyl groups.

In a still more specific embodiment, this invention provides a compound of formula IXA, in which $R_1$ is 4-cyano; $R_2$ is 2-methyl; $R_3$ and $R_4$ are H or methyl; R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula IXA, in which $R_1$ is 2-methyl; $R_2$ is 4- or 5-hydroxy; $R_3$ and $R_4$ are, independently, H, hydroxy, methoxy, halo, or methyl; R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In a still more specific embodiment, this invention provides a compound of formula IXA, in which $R_1$ is 2-hydroxymethyl; $R_2$-$R_4$ are H; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In another specific embodiment, this invention provides a compound of formula IXA, in which $R_1$ is 2-methoxy; $R_2$ is H, halo, or methyl; $R_3$ and $R_4$ are, independently, H or methyl; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In a still more specific embodiment, this invention provides a compound of formula IXA, in which $R_1$ is 4-methoxy; $R_2$-$R_4$ are H; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula IXA, in which $R_1$ is 2-, 3-, or 4-dimethylamino; $R_2$; $R_3$; and $R_4$ are H; R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl, or R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-acetyl; $R_2$, $R_3$, and $R_4$ are H; and R' is $C_1$-$C_6$ alkyl, optionally substituted with one or two or hydroxyl groups.

In a still more specific embodiment, this invention contemplates a compound of formula IXA, in which $R_1$ is 2-, 3-, or 4-acetoxy; $R_2$, $R_3$, and $R_4$ are H; and R' is —$(CH_2)_n$-G, where n is 1 or 2, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention contemplates a compound of formula IXA, in which $R_1$ is 4-methyloxycarbonyl; $R_2$ is H or methyl; $R_3$ and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula IXA, in which $R_1$ is 2-, 3-, or 4-acetyl; $R_2$, $R_3$, and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula IXA, in which $R_1$ is 2-, 3-, or 4-acetoxy; $R_2$; $R_3$; and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula IXA, in which $R_1$ is 2-, 3-, or 4-$CH_2F$; $R_2$; $R_3$; and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 2-, 3-, or 4-cyano; $R_2$-$R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 2-, 3-, or 4-ethoxy; $R_2$-$R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 2-, 3-, or 4-trifluoromethoxy; $R_2$-$R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 2-, 3-, or 4-chloromethoxy; $R_2$-$R_4$ are H; and R' is —$(CH_2)_n$-G, where n is 1 or 2, and G is isothiazolyl, isoxazolyl, oxazolyl, oxazolinyl, oxazolidinyl, thiazolyl, thienyl, furyl, pyrrolyl, pyrrolinyl, pyrrolidinyl, pyrrolidinonyl, morpholyl, or imidazolyl.

In another more specific embodiment, this invention provides a compound of formula IXA, in which $R_1$ is 2-, 3-, or 4-methoxy; $R_2$-$R_4$ are H; and R' is —$(CH_2)_n$-G, where n is 1 or 2, and G is 5-oxazolidinyl, 4-thiazolyl, 3-thienyl, 2-furyl, 3-pyrrolyl, 2-pyrrolidinyl, N-pyrrolidinonyl, N-morpholyl, or 4-imidazolyl.

In another more specific embodiment, this invention provides a compound of formula IXA, in which $R_1$ is 3- or 4-methylsulfonyl $R_2$ is 2-(2-methyl cyclopropyl); $R_3$ and $R_4$ are H; and R' is —$(CH_2)_n$-G, where n is 1 or 2, and G is 3-methyl-2-isothiazolyl, 3-methyl-2-isoxazolyl, 3-methyl-4-oxazolyl, 3-methyl-2-pyrrolyl, 3-methyl-2-pyridyl, N-pyrrolidonyl, or m-tolyl.

In another more specific embodiment, this invention provides a compound of formula IXA, in which $R_1$ is 2-, 3-, or 4-methoxy; $R_2$-$R_4$ are H; and R' is —$(CH_2)_n$-G, where n is 1 or 2, and G is cyclopentyl, cyclopenten-3-yl, cyclopentadien-4-yl; cyclohexyl, or cyclohexen-2-yl.

In another more specific embodiment, this invention provides a compound of formula IXA, in which $R_1$ is 4-bromo or 4-bromomethyl; $R_2$-$R_4$ are H; and R' is —$(CH_2)_n$-G, where n is 1 or 2, and G is cyclopentyl, cyclopenten-3-yl, cyclopentadien-4-yl; cyclohexyl, or cyclohexen-2-yl.

In another more specific embodiment, this invention provides a compound of formula IXA, in which $R_1$ is 2- or 3-chloro; $R_2$ is 4-(2-cyclopropylethyl); $R_3$ and $R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula IXA, in which $R_1$ is cyclopropyl or cyclopropylmethyl; $R_2$-$R_4$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula IXA, in which $R_1$ is trans-3-(2-methylcyclopropyl); $R_2$ is 6-chloro; $R_3$ and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 3- or 4-cyclopropyl; $R_2$ is 5-chloro; $R_3$ is 2-(2-fluoroethyl); and $R_4$ is H, hydroxy, methoxy, or halo; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula IXA, in which $R_1$ is 2- or 3-cyclopropyl; $R_2$ is 6-chloro; $R_3$ is 3-chloro; $R_4$ is methyl; and R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In another embodiment, this invention provides a compound of formula IXA, in which $R_1$ and $R_2$ are halogen or methyl; $R_3$ and $R_4$ are H; and R' is methyl, ethyl, isopropyl, or sec-butyl.

In another more specific embodiment, this invention provides a compound of formula IXA, in which $R_1$ is halogen or methyl; $R_2$-$R_4$ are H; and R' is methyl, ethyl, isopropyl, or sec-butyl.

In another more specific embodiment, this invention provides a compound of formula IXA, in which $R_1$ and $R_2$ are, independently, halogen or methyl; $R_3$ and $R_4$ are H; and R' is 1,2-chloropropan-3-yl.

In another more specific embodiment, this invention provides a compound of formula IXA, in which $R_1$ and $R_2$ are, independently, halogen or methyl; $R_3$ and $R_4$ are H; and R' is 1-hydroxy-butan-3-yl.

In another more specific embodiment, this invention provides a compound of formula IXA, in which $R_1$ is bromo; $R_2$-$R_4$ are H; and R' is isopropyl.

In another more specific embodiment, this invention provides a compound of formula IXA, in which $R_1$ and $R_2$ are, independently, halogen or methyl; $R_3$ and $R_4$ are H; and R' is 1,2-dihydroxy-propan-3-yl.

In another more specific embodiment, this invention provides a compound of formula IXA, in which $R_1$ and $R_2$ are, independently, halogen or methyl; $R_3$ and $R_4$ are H; and R' is 2-hydroxyethyl.

In another more specific embodiment, this invention provides a compound of formula IXA, in which $R_1$ and $R_2$ are, independently, halogen or methyl; $R_3$ and $R_4$ are H; and R' is 4-hydroxybutyl.

In another more specific embodiment, this invention provides a compound of formula IXA, in which $R_1$ and $R_2$ are, independently, halogen or methyl; $R_3$ and $R_4$ are H; and R' is 1,2-dihydroxybutan-4-yl.

In another more specific embodiment, this invention provides a compound of formula IXA, in which $R_1$ and $R_2$ are, independently, halogen or methyl; $R_3$ and $R_4$ are $C_1$-$C_6$ alkyl; and R' is 1,2-dihydroxybutan-3-yl.

In another more specific embodiment, this invention provides a compound of formula IXA, in which $R_1$ and $R_2$ are halogen or methyl; $R_3$ and $R_4$ are H; and R' is 4-methoxybutyl.

In another more specific embodiment, this invention provides a compound of formula IXA, in which $R_1$ and $R_2$ are, independently, halogen or methyl; $R_3$ and $R_4$ are H; and R' is 3-hydroxypropyl.

In another more specific embodiment, this invention provides a compound of formula IXA, where $R_1$ and $R_2$ together are fused cyclohexyl or fused cyclopentyl; $R_3$ and $R_4$ are H; and R' is isopropyl, (2-tetrahydrofuryl)methyl, 2-hydroxyethyl, 2,3-dihydroxy-1-propyl, or 3,4-dihydroxy-2-butyl.

In another more specific embodiment, this invention contemplates a compound of formula IXA, where $R_1$ and $R_2$, at positions 3 and 4, are fused (4,5)-imidazolo; $R_3$ and $R_4$ are H; and R' is isopropyl, (2-tetrahydrofuryl)methyl, 2-hydroxyethyl, 2,3-dihydroxy-1-propyl, or 3,4-dihydroxy-2-Butyl.

In another more specific embodiment, this invention contemplates a compound of formula IXA, where $R_1$ and $R_2$, at positions 3 and 4, are fused (2,3)-furyl; $R_3$ and $R_4$ are H; and R' is isopropyl, (2-tetrahydrofuryl)methyl, 2-hydroxyethyl, 2,3-dihydroxy-1-propyl, or 3,4-dihydroxy-2-butyl.

In another more specific embodiment, this invention contemplates a compound of formula IXA, where $R_1$ and $R_2$, at positions 3 and 4, are fused (2,3)-pyrido; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 3 and 4, are fused (3,4)pyrrolyl; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 2 and 3, are fused cyclopentyl; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 3 and 4, are fused cyclopentyl; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 2 and 3, are benzo; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 2 and 3, are benzo, substituted at one or both ortho positions; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention contemplates a compound of formula IXA, where $R_1$ and $R_2$, at positions 3 and 4, are benzo; $R_3$ and $R_4$ are H; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

Specific prophetic examples of compounds of formula IXA are shown below,

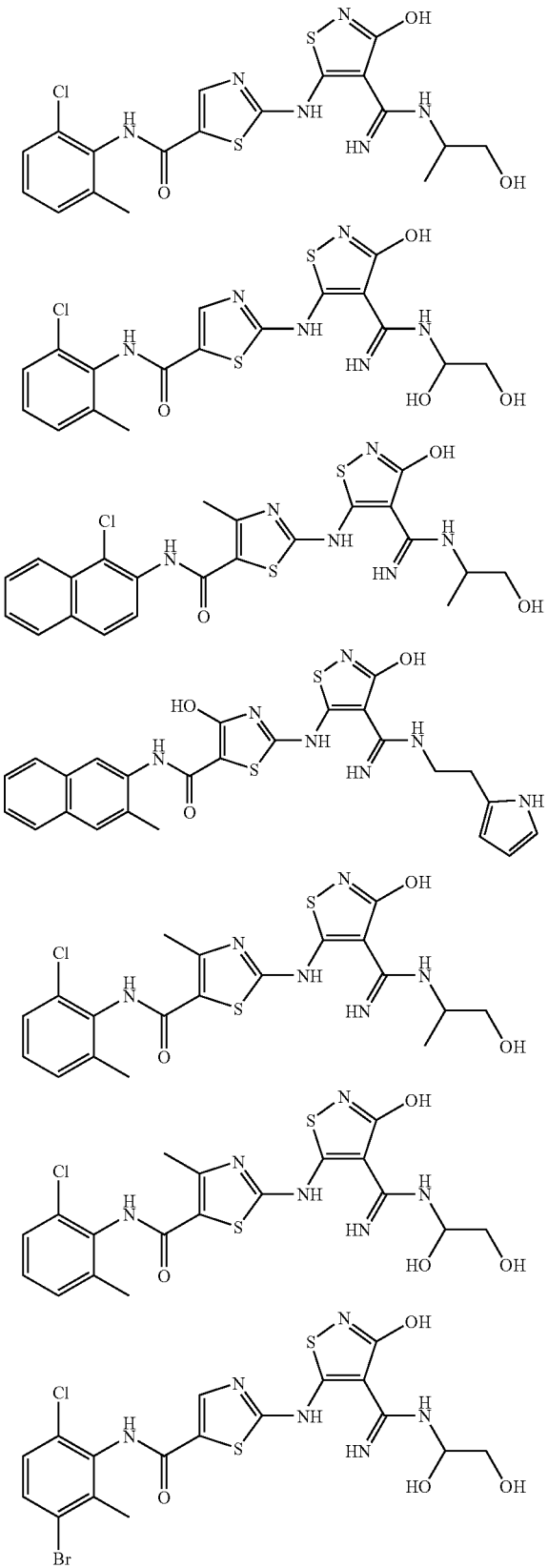

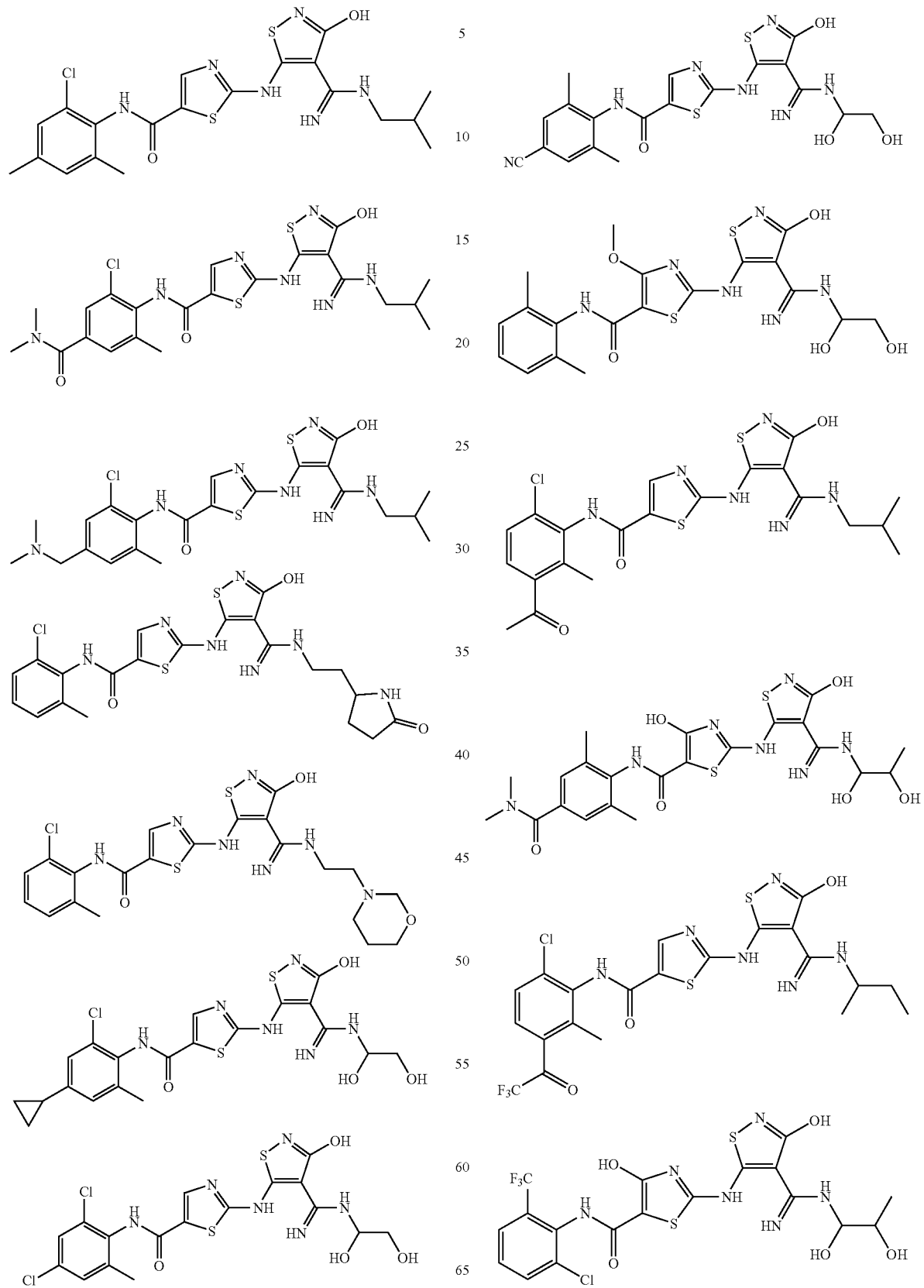

Subgeneric embodiments of formula IXB are shown below:
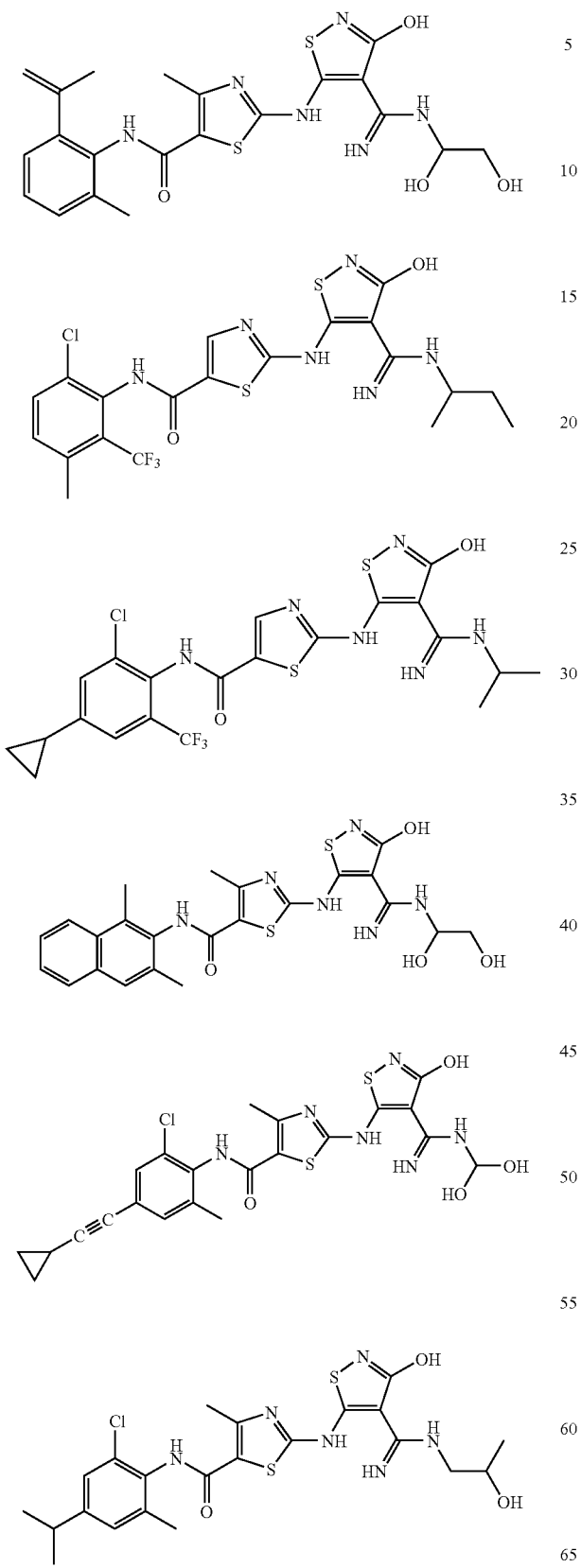

-continued

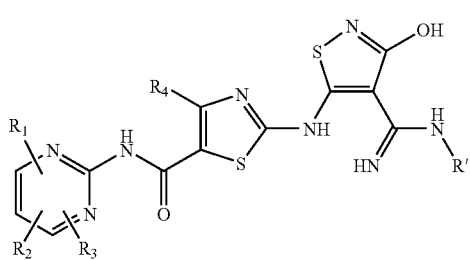

IXB-6

In one subgeneric embodiment, this invention provides a compound of any of formulas IXB-1-IXB-6, in which $R_1$, $R_2$, and $R_4$ are, independently, H, $C_1$-$C_4$ alkyl, alkenyl, alkynyl, cycloalkyl, cyano, acetyl, acetoxy, acetamido, methylcarbamoyl, dimethylamino, or halo; $R_3$ is H, and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl, optionally substituted as described above, or R' is $C_1$-$C_6$ alkyl, optionally substituted with one or two or hydroxyl groups.

In a more specific embodiment, this invention provides a compound according to formula IXB-1, where $R_1$ is 3-methyl or 3-halo; $R_2$ and $R_3$ are H; $R_4$ is H, vinyl, cyano, halo, hydroxy, or methyl; and R' is $C_1$-$C_6$ alkyl, optionally substituted with one or two or hydroxyl groups.

In a more specific embodiment, this invention provides a compound according to formula IXB-1, where $R_1$ is 3-methyl or 3-halo; $R_2$ and $R_3$ are H; $R_4$ is H or methyl; and R' is $C_1$-$C_6$ alkyl, optionally substituted with one or two or hydroxyl groups.

In another more specific embodiment, this invention provides a compound according to formula IXB-2, where $R_1$ is 2-methyl or 2-halo; $R_2$ and $R_3$ are, independently, H, halo, $C_1$-$C_6$ alkyl, or $C_1$-$C_6$ alkenyl, said alkyl and alkenyl groups optionally substituted as described above; $R_4$ is H, vinyl, cyano, halo, hydroxy, or $C_1$-$C_6$ alkyl; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound according to formula IXB-2, where $R_1$ is 4-methyl or 4-halo; $R_2$ and $R_3$ are H; $R_4$ is H, OH, halo, or methyl; and R' is $C_1$-$C_6$ alkyl, optionally substituted with one or two or hydroxyl groups or R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound according to formula IXB-2, where $R_1$ is 2-methyl; $R_2$ is 4-halo; $R_3$ is H; $R_4$ is H, OH, halo, or methyl; and R' is $C_1$-$C_6$ alkyl, optionally substituted with one or two or hydroxyl groups.

In another more specific embodiment, this invention provides a compound according to formula IXB-2, where $R_1$ is 2-halo; $R_2$ is 4-methyl; $R_3$ is H; $R_4$ is H, OH, halo, or methyl; and R' is $C_1$-$C_6$ alkyl, optionally substituted with one or two or hydroxyl groups.

In another more specific embodiment, this invention provides a compound according to formula IXB-2, where $R_1$ is 2-methyl; $R_2$ is 4-chloro; $R_3$ is H; $R_4$ is H, OH, or methyl; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention provides a compound according to formula IXB-2, where $R_1$ is 2-chloro; $R_2$ is 4-methyl; $R_3$ is H; $R_4$ is H, OH, or methyl; and R' is isopropyl, (2-tetrahydrofuryl)methyl, 2-hydroxyethyl, 1-hydroxy-2-propyl, 2,3-dihydroxy-1-propyl, or 3,4-dihydroxy-2-butyl.

In another more specific embodiment, this invention provides a compound according to formula IXB-3, where $R_1$ is 4-methyl or 4-halo; $R_2$ and $R_3$ are H; $R_4$ is H, vinyl, cyano, halo, hydroxy, or methyl; and R' is $C_1$-$C_6$ alkyl, optionally substituted with one or two or hydroxyl groups.

In another more specific embodiment, this invention provides a compound according to formula IXB-3, where $R_1$ is 4-methyl or 4-halo; $R_2$ is 6-methyl or 6-halo; $R_3$ is H; $R_4$ is H, hydroxy, or methyl; and R' is $C_1$-$C_6$ alkyl, optionally substituted with one or two or hydroxyl groups.

In another more specific embodiment, this invention provides a compound according to formula IXB-3, where $R_1$ is 4-methyl or 4-halo; $R_2$ is 6-methyl or 6-halo; $R_3$ is H; $R_4$ is H or methyl; and R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In another more specific embodiment, this invention provides a compound according to formula IXB-3, where $R_1$ is 4-methyl or 4-halo; $R_2$ is 6-methyl or 6-halo; $R_3$ is H; $R_4$ is H or methyl; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound according to formula IXB-3, where $R_1$ is 4-methyl or 4-halo; $R_2$ is H, 6-methyl, or 6-halo; $R_3$ is H, $C_1$-$C_3$ alkyl, dimethylamino methyl; chloromethyl, or bromomethyl; $R_4$ is H or methyl; and R' is $C_1$-$C_6$ alkyl, optionally substituted with one or two or hydroxyl groups or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-3, where $R_1$ is 4-methyl; $R_2$ is 6-chloro; $R_3$ is H; $R_4$ is H, OH, or methyl; and R' is isopropyl, 1-hydroxy-2-propyl, 2-hydroxyethyl, 2,3-dihydroxy-1-propyl, or 3,4-dihydroxy-2-butyl, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-3, where $R_1$ is 4-chloro; $R_2$ is 6-methyl; $R_3$ is H; $R_4$ is H, OH, or methyl; and R' is isopropyl, 1-hydroxy-2-propyl, 2-hydroxyethyl, 2,3-dihydroxy-1-propyl, or 3,4-dihydroxy-2-butyl, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-4, where $R_1$ is 5-methyl or 4-halo; $R_2$ is 6-methyl or 6-halo; $R_3$ is H; 4 is H, hydroxy, halo, $C_1$-$C_6$ alkyl, or $C_1$-$C_6$ alkenyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-4, where $R_1$ is 5-methyl; $R_2$ is H, 6-methyl, or 6-chloro; $R_3$ is H; $R_4$ is H, OH, or methyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-4, where $R_1$ and $R_2$, at positions 5 and 6, are fused benzo or pyrido; $R_3$ is H; $R_4$ is H, OH, or methyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In another more specific embodiment, this invention provides a compound according to formula IXB-4, where $R_1$ is 5-chloro; $R_2$ is H, 6-methyl, or 6-chloro; $R_3$ is H; $R_4$ is H, OH, or methyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In a more specific embodiment, this invention provides a compound according to formula IXB-5, where $R_1$ is 3-($C_1$-$C_4$ alkyl), 3-($C_1$-$C_4$ alkenyl), or 3-halo; $R_2$ and $R_3$ are H; $R_4$ is H, vinyl, cyano, halo, hydroxy, or methyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl.

In a more specific embodiment, this invention provides a compound according to formula IXB-5, where $R_1$ is 3-methyl or 3-halo; $R_2$ is 5-methyl or 5-halo; $R_3$ is H; $R_4$ is H, OH, or methyl; and R' is $C_1$-$C_6$ alkyl, optionally substituted with one or two or hydroxyl groups, or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl or R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In a still more specific embodiment, this invention provides a compound according to formula IXB-5, where $R_1$ is 3-methyl; $R_2$ is 5-chloro; $R_3$ is H; $R_4$ is H, OH, or methyl; and R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In a still more specific embodiment, this invention provides a compound according to formula IXB-5, where $R_1$ and $R_2$, at positions 2 and 3, are fused benzo, pyrido, pyrrolo, or imidazolo, optionally substituted with halogen, methyl, halomethyl, or hydroxy; $R_3$ is H; $R_4$ is H, OH, or methyl; and R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In a still more specific embodiment, this invention provides a compound according to formula IXB-5, where $R_1$ is 3-methyl; $R_2$ is 5-chloro; $R_3$ is H; $R_4$ is H, OH, or methyl; and R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In another more specific embodiment, this invention provides a compound according to formula IXB-5, where $R_1$ is H, 2-methyl, 2-nitro, 2-methylcarbamoyl, or 2-halo; $R_2$ is 3-methyl or 3-chloro, and $R_3$ is H, 5-methyl, or 5-chloro; $R_4$ is H, OH, or methyl; and R' is $C_1$-$C_6$ alkyl, optionally substituted with one or two or hydroxyl groups or R' is —$(CH_2)_n$-G, where n is 1 or 2, and G is N-pyrrolidinonyl, 4-morpholyl, 2,6-dimethyl-4-morpholyl, 2-tetrahydrofuryl, or 4-imidazolyl or R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In another more specific embodiment, this invention provides a compound according to formula IXB-5, where $R_1$ is H, 2-acetyl, 2-acetamido, 2-dimethylamino, or 2-halomethyl; $R_2$ is 3-methyl or 3-chloro, and $R_3$ is H, 5-methyl, or 5-chloro; $R_4$ is H or methyl; and R' is $C_1$-$C_6$ alkyl, optionally substituted with one or two or hydroxyl groups.

In another still more specific embodiment, this invention provides a compound according to formula IXB-5, where $R_1$ is 3-methyl; $R_2$ is H or 5-chloro; $R_3$ is H; $R_4$ is H; and R' is isopropyl, 1-hydroxy-2-propyl, 2-hydroxyethyl, 2,3-dihydroxy-1-propyl, or 3,4-dihydroxy-2-butyl.

In another more specific embodiment, this invention provides a compound according to formula IXB-5, where $R_1$ is H, 2-bromomethyl, 2-ethynyl, 2-cyano; $R_2$ is 3-chloro; $R_3$ is H or 5-methyl; $R_4$ is H or methyl; and R' is $C_1$-$C_6$ alkyl, optionally substituted with one or two or hydroxyl groups.

In another more specific embodiment, this invention provides a compound according to formula IXB-5, where $R_1$ is H or 2-chloro; $R_2$ is 3-chloro; $R_3$ is H or 5-chloro; $R_4$ is H or methyl; and R' is $C_1$-$C_6$ alkyl, optionally substituted with one or two or hydroxyl groups.

In another more specific embodiment, this invention provides a compound according to formula IXB-5, where $R_1$ is H or 2-chloro; $R_2$ is 3-chloro; $R_3$ is H or 5-chloro; $R_4$ is H or methyl; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound according to formula IXB-6, where $R_1$ is H, 4-acetyl, 4-acetamido, 4-dimethylamino, 4-$C_1$-$C_4$ alkyl, alkenyl, alkynyl, or cycloalkyl, or 4-halomethyl; $R_2$ is H, 5-methyl or 5-halo, and $R_3$ is H, 6-methyl, or 6-chloro; $R_4$ is H, hydroxy, or methyl; and R' is $C_1$-$C_6$ alkyl, optionally substituted with one or two or hydroxyl groups.

In another more specific embodiment, this invention provides a compound according to formula IXB-6, where $R_1$ is 4-methyl; $R_2$ is H or 5-chloro; $R_3$ is H or 6-chloro; $R_4$ is H or methyl; and R' is isopropyl, 1-hydroxy-2-propyl, 2-hydroxyethyl, 2,3-dihydroxy-1-propyl, or 3,4-dihydroxy-2-butyl.

In another more specific embodiment, this invention provides a compound according to formula IXB-6, where $R_1$ is H, 4-bromomethyl, 4-ethynyl, 4-cyano; $R_2$ is H, 5-methyl, or 5-chloro; $R_3$ is H, 6-acetyl, 6-acetoxy, 6-acetamido, or 6-methylcarbamoyl; $R_4$ is H, vinyl, chloromethyl, hydroxy, or methyl; and R' is $C_1$-$C_6$ alkyl, optionally substituted with one or two or hydroxyl groups.

In another more specific embodiment, this invention provides a compound according to formula IXB-6, where $R_1$ and $R_2$, at positions 4 and 5, are fused benzo; $R_3$ is H or 6-methyl; $R_4$ is H, halo, halomethyl, hydroxy, or methyl; and R' is $C_1$-$C_6$ alkyl, optionally substituted with one or two or hydroxyl groups or R' is —$(CH_2)_n$-G, where n is 1 or 2, and G is N-pyrrolidinonyl, 4-morpholyl, 2,6-dimethyl-4-morpholyl, or 4-imidazolyl, or R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In another more specific embodiment, this invention provides a compound according to formula IXB-6, where $R_1$ and $R_2$, at positions 4 and 5, are (2,3) fused imidazolo, pyrido, or pyrrolo; $R_3$ is H or 6-methyl; $R_4$ is H, halo, halomethyl, or methyl; and R' is —$(CH_2)_n$-G, where n is 1 or 2, and G is N-pyrrolidinonyl, 4-morpholyl, 2,6-dimethyl-4-morpholyl, or 4-imidazolyl or R' is $C_1$-$C_6$ alkyl, optionally substituted with one or two or hydroxyl groups.

Prophetic examples of additional compounds of formula IXB are shown below

IXB-1a
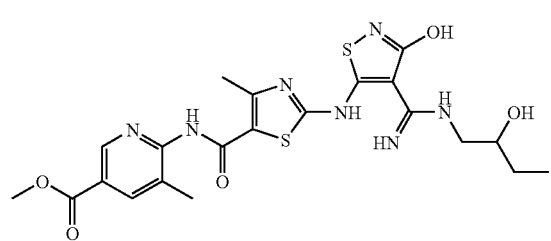
IXB-1b
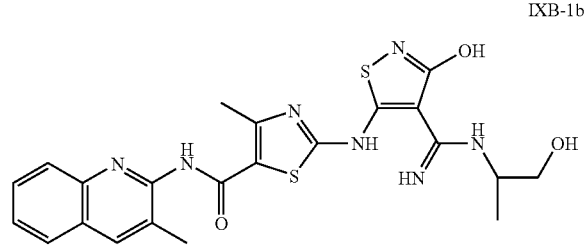
IXB-2a
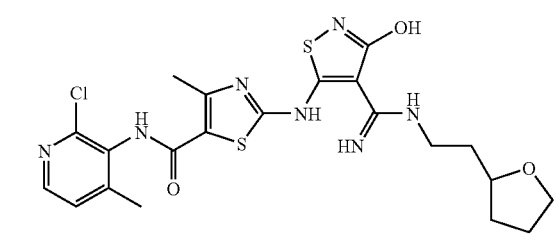
IXB-2b
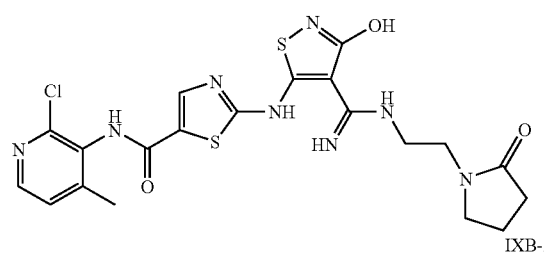
IXB-2c
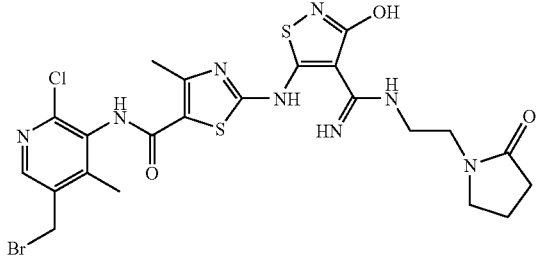
IXB-2d
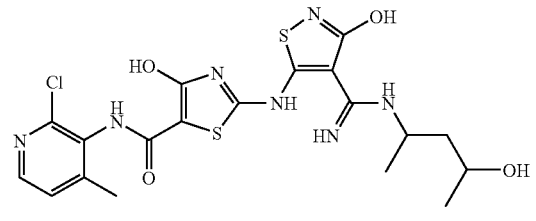
IXB-2e
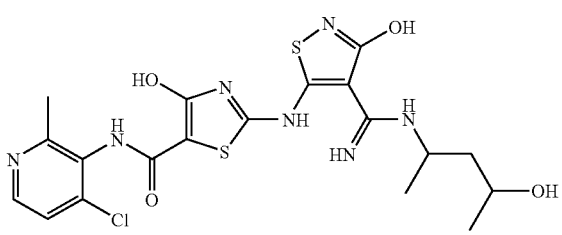
IXB-2f
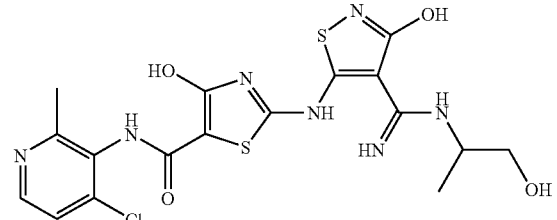
IXB-2g
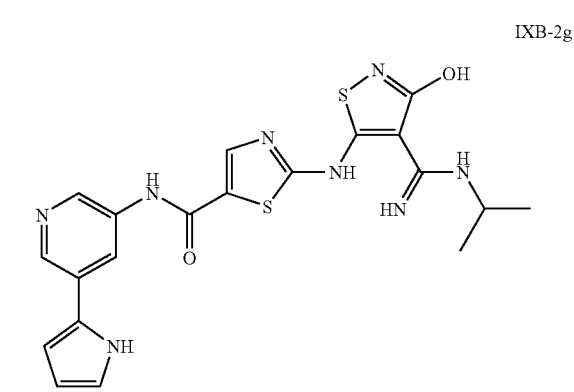
IXB-2h
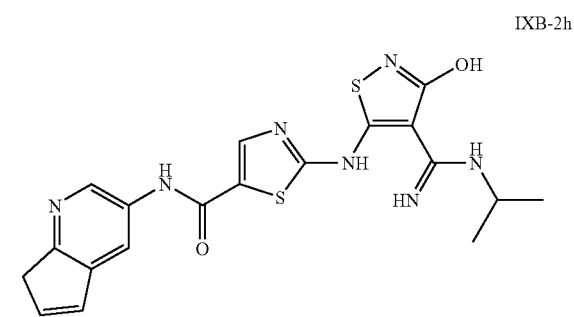
IXB-3a
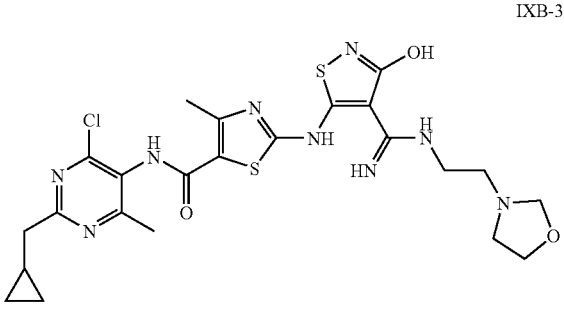

-continued

-continued

IXB-6c

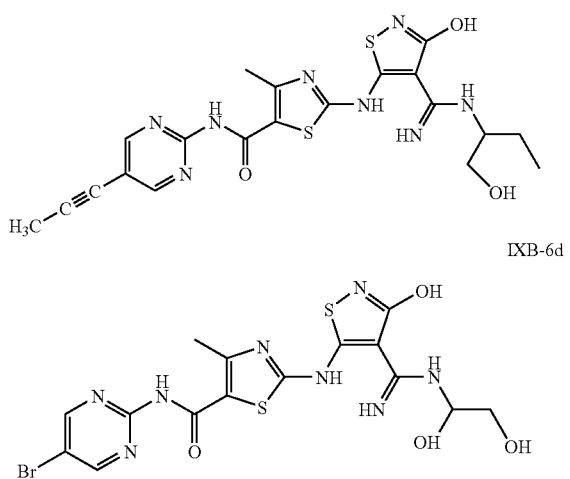

IXB-6d

In another generic embodiment, this invention provides a compound of formula X

X

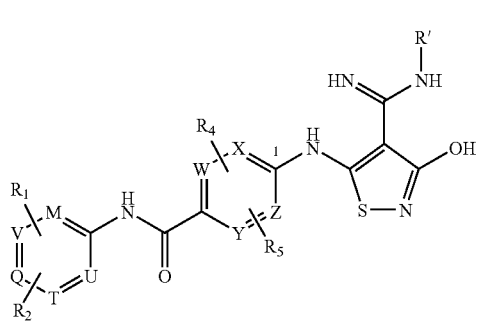

where M, Q, T, U, V, W, X, Y, and Z represent N, CH, or $CR_{1, 2, 3, or 4}$, where $R_1$-$R_4$ are defined as for formula I.

In a subgeneric embodiment, this invention provides a compound of formula XA where M, Q, T, U, V, W, X, Y, and Z are all CH or $CR_{1, 2, 3, or 4}$.

In another subgeneric embodiment, this invention provides a compound of formula XB,

XB

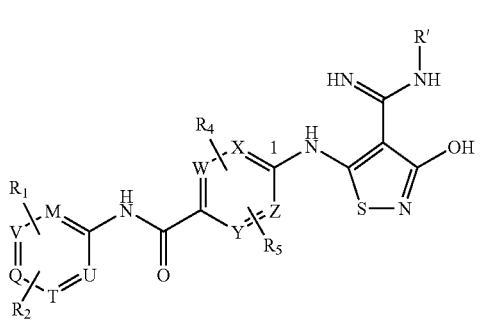

where all substituents are as defined for formula I, and where at least one of M, Q, T, U, V, W, X, Y, and Z is N, provided that no ring contains 2 adjacent nitrogen atoms.

In one subgeneric embodiment, this invention provides a compound of formula XA, where R' is —$(CH_2)_n$-G, where n is 1 or 2; and G is isothiazolyl, isoxazolyl, oxazolyl, oxazolinyl, oxazolidinyl, oxazolidinonyl, thiazolyl, thienyl, furyl, pyrrolyl, pyrrolinyl, pyrrolidinyl, pyrrolidinonyl, thiazolinyl, thiazolidinyl, thiazolidinonyl, isothiazolinyl, isothiazolidinyl, isothiazolidinonyl, imidazolinyl, imidazolyl, imidazolinonyl, pyridyl, pyrazyl, pyranyl, pyridazolyl, piperidinonyl, morpholyl, 2,6-dimethyl morpholyl, tetrahydrofuryl, piperazinyl, 1-methyl-piperazin-4-yl, piperazinonyl, 2-pyrrolidonyl, tolyl, phenyl, piperidinyl, pyrimidinyl, pyrazolyl, isoxazolyl, isoxazolinyl, isoxazolidinyl, isoxazolidinonyl, isothiazolinyl, isothiazolidinyl, indolyl, oxindolyl, isoindolyl, quinolyl, isoquinolyl, or naphthyl.

In another preferred embodiment, this invention provides a compound of formula XA, where R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl.

In another preferred embodiment, this invention provides a compound of formula XA, where R' is $C_1$-$C_6$ alkyl, optionally substituted with one or two or hydroxyl groups.

In another preferred embodiment, this invention provides a compound of formula XA, where $R_1$ and $R_2$ are both ortho substituents.

In another preferred embodiment, this invention provides a compound of formula XA, where $R_4$ and $R_5$ occupy the 3- and 5-positions.

In a more specific embodiment, this invention provides a compound of formula XA, where $R_1$ and $R_2$ are as defined for formula I; $R_4$ and $R_5$ are both H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula XA, where $R_1$ and $R_2$ are defined as in formula XA; $R_4$ and $R_5$ are both H; and R' is $C_1$-$C_6$ alkyl or O—$C_1$-$C_6$ alkyl, both optionally substituted as described above.

In a still more specific embodiment, this invention provides a compound of formula XA, where $R_1$ and $R_2$ are H, halo, or $C_1$-$C_3$ alkyl; $R_4$ and $R_5$ are both H; and R' is $C_1$-$C_6$ alkyl, optionally substituted with one or two or hydroxyl groups.

In a preferred and more specific embodiment, this invention provides a compound of formula XA, in which $R_1$ is 2-halo; $R_2$ is 6-methyl; $R_4$ and $R_5$ are, independently, H, $C_1$-$C_3$ alkyl, or halo; and R' is isopropyl or mono- or di-hydroxy $C_1$-$C_4$ alkyl.

In another more preferred specific embodiment, this invention provides a compound of formula XA, in which $R_1$ is 2-chloro; $R_2$ is 6-methyl; $R_4$ and $R_5$ are, independently, H, $C_1$-$C_3$ alkyl, or halo; and R' is isopropyl or mono- or di-hydroxy $C_1$-$C_4$ alkyl.

In another more preferred specific embodiment, this invention provides a compound of formula XA, in which $R_1$ and $R_2$ are H; $R_4$ and $R_5$ are, independently, methyl or halo; and R' is isopropyl or mono- or di-hydroxy $C_1$-$C_4$ alkyl.

In another more preferred specific embodiment, this invention provides a compound of formula XA, in which $R_1$ and $R_2$ are H; $R_4$ and $R_5$ are, independently, methyl or chloro; and R' is isopropyl or mono- or di-hydroxy $C_1$-$C_4$ alkyl.

In another more preferred specific embodiment, this invention provides a compound of formula XA, in which $R_1$ and $R_2$ are H; $R_4$ and $R_5$ are 3-chloro and 5-methyl; and R' is isopropyl or mono- or di-hydroxy $C_1$-$C_4$ alkyl.

In another more preferred specific embodiment, this invention provides a compound of formula XA, in which $R_1$ and $R_2$ are H; $R_5$ is 2-chloro or 3-chloro; $R_4$ is H; and R' is isopropyl or mono- or di-hydroxy $C_1$-$C_4$ alkyl.

In another more preferred specific embodiment, this invention provides a compound of formula XA, in which $R_1$ and $R_2$ are H; $R_5$ is 2-methyl or 3-methyl; $R_4$ is H; and R' is isopropyl or mono- or di-hydroxy $C_1$-$C_4$ alkyl.

In another more preferred subgeneric embodiment, this invention provides a compound of formula XA, in which $R_1$ is 2-chloro; $R_2$ is 6-methyl; $R_4$ and $R_5$ are, independently, H, $C_1$-$C_3$ alkyl, or halo; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula XA, where $R_1$ is $C_2$-$C_6$ alkenyl, $C_2$-$C_6$ alkynyl, or $C_1$-$C_6$ cycloalkyl; $R_2$-$R_5$ are H; and R' is $C_1$-$C_6$ alkyl, optionally substituted with one or two or hydroxyl groups.

In another more specific embodiment, this invention provides a compound of formula XA, where $R_1$ is amino, methyl amino, dimethylamino, dimethylaminomethyl, or acetylamino; $R_2$-$R_5$ are H and R' is $C_1$-$C_6$ alkyl, optionally substituted with one or two or hydroxyl groups.

In another more specific embodiment, this invention provides a compound of formula XA, where $R_1$ is nitro, cyano, methylcarbamoyl, dimethylcarbamoyl, or aminosulfonyl; $R_2$-$R_5$ are H and R' is $C_1$-$C_6$ alkyl, optionally substituted with one or two or hydroxyl groups.

In another more specific embodiment, this invention provides a compound of formula XA, where $R_1$ is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl; $R_2$-$R_5$ are H; and R' is $C_1$-$C_6$ alkyl, optionally substituted with one or two or hydroxyl groups.

In a still more specific embodiment, this invention provides a compound of formula XA, in which $R_1$ and $R_2$ are both halogen; $R_5$ is 2-methyl; and $R_4$ is H; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidyl, or R' is $C_1$-$C_6$ alkyl, optionally substituted with one or two or hydroxyl groups.

In a still more specific embodiment, this invention provides a compound of formula XA, in which $R_1$ and $R_2$ are both H; $R_5$ is 2-chloro; $R_4$ is 3-methyl; R' is —$(CH_2)_n$-G, where n is 1, and G is piperazinyl, piperazinonyl, piperidinyl, piperidinonyl, morpholyl, furyl, or tetrahydrofuryl, or R' is $C_1$-$C_6$ alkyl, optionally substituted with one or two or hydroxyl groups.

In a still more specific embodiment, this invention provides a compound of formula XA, in which $R_1$ and $R_2$ are both H; $R_5$ is 3-methyl; $R_4$ is 6-(2-chloroethyl); R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention provides a compound of formula XA, in which $R_1$ is 2-hydroxymethyl; $R_5$ is 4-$CF_3$; $R_2$ and $R_4$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention provides a compound of formula XA, in which $R_1$ and $R_2$ are both H; $R_5$ is 3-methyl; $R_4$ is 5-chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another specific embodiment, this invention provides a compound of formula XA, in which one or both of $R_1$ and $R_2$ are $CF_3$; $R_4$ and $R_5$ are H; and R' is —$(CH_2)_n$-G, where n is 1, and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another subgeneric embodiment, this invention provides a compound of formula XA, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl; $R_2$; $R_4$; and $R_5$ are H; and R' is —$(CH_2)_n$-G, where n is 1 or 2; and G is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, or naphthyl, or R' is $C_1$-$C_6$ alkyl, optionally substituted with one or two or hydroxyl groups.

In a still more specific embodiment, this invention contemplates the compound of formula XA, in which $R_1$ is 3-chloro; $R_2$; $R_4$ and $R_5$ are H; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ is 2-chloro; $R_2$ is 6-methyl; $R_4$ and $R_5$ are H; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ is 4-chloro; $R_2$; $R_4$ and $R_5$ are H; R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ and $R_2$ are 2,6-di-chloro; $R_2$; $R_4$ and $R_5$ are H; and R' is —$(CH_2)_n$-G, where n is 1, and G is pyridyl; piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ is 2-bromo; $R_2$; $R_4$ and $R_5$ are H; and R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 3-bromo; $R_2$; $R_4$ and $R_5$ are H; and R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 4-bromo; $R_2$; $R_4$ and $R_5$ are H; and R' is —$(CH_2)_n$-G, where n is 1, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 2-, 3-, or 4-bromo; $R_2$; $R_4$ and $R_5$ are H; and R' is —$(CH_2)_n$-G, where n is 1, and G is R' is $C_1$-$C_6$ alkyl, optionally substituted with one or two or hydroxyl groups.

In another specific embodiment, this invention contemplates the compound of formula XA, in which $R_1$ is 4-bromo; $R_2$ is 2-methyl; $R_5$ is 3-methyl; $R_4$ is H, 5-methyl, or 5-halo; and R' is $C_1$-$C_6$ alkyl, optionally substituted with one or two or hydroxyl groups.

In another specific embodiment, this invention contemplates the compound of formula XA, in which $R_1$ is 2-bromo; $R_2$ is 6-methyl; $R_5$ is 3-methyl; $R_4$ is H, 5-methyl, or 5-halo; and R' is $C_1$-$C_6$ alkyl, optionally substituted with one or two or hydroxyl groups.

In another specific embodiment, this invention contemplates the compound of formula XA, in which $R_1$ is 3-bromo; $R_2$ is 6-methyl; $R_5$ is 3-methyl; $R_4$ is H, 5-methyl, or 5-halo; and R' is $C_1$-$C_6$ alkyl, optionally substituted with one or two or hydroxyl groups.

In a still more specific embodiment, this invention contemplates the compound of formula XA, in which $R_1$ is 2-chloro; $R_2$ is 4-chloro; $R_4$ and $R_5$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates the compound of formula XA, in which $R_1$ is 2-methyl; $R_2$ is 6-methyl; $R_4$ and $R_5$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention provides a compound of formula XA, in which one or both of $R_1$ and $R_2$ are $CF_3$; $R_4$ and $R_5$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In a still more specific embodiment, this invention contemplates a compound of formula XA, in which $R_1$ is 2-$CF_3$; $R_2$; $R_4$ and $R_5$ are H; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula XA, in which $R_1$ and $R_2$, in positions 2 and 6, are methyl or halogen; $R_5$ is 2-chloromethyl, 4 is H; and R' is —$(CH_2)_n$-G, where n is 1 or 2; and G is 2-pyridyl, 3-pyridyl, 4-pyridyl, 2-piperidyl, 3-piperidyl, or 4-piperidyl or R' is isopropyl or mono- or di-hydroxy $C_1$-$C_4$ alkyl.

In another more specific embodiment, this invention provides a compound of formula XA, in which $R_1$ and $R_2$, in positions 2 and 6, are methyl or halogen; $R_5$ is 3-fluoromethyl; and $R_4$ is H; R' is —$(CH_2)_n$-G, where n is 1 or 2; and G is 2-pyrimidyl, 4-pyrimidyl, 2-morpholyl, or 3-morpholyl or R' is isopropyl or mono- or di-hydroxy $C_1$-$C_4$ alkyl.

In another more specific embodiment, this invention provides a compound of formula XA, in which $R_1$ and $R_2$, in positions 2 and 6, are methyl or halogen; $R_5$ is 3-methyl; and $R_4$ is H; R' is —$(CH_2)_n$-G, where n is 1 or 2; and G is 2-pyridyl, 3-pyridyl, 4-pyridyl, 2-piperidyl, 3-piperidyl, or 4-piperidyl.

In another more specific embodiment, this invention provides a compound of formula XA, in which $R_1$ and $R_2$, in positions 2 and 6, are methyl or halogen; $R_5$ is 3-fluoromethyl; and $R_4$ is H; R' is —$(CH_2)_n$-G, where n is 1 or 2; and G is 4-bromo-2-pyrimidyl, 2-chloro-4-pyrimidyl, 2-morpholyl, or 3-morpholyl.

In a still more specific embodiment, this invention provides a compound of formula XA, in which $R_1$ is 3-cyano; $R_2$ is H or 6-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula XA, in which $R_1$ is 3-hydroxy; $R_2$ is H or 6-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XA, in which $R_1$ is 4-hydroxy; $R_2$ is H or 2-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula XA, in which $R_1$ is 2-, 3-, or 4-methoxy; $R_2$ is H or 2-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In a still more specific embodiment, this invention provides a compound of formula XA, in which $R_1$ is 2-, 3-, or 4-methoxy; $R_2$ is H or 2-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is isopropyl or mono- or di-hydroxy $C_1$-$C_4$ alkyl.

In another more specific embodiment, this invention provides a compound of formula XA, in which $R_1$ is 2-, 3-, or 4-ethoxymethyl; $R_2$ is H or 2-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XA, in which R is 2-, 3-, or 4-methoxymethyl; $R_2$ is H or 2-methyl; $R_4$ and $R_5$ are H, halo, or methyl; and R' is $C_1$-$C_6$ alkyl, optionally substituted with one or two or hydroxyl groups.

In another more specific embodiment, this invention provides a compound of formula XA, in which $R_1$ is 3-(2-methoxyethyl); $R_2$ is H, 2-methyl, or 6-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In a still more specific embodiment, this invention provides a compound of formula XA, in which $R_1$ is 4-(2-methoxyethyl); $R_2$ is H, 2-methyl, or 6-methyl; $R_4$ and $R_5$ are H or methyl; and R' is —$(CH_2)_n$-G, where n is 1 or 2; and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In a still more specific embodiment, this invention contemplates a compound of formula XA, in which $R_1$ is 2-, 3-, or 4-dimethylamino; $R_2$ is H or 6-methyl; $R_4$ and $R_5$ are H; and R' is $C_1$-$C_6$ alkyl, optionally substituted with one or two or hydroxyl groups.

In a still more specific embodiment, this invention contemplates a compound of formula XA, in which $R_1$ is 2-, 3-, or 4-dimethylamino; $R_2$ is H or 6-methyl; $R_5$ is 3-methyl; $R_4$ are 5-methyl, 5-halo, or H; and R' is $C_1$-$C_6$ alkyl, optionally substituted with one or two or hydroxyl groups.

In another more specific embodiment, this invention contemplates a compound of formula XA, in which $R_1$ is 2-, 3-, or 4-dimethylaminocarbonyl; $R_2$ is H or 6-methyl; $R_5$ is H or 3-methyl; $R_4$ is H; and R' is $C_1$-$C_6$ alkyl, optionally substituted with one or two or hydroxyl groups.

In a still more specific embodiment, this invention contemplates a compound of formula XA, in which $R_1$ is 2-, 3-, or 4-methyloxycarbonyl; $R_2$ is H or 6-methyl; $R_5$ is H or 3-methyl, $R_4$ is H; and R' is $C_1$-$C_6$ alkyl, optionally substituted with one or two or hydroxyl groups.

In a still more specific embodiment, this invention contemplates a compound of formula XA, in which $R_1$ is 2-, 3-, or 4-acetyl; $R_2$ is H or 6-methyl, $R_5$ is H, 3-chloro, or 3-methyl; $R_4$ is H or 5-methyl; and R' is $C_1$-$C_6$ alkyl, optionally substituted with one or two or hydroxyl groups.

In a still more specific embodiment, this invention contemplates a compound of formula XA, in which $R_1$ is 2-, 3-, or 4-acetoxy; $R_2$ is H or 6-methyl; $R_5$ is H or 3-methyl; $R_4$ is H or 5-chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates a compound of formula XA, in which $R_1$ is 2-, 3-, or 4-dimethylamino; $R_2$ is H or 6-methyl; $R_5$ is H or 3-methyl; $R_4$ is H or 5-chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention contemplates a compound of formula XA, in which $R_1$ is 2-, 3- or 4-dimethylaminocarbonyl; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention contemplates a compound of formula XA, in which $R_1$ is 2-, 3-, or 4-methyloxycarbonyl; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention contemplates a compound of formula XA, in which $R_1$ is 2-, 3- or 4-chloroacetyl; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention contemplates a compound of formula XA, in which $R_1$ is 2-, 3- or 4-acetoxy; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention contemplates a compound of formula XA, in which $R_1$ is 2-, 3- or 4-fluoromethyl; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention provides a compound of formula XA, in which $R_1$ is 4-cyano; $R_2$ is H or 6-methyl; $R_5$ is H or 3-methyl; $R_4$ is H or 5-chloro; and R' is $C_1$-$C_6$ alkyl, optionally substituted with one or two or hydroxyl groups, or R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula XA, in which $R_1$ is 2-, 3- or 4-ethoxy; $R_2$ is H or 6-methyl; $R_5$ is H or 3-methyl; $R_4$ is H or 5-chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula XA, in which $R_1$ is 2-, 3-, or 4-vinyl; $R_2$ is H or 6-methyl; $R_5$ is H or 3-methyl; $R_4$ is H or 5-chloro; and R' is —$(CH_2)_n$-G, where n is 1 or 2; and G is 4-imidazolyl, 4-morpholyl, 4-(2,6-dimethyl morpholyl), 2-tetrahydrofuryl, piperazin-1-yl, 1-methyl-piperazin-4-yl, piperazin-2-on-4-yl, or 2-pyrrolidonyl, or R' is $C_1$-$C_6$ alkyl, optionally substituted with one or two or hydroxyl groups.

In another more specific embodiment, this invention provides a compound of formula XA, in which $R_1$ is 2-, 3-, or 4-chloromethoxy; $R_2$ is H or 6-methyl; $R_5$ is H or 3-methyl; $R_4$ is H or 5-chloro; and R' is $C_1$-$C_6$ alkyl, optionally substituted with one or two or hydroxyl groups.

In another more specific embodiment, this invention provides a compound of formula XA, in which $R_1$ is 4-methoxy; $R_2$-$R_5$ are H; R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula XA, in which $R_1$ is 2-methyl; $R_2$ is 4-methylsulfonyl; $R_4$ and $R_5$ are H or methyl; and R' is —$(CH_2)_n$-G, where n is 1, and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another more specific embodiment, this invention provides a compound of formula XA, in which $R_1$ is 2-, 3-, or 4-methoxy; $R_2$ is H or 6-methyl; $R_5$ is H or 3-methyl; $R_4$ is H or 5-chloro; and R' is —$(CH_2)_n$-G, where n is 1, and G is cyclopentyl, cyclopenten-3-yl, cyclopentadien-4-yl; cyclohexyl, or cyclohexen-2-yl.

In another more specific embodiment, this invention provides a compound of formula XA, in which $R_1$ is 2-, 3-, or 4-bromo; $R_2$ is H or 6-methyl; $R_5$ is H or 3-methyl; $R_4$ is H or 5-chloro; and R' is —$(CH_2)_n$-G, where n is 1, and G is cyclopentyl, cyclopenten-3-yl, cyclopentadien-4-yl; cyclohexyl, or cyclohexen-2-yl.

In another more specific embodiment, this invention provides a compound of formula XA, in which $R_1$ is 2-chloro; $R_2$ is 3-, 4-, 5-, or 6-cyclopropyl, R and $R_5$ are H, halo, or methyl; and R' is $C_1$-$C_6$ alkyl, optionally substituted with one or two or hydroxyl groups.

In another more specific embodiment, this invention provides a compound of formula XA, in which $R_1$ is 3-cyclopropyl; $R_2$-$R_5$ are H; and R' is $C_1$-$C_6$ alkyl, optionally substituted with one or two or hydroxyl groups.

In another more specific embodiment, this invention provides a compound of formula XA, in which $R_1$ is 3-cyclopropyl; $R_2$ is 2-, 4-, 5-, or 6-chloro; $R_4$ and $R_5$ are H; and R' is $C_1$-$C_6$ alkyl, optionally substituted with one or two or hydroxyl groups.

In another more specific embodiment, this invention provides a compound of formula XA, in which $R_1$ is 2-chloro; $R_2$ is trans-4-(2-methylcyclopropyl); R4 and R5 are H; R' is —$(CH_2)_n$-G, where n is 1, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula XA, in which $R_1$ is 4-cyclopropyl; $R_2$ is 2- or 3-chloro; $R_4$ and $R_5$ are H, halo, or $C_1$-$C_3$ alkyl; and R' is $C_1$-$C_6$ alkyl, optionally substituted with one or two or hydroxyl groups.

In another more specific embodiment, this invention provides a compound of formula XA, in which $R_1$ is 4-isopropyl; $R_2$ is 2-chloro; $R_5$ is 2- or 3-chloro; $R_4$ is 5- or 6-methyl; and R' is —$(CH_2)_n$-G, where n is 1, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl or R' is $C_1$-$C_6$ alkyl, optionally substituted with one or two or hydroxyl groups.

In another more specific embodiment, this invention provides a compound of formula XA, in which $R_1$ and $R_2$ are both halogen; $R_5$ is 3-methyl; $R_4$ is H; and R' is $C_1$-$C_6$ alkyl, optionally substituted with one or two or hydroxyl groups.

In another more specific embodiment, this invention provides a compound of formula XA, in which $R_1$ and $R_2$ are both H; $R_5$ is 3-chloro; $R_4$ is 5-methyl; and R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl or R' is $C_1$-$C_6$ alkyl, optionally substituted with one or two or hydroxyl groups or R' is $C_1$-$C_6$ alkyl, optionally substituted with one or two or hydroxyl groups.

In another more specific embodiment, this invention provides a compound of formula XA, in which $R_1$ and $R_2$ are both H; $R_5$ is 2-(2-chloroethyl); 4 is 3-methyl; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In another more specific embodiment, this invention provides a compound of formula XA, in which $R_1$ is 2-hydroxymethyl; $R_2$ is 4-$CF_3$; $R_4$ and $R_5$ are H; R' is —$(CH_2)_n$-G, where n is 2, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula XA, in which $R_1$ and $R_2$ are both H; $R_5$ is 3-chloro; $R_4$ is 5-methyl; and R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In another more specific embodiment, this invention provides a compound of formula XA, in which one or both of $R_1$ and $R_2$ are $CF_3$; $R_4$ and $R_5$ are H; R' is —$(CH_2)_n$-G, where n is 1 or 2; and G is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another subgeneric embodiment, this invention provides a compound of formula XA, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$; $R_5$; and $R_4$ are H; R' is —$(CH_2)_n$-G, where n is 1 or 2; and G is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a more specific embodiment, this invention contemplates the compound of formula XA, in which $R_1$ is 4-chloro; $R_5$ is 3-chloro; $R_2$ and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ is 2-, 3-, or 4-fluoro; $R_2$, $R_4$ and $R_5$ are H; and R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is fluoro; $R_2$ is methyl; $R_4$ and $R_5$ are H; R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl, or R' is $C_1$-$C_6$ alkyl, optionally substituted with one or two or hydroxyl groups.

In a still more specific embodiment, this invention contemplates the compound of formula XA, in which $R_1$ is 6-chloro; $R_2$, $R_4$ and $R_5$ are H; R' is —$(CH_2)_n$-G, where n is 1 or 2; and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 2-bromo; $R_2$ is methyl; R5; and $R_4$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 3-bromo; $R_2$; $R_4$ and $R_5$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 4-bromo; $R_2$, $R_4$ and $R_5$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XA, in which $R_1$ is 2-(2-chloroethyl); $R_2$ is 6-chloro; $R_4$ and $R_5$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl or R' is $C_1$-$C_6$ alkyl, optionally substituted with one or two or hydroxyl groups.

In a still more specific embodiment, this invention contemplates the compound of formula XA, in which $R_1$ is 4-(3-chloropropyl); $R_2$ is 2-bromomethyl; $R_4$ and $R_5$ are H; R' is —$(CH_2)_n$-G, where n is 2, and G is pyridyl, piperazinyl, piperazinonyl, piperidinyl, piperidinonyl, morpholyl, furyl, tetrahydrofuryl, or pyrimidinyl.

In a still more specific embodiment, this invention contemplates a compound of formula XA, in which $R_1$ is 2-$CF_3$; $R_2$, $R_4$ and $R_5$ are H; R' is —$(CH_2)_n$-G, where n is 1 or 2, and G is isothiazol-4-yl, isoxazol-4-yl, oxazol-2-yl, 2-oxazolin-4-yl, oxazolidin-5-yl, or thiazol-2-yl, or R' is $C_1$-$C_6$ alkyl, optionally substituted with one or two or hydroxyl groups.

In a still more specific embodiment, this invention provides a compound of formula XA, in which $R_1$ is 4-cyano; $R_2$ is 2-methyl; $R_4$ and $R_5$ are H or methyl; R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XA, in which $R_1$ is 2-methyl; $R_2$ is 4- or 5-hydroxy; $R_4$ and $R_5$ are H or methyl; R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In a still more specific embodiment, this invention provides a compound of formula XA, in which $R_1$ is 2-hydroxymethyl; $R_2$-$R_5$ are H; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In another specific embodiment, this invention provides a compound of formula XA, in which $R_1$ is 2-methoxy; $R_2$ is H, halo, or methyl; $R_4$ and $R_5$ are H or methyl; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl, or R' is $C_1$-$C_6$ alkyl, optionally substituted with one or two or hydroxyl groups.

In a still more specific embodiment, this invention provides a compound of formula XA, in which $R_1$ is 4-methoxy; $R_2$-$R_5$ are H; R' is —$(CH_2)_n$-G, where n is 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula XA, in which $R_1$ is 2-, 3-, or 4-dimethylamino; $R_2$, $R_4$, and $R_5$ are H; R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl, or R' is $C_1$-$C_6$ alkyl, optionally substituted with one or two or hydroxyl groups.

In a still more specific embodiment, this invention contemplates a compound of formula XA, in which $R_1$ is 2-, 3-, or 4-dimethylaminocarbonyl; $R_2$ is H or 6-methyl, $R_4$ and $R_5$ are H, halo, or methyl; and R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl, or R' is $C_1$-$C_6$ alkyl, optionally substituted with one or two or hydroxyl groups.

In a still more specific embodiment, this invention contemplates a compound of formula XA, in which $R_1$ is 2-, 3-, or 4-methyloxycarbonyl; $R_2$ is H, 6-methyl, or 6-halo; $R_4$ and $R_5$ are H, halo, or methyl; and R' is —$(CH_2)_n$-G, where n is 1 or 2; and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl, or R' is $C_1$-$C_6$ alkyl, optionally substituted with one or two or hydroxyl groups.

In a still more specific embodiment, this invention contemplates a compound of formula XA, in which $R_1$ is 2-, 3-, or 4-acetyl; $R_2$, $R_4$, and $R_5$ are H; and R' is $C_1$-$C_6$ alkyl, optionally substituted with one or two or hydroxyl groups.

In a still more specific embodiment, this invention contemplates a compound of formula XA, in which $R_1$ is 2-, 3-, or 4-acetoxy; $R_2$, $R_4$, and $R_5$ are H; and R' is —$(CH_2)_n$-G, where n is 2, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XA, in which $R_1$ is 4-dimethylamino; $R_2$ is 2-methyl; $R_4$ and $R_5$ are H or methyl; and R' is —$(CH_2)_n$-G, where n is 1 or 2, and G is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention contemplates a compound of formula XA, in which $R_1$ is 4-dimethylaminocarbonyl; $R_2$ is 2-methyl; $R_4$ and $R_5$ are H or methyl; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula XA, in which $R_1$ is 4-methyloxycarbonyl; $R_2$ is H or methyl; $R_4$ and $R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula XA, in which $R_1$ is 2-, 3-, or 4-acetyl; $R_2$, $R_4$, and $R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula XA, in which $R_1$ is 2-, 3-, or 4-acetoxy; $R_2$; $R_5$; and $R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention contemplates a compound of formula XA, in which $R_1$ is 2-, 3-, or 4-$CH_2F$; $R_2$; $R_4$; and $R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 2-, 3-, or 4-cyano; $R_2$-$R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 2-, 3-, or 4-ethoxy; $R_2$-$R_4$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 2-, 3-, or 4-trifluoromethoxy; $R_2$-$R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 2-, 3-, or 4-chloromethoxy; $R_2$-$R_5$ are H; and R' is —$(CH_2)_n$-(G, where n is 1 or 2, and G is isothiazolyl, isoxazolyl, oxazolyl, oxazolinyl, oxazolidinyl, thiazolyl, thienyl, furyl, pyrrolyl, pyrrolinyl, pyrrolidinyl, pyrrolidinonyl, morpholyl, or imidazolyl.

In another more specific embodiment, this invention provides a compound of formula XA, in which $R_1$ is 2-, 3-, or 4-methoxy; $R_2$-$R_5$ are H; and R' is —$(CH_2)_n$-G, where n is 1 or 2, and G is 5-oxazolidinyl, 4-thiazolyl, 3-thienyl, 2-furyl, 3-pyrrolyl, 2-pyrrolidinyl, N-pyrrolidinonyl, N-morpholyl, or 4-imidazolyl.

In another more specific embodiment, this invention provides a compound of formula XA, in which $R_1$ is 3- or 4-methylsulfonyl $R_2$ is 2-(2-methyl cyclopropyl); $R_4$ and $R_5$ are H; and R' is —$(CH_2)_n$-G, where n is 1 or 2, and G is 3-methyl-2-isothiazolyl, 3-methyl-2-isoxazolyl, 3-methyl-4-oxazolyl, 3-methyl-2-pyrrolyl, 3-methyl-2-pyridyl, N-pyrrolidonyl, or m-tolyl.

In another more specific embodiment, this invention provides a compound of formula XA, in which $R_1$ is 2-, 3-, or 4-methoxy; $R_2$-$R_5$ are H; and R' is —$(CH_2)_n$-G, where n is 1 or 2, and G is cyclopentyl, cyclopenten-3-yl, cyclopentadien-4-yl; cyclohexyl, or cyclohexen-2-yl.

In another more specific embodiment, this invention provides a compound of formula XA, in which $R_1$ is 4-bromo or 4-bromomethyl; $R_2$-$R_5$ are H; and R' is —$(CH_2)_n$-G, where n is 1 or 2, and G is cyclopentyl, cyclopenten-3-yl, cyclopentadien-4-yl; cyclohexyl, or cyclohexen-2-yl.

In another more specific embodiment, this invention provides a compound of formula XA, in which $R_1$ is 2- or 3-chloro; $R_2$ is 4-(2-cyclopropylethyl); $R_4$ and $R_5$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula XA, in which $R_1$ is cyclopropyl or cyclopropylmethyl; $R_2$-$R_5$ are H; and R' is —$(CH_2)_n$-G, where n is 1 or 2, and G is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula XA, in which $R_1$ is trans-3-(2-methylcyclopropyl); $R_2$ is 6-chloro; $R_4$ and $R_5$ are H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 3- or 4-cyclopropyl; $R_2$ is 5-chloro; $R_5$ is 2-(2-fluoroethyl); and $R_4$ is H; and R' is —$(CH_2)_n$-G, where n is 1 or 2, and G is N-pyrrolidinonyl, 4-morpholyl, 2,6-dimethyl-4-morpholyl, or 4-imidazolyl.

In another more specific embodiment, this invention provides a compound of formula XA, in which $R_1$ is 2- or 3-cyclopropyl; $R_2$ is 6-chloro; $R_5$ is 3-chloro; $R_4$ is 5-methyl; and R' is —$(CH_2)_n$-G, where n is 1 or 2, and G is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In another embodiment, this invention provides a compound of formula XA, in which $R_1$ and $R_2$ are halogen or methyl; $R_4$ and $R_5$ are H; and R' is methyl, ethyl, isopropyl, or sec-butyl.

In another more specific embodiment, this invention provides a compound of formula XA, in which $R_1$ is halogen or methyl; $R_2$-$R_5$ are H; and R' is methyl, ethyl, isopropyl, or sec-butyl.

In another more specific embodiment, this invention provides a compound of formula XA, in which $R_1$ and $R_2$ are halogen or methyl; $R_4$ and $R_5$ are H; and R' is 1,2-chloropropan-3-yl.

In another more specific embodiment, this invention provides a compound of formula XA, in which $R_1$ and $R_2$ are halogen or methyl; $R_4$ and $R_5$ are H; and R' is 1-hydroxybutan-3-yl.

In another more specific embodiment, this invention provides a compound of formula XA, in which $R_1$ is bromo; $R_2$-$R_5$ are H; and R' is isopropyl.

In another more specific embodiment, this invention provides a compound of formula XA, in which $R_1$ and $R_2$ are halogen or methyl; $R_4$ and $R_5$ are H; and R' is 1,2-dihydroxypropan-3-yl.

In another more specific embodiment, this invention provides a compound of formula XA, in which $R_1$ and $R_2$ are halogen or methyl; $R_4$ and $R_5$ are H; and R' is 2-hydroxyethyl.

In another more specific embodiment, this invention provides a compound of formula XA, in which $R_1$ and $R_2$ are halogen or methyl; $R_4$ and $R_5$ are H; and R' is 4-hydroxybutyl.

In another more specific embodiment, this invention provides a compound of formula XA, in which $R_1$ and $R_2$ are halogen or methyl; $R_4$ and $R_5$ are H; and R' is 1,2-dihydroxybutan-4-yl.

In another more specific embodiment, this invention provides a compound of formula XA, in which $R_1$ and $R_2$ are halogen or methyl; $R_4$ and $R_5$ are $C_1$-$C_6$ alkyl; and R' is 1,2-dihydroxybutan-3-yl.

In another more specific embodiment, this invention provides a compound of formula XA, in which $R_1$ and $R_2$ are halogen or methyl; $R_4$ and $R_5$ are H; and R' is 4-methoxybutyl.

In another more specific embodiment, this invention provides a compound of formula XA, in which $R_1$ and $R_2$ are halogen or methyl; $R_4$ and $R_5$ are H; and R' is 3-hydroxypropyl.

In another more specific embodiment, this invention provides a compound of formula XA, where $R_1$ and $R_2$ are fused cyclohexyl or fused cyclopentyl; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 3 and 4, are fused (4,5)-imidazolo; $R_4$ and $R_5$ are H; and R' is isopropyl, 2-(2-furyl)ethyl, 2-hydroxyethyl, 2,3-dihydroxy-1-propyl, or 3,4-dihydroxy-2-Butyl.

In another more specific embodiment, this invention contemplates a compound of formula XA, where $R_1$ and $R_2$, at positions 3 and 4, are fused (2,3)-furyl; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 3 and 4, are fused (2,3)-pyrido; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 3 and 4, are fused (3,4)pyrrolyl; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 2 and 3, are fused cyclopentyl; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 3 and 4, are fused cyclopentyl; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 2 and 3, are benzo; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 2 and 3, are benzo, substituted at one or both ortho positions; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XA, where $R_1$ and $R_2$, at positions 3 and 4, are benzo; $R_4$ and $R_5$ are H; and R' is isopropyl, 2-(2-furyl)ethyl, 2-hydroxyethyl, 2,3-dihydroxy-1-propyl, or 3,4-dihydroxy-2-butyl.

The prophetic examples below show specific embodiments of this invention.

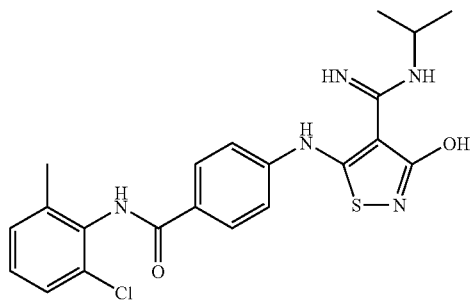

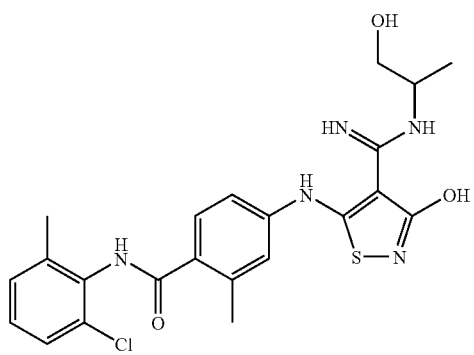

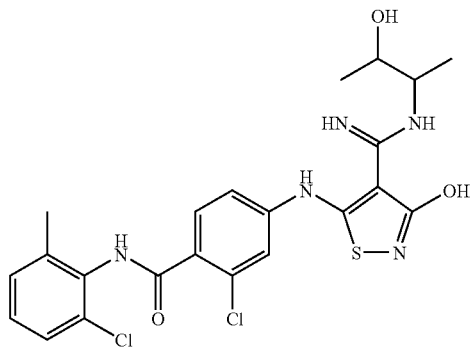

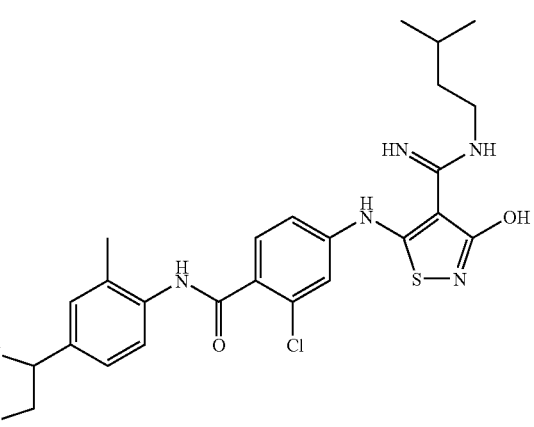

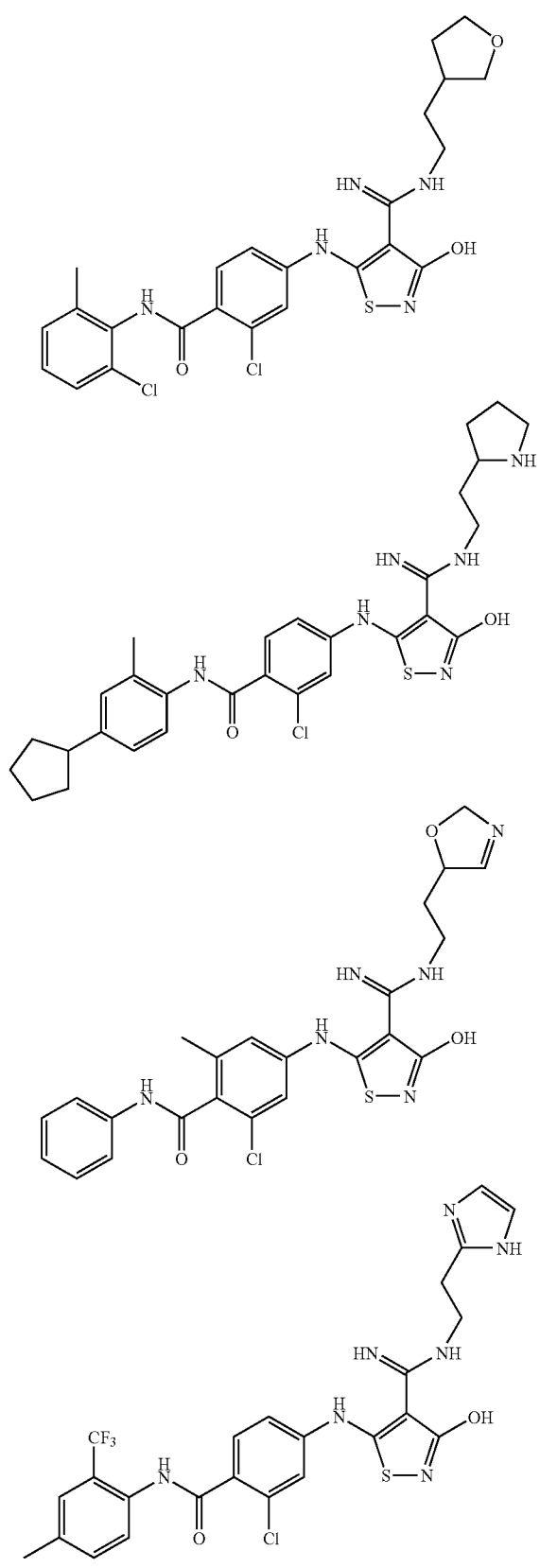
In additional subgeneric embodiments, this invention provides aza-substituted compounds of the types shown below, where substituents $R_1$-R' are as defined above.
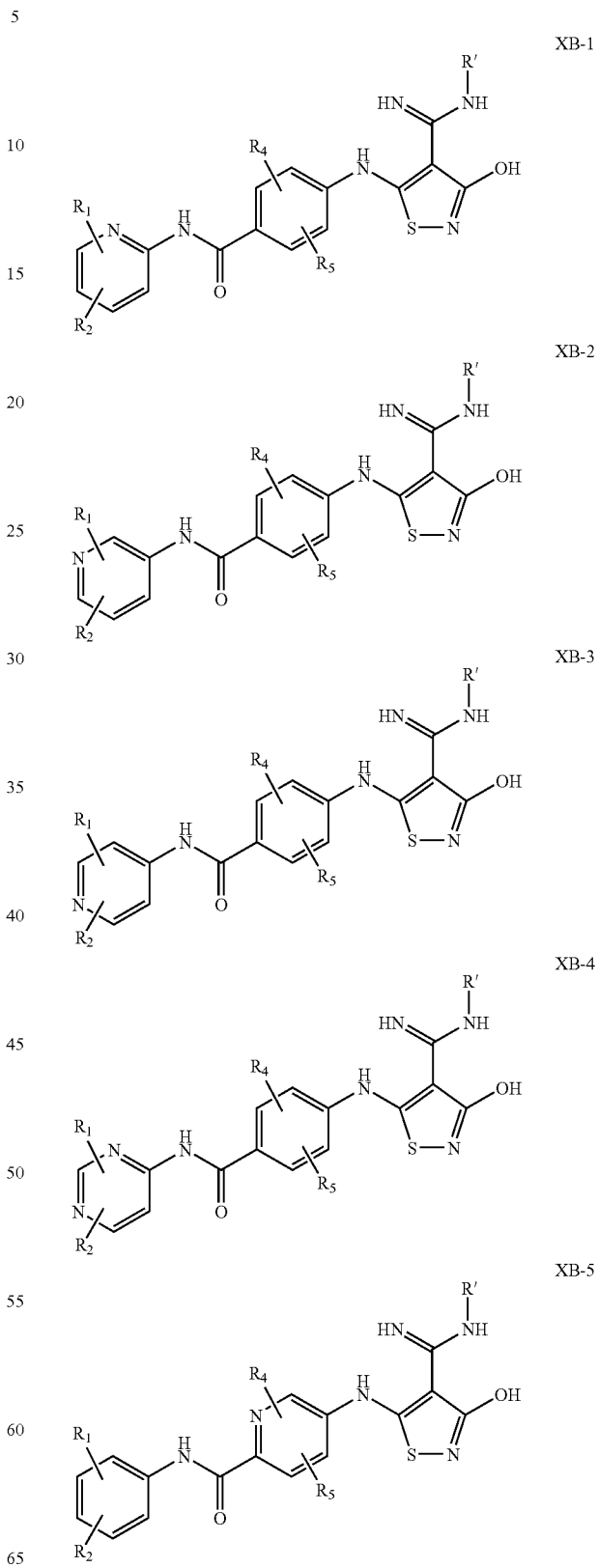

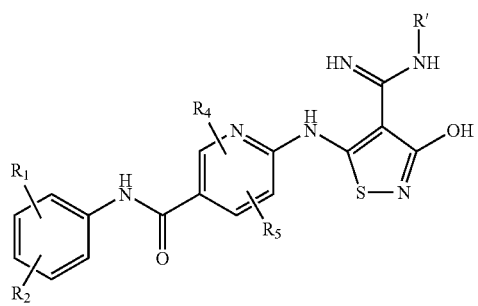
XB-6

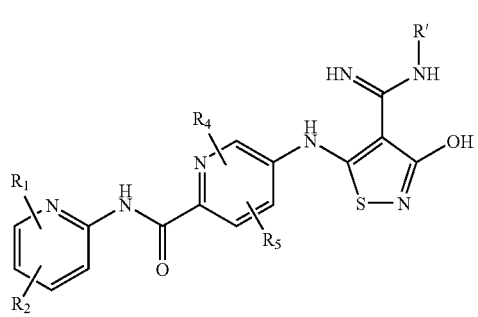
XB-7

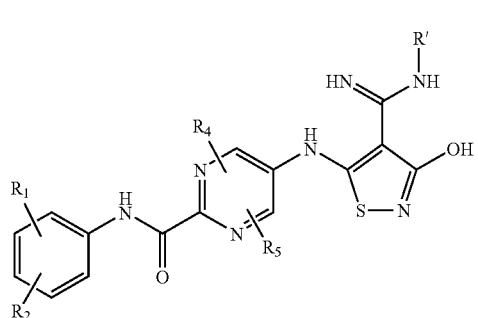
XB-8

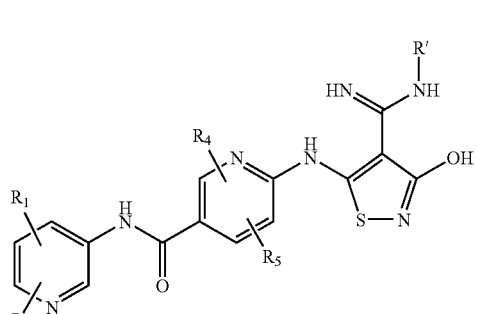
XB-9

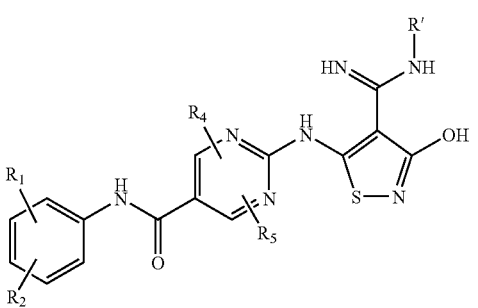
XB-10

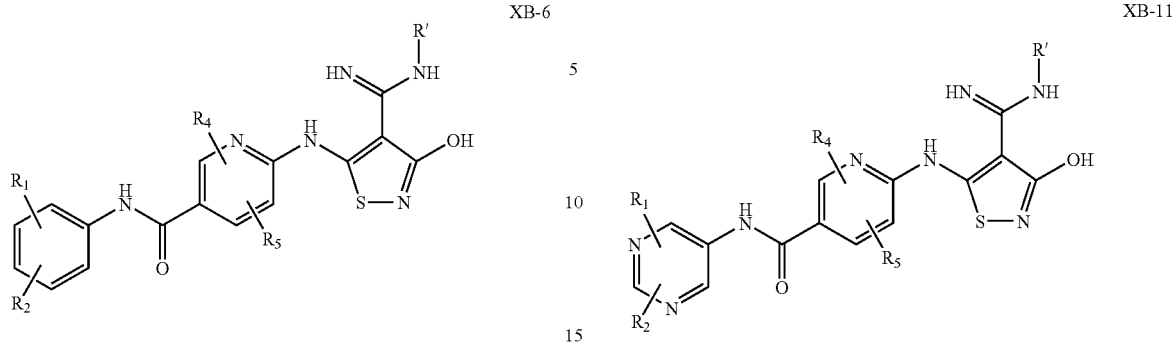
XB-11

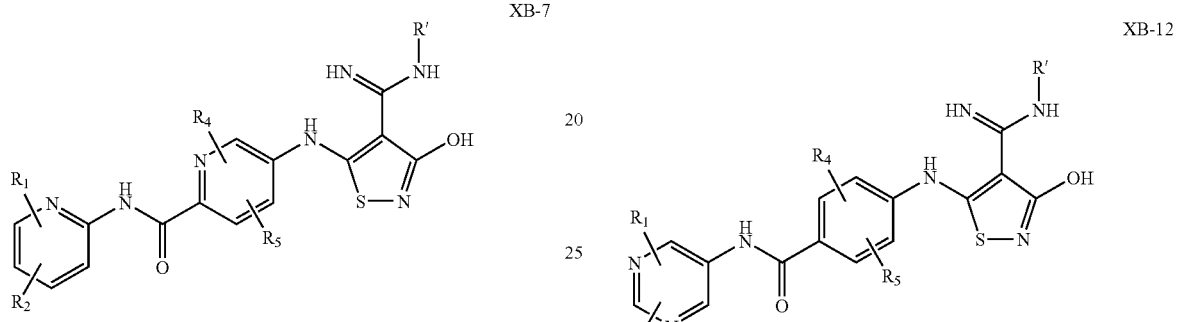
XB-12

In one more specific embodiment, this invention provides a compound of formula XB1, where $R_1$-$R_5$ are, independently, H, methyl, halo, nitro, cyano, 1-propynyl, amino, dimethylamino, or acetamido, and R' is —$(CH_2)_n$-G, as described above, or $C_1$-$C_6$ alkyl, optionally substituted with one or two or hydroxyl groups.

In another more specific embodiment, this invention provides a compound of formula XB2, where $R_1$-$R_5$ are, independently, H, methyl, halo, nitro, cyano, 1-propynyl, amino, dimethylamino, or acetamido, and R' is —$(CH_2)_n$-G, as described above, or $C_1$-$C_6$ alkyl, optionally substituted with one or two or hydroxyl groups.

In another more specific embodiment, this invention provides a compound of formula XB3, where $R_1$-$R_5$ are, independently, H, methyl, halo, nitro, cyano, 1-propynyl, amino, dimethylamino, or acetamido, and R' is —$(CH_2)_n$-G, as described above, or $C_1$-$C_6$ alkyl, optionally substituted with one or two or hydroxyl groups.

In another more specific embodiment, this invention provides a compound of formula XB4, where $R_1$-$R_5$ are, independently, H, methyl, halo, nitro, cyano, 1-propynyl, amino, dimethylamino, or acetamido, and R' is —$(CH_2)_n$-G, as described above, or $C_1$-$C_6$ alkyl, optionally substituted with one or two or hydroxyl groups.

In another more specific embodiment, this invention provides a compound of formula XB5, where $R_1$-$R_5$ are, independently, H, methyl, halo, nitro, cyano, 1-propynyl, amino, dimethylamino, or acetamido, and R' is —$(CH_2)_n$-G, as described above, or $C_1$-$C_6$ alkyl, optionally substituted with one or two or hydroxyl groups.

In another more specific embodiment, this invention provides a compound of formula XB6, where $R_1$-$R_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB7, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB8, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB9, where R$_1$-R$_4$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB10, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In one more specific embodiment, this invention provides a compound of formula XB11, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In one more specific embodiment, this invention provides a compound of formula XB12, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB1, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB2, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB3, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB4, where R$_1$-R$_4$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB5, where R$_1$-R$_5$ are, independently, H, methyl, halo, nitro, cyano, 1-propynyl, amino, dimethylamino, or acetamido, and R' is —(CH$_2$)$_n$-G, as described above, or C$_1$-C$_6$ alkyl, optionally substituted with one or two or hydroxyl groups.

In another more specific embodiment, this invention provides a compound of formula XB6, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB7, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB8, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB9, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB10, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB11, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In another more specific embodiment, this invention provides a compound of formula XB12, where R$_1$-R$_5$ are, independently, H, methyl, halo, acetyl, acetoxy, methyloxycarbonyl, or methylsulfonyl, and R' is —(CH$_2$)$_n$-G, as described above, or C$_1$-C$_6$ alkyl, optionally substituted with one or two or hydroxyl groups.

In one more specific embodiment, this invention provides a compound of formula XB1, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB2, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB3, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB4, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB5, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB6, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB7, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB8, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB9, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In another more specific embodiment, this invention provides a compound of formula XB10, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In one more specific embodiment, this invention provides a compound of formula XB11, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In one more specific embodiment, this invention provides a compound of formula XB12, where R$_1$-R$_5$ are, independently, H, halo, or C$_1$-C$_5$ alkyl, cycloalkyl, or alkenyl, optionally substituted with halogen, alkoxy, hydroxy, or phenyl, and R' is —(CH$_2$)$_n$-G, as described above, or C$_1$-C$_6$ alkyl, optionally substituted with one or two or hydroxyl groups.

In a still more specific embodiment, this invention provides a compound of formula XB1, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB2, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB3, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB4, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB5, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB6, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB7, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB8, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB9, where R$_1$-R$_5$ are, independently, H, halo, methyl, or halomethyl, and R' is C$_1$-C$_6$ alkyl, optionally substituted with one or two or hydroxyl groups.

In another more specific embodiment, this invention provides a compound of formula XB10, where R$_1$-R$_5$ are, independently, H, halo, methyl, or halomethyl, and R' is C$_1$-C$_6$ alkyl, optionally substituted with one or two or hydroxyl groups.

In a still more specific embodiment, this invention provides a compound of formula XB111, where R$_1$-R$_5$ are, independently, H, halo, methyl, or halomethyl, and R' is C$_1$-C$_6$ alkyl, optionally substituted with one or two or hydroxyl groups.

In a still more specific embodiment, this invention provides a compound of formula XB12, where R$_1$-R$_5$ are, independently, H, halo, methyl, or halomethyl, and R' is C$_1$-C$_6$ alkyl, optionally substituted with one or two or hydroxyl groups.

Additional subgeneric embodiments are shown below.

In an even more specific and preferred embodiment, this invention provides a compound of formula XB1, where R$_1$-R$_4$ are, independently, H, chloro, or methyl, R$_5$ is H, and R' is C$_1$-C$_4$ alkyl, optionally substituted with one or two or hydroxyl groups.

In an additional more specific and preferred embodiment, this invention provides a compound of formula XB2, where R$_1$-R$_5$ are, independently, H, chloro, or methyl, R$_4$ is H, and R' is C$_1$-C$_4$ alkyl, optionally substituted with one or two or hydroxyl groups.

In an additional more specific and preferred embodiment, this invention provides a compound of formula XB3, where R$_1$-R$_5$ are, independently, H, chloro, or methyl, R$_4$ is H, and R' is C$_1$-C$_4$ alkyl, optionally substituted with one or two or hydroxyl groups.

In an additional more specific and preferred embodiment, this invention provides a compound of formula XB4, where R$_1$-R$_5$ are, independently, H, chloro, or methyl, R$_4$ is H, and R' is C$_1$-C$_4$ alkyl, optionally substituted with one or two or hydroxyl groups.

In an additional more specific and preferred embodiment, this invention provides a compound of formula XB5, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB6, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB7, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB8, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB9, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB10, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB11, where $R_1$-$R_5$ are, independently, H, chloro, or methyl, $R_4$ is H, and R' is $C_1$-$C_4$ alkyl, optionally substituted with one or two or hydroxyl groups.

In an additional more specific and preferred embodiment, this invention provides a compound of formula XB12, where $R_1$-$R_5$ are, independently, H, chloro, or methyl, $R_4$ is H, and R' is $C_1$-$C_4$ alkyl, optionally substituted with one or two or hydroxyl groups.

The prophetic examples below provide specific examples of subgeneric structures XB-1-XB-12.

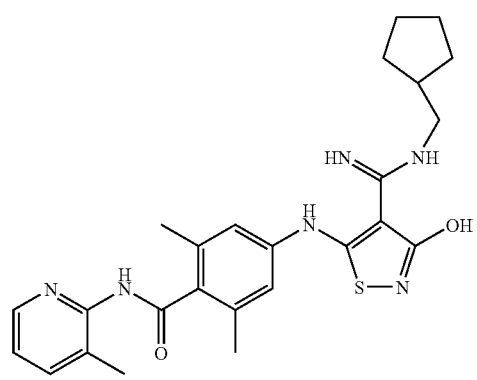

XB-1a

-continued

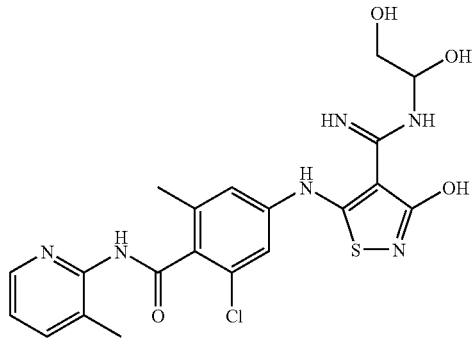

XB-1b

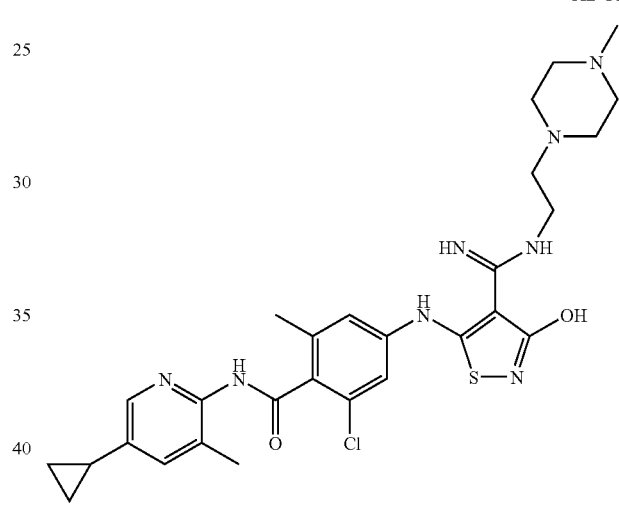

XB-1c

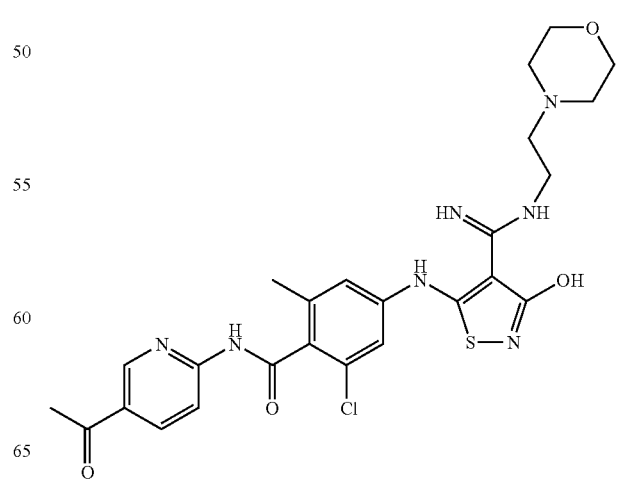

XB-1d

-continued
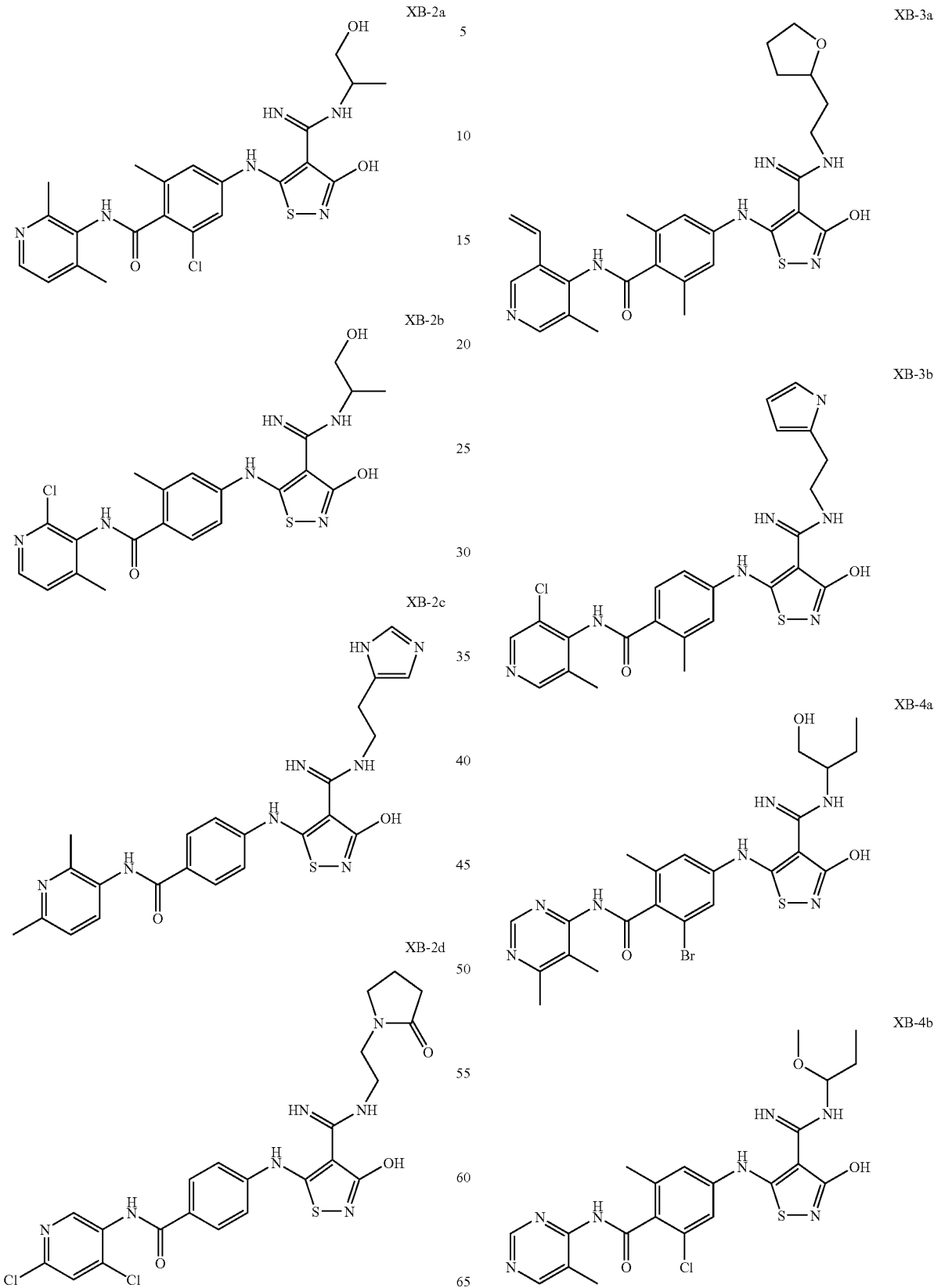

-continued
XB-5a
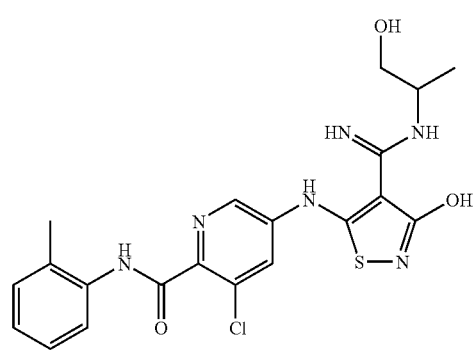
XB-5b
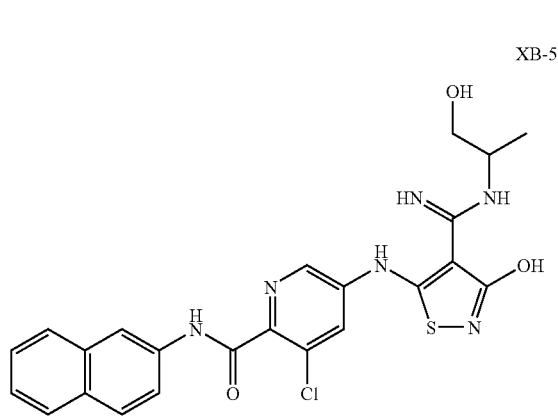
XB-6a
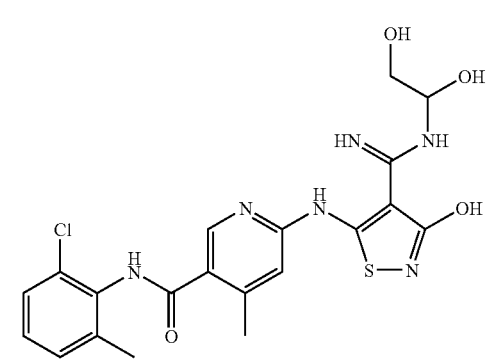
XB-6b
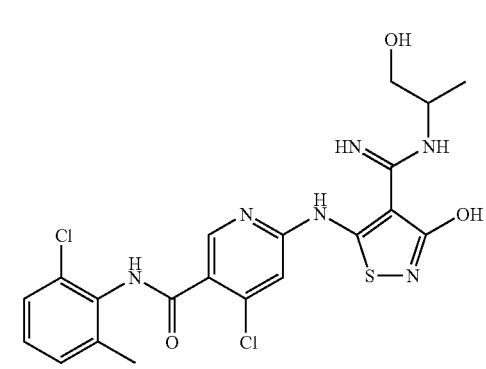
-continued
XB-7a
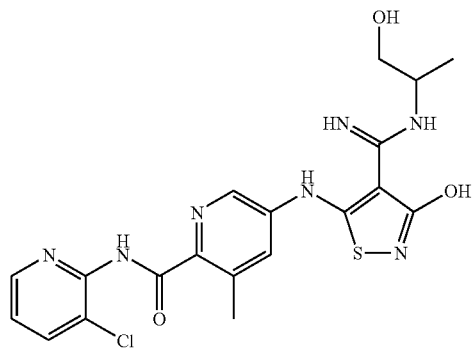
XB-7b
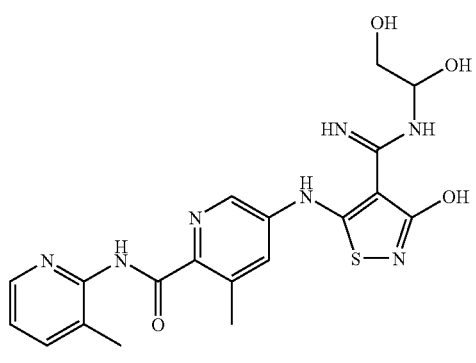
XB-8a
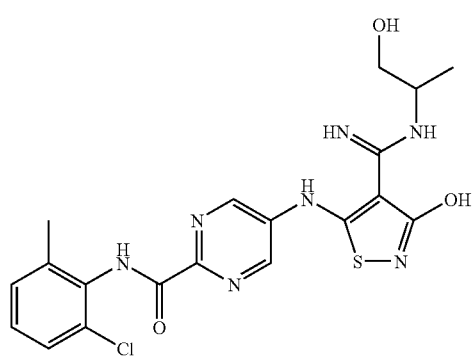
XB-8b
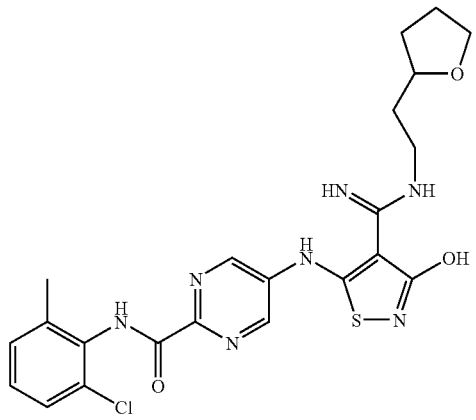

-continued
XB-9a
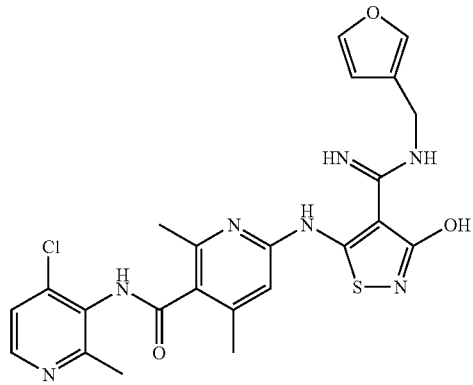
XB-9b
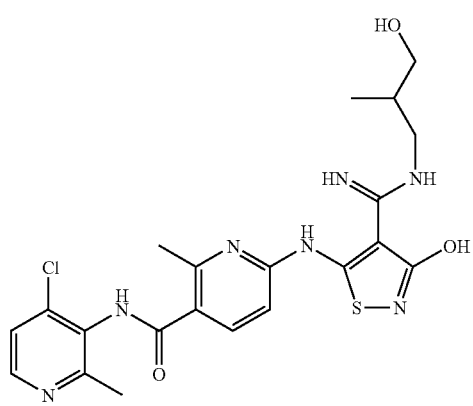
XB-10a
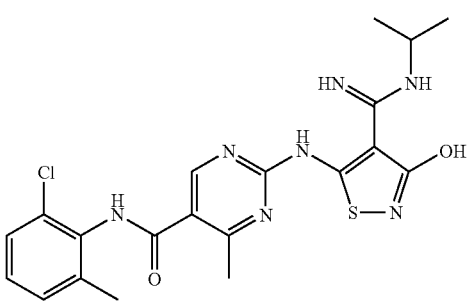
XB-10b
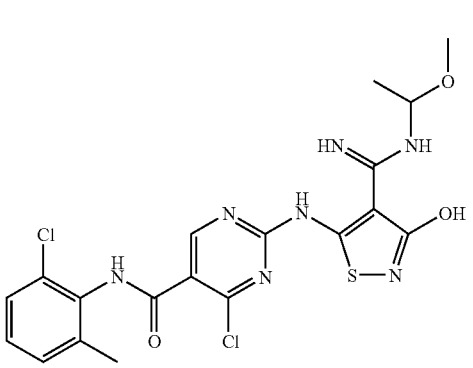
-continued
XB-11a
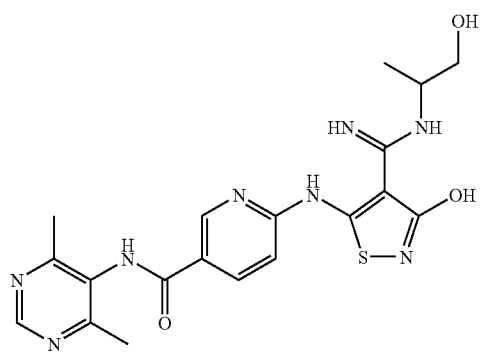
XB-11b
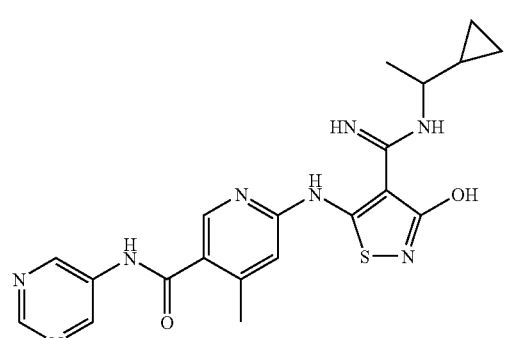
XB-12a
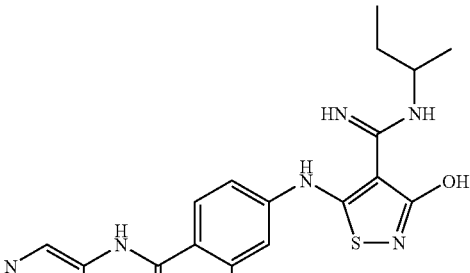
XB-12b
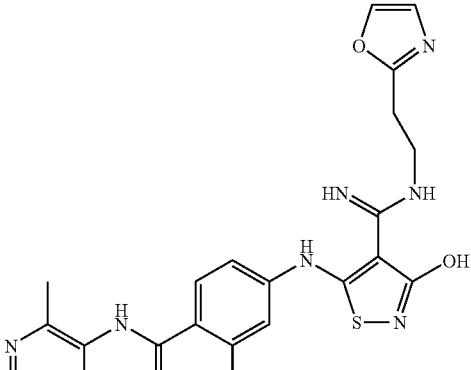

In another generic embodiment, this invention provides a compound of formula XI below,

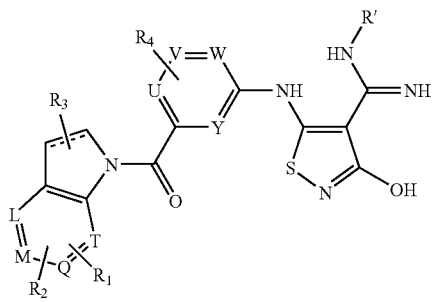

XI where the dashed bond represents an optional double bond, where symbols L, T, U, V, and W-Z represent N, CH, or $CR_{1, 2, or 4}$, provided that no two nitrogen atoms are adjacent, where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$; $CH_3CH_2OC(O)$; $C_1$-$C_5$ alkyl-C(O)—; $C_1$-$C_5$ alkyl-C(O)O—; —$NR_6R_7$, —$CH_2NR_6R_7$, —NH—C(O)—$R_6$, —C(O)$NR_8R_9$; $CH_3S(O)_2$—, or —$S(O)_2NR_8R_9$, where $R_6$-$R_9$ are, independently, H or $C_1$-$C_4$ alkyl; or any of the pairs $R_1$ and $R_2$, $R_6$ and $R_7$, or $R_8$ and $R_9$, together with the ring atoms to which they are attached, form an additional, five- or six-membered ring, optionally containing one or two heteroatoms selected from O, N, and S, which ring may be aromatic or aliphatic, and which ring is fused in the case of $R_1$ and $R_2$; and where $R_1$ may also be isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, tolyl, or phenyl, wherein all alkyl, alkenyl, and cycloalkyl groups and all rings are optionally substituted with 1-3 halogen atoms, $C_1$-$C_3$ alkyl groups, or trifluoromethyl groups; R' is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or R' is —$(CH_2)_n$-G where n is 1 or 2 and G is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

In one subgeneric embodiment, this invention provides a compound of formula XIA-1,

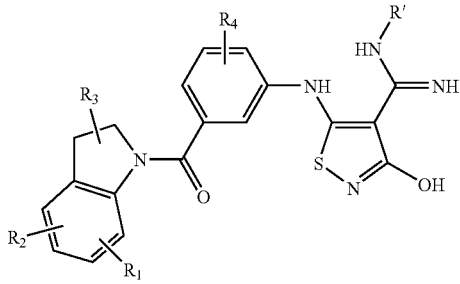

XIA-1 where $R_1$-R' are as defined above for formula I.

In a more specific embodiment, this invention provides a compound of formula XIA-1, where $R_1$-$R_4$ are as described above for formula I, and where R' is $C_1$-$C_6$ alkyl, optionally substituted with one or two or hydroxyl groups, or R' is —$(CH_2)_n$-G, where n is 1 or 2; and G is isothiazolyl, isoxazolyl, isoxazolidinyl, isoxazolidinonyl, oxazolyl, oxazolinyl, oxazolidinyl, oxazolidinonyl, thiazolyl, thienyl, furyl, pyrrolyl, pyrrolinyl, pyrrolidinyl, pyrrolidinonyl, thiazolinyl, thiazolidinyl, thiazolidinonyl, isothiazolinyl, isothiazolidinyl, isothiazolidinonyl, imidazolinyl, imidazolyl, pyridyl, or phenyl.

In another more specific embodiment, this invention provides a compound of formula XIA-1, where $R_3$ and $R_4$ are both H and R' is $C_1$-$C_6$ alkyl or O—$C_1$-$C_6$ alkyl, both optionally substituted as described above.

In another more specific embodiment, this invention provides a compound of formula XIA-1, where $R_2$-$R_5$ are H and R' is $C_1$-$C_6$ alkyl, optionally substituted with halogen, $C_1$-$C_3$ alkoxy, or hydroxy.

In another more specific embodiment, this invention provides a compound of formula XIA-1, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIA-1, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIA-1, in which $R_1$ and $R_2$ are both halogen, $R_3$ is 2-methyl, and $R_4$ is H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a more specific embodiment, this invention contemplates a compound of formula XIA-1, where $R_1$-$R_4$ are H and R' is 2-(2-furyl)ethyl, 2-hydroxyethyl, or 2,3-dihydroxy-1-propyl.

In another more specific embodiment, this invention contemplates a compound of formula XIA-1, in which $R_1$ and $R_2$ together, at positions 3 and 4, are fused cyclopentyl, $R_3$ and $R_4$ are H, and R' is isopropyl.

In another more specific embodiment, this invention contemplates a compound of formula XIA-1, in which $R_1$ and $R_2$ together, at positions 3 and 4, are benzo, $R_3$ and $R_4$ are H, and R' is isopropyl.

In another more specific embodiment, this invention contemplates a compound of formula XIA-1, in which $R_1$ and $R_2$ together, at positions 3 and 4, are 2,3-pyrido, $R_3$ and $R_4$ are H, and R' is isopropyl.

In another more specific embodiment, this invention contemplates a compound of formula XIA-1, in which $R_1$ and $R_2$ together, at positions 3 and 4, are 2,3-pyrrolo, $R_3$ and $R_4$ are H, and R' is isopropyl.

In another more specific embodiment, this invention contemplates a compound of formula XIA-1, in which $R_1$ and $R_2$ together, at positions 4 and 5, are fused (2,3)-furyl, $R_3$ and $R_4$ are H, and R' is 1,2-dihydroxy-propan-3-yl.

In another more specific embodiment, this invention contemplates a compound of formula XIA-1, in which $R_1$ and $R_2$ together, at positions 3 and 4, are fused (2,3)thienyl, $R_3$ and $R_4$ are H, and R' is 2-hydroxyethyl.

In a still more specific embodiment, this invention provides a compound of formula XIA-1, in which $R_1$ and $R_2$ are both H, $R_3$ is 3-methyl, $R_4$ is 2-chloro, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ and $R_2$ are both H, $R_3$ is 3-methyl, $R_4$ is 2-(2-chloroethyl), R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ is 4-$CF_3$, $R_3$ is 2-hydroxymethyl, $R_2$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ and $R_2$ are both H, $R_3$ is 3-methyl, $R_4$ is 2-chloro, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which one or both of $R_1$ and $R_2$ are $CF_3$, $R_3$ and $R_4$ are H, R' is —$(CH_2)_n$—B, where n is 1, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIA-1, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a still more specific embodiment, this invention contemplates the compound of formula XIA-1, in which $R_1$ is 2-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 4-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 5-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 4-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 5-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 2-chloro, $R_2$ is 4-chloro, $R_3$ and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-chloro, $R_2$ is 4-chloro, $R_3$ and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which one or both of $R_1$ and $R_2$ are $CF_3$, $R_3$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention contemplates a compound of formula XIA-1, in which $R_1$ is 3-$CF_3$, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention provides a compound of formula XIA-1, in which $R_1$ is 3-cyano, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 3-hydroxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 4-hydroxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 3-methoxy, $R_2$-$R_4$ are H, R' is —(CH$_2$)$_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 4-methoxy, $R_2$-$R_4$ are H, R' is —(CH$_2$)$_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula XIA-1, in which $R_1$ is 3-dimethylamino, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-dimethylaminocarbonyl, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-methyloxycarbonyl, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-acetyl, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-acetoxy, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-dimethylamino, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-dimethylaminocarbonyl, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-methyloxycarbonyl, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-acetyl, $R_2$, $R_3$, and R are H. R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-acetoxy, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-CH$_2$F, $R_2$, $R_3$, and $R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyano, $R_2$-$R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-ethoxy, $R_2$-$R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 4-ethoxy, $R_2$-$R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-chloromethoxy, $R_2$-$R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 4-methoxy, $R_2$-$R_4$ are H, R' is —(CH$_2$)$_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 2-methyl, $R_2$ is 4-methylsulfonyl, $R_3$ and $R_4$ are H, R' is —$(CH_2)_n$—B, where n is 1, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIA-1, in which $R_1$ is 4-methoxy, $R_2$-$R_4$ are H, R' is —$(CH_2)_n$—B, where n is 1, and B is cyclopentyl, cyclopenten-3-yl, cyclopentadien-4-yl; cyclohexyl, or cyclohexen-2-yl.

In a still more specific embodiment, this invention provides a compound of formula XIA-1, in which $R_1$ is 4-bromo, $R_2$-$R_4$ are H, R' is —$(CH_2)_n$—B, where n is 1, and B is cyclopentyl, cyclopenten-3-yl, cyclopentadien-4-yl; cyclohexyl, or cyclohexen-2-yl.

In a still more specific embodiment, this invention provides a compound of formula XIA-1, in which $R_1$ is 3-cyclopropyl, $R_2$ is 4-chloro, $R_3$ and $R_4$ are H, R' is —$(CH_2)_n$and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIA-1, in which $R_1$ is 3-cyclopropyl, $R_2$-$R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ is 3-cyclopropyl, $R_2$ is 4-chloro, $R_3$ and $R_4$ are H, R' is —$(CH_2)_n$and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is trans-3-(2-methylcyclopropyl), $R_2$ is 4-chloro, $R_3$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyclopropyl, $R_2$ is 4-chloro, $R_3$ is 2-(2-fluoroethyl), and $R_4$ is H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyclopropyl, $R_2$ is 4-chloro, $R_3$ is 2-chloro, $R_4$ is 2-fluoro, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ and $R_2$ are both halogen, $R_3$ is 2-methyl, and $R_4$ is H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ and $R_2$ are both H, $R_3$ is 3-methyl, $R_4$ is 2-chloro, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ and $R_2$ are both H, $R_3$ is 3-methyl, $R_4$ is 2-(2-chloroethyl), R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ is 4-$CF_3$, $R_3$ is 2-hydroxymethyl, $R_2$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ and $R_2$ are both H. $R_3$ is 3-methyl, $R_4$ is 2-chloro, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which one or both of $R_1$ and $R_2$ are $CF_3$, $R_3$ and $R_4$ are H, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIA-1, in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, pyrimidinyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, or naphthyl.

In a still more specific embodiment, this invention contemplates the compound of formula XIA-1, in which $R_1$ is 2-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 4-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 5-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 4-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 5-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 2-chloro, $R_2$ is 4-chloro, $R_3$ and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention contemplates the compound of formula XIA-1, in which $R_1$ is 3-chloro, $R_2$ is 4-chloro, $R_3$ and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which one or both of $R_1$ and $R_2$ are $CF_3$, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention contemplates a compound of formula XIA-1, in which $R_1$ is 3-$CF_3$, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolidinyl, isothiazolidinyl, imidazolinyl, imidazolyl, pyridyl, phenyl.

In a still more specific embodiment, this invention provides a compound of formula XIA-1, in which $R_1$ is 3-cyano, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 3-hydroxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 4-hydroxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 3-methoxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention provides a compound of formula XIA-1, in which $R_1$ is 4-methoxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In a still more specific embodiment, this invention contemplates a compound of formula XIA-1, in which $R_1$ is 3-dimethylamino, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-dimethylaminocarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-methyloxycarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-acetyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-acetoxy, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-dimethylamino, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-dimethylaminocarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-methyloxycarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-acetyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 4-acetoxy, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIA-1, in which $R_1$ is 3-$CH_2F$, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyano, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-ethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 4-ethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-chloromethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 4-methoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 2-methyl, $R_2$ is 4-methylsulfonyl, $R_3$ and $R_4$ are H, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIA-1, in which $R_1$ is 4-methoxy, $R_2$-$R_4$ are H, R' is —$(CH_2)_n$—B, where n is 2, and B is cyclopentyl, cyclopenten-3-yl, cyclopentadien-4-yl; cyclohexyl, or cyclohexen-2-yl.

In a still more specific embodiment, this invention provides a compound of formula XIA-1, in which $R_1$ is 4-bromo, $R_2$-$R_4$ are H, R' is —$(CH_2)_n$—B, where n is 2, and B is cyclopentyl, cyclopenten-3-yl, cyclopentadien-4-yl; cyclohexyl, or cyclohexen-2-yl.

In a still more specific embodiment, this invention provides a compound of formula XIA-1, in which $R_1$ is 3-cyclopropyl, $R_2$ is 4-chloro, $R_3$ and $R_4$ are H, R' is —$(CH_2)_n$ and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ is 3-cyclopropyl, $R_2$-$R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In a still more specific embodiment, this invention provides a compound of formula XIA-1, in which $R_1$ is 3-cyclopropyl, $R_2$ is 4-chloro, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is trans-3-(2-methylcyclopropyl), $R_2$ is 4-chloro, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyclopropyl, $R_2$ is 4-chloro, $R_3$ is 2-(2-fluoroethyl), and $R_4$ is H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIA-1, in which $R_1$ is 3-cyclopropyl, $R_2$ is 4-chloro, $R_3$ is 2-chloro, $R_4$ is 2-fluoro, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidinyl.

In another more specific embodiment, this invention provides a compound of formula XIA-1, in which $R_1$ and $R_2$ are halogen, $R_3$ and $R_4$ are H, and R' is methyl.

In another more specific embodiment, this invention provides a compound of formula XIA-1, in which $R_1$ and $R_2$ are halogen, $R_3$ and $R_4$ are H, and R' is ethyl.

In another more specific embodiment, this invention provides a compound of formula XIA-1, in which $R_1$ and $R_2$ are halogen, $R_3$ and $R_4$ are H, and R' is 1,2-chloropropan-3-yl.

In another more specific embodiment, this invention provides a compound of formula XIA-1, in which $R_1$ and $R_2$ are halogen, $R_3$ and $R_4$ are H, and R' is 1-hydroxy-butan-3-yl.

In another more specific embodiment, this invention contemplates a compound of formula XIA-1, in which $R_1$ is 4-(methylcarbamoyl), $R_2$ is 5-fluoro, $R_3$ and $R_4$ are H, and R' is isopropyl.

In another more specific embodiment, this invention contemplates a compound of formula XIA-1, in which $R_1$ is 4-acetamido, $R_2$ is 5-fluoro, $R_3$ and $R_4$ are H, and R' is 1,2-dihydroxy-propan-3-yl.

In another more specific embodiment, this invention contemplates a compound of formula XIA-1, in which $R_1$ and $R_2$ are 4-fluoro and 5-fluoro, $R_3$ and $R_4$ are H, and R' is 2-hydroxyethyl.

In another more specific embodiment, this invention contemplates a compound of formula XIA-1, in which $R_1$ and $R_2$ are 4-chloro and 5-chloro, $R_3$ and $R_4$ are H, and R' is 4-hydroxybutyl.

In another more specific embodiment, this invention contemplates a compound of formula XIA-1, in which $R_1$ and $R_2$ are 4-fluoro and 5-fluoro, $R_3$ and $R_4$ are H, and R' is 4-hydroxybutyl.

In another more specific embodiment, this invention contemplates a compound of formula XIA-1, in which $R_1$ is 2-methoxymethyl, and $R_2$ is 3-chloro, $R_3$ and $R_4$ are H, and R' is 1,2-dihydroxybutan-4-yl.

In another more specific embodiment, this invention contemplates a compound of formula XIA-1, in which $R_1$ is 2-ethoxymethyl, and $R_2$ is 3-chloro, $R_3$ and $R_4$ are H, and R' is 1,2-dihydroxybutan-3-yl.

In another more specific embodiment, this invention contemplates a compound of formula XIA-1, in which $R_1$ is 3-methoxymethyl, $R_2$ is 4-chloro, $R_3$ and $R_4$ are H, and R' is 1,2-dihydroxybutan-4-yl.

In another more specific embodiment, this invention contemplates a compound of formula XIA-1, in which $R_1$ is 3-nitro, $R_2$ is 4-methoxy, $R_3$ and $R_4$ are H, and R' is 1,2-dihydroxybutan-3-yl.

In another more specific embodiment, this invention contemplates a compound of formula XIA-1, in which $R_1$ is 5-nitro, $R_2$-$R_4$ are H, and R' is 4-hydroxybutyl.

In another more specific embodiment, this invention contemplates a compound of formula XIA-1, in which $R_1$ is 3-cyano, $R_2$-$R_4$ are H, and R' is 4-hydroxybutyl.

In another more specific embodiment, this invention contemplates a compound of formula XIA-1, in which $R_1$ is 3-(2-methoxyethenyl), $R_2$-$R_4$ are H, and R' is 4-hydroxybutyl.

In another more specific embodiment, this invention contemplates a compound of formula XIA-1, in which $R_1$ is 4-cyano, $R_2$-$R_4$ are H, and R' is 4-hydroxybutyl.

In another more specific embodiment, this invention contemplates a compound of formula XIA-1, in which $R_1$ and $R_2$ are 3-chloromethyl and 4-chloromethyl, $R_3$ and $R_4$ are H, and R' is 3-hydroxypropyl.

In another subgeneric embodiment, this invention provides a compound of formula XIA-2, where $R_1$-R' are defined as for formula I.

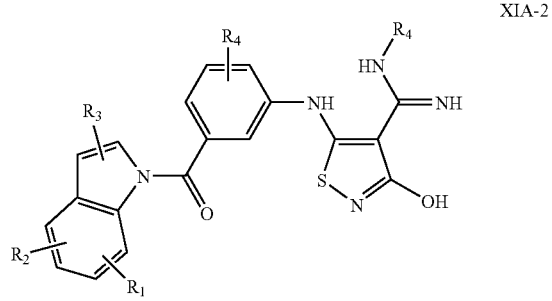

In a more specific embodiment, this invention provides a compound of formula XIA-2 where $R_1$-$R_4$ are H and R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula XIA-2 where $R_1$-$R_4$ are H and R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In another more specific embodiment, this invention provides a compound of formula XIA-2 where $R_1$-$R_4$ are H and R' is isopropyl, 2-(2-furyl)ethyl, 2-hydroxyethyl, 2,3-dihydroxy-1-propyl, or 3,4-dihydroxy-2-butyl.

In a more specific embodiment, this invention provides a compound of formula XIA-2 where $R_1$-$R_4$ are H and R' is isopropyl, 2-butyl, 2-(2-furyl)ethyl, 2-hydroxyethyl, 2,3-dihydroxy-1-propyl, or 3,4-duhydroxy-2-butyl.

In another more specific embodiment, this invention provides a compound of formula XIA-2, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIA-2, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In a more specific embodiment, this invention provides a compound of formula XIA-2, where R is 4-acetyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention provides a compound of formula XIA-2, where $R_1$ is 4-bromo, $R_2$, $R_3$, and $R_4$ are H, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another more specific embodiment, this invention contemplates a compound of formula XIA-2, where $R_1$ is 5-bromo, $R_2$ and $R_3$ are H, $R_4$ is 2-fluoro, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In another more specific embodiment, this invention contemplates a compound of formula XIA-2, where $R_1$ is 5-cyano, $R_2$ is H, $R_3$ is 2-trifluoromethyl, $R_4$ is 2-fluoro, R' is —$(CH_2)_n$—B, where n is 1, and B is 5-methyl-2-furyl, 5-methyl-2-pyrrolyl, or 3-pyrrolyl.

In another more specific embodiment, this invention contemplates a compound of formula XIA-2, where $R_1$ is 4-fluoro, $R_2$ is 5-fluoro, $R_3$ is 3-acetamido, $R_4$ is 2-fluoro, R' is —$(CH_2)_n$—B, where n is 1, and B is 5-methyl-2-furyl, 5-methyl-2-pyrrolyl, or 3-pyrrolyl.

In a more specific embodiment, this invention contemplates a compound of formula XIA-2 where $R_1$-$R_4$ are H and R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In another more specific embodiment, this invention contemplates a compound of formula XIA-2 where $R_1$-$R_4$ are H and R' is —$(CH_2)_n$—B, where n is 2, and B is pyridyl, piperazinyl, piperazinonyl, piperidinyl, piperidinonyl, morpholyl, furyl, tetrahydrofuryl, or pyrimidinyl.

In another more specific embodiment, this invention contemplates a compound of formula XIA-2 where $R_1$-$R_4$ are H and R' is isopropyl, 2-(2-furyl)ethyl, 2-hydroxyethyl, 2,3-dihydroxy-1-propyl, or 3,4-duhydroxy-2-butyl.

In another more specific embodiment, this invention contemplates a compound of formula XIA-2, where $R_1$ and $R_2$ together, at positions 3 and 4, are fused cyclopentyl, $R_3$ and $R_4$ are H, and R' is 1-hydroxy-butan-3-yl.

In another more specific embodiment, this invention contemplates a compound of formula XIA-2 in which $R_1$ and $R_2$ together, at positions 3 and 4, are fused cyclopentyl, $R_3$ and $R_4$ are H, and R' is isopropyl.

In another more specific embodiment, this invention contemplates a compound of formula XIA-2 in which $R_1$ and $R_2$ together, at positions 4 and 5, are fused (2,3)-furyl, $R_3$ and $R_4$ are H, and R' is 1,2-dihydroxy-propan-3-yl.

In another more specific embodiment, this invention contemplates a compound of formula XIA-2 in which $R_1$ and $R_2$ together, at positions 3 and 4, are fused (2,3)thienyl, $R_3$ and $R_4$ are H, and R' is 2-hydroxyethyl.

In another more specific embodiment, this invention contemplates a compound of formula XIA-2 in which $R_1$ and $R_2$ together, at positions 3 and 4, are fused cyclopentyl, $R_3$ and $R_4$ are H, and R' is 4-hydroxybutyl.

In another more specific embodiment, this invention provides a compound of formula XIA-2, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIA-2, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In another more specific embodiment, this invention contemplates a compound of formula XIA-2, where $R_1$ and $R_2$ together, at positions 3 and 4, are fused cyclopentyl, $R_3$ and $R_4$ are H, and R' is 1-hydroxy-butan-3-yl.

In another more specific embodiment, this invention contemplates a compound of formula XIA-2 in which $R_1$ and $R_2$ together, at positions 3 and 4, are fused cyclopentyl, $R_3$ and $R_4$ are H, and R' is isopropyl.

In another more specific embodiment, this invention contemplates a compound of formula XIA-2 in which $R_1$ and $R_2$ together, at positions 4 and 5, are fused (2,3)-furyl, $R_3$ and $R_4$ are H, and R' is 1,2-dihydroxy-propan-3-yl.

In another more specific embodiment, this invention contemplates a compound of formula XIA-2 in which $R_1$ and $R_2$ together, at positions 3 and 4, are fused (2,3)thienyl, $R_3$ and $R_4$ are H, and R' is 2-hydroxyethyl.

In another more specific embodiment, this invention contemplates a compound of formula XIA-2 in which $R_1$ and $R_2$ together, at positions 3 and 4, are fused cyclopentyl, $R_3$ and $R_4$ are H, and R' is 4-hydroxybutyl.

In another more specific embodiment, this invention contemplates a compound of formula XIA-2 in which $R_1$ and $R_2$ together are fused furyl, $R_3$ and $R_4$ are H, and R' is 1,2-dihydroxybutan-4-yl.

In another more specific embodiment, this invention contemplates a compound of formula XIA-2 in which $R_1$ and $R_2$ together are fused cyclopentyl, $R_3$ and $R_4$ are H, and R' is 1,2-dihydroxybutan-4-yl.

In another specific embodiment, this invention contemplates a compound of formula XIA-2 in which $R_1$ and $R_2$ are both H, $R_3$ is 3-methyl, $R_4$ is 2-(2-chloroethyl), R' is —$(CH_2)_n$—B, where n is 1, and B is pyridyl, piperazinyl, piperazinonyl, piperidinyl, piperidinonyl, morpholyl, furyl, tetrahydrofuryl, or pyrimidinyl.

In a more specific embodiment, this invention provides a compound of formula XIA-2 in which $R_1$ is 4-$CF_3$, $R_3$ is 2-hydroxymethyl, $R_2$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another more specific embodiment, this invention contemplates a compound of formula XIA-2 in which $R_1$ is 3-$CH_2F$, $R_2$ is 5-cyano, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In another generic embodiment, this invention provides a compound of formula B, where $R_1$-R' are defined as for formula A, where the dashed line represents an optional double bond, and where symbols L, T, U, V, and W-Z represent N, CH, or $CR_{1, 2, or 4}$, provided that at least one of L, T, U, V, and W-Z is N, and further provided that no two nitrogen atoms are adjacent.

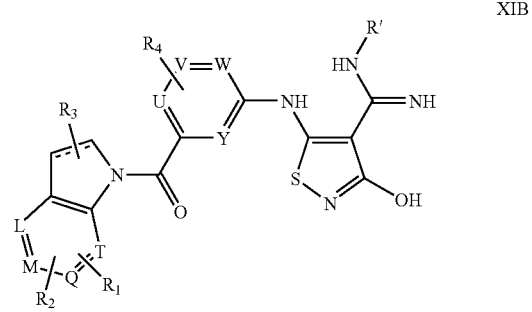

XIB

In one subgeneric embodiment, this invention provides a compound of formula XIB-1,

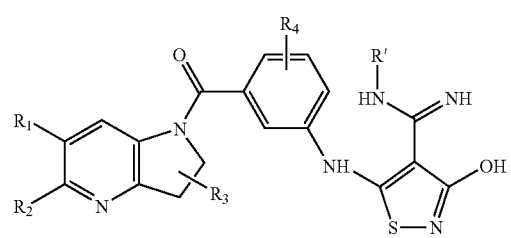

XIB-1 where all substituents are defined as for formula I.

In a more specific embodiment, this invention provides a compound of formula XIB-1, where $R_1$-$R_4$ are, independently, H, $C_1$-$C_6$ alkyl, hydroxy, or halogen, and R' is —$(CH_2)_n$—B, where n is 1 or 2, and B is pyridyl, piperazinyl, piperazinonyl, piperidinyl, piperidinonyl, 1-pyrrolidonyl, 2,6-dimethyl-4-morpholyl, 4-morpholyl, furyl, tetrahydrofuryl, or pyrimidinyl.

In another more specific embodiment, this invention provides a compound of formula XIB-1, where $R_1$-$R_4$ are, independently, H, $C_1$-$C_6$ alkyl, hydroxy, or halogen, and R' is $C_1$-$C_4$ alkyl, optionally substituted with one or two halogen atoms, hydroxy groups, or $C_1$-$C_3$ alkoxy groups.

In a still more specific embodiment, this invention provides a compound of formula XIB-1, where $R_1$-$R_4$ are, independently, H. $C_1$-$C_4$ alkyl, hydroxy, or halogen, and R' is isopropyl, 2-(2-furyl)ethyl, 2-hydroxyethyl, 1-hydroxy-2-propyl, 2,3-dihydroxy-1-propyl, or 3,4-dihydroxy-2-butyl.

In another more specific embodiment, this invention provides a compound of formula XIB-1 where one of $R_1$ and $R_2$ is H and the other is amino, methyl amino, dimethylamino, dimethylaminomethyl, or acetylamino; $R_3$-$R_4$ are, independently, H, chloro, methyl, or hydroxy; and R' is $C_1$-$C_6$ alkyl, optionally substituted with halogen, $C_1$-$C_3$ alkoxy, or hydroxy.

In another more specific embodiment, this invention provides a compound of formula XIB-1, where one of $R_1$ and $R_2$ is H and the other is nitro, cyano, methylcarbamoyl, dimethylcarbamoyl, or aminosulfonyl; $R_3$-$R_4$ are, independently, H, chloro, methyl, or hydroxy; and R' is $C_1$-$C_6$ alkyl, optionally substituted with halogen, $C_1$-$C_3$ alkoxy, or hydroxy.

In another more specific embodiment, this invention provides a compound of formula XIB-1, where $R_1$ and $R_2$ are fused cyclohexyl or fused cyclopentyl, $R_3$ and $R_4$ are, independently, H, chloro, methyl, or hydroxy; and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula XIB-1, where $R_1$ and $R_2$ are fused benzo; $R_3$ and $R_4$ are, independently, H, chloro, methyl, or hydroxy; and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula XIB-1, wherein $R_1$ and $R_2$ are, independently, H or halogen, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In a more specific embodiment, this invention provides a compound of formula XIB-1, where $R_1$-$R_3$ are H, $R_4$ is 2-halo, 2-cyano, 2-hydroxy, or 2-methoxy, and R' is —$(CH_2)_n$—B, where n is 1 or 2, and B is 4-methyl-1-piperazinyl, 1-piperidinyl, piperidinonyl, 4-morpholyl, 2,6-dimethyl-4-morpholyl, 2-furyl, 2-tetrahydrofuryl, 1-pyrrolidonyl, or pyrimidinyl.

In another more specific embodiment, this invention provides a compound of formula XIB-1, where $R_1$ is halo, $R_2$-$R_4$ are H and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidinyl.

In a still more specific embodiment, the invention contemplates a compound of formula XIB-1, where $R_1$ is chloro or bromo; $R_2$-$R_4$ are H; and R' is isopropyl, 2-hydroxyethyl, 1-hydroxy-2-propyl, or 2,3-dihydroxy-1-propyl.

In another embodiment, this invention provides a compound of formula XIB-2,

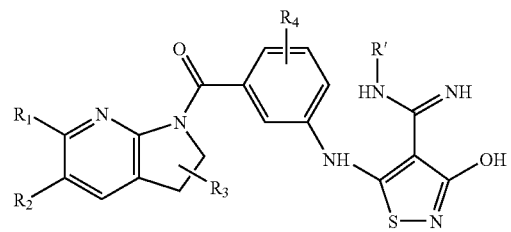

XIB-2 where substituents are defined as for formula I.

In a more specific embodiment, this invention provides a compound of formula XIB-2, where $R_1$-$R_4$ are, independently, H or halogen, and R' is isopropyl, 2-(2-furyl)ethyl, 2-hydroxyethyl, 2-methoxyethyl, 1-hydroxy-2-propyl,1,2-dihydroxy-3-propyl, or 3,4-dihydroxy-2-butyl.

In another more specific embodiment, this invention provides a compound of formula XIB-2, where one of $R_1$ and $R_2$ is H and the other is amino, methyl amino, dimethylamino, dimethylaminomethyl, or acetylamino, $R_3$-$R_4$ are H, and R' is $C_1$-$C_6$ alkyl, optionally substituted with halogen, $C_1$-$C_3$ alkoxy, or hydroxy.

In another more specific embodiment, this invention provides a compound of formula XIB-2, where one of $R_1$ and $R_2$ is H and the other is nitro, cyano, methylcarbamoyl, dimethylcarbamoyl, or aminosulfonyl, $R_3$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIB-2, where $R_1$ and $R_2$ are H, $R_3$ is methyl, methoxy, acetamido, or acetyl, $R_4$ is nitro, cyano, halo, halomethyl, dimethylamino, or methylaminocarbonyl, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates a compound of formula XIB-2, where $R_1$ and $R_2$ are fused cyclohexyl or are both H, $R_3$ and $R_4$ are H, and R' is isopropyl or 1-hydroxy-2-propyl.

Additional embodiments of generic structure B are shown below.

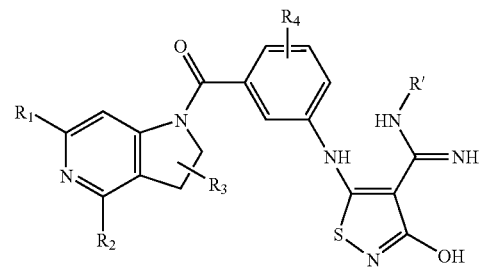

XIB-3

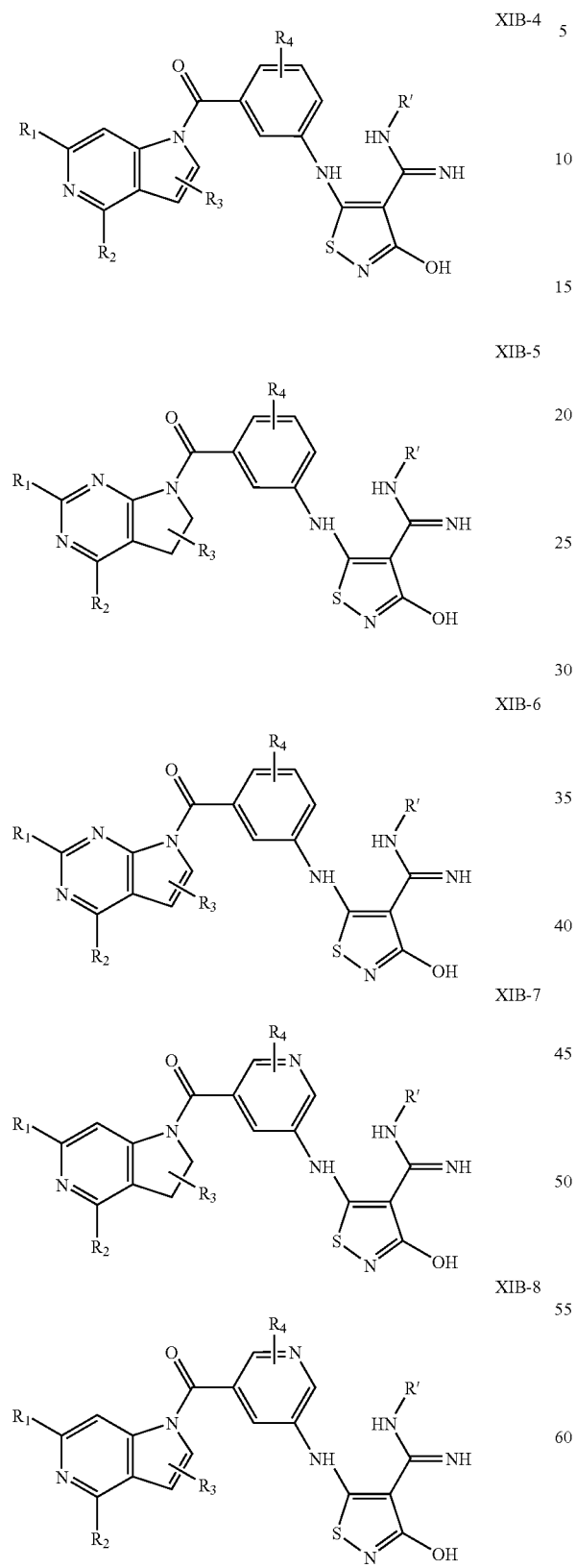
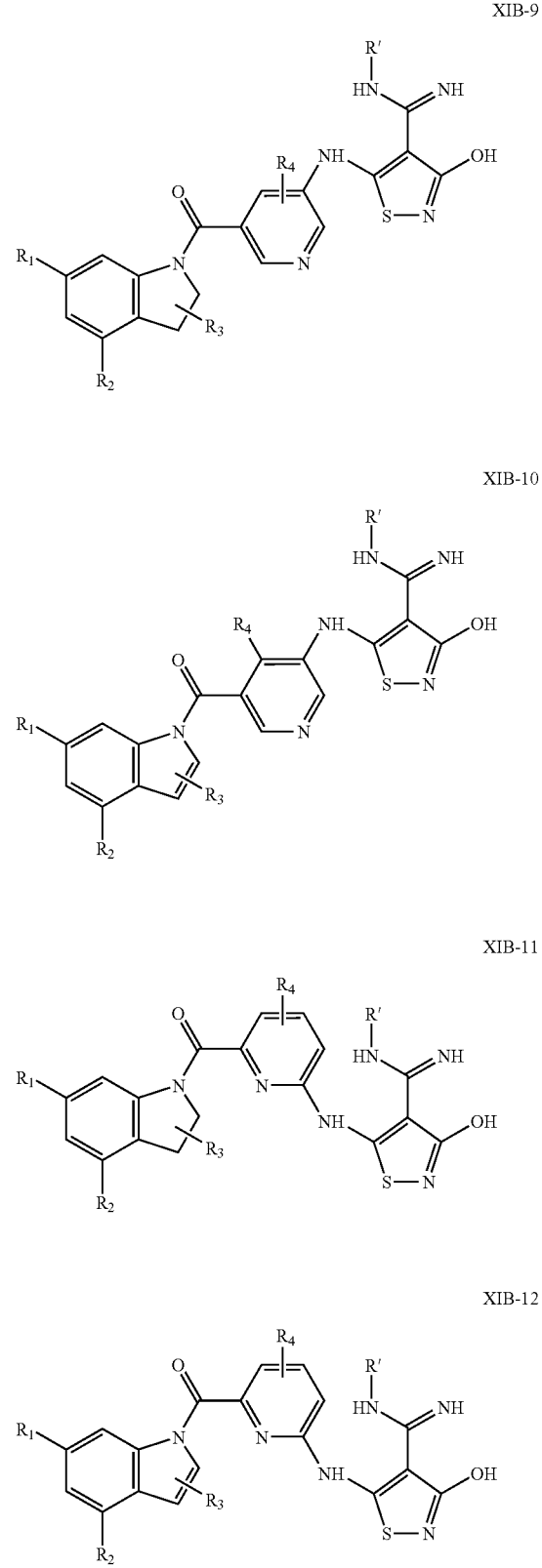

XIB-13
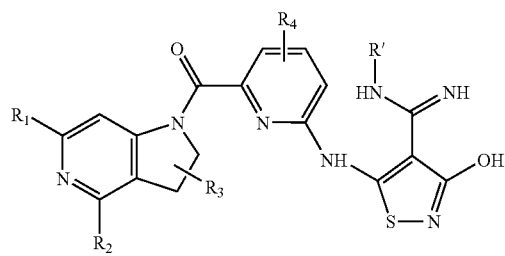
XIB-14
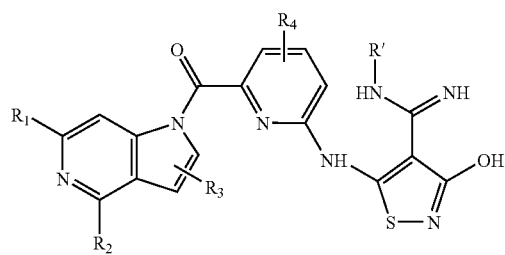
XIB-15
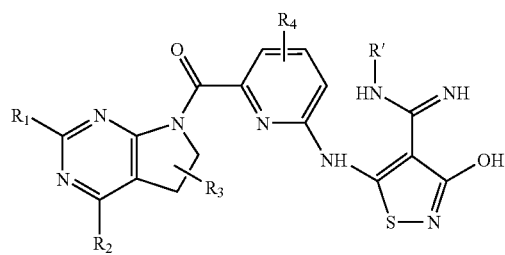
XIB-16
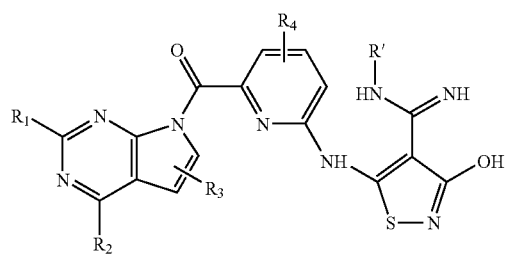
XIB-17
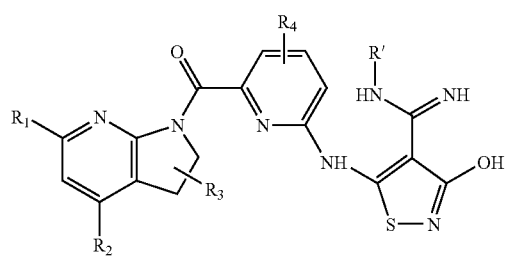
XIB-18
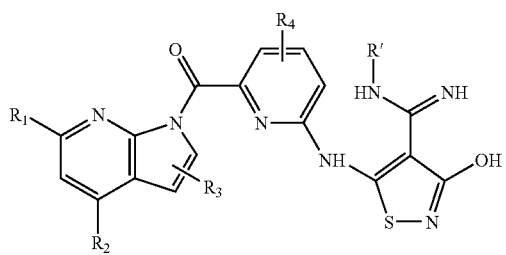
XIB-19
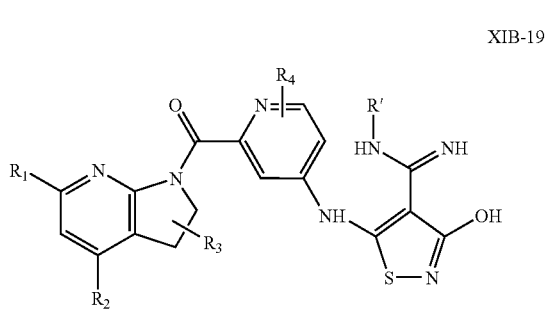
XIB-20
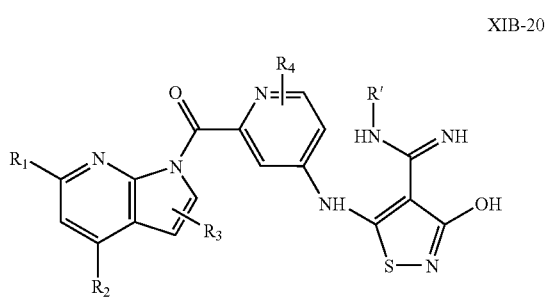
XIB-21
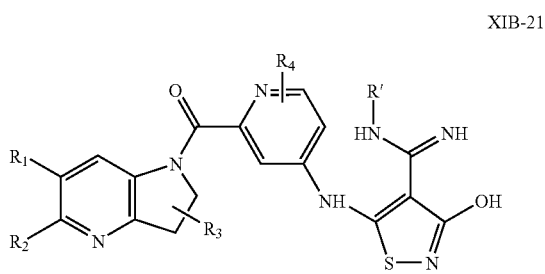
XIB-22
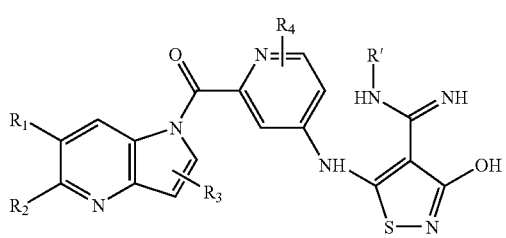

XIB-23
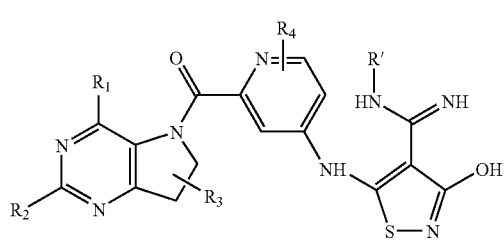
XIB-24
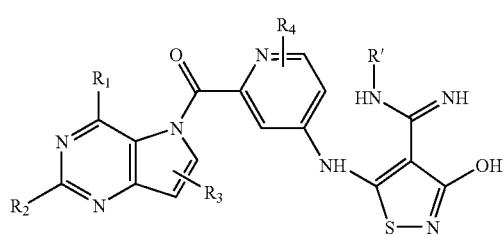
XIB-25
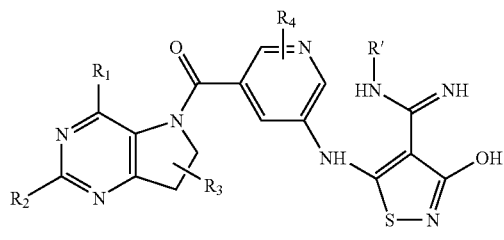
XIB-26
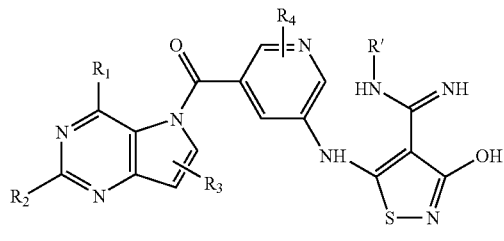
XIB-27
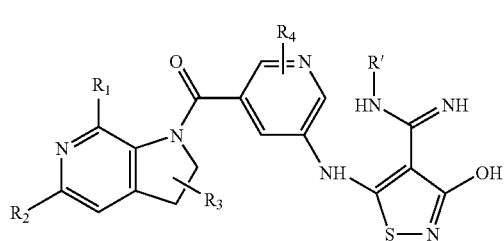
XIB-28
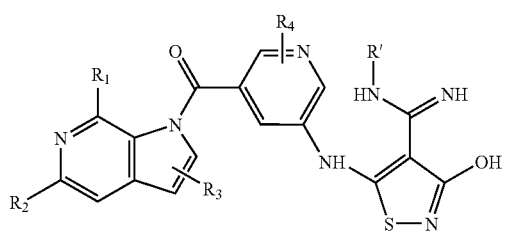
XIB-29
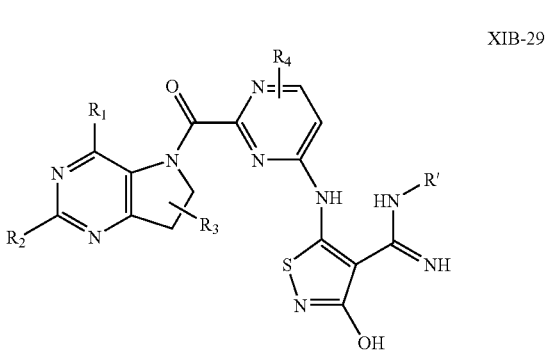
XIB-30
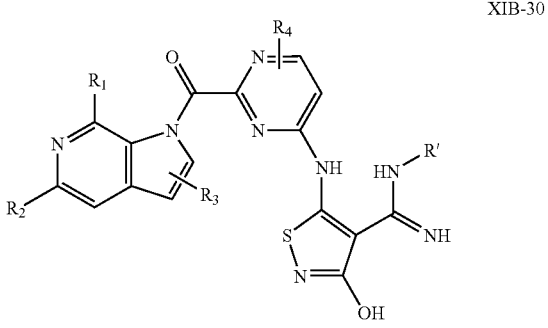
XIB-31
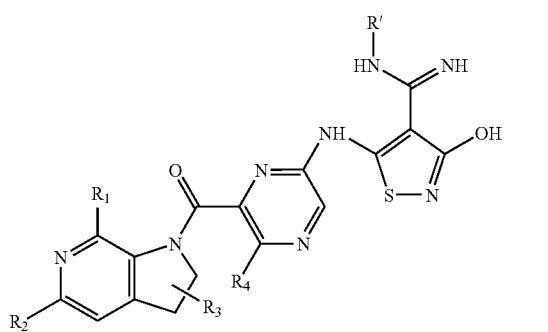

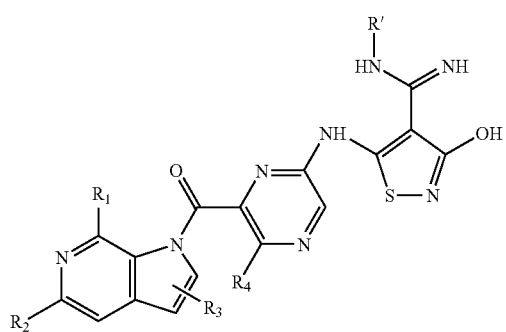
XIB-32
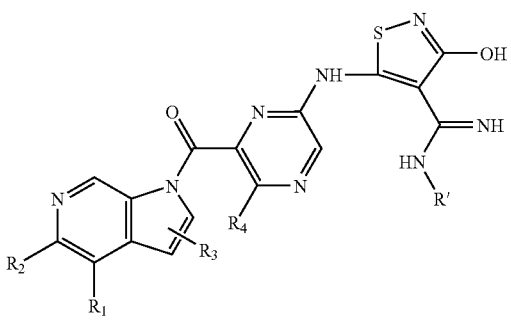
XIB-33
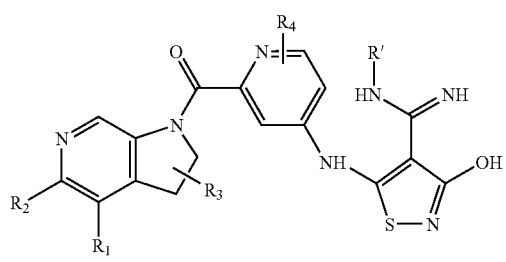
XIB-34
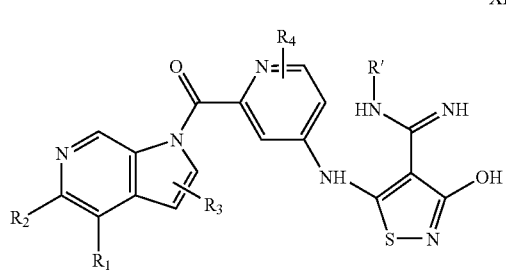
XIB-35
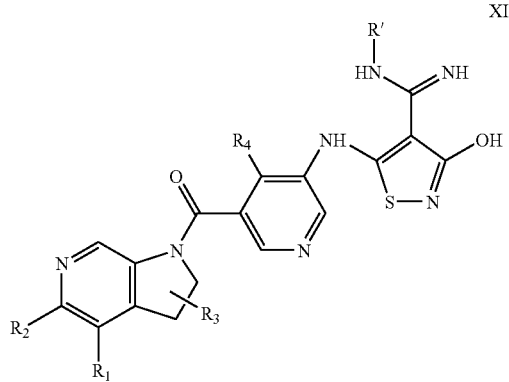
XIB-36
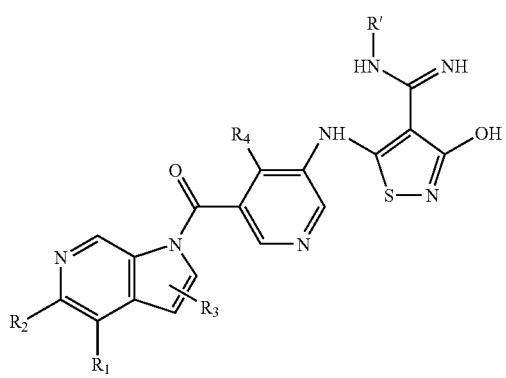
XIB-37
XIB-38
XIB-39
XIB-40
XIB-41

-continued

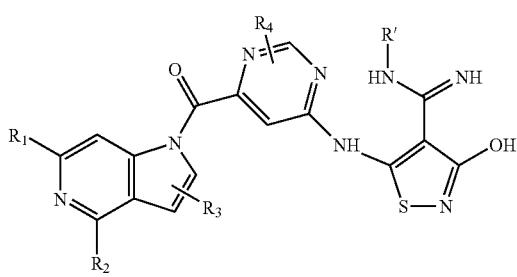

XIB-42

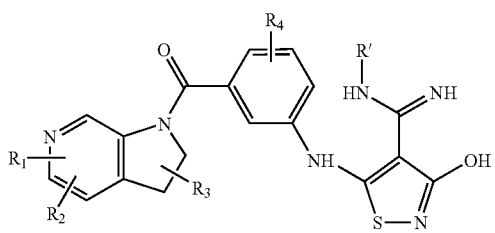

XIB-43

In more specific embodiments, the invention provides compounds according to any of formulas XIB-1 to XIB-43, wherein $R_1$-$R_4$ are all independently methyl, methoxy, ethyl, vinyl, ethynyl, halo, or H, and R' is —$(CH_2)_n$—B, where n is 1 or 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, cyclopentyl, cyclopentenyl, cyclopentadien-4-yl; cyclohexyl, or cyclohexen-2-yl.

In additional more specific embodiments, the invention provides compounds according to any of formulas XIB-1 to XIB-43, wherein $R_1$-$R_4$ are all independently halo, halomethyl, dihalomethyl, or H, and R' is —$(CH_2)_n$—B, where n is 1 or 2, and B is phenyl, pyridyl, piperazinyl, piperazinonyl, piperidinyl, piperidinonyl, morpholyl, furyl, tetrahydrofuryl, or pyrimidinyl.

In additional more specific embodiments, the invention contemplates compounds according to any of formulas XIB-1 to XIB-43, where $R_1$ is bromo; $R_2$-$R_4$ are all H; and R' is isopropyl, 2-hydroxyethyl, 1-hydroxy-2-propyl, 2,3-dihydroxy-1-propyl, or 3,4-dihydroxy-2-butyl.

In additional more specific embodiments, the invention contemplates compounds according to any of formulas XIB-1 to XIB-43, where $R_1$ is chloro; $R_2$-$R_4$ are all H; and R' is isopropyl, 2-hydroxyethyl, 1-hydroxy-2-propyl, 2,3-dihydroxy-1-propyl, or 3,4-dihydroxy-2-butyl.

In additional more specific embodiments, the invention contemplates compounds according to any of formulas XIB-1 to XIB-43, where $R_3$ is chloro; $R_1$, $R_2$, and $R_4$ are all H; and R' is isopropyl, 2-hydroxyethyl, 1-hydroxy-2-propyl, 2,3-dihydroxy-1-propyl, or 3,4-dihydroxy-2-butyl.

In additional more specific embodiments, the invention contemplates compounds according to any of formulas XIB-1 to XIB-43, where $R_4$ is chloro or hydroxy; $R_1$-$R_3$ are all H; and R' is isopropyl, 2-hydroxyethyl, 1-hydroxy-2-propyl, 2,3-dihydroxy-1-propyl, or 3,4-dihydroxy-2-butyl.

In still more specific embodiments, the invention contemplates compounds according to any of formulas XIB-1 to XIB-43, where $R_1$-$R_4$ are all H and R' is isopropyl, 1-hydroxy-2-propyl, or 2,3-dihydroxy-1-propyl.

In still more specific embodiments, the invention contemplates compounds according to any of formulas XIB-1 to XIB-28 and XIB-30 to XIB-42, where $R_1$-$R_3$ are all H; $R_4$ is ortho to the amide group and is chloro or hydroxy; and R' is isopropyl, 1-hydroxy-2-propyl, 2,3-dihydroxy-1-propyl, or (2-tetrahydrofuryl)methyl.

Additional contemplated examples of compounds according to formulas XIB-1 to XIB-43 are shown below.

example of XIB-1

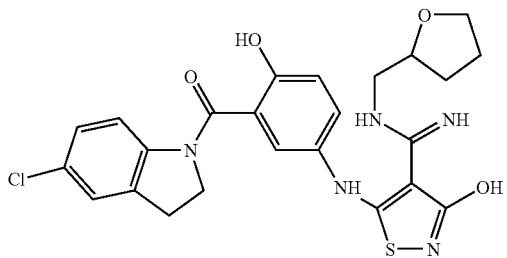

example of XIB-1

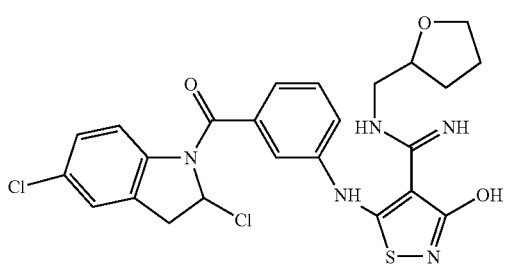

example of XIB-1

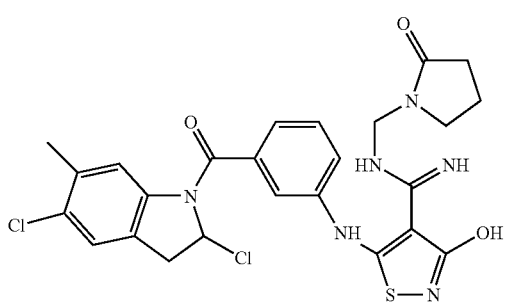

example of XIB-1

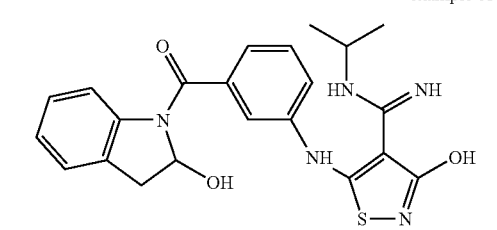

-continued
example for XIB-2
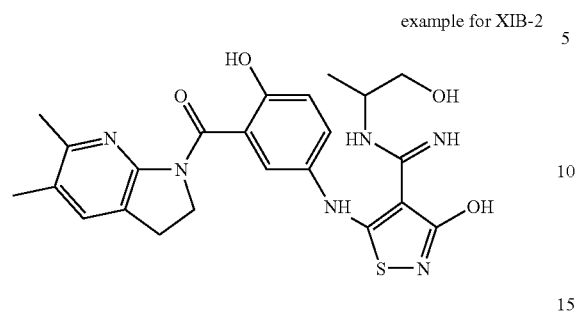
example for XIB-2
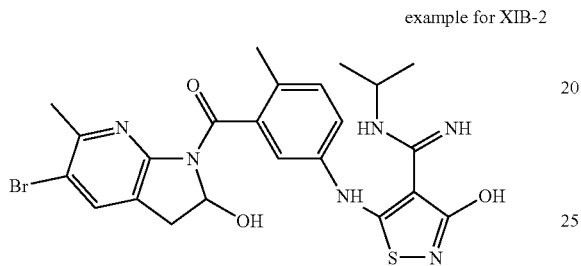
example for XIB-2
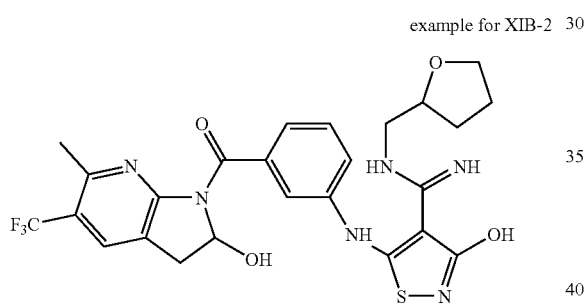
example for XIB-2
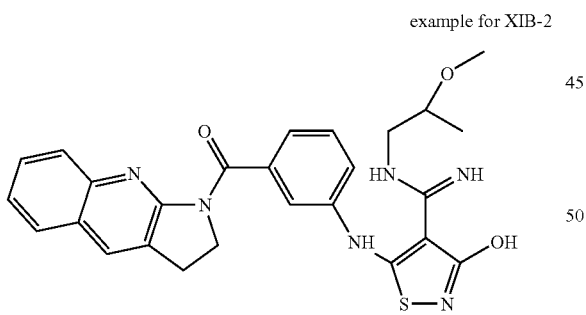
example for XIB-2
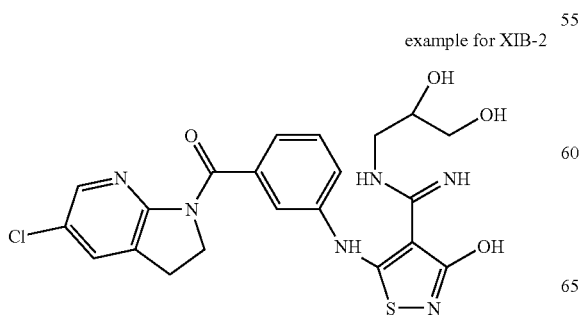
-continued
example for XIB-3
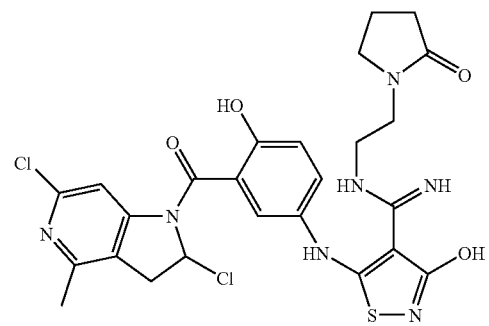
example for XIB-3
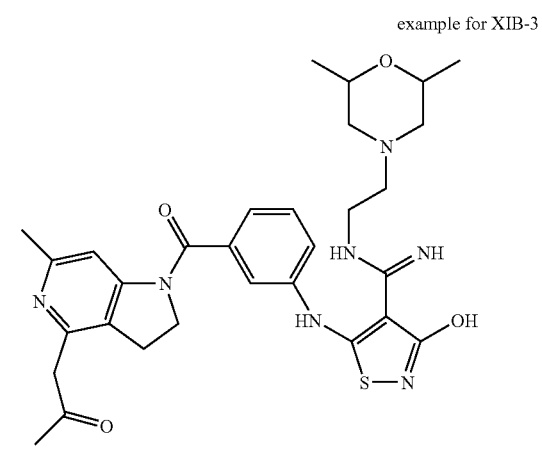
example for XIB-4
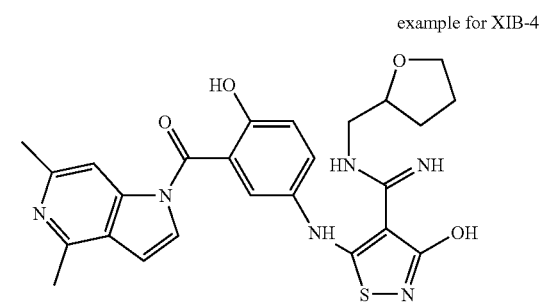
example for XIB-5
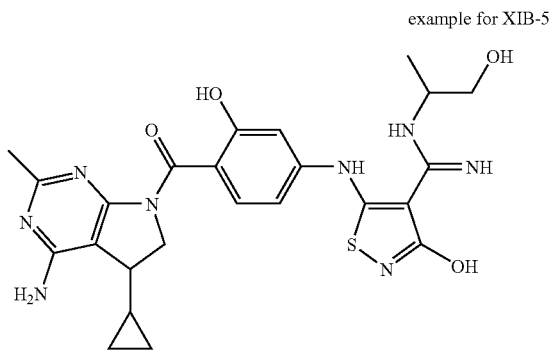

example for XIB-6
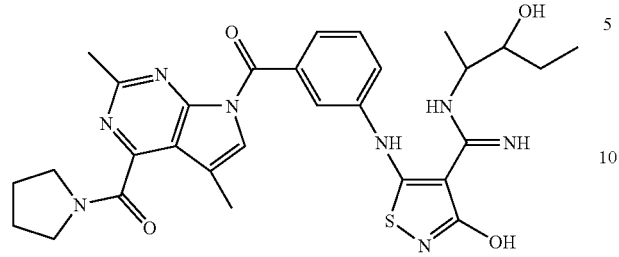
example for XIB-7
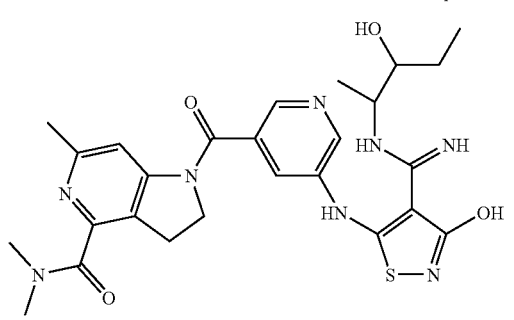
example for XIB-7
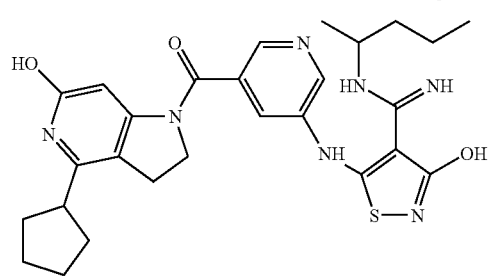
example for XIB-8
example for XIB-8
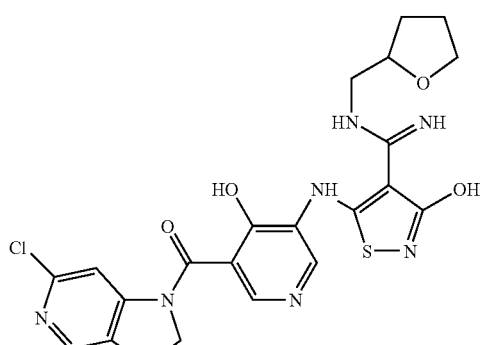
example for XIB-9
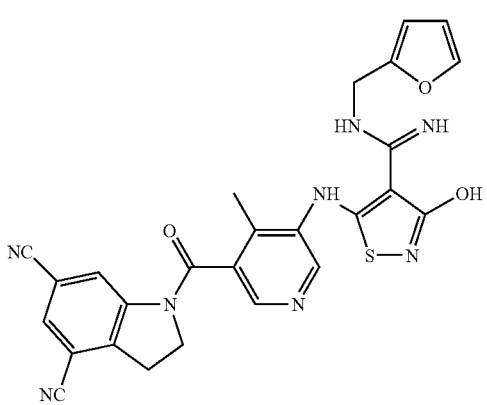
example for XIB-9
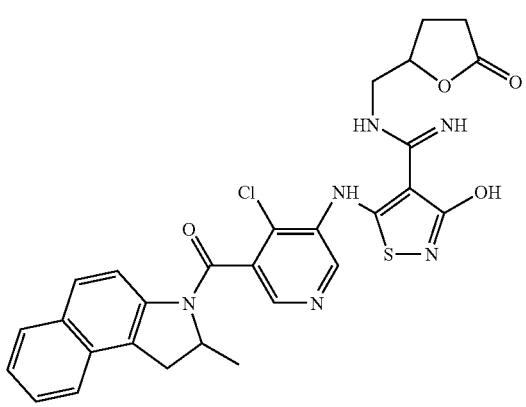

-continued
example for XIB-9
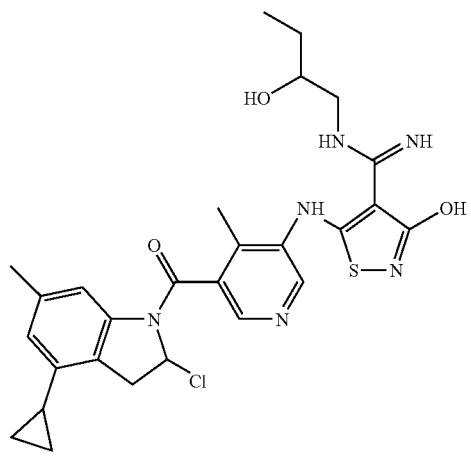
example for XIB-9
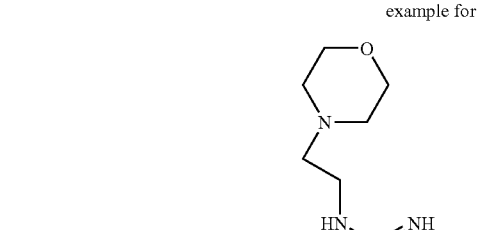
example for XIB-10
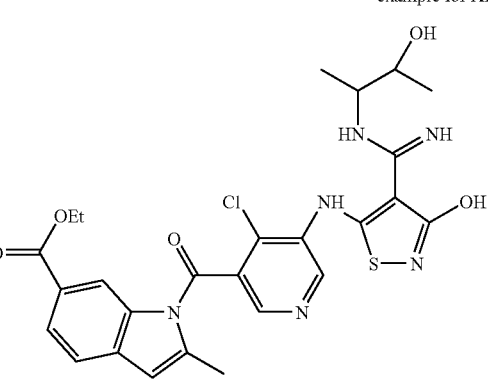
-continued
example for XIB-10
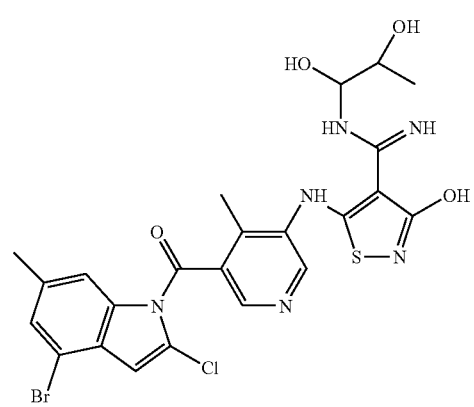
example for XIB-11
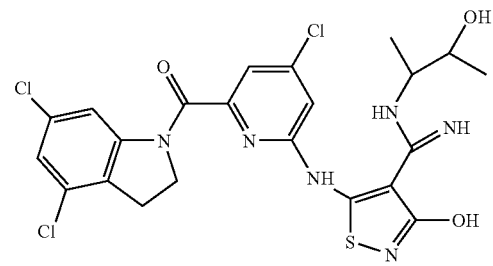
example for XIB-11
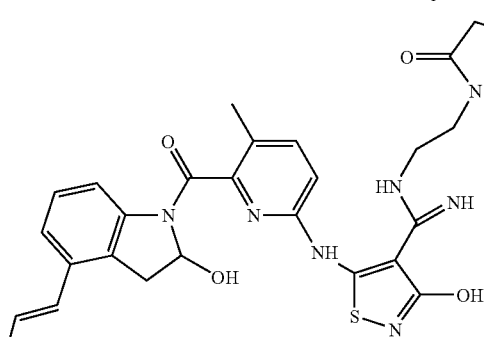
example for XIB-12
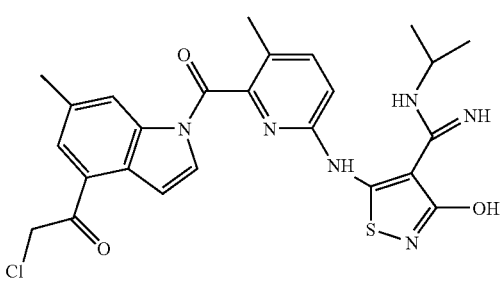

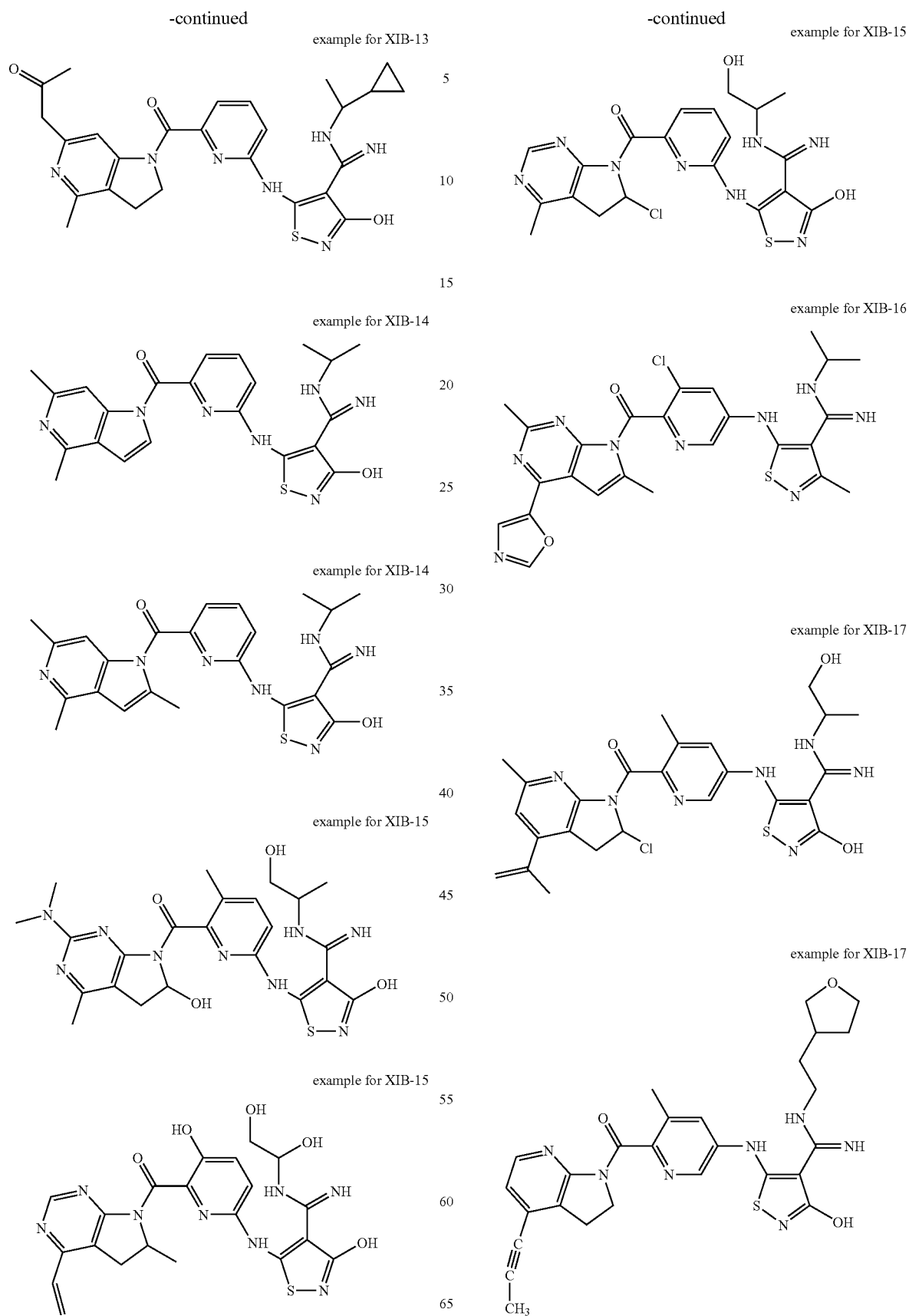

-continued
example for XIB-17
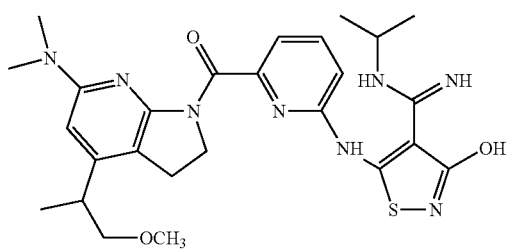
example for XIB-18
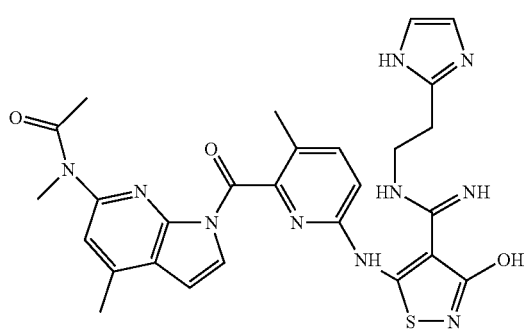
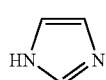
example for XIB-18
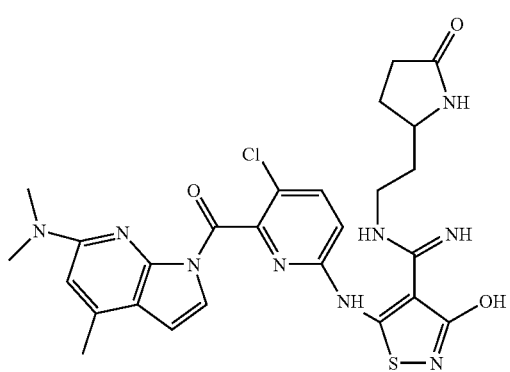
example for XIB-18
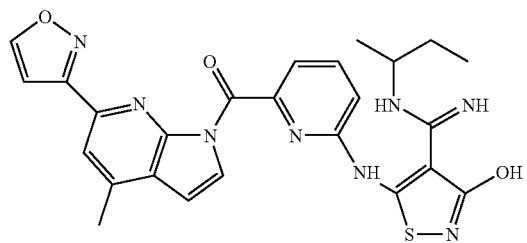
-continued
example for XIB-19
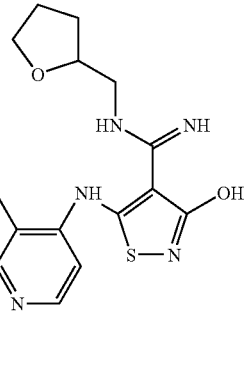
example for XIB-19
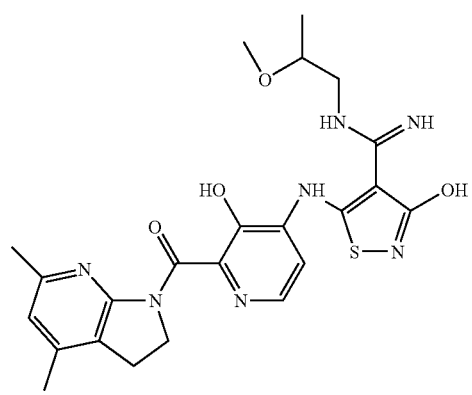
example for XIB-19
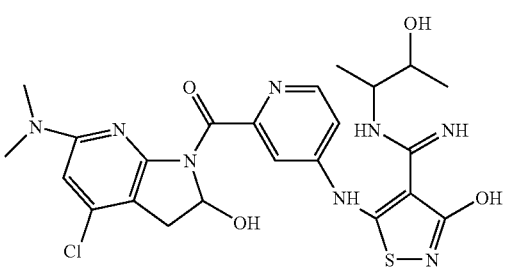
example for XIB-20
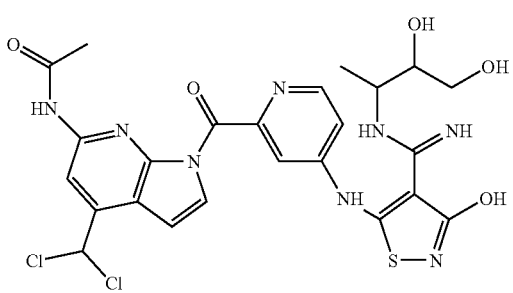

175
-continued
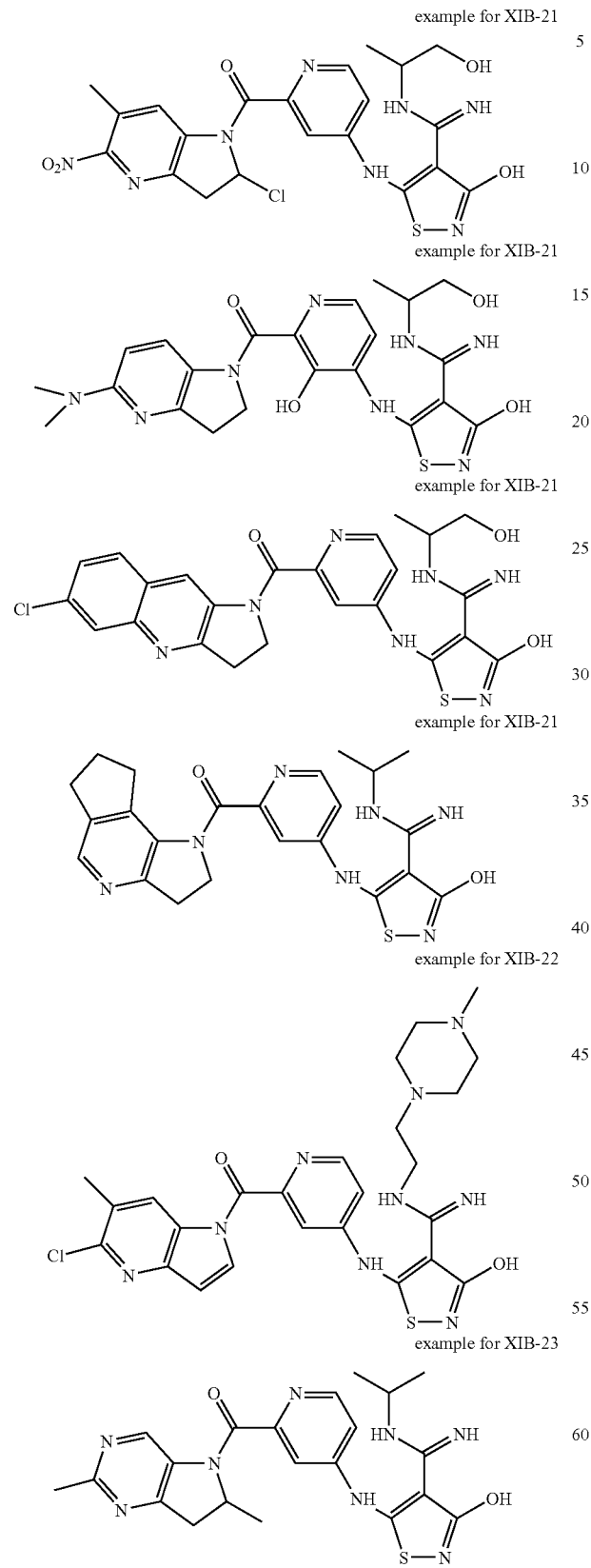
176
-continued
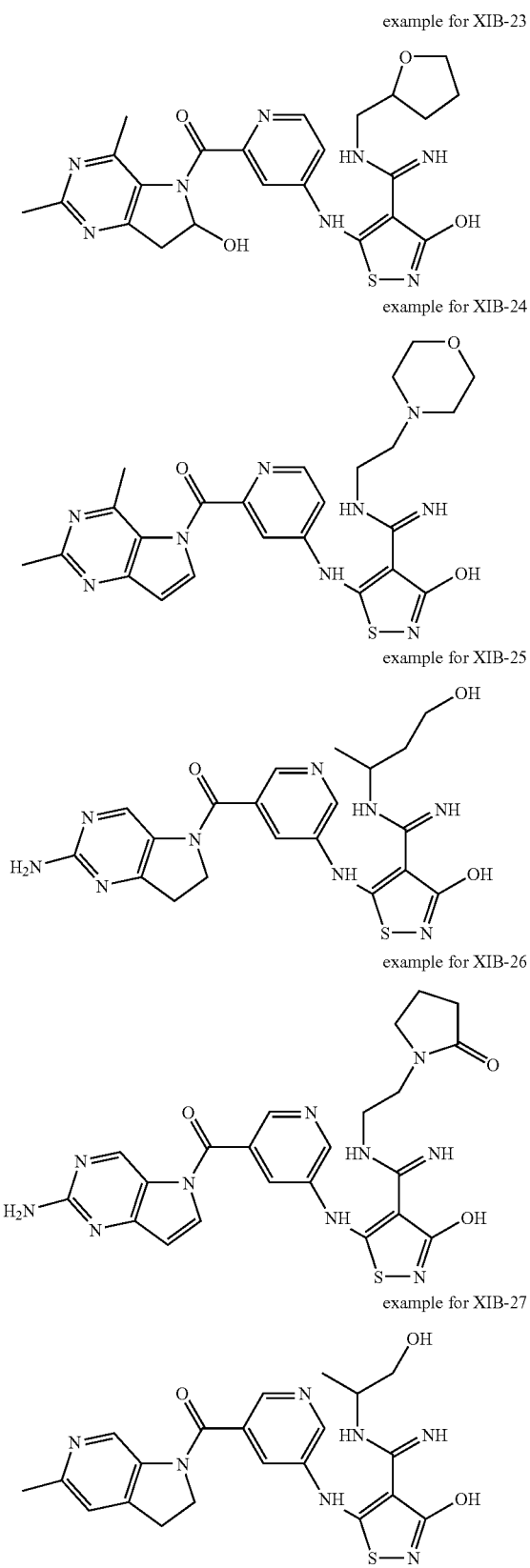

-continued
example for XIB-28
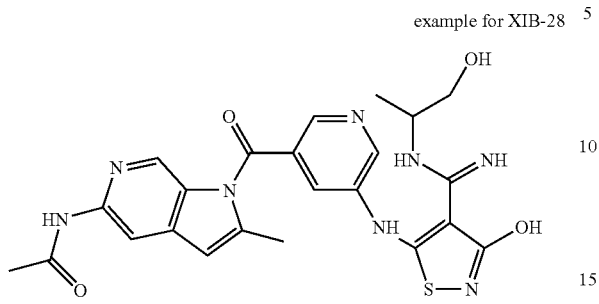
example for XIB-29
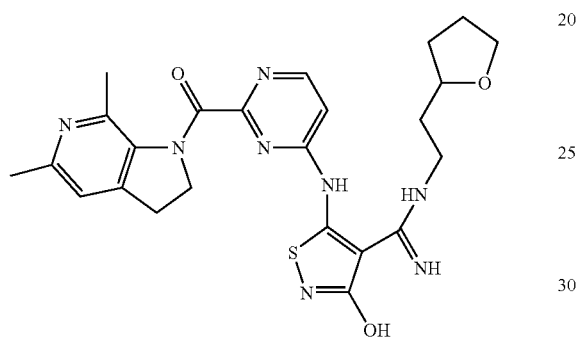
example for XIB-30
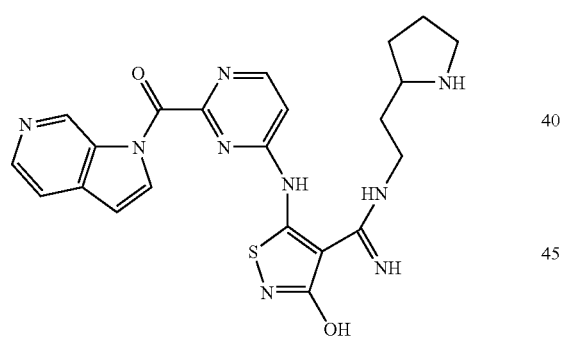
example for XIB-31
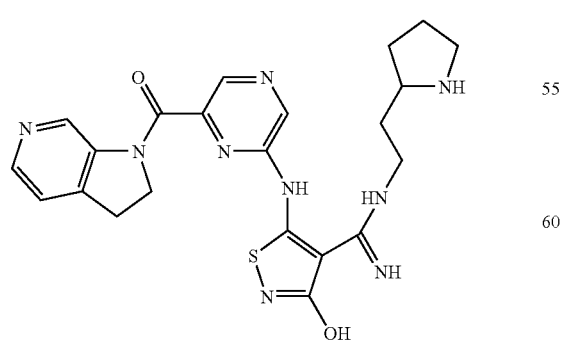
-continued
example for XIB-32
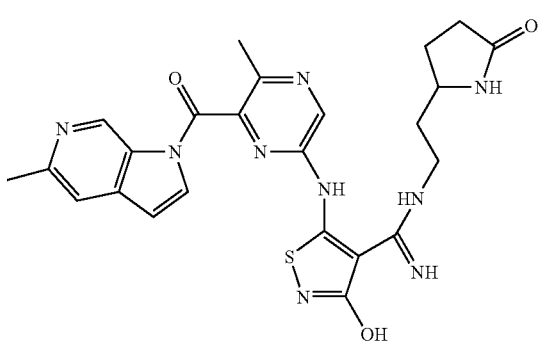
example for XIB-33
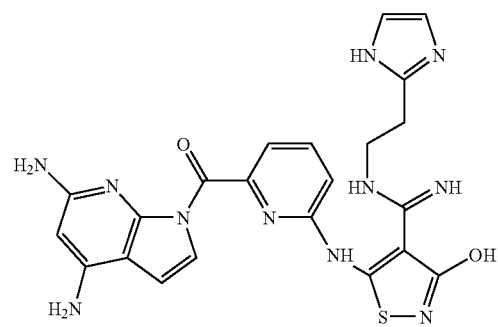
example for XIB-34
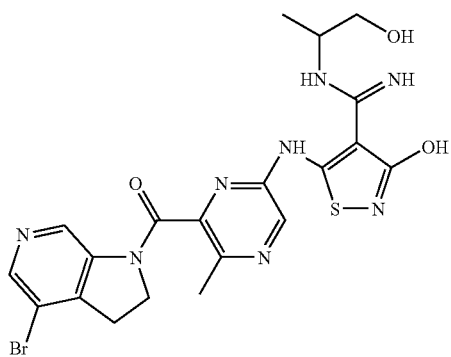
example for XIB-35
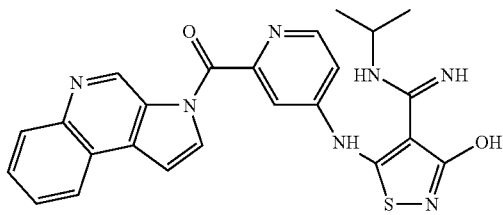

example for XIB-36
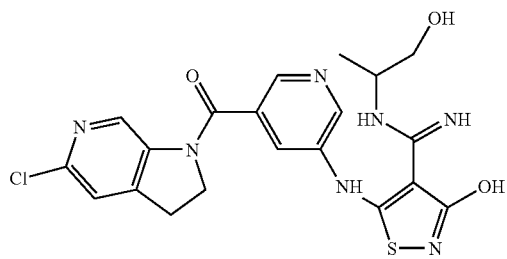
example for XIB-38
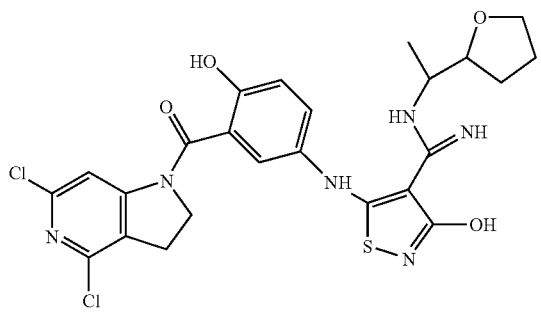
example for XIB-37
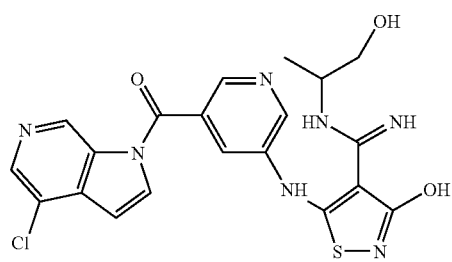
example for XIB-40
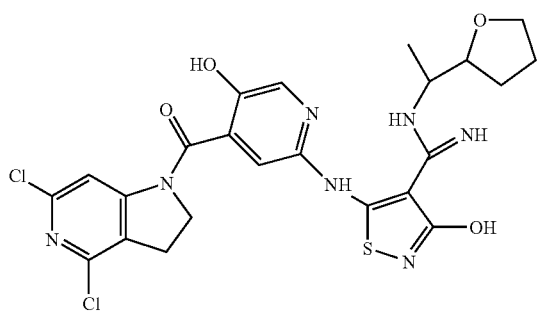
example for XIB-37
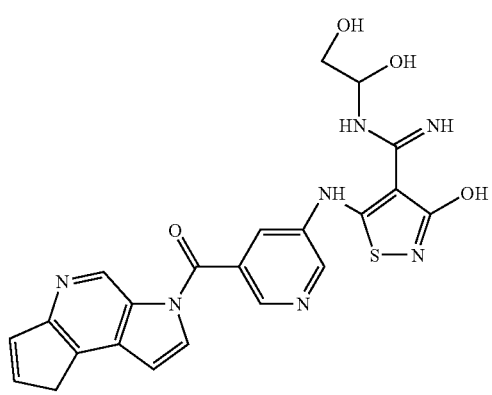
example for XIB-40
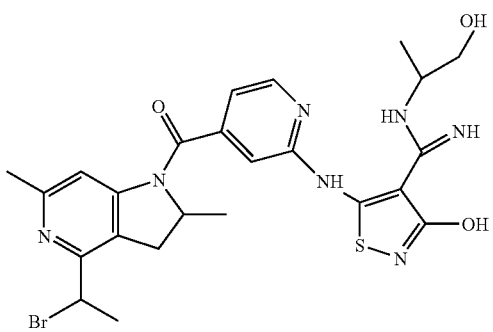
example for XIB-38
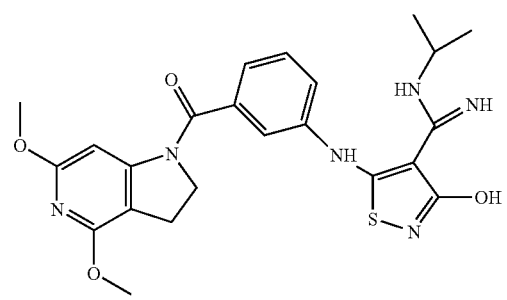
example for XIB-41
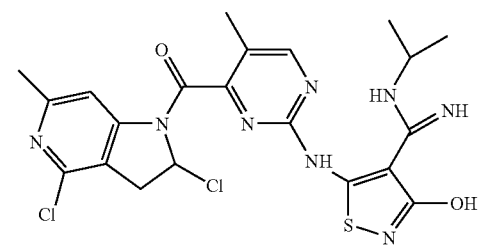

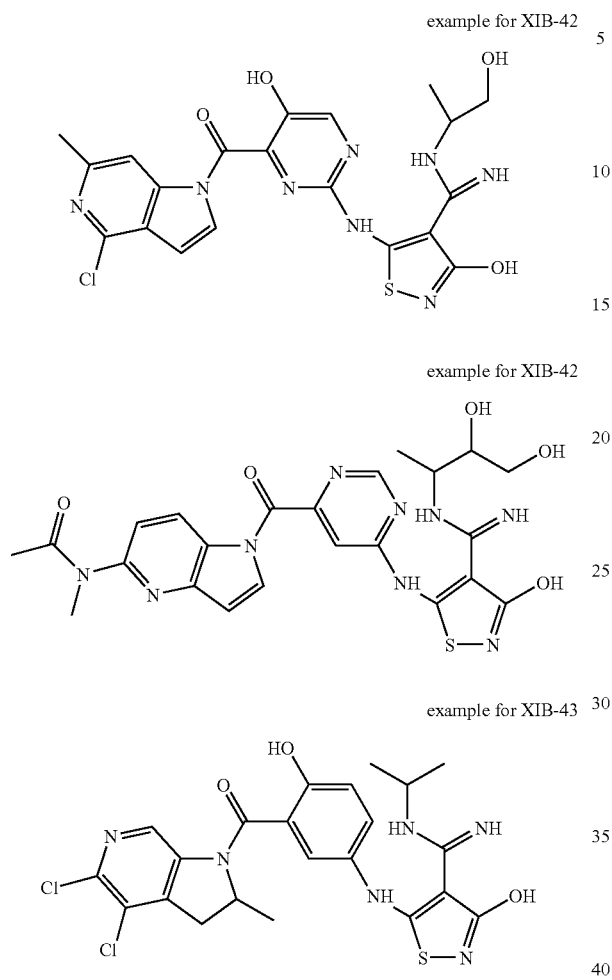
Additional contemplated compounds for subgeneric embodiments XIA-1 and XIA-2 are shown in the tables below
| Cpd # | Structure |
|---|---|
| 1 | 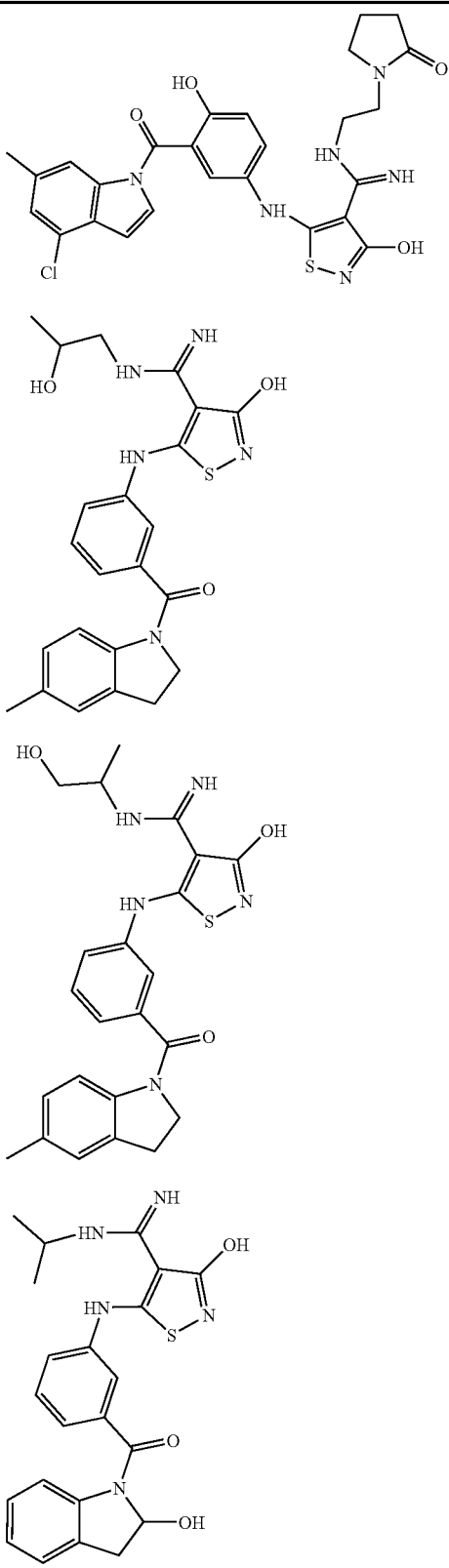 |

| Cpd # | Structure |
|---|---|
| 6 | 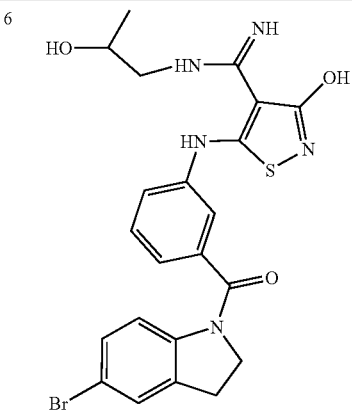 |
| 7 | 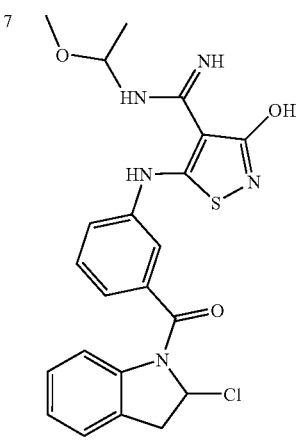 |
| 8 | 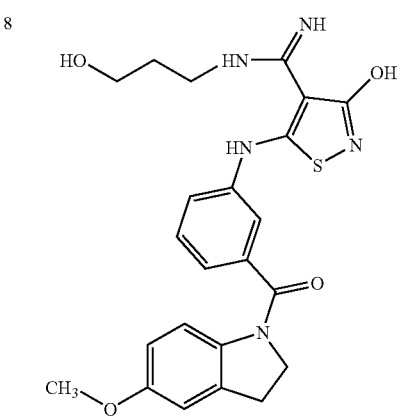 |
| Cpd # | Structure |
|---|---|
| 9 | 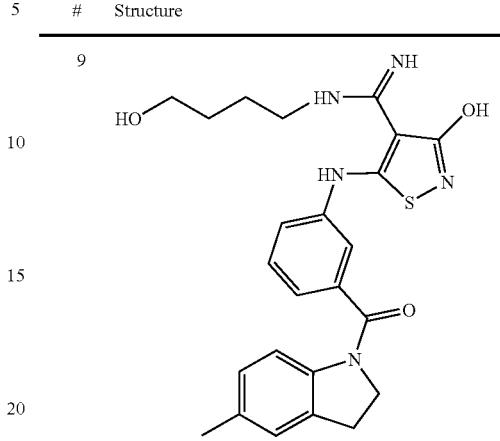 |
| 10 | 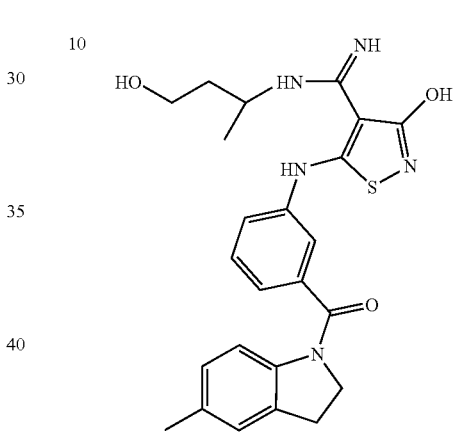 |
| 11 | 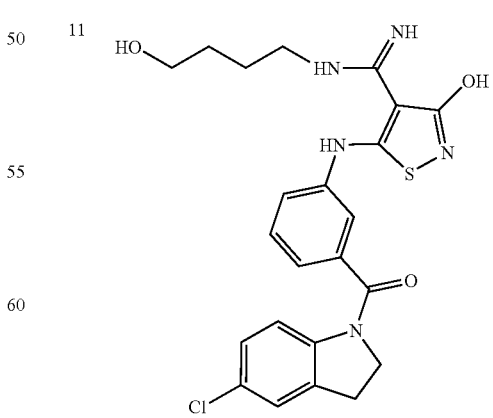 |

-continued
| Cpd # | Structure |
|---|---|
| 12 | 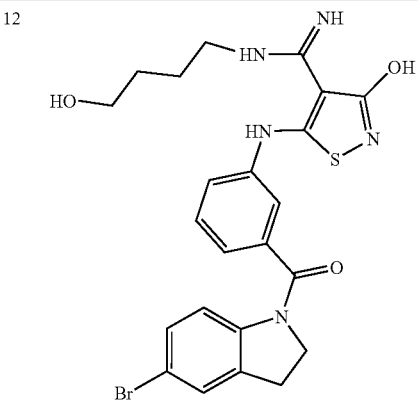 |
| 13 | 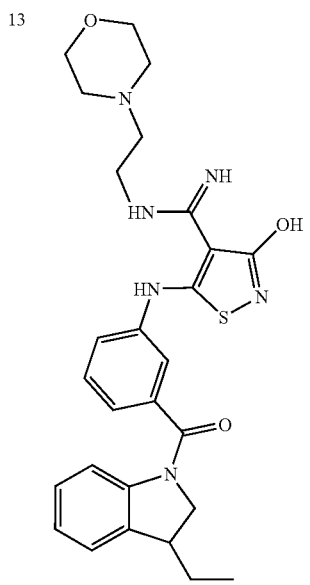 |
| 14 | 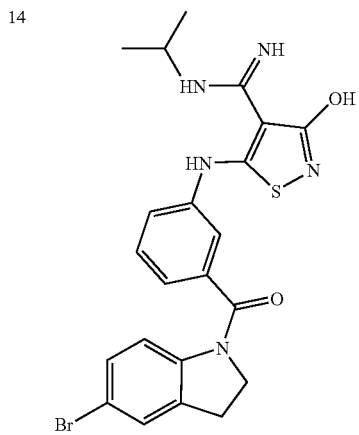 |
-continued
| Cpd # | Structure |
|---|---|
| 15 | 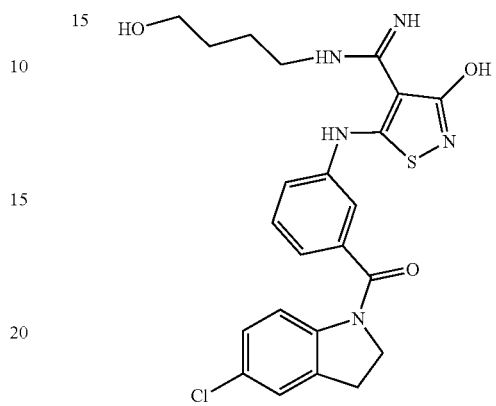 |
| 16 | 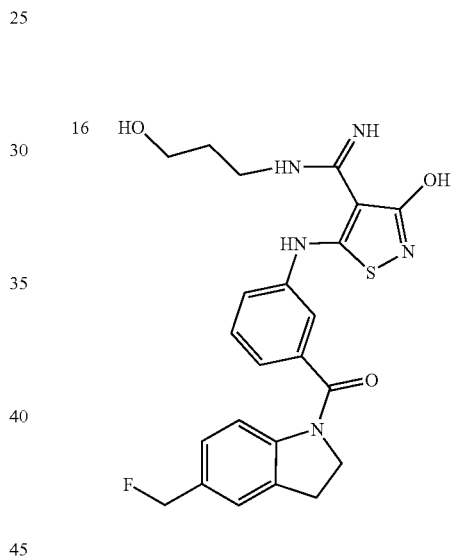 |
| 17 | 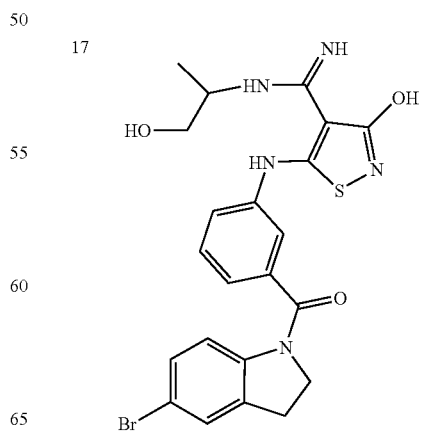 |

-continued

| Cpd # | Structure |
|---|---|
| 18 | 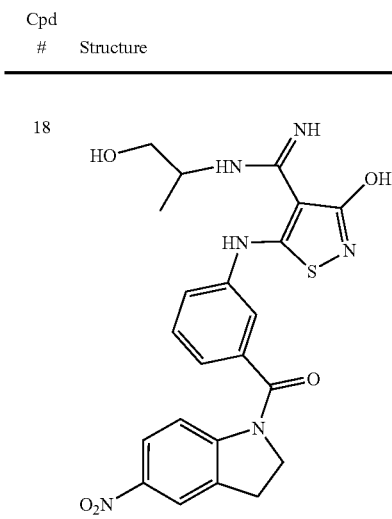 |
| 19 | 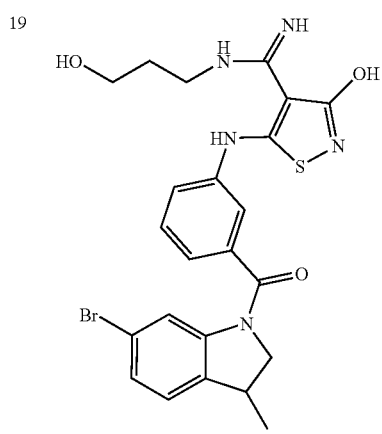 |
| 20 | 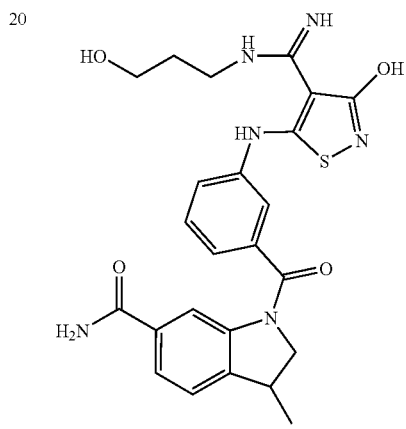 |

-continued

| Cpd # | Structure |
|---|---|
| 21 | 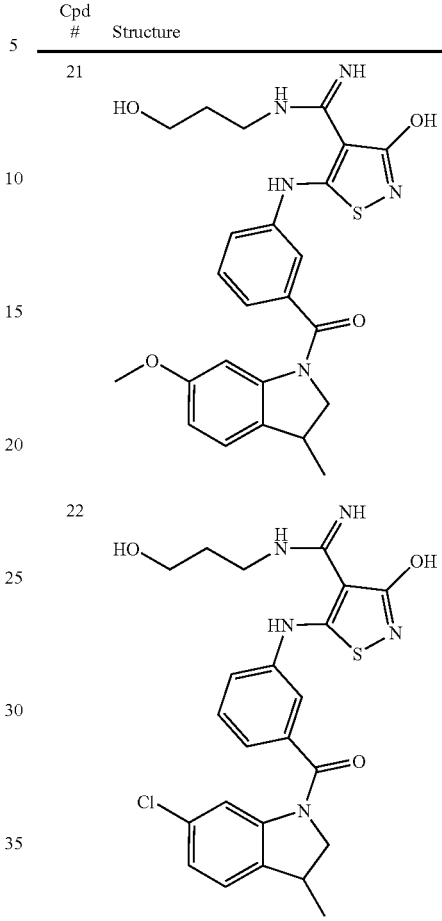 |
| 22 | 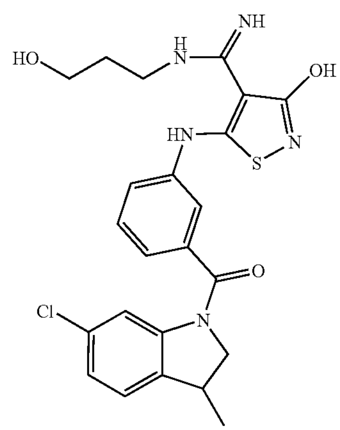 |

In another generic embodiment, this invention provides a compound of formula XII below, where the dashed bond represents an optional double bond, and where symbols T-Z represent N, CH, or $CR_{1, 2, or 4}$, that at most two of W, X, Y, and Z and at most 2 of T, U, and V are N;

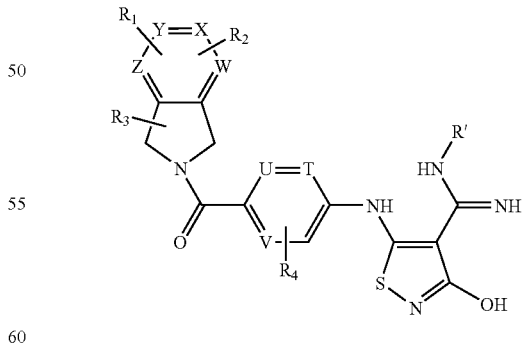

XII where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$; $CH_3CH_2OC(O)$; $C_1$-$C_5$ alkyl-C(O)—; $C_1$-$C_5$ alkyl-C(O)O—; —$NR_6R_7$, —$CH_2NR_6R_7$, —NH—C(O)—$R_6$, —C(O)$NR_8R_9$; $CH_3S(O)_2$—, or —$S(O)_2NR_8R_9$, where $R_6$-$R_9$ are, independently, H or $C_1$-$C_4$ alkyl; or any of the pairs $R_1$ and $R_2$, $R_6$ and $R_7$, or $R_8$ and $R_9$ are attached to adjacent carbons and, together with the ring atoms to which they are attached, form an additional, fused, five- or six-membered ring, optionally containing one or two heteroatoms selected from O, N, and S, which ring may be aromatic or aliphatic; wherein all alkyl, alkenyl, and cycloalkyl groups and all rings are optionally substituted with 1-3 halogen atoms; R' is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or R' is —$(CH_2)_n$—B where n is 1 or 2 and B is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

In one subgeneric embodiment, this invention provides a compound of formula XIIA-1,

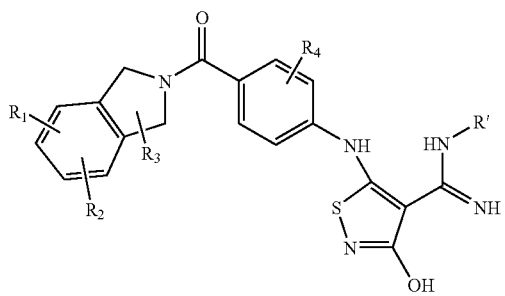

XIIA-1 where all substituents are defined as for formula XII.

In a more specific embodiment, this invention provides a compound of formula XIIA-1 where $R_3$ and $R_4$ are both H and R' is —$(CH_2)_n$—B, where n is 1 or 2 and B is defined as above.

In another more specific embodiment, this invention provides a compound of formula XIIA-1 where R' is $C_1$-$C_6$ alkyl or O—$C_1$-$C_6$ alkyl, both optionally substituted as described above.

In another more specific embodiment, this invention provides a compound of formula XIIA-1 where $R_3$ and $R_4$ are both H and R' is $C_1$-$C_6$ alkyl or O—$C_1$-$C_6$ alkyl, both optionally substituted as described above.

In another more specific embodiment, this invention provides a compound of formula XIIA-1, where $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIIA-1, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIIA-1, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

In a still more specific embodiment, this invention provides a compound of formula XIIA-1 in which $R_1$ and $R_2$ are both halogen, $R_3$ is 2-methyl, and $R_4$ is H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ and $R_2$ are both H, $R_3$ is 3-methyl, $R_4$ is 2-chloro, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ and $R_2$ are both H, $R_3$ is 3-methyl, $R_4$ is 2-(2-chloroethyl), R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 4-$CF_3$, $R_3$ is 2-hydroxymethyl, $R_2$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ and $R_2$ are both H, $R_3$ is 3-methyl, $R_4$ is 2-chloro, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which one or both of $R_1$ and $R_2$ are $CF_3$, $R_3$ and $R_4$ are H, R' is —$(CH_2)_n$—B, where n is 1, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIIA-1 in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, pyrimidyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a still more specific embodiment, this invention contemplates the compound of formula XIIA-1 in which $R_1$ is 2-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 4-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 5-chloro, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 4-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 5-bromo, $R_2$, $R_3$, and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 2-chloro, $R_2$ is 4-chloro, $R_3$ and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-chloro, $R_2$ is 4-chloro, $R_3$ and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which one or both of $R_1$ and $R_2$ are $CF_3$, $R_3$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention contemplates a compound of formula XIIA-1 in which $R_1$ is 3-$CF_3$, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention provides a compound of formula XIIA-1 in which $R_1$ is 3-cyano, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 3-hydroxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 4-hydroxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 3-methoxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 4-methoxy, $R_2$-$R_4$ are H, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention contemplates a compound of formula XIIA-1 in which $R_1$ is 3-dimethylamino, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-dimethylaminocarbonyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-methyloxycarbonyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-acetyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-acetoxy, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-dimethylamino, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-dimethylaminocarbonyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-methyloxycarbonyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-acetyl, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-acetoxy, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-$CH_2F$, $R_2$, $R_3$, and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyano, $R_2$-$R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-ethoxy, $R_2$-$R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 4-ethoxy, $R_2$-$R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-chloromethoxy, $R_2$-$R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 4-methoxy, $R_2$-$R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 2-methyl, $R_2$ is 4-methylsulfonyl, $R_3$ and $R_4$ are H, R' is —$(CH_2)_n$—B, where n is 1, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIIA-1 in which $R_1$ is 4-methoxy, $R_2$-$R_4$ are H, R' is —$(CH_2)_n$—B, where n is 1, and B is cyclopentyl, cyclopenten-3-yl, cyclopentadien-4-yl; cyclohexyl, or cyclohexen-2-yl.

In a still more specific embodiment, this invention provides a compound of formula XIIA-1 in which $R_1$ is 4-bromo, $R_2$-$R_4$ are H, R' is —$(CH_2)_n$—B, where n is 1, and B is cyclopentyl, cyclopenten-3-yl, cyclopentadien-4-yl; cyclohexyl, or cyclohexen-2-yl.

In a still more specific embodiment, this invention provides a compound of formula XIIA-1 in which $R_1$ is 3-cyclopropyl, $R_2$ is 4-chloro, $R_3$ and $R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 3-cyclopropyl, $R_2$-$R_4$ are H, R' is —$(CH_2)_n$—B, where n is 1, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 3-cyclopropyl, $R_2$ is 4-chloro, $R_3$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is trans-3-(2-methylcyclopropyl), $R_2$ is 4-chloro, $R_3$ and $R_4$ are H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyclopropyl, $R_2$ is 4-chloro, $R_3$ is 2-(2-fluoroethyl), and $R_4$ is H, R' is —$(CH_2)_n$—B, where n is 1, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyclopropyl, $R_2$ is 4-chloro, $R_3$ is 2-chloro, $R_4$ is 2-fluoro, R' is —$(CH_2)_n$—B, where n is 1, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ and $R_2$ are both halogen, $R_3$ is 2-methyl, and $R_4$ is H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ and $R_2$ are H, $R_3$ is 3-methyl, $R_4$ is 2-chloro, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ and $R_2$ are both H, $R_3$ is 3-methyl, $R_4$ is 2-(2-chloroethyl), R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 4-$CF_3$, $R_3$ is 2-hydroxymethyl, $R_2$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ and $R_2$ are both H, $R_3$ is 3-methyl, $R_4$ is 2-chloro, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which one or both of $R_1$ and $R_2$ are $CF_3$, $R_3$ and $R_4$ are H, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIIA-1 in which $R_1$ is isothiazolyl, isoxazolyl, oxazolyl, oxazolidyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl; $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, pyrimidyl, pyrrolyl, pyrrolinyl, pyrrolidinyl, pyrrolidinonyl, pyrazolyl, imidazolyl, imidazolinonyl; oxazolyl, oxazolinyl, oxazolidinyl, oxazolidinonyl, isoxazolyl, isoxazolinyl, isoxazolidinyl, isoxazolidinonyl, thiazolyl, thiazolinyl, thiazolidinyl, thiazolidinonyl, isothiazolyl, isothiazolinyl, isothiazolidinyl, isothiazolidinonyl, indolyl, indolyl, oxindolyl, isoindolyl, quinolyl, isoquinolyl, and naphthyl.

In a still more specific embodiment, this invention contemplates the compound of formula XIIA-1 in which $R_1$ is 2-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 4-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 5-chloro, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 4-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 5-bromo, $R_2$, $R_3$, and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 2-chloro, $R_2$ is 4-chloro, $R_3$ and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention contemplates the compound of formula XIIA-1 in which $R_1$ is 3-chloro, $R_2$ is 4-chloro, $R_3$ and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which one or both of $R_1$ and $R_2$ are $CF_3$, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention contemplates a compound of formula XIIA-1 in which $R_1$ is 3-$CF_3$, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, phenyl.

In a still more specific embodiment, this invention provides a compound of formula XIIA-1 in which $R_1$ is 3-cyano, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 3-hydroxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 4-hydroxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 3-methoxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention provides a compound of formula XIIA-1 in which $R_1$ is 4-methoxy, $R_2$-$R_4$ are H, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In a still more specific embodiment, this invention contemplates a compound of formula XIIA-1 in which $R_1$ is 3-dimethylamino, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-dimethylaminocarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-methyloxycarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-acetyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-acetoxy, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-dimethylamino, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-dimethylaminocarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-methyloxycarbonyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-acetyl, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 4-acetoxy, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention contemplates a compound of formula XIIA-1 in which $R_1$ is 3-$CH_2F$, $R_2$, $R_3$, and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyano, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-ethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 4-ethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-chloromethoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 4-methoxy, $R_2$-$R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 2-methyl, $R_2$ is 4-methylsulfonyl, $R_3$ and $R_4$ are H, R' is —$(CH_2)_n$—B, where n is 2, and B is 3-methyl-2-isothiazolyl, 3-methyl-2-isoxazolyl, 3-methyl-4-oxazolyl, 3-methyl-2-pyrrolyl, 3-methyl-2-pyridyl, or m-tolyl.

In a still more specific embodiment, this invention provides a compound of formula XIIA-1 in which $R_1$ is 4-methoxy, $R_2$-$R_4$ are H, R' is —$(CH_2)_n$—B, where n is 2, and B is cyclopentyl, cyclopenten-3-yl, cyclopentadien-4-yl; cyclohexyl, or cyclohexen-2-yl.

In a still more specific embodiment, this invention provides a compound of formula XIIA-1 in which $R_1$ is 4-bromo, $R_2$-$R_4$ are H, R' is —$(CH_2)_n$—B, where n is 2, and B is cyclopentyl, cyclopenten-3-yl, cyclopentadien-4-yl; cyclohexyl, or cyclohexen-2-yl.

In a still more specific embodiment, this invention provides a compound of formula XIIA-1 in which $R_1$ is 3-cyclopropyl, $R_2$ is 4-chloro, $R_3$ and $R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 3-cyclopropyl, $R_2$-$R_4$ are H, R' is —$(CH_2)_n$—B, where n is 2, and B is pyridyl, piperazinyl, piperazinonyl, piperidinyl, piperidinonyl, morpholyl, furyl, tetrahydrofuryl, or pyrimidyl.

In a still more specific embodiment, this invention provides a compound of formula XIIA-1 in which $R_1$ is 3-cyclopropyl, $R_2$ is 4-chloro, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is trans-3-(2-methylcyclopropyl), $R_2$ is 4-chloro, $R_3$ and $R_4$ are H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyclopropyl, $R_2$ is 4-chloro, $R_3$ is 2-(2-fluoroethyl), and $R_4$ is H, R' is —$(CH_2)_n$—B, where n is 2, and B is isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, or phenyl.

In a still more specific embodiment, this invention provides a compound of formula XIIA-1 in which $R_1$ is 3-cyclopropyl, $R_2$ is 4-chloro, $R_3$ is 2-chloro, $R_4$ is 2-fluoro, R' is —$(CH_2)_n$—B, where n is 2, and B is 3-methyl-2-pyridyl, 3-methyl-2-piperazinyl, 3-methylpiperazin-2-on-1-yl, 3-methyl-1-piperidinyl, 3-methyl-2-piperidinonyl, 3-methyl-1-morpholyl, 3-methyl-2-furyl, 3-methyl-2-tetrahydrofuryl, or 2-methyl-1-pyrimidyl.

In another more specific embodiment, this invention provides a compound of formula XIIA-1 in which $R_1$ and $R_2$ are halogen, $R_3$ and $R_4$ are H, and R' is methyl, ethyl, isopropyl, or sec-butyl.

In another more specific embodiment, this invention provides a compound of formula XIIA-1 in which $R_1$ is halogen, $R_2$-$R_4$ are H, and R' is methyl, ethyl, isopropyl, or sec-butyl.

In another more specific embodiment, this invention provides a compound of formula XIIA-1 in which $R_1$ and $R_2$ are halogen, $R_3$ and $R_4$ are H, and R' is 1,2-chloropropan-3-yl.

In another more specific embodiment, this invention provides a compound of formula XIIA-1 in which $R_1$ and $R_2$ are halogen, $R_3$ and $R_4$ are H, and R' is 1-hydroxy-butan-3-yl.

In another more specific embodiment, this invention provides a compound of formula XIIA-1 in which $R_1$ is bromo, $R_2$-$R_4$ are H, and R' is isopropyl.

In another more specific embodiment, this invention provides a compound of formula XIIA-1 in which $R_1$ and $R_2$ are halogen, $R_3$ and $R_4$ are H, and R' is 1,2-dihydroxy-propan-3-yl.

In another more specific embodiment, this invention provides a compound of formula XIIA-1 in which $R_1$ and $R_2$ are halogen, $R_3$ and $R_4$ are H, and R' is 2-hydroxyethyl.

In another more specific embodiment, this invention provides a compound of formula XIIA-1 in which $R_1$ and $R_2$ are halogen, $R_3$ and $R_4$ are H, and R' is 4-hydroxybutyl.

In another more specific embodiment, this invention provides a compound of formula XIIA-1 in which $R_1$ and $R_2$ are halogen, $R_3$ and R are H, and R' is 1,2-dihydroxybutan-4-yl.

In another more specific embodiment, this invention provides a compound of formula XIIA-1 in which $R_1$ and $R_2$ are halogen, $R_3$ and $R_4$ are $C_1$-$C_6$ alkyl, and R' is 1,2-dihydroxybutan-3-yl.

In another more specific embodiment, this invention provides a compound of formula XIIA-1 in which $R_1$ and $R_2$ are halogen, $R_3$ and $R_4$ are H, and R' is 4-hydroxybutyl.

In another more specific embodiment, this invention provides a compound of formula XIIA-1 in which $R_1$ and $R_2$ are halogen, $R_3$ and $R_4$ are H, and R' is 3-hydroxypropyl.

In another more specific embodiment, this invention provides a compound of formula XIIA-1, where $R_1$ and $R_2$ are fused cyclohexyl or fused cyclopentyl, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula XIIA-1, where $R_1$ and $R_2$ are benzo, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XIIA-1, where $R_1$ and $R_2$, at positions 2 and 3, are fused cyclopentyl, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XIIA-1, where $R_1$ and $R_2$, at positions 3 and 4, are benzo, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

In another more specific embodiment, this invention contemplates a compound of formula XIIA-1, where $R_1$ and $R_2$, at positions 3 and 4, are benzo, said benzo bearing fluoro at each ortho position, $R_3$ and $R_4$ are H, and R' is isopropyl, 2-(2-furyl)ethyl, 2-hydroxyethyl, 2,3-dihydroxy-1-propyl, or 3,4-dihydroxy-2-butyl.

Additional contemplated compounds for generic embodiment XIIA-1 are shown in the table below

| Cpd # | Structure |
|---|---|
| 1. | 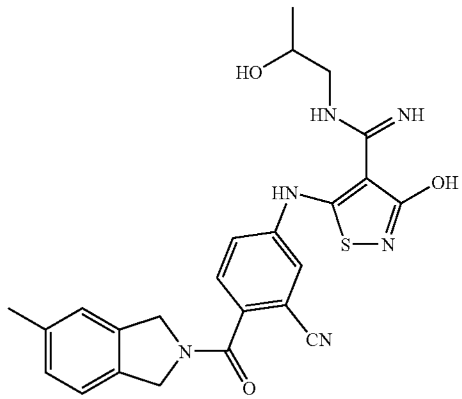 |
| 2. | 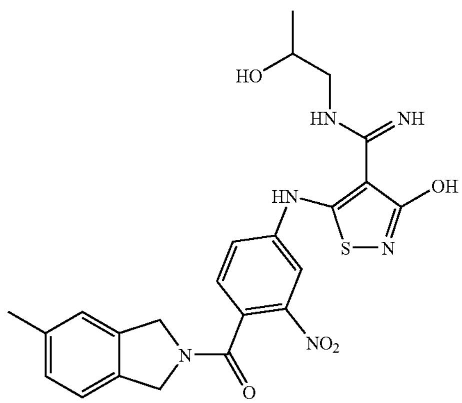 |
| 3. | 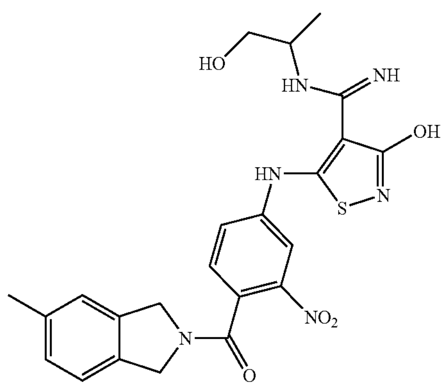 |
| 4. | 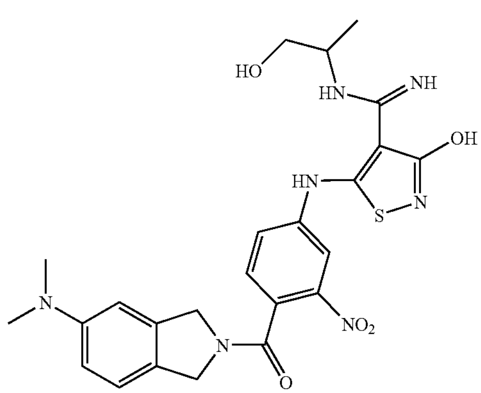 |

-continued

| Cpd # | Structure |
|---|---|
| 5. | 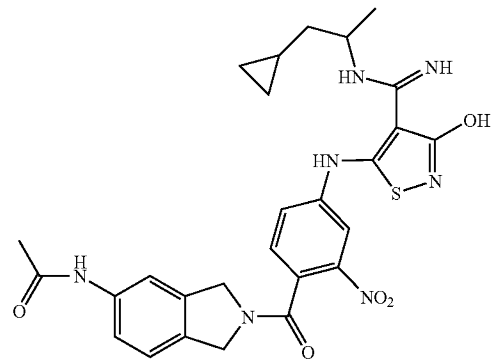 |
| 6. | 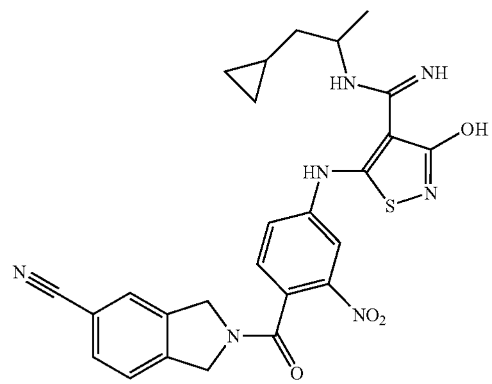 |
| 7. | 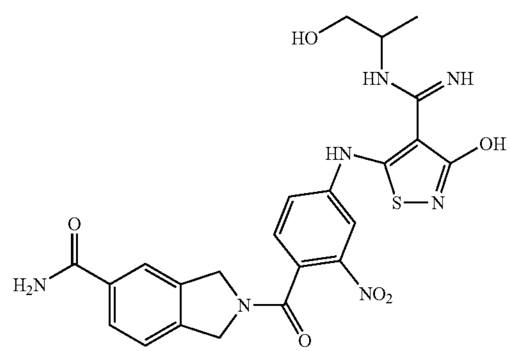 |
| 8. | 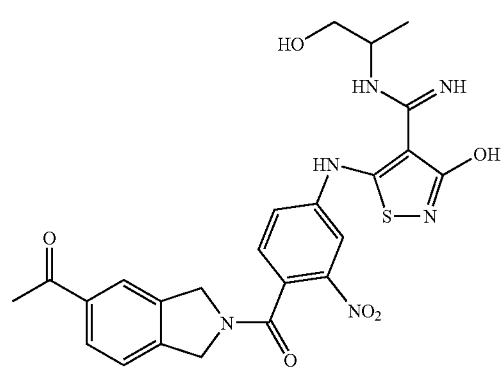 |

| Cpd # | Structure |
|---|---|
| 9. | 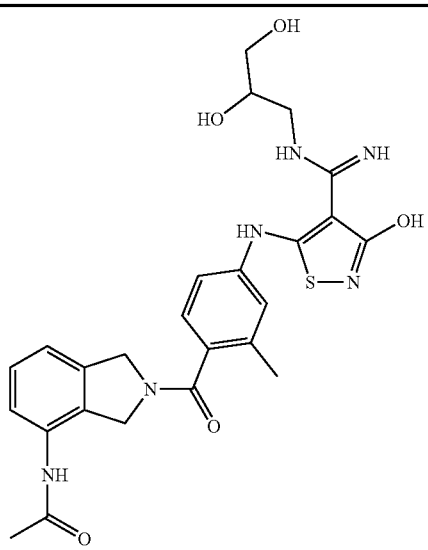 |
| 10. | 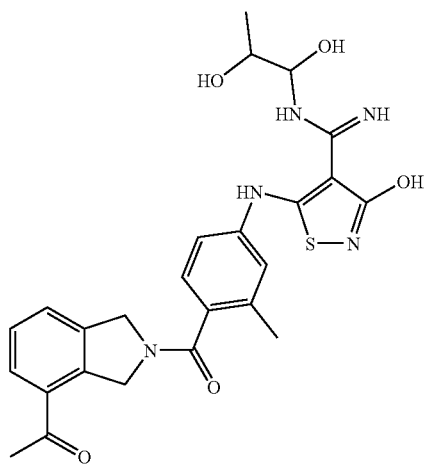 |
| 11. | 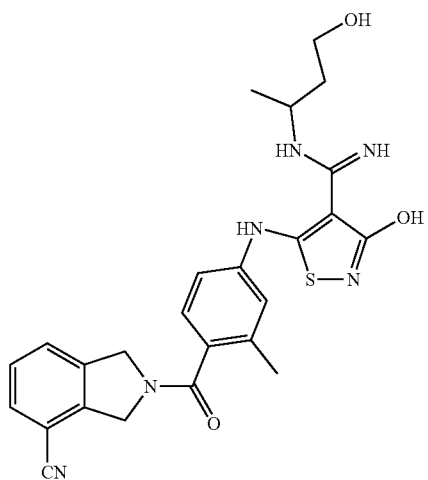 |
| 12. | 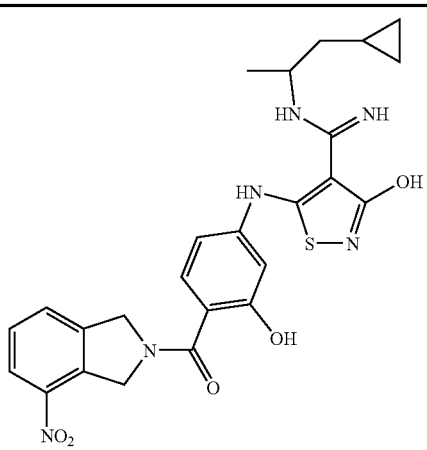 |
| 13. | 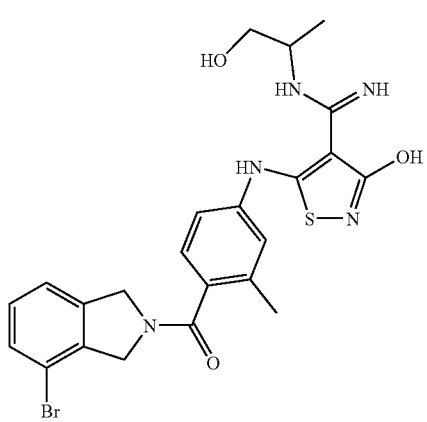 |
| 14. | 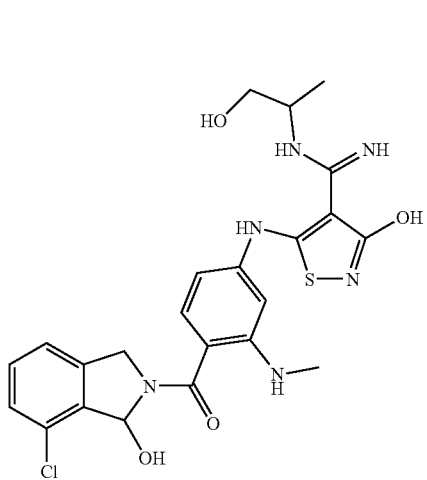 |

-continued
| Cpd # | Structure |
|---|---|
| 15. | 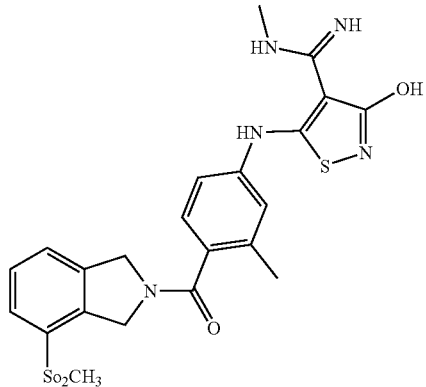 |
| 16. | 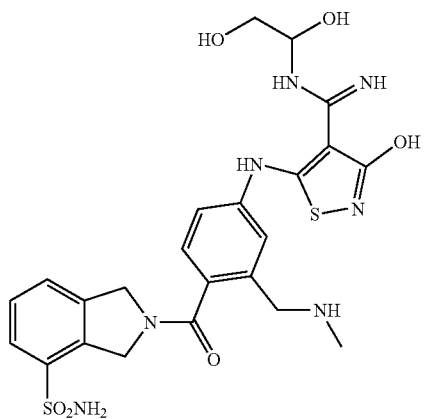 |
| 17. | 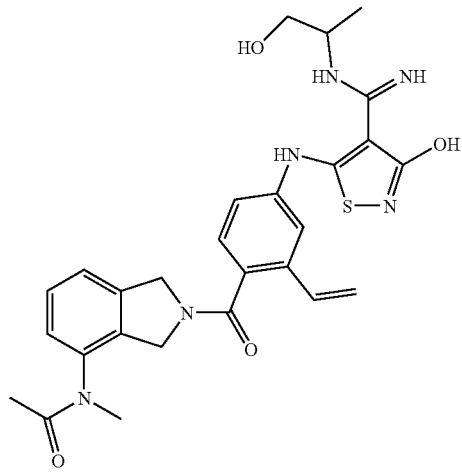 |
-continued
| Cpd # | Structure |
|---|---|
| 18. | 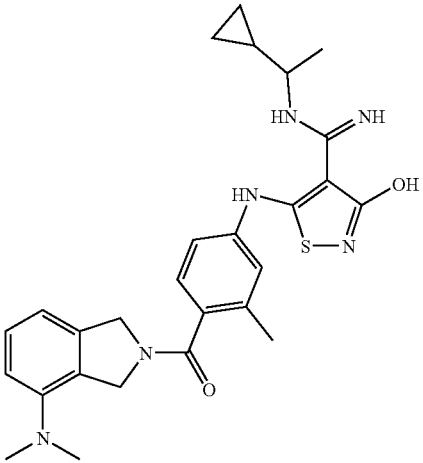 |
| 19. | 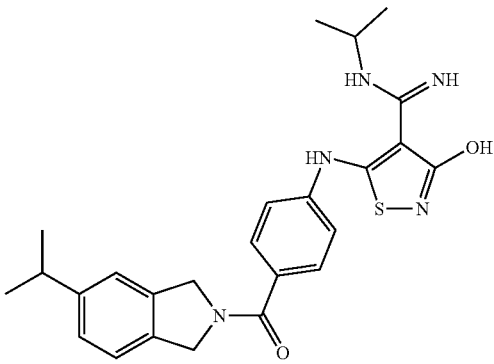 |
| 20. | 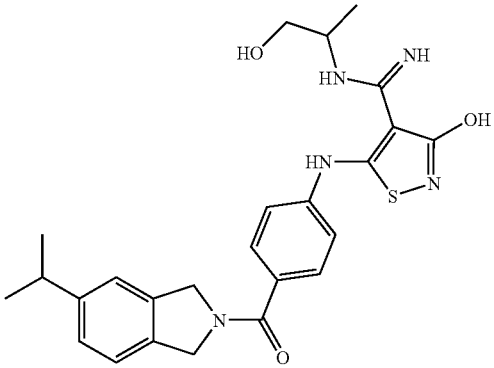 |

-continued

| Cpd # | Structure |
|---|---|
| 21. | 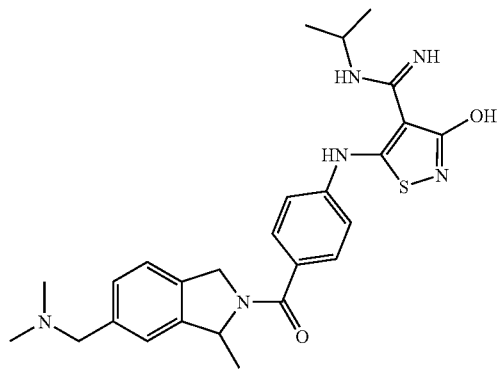 |
| 22. | 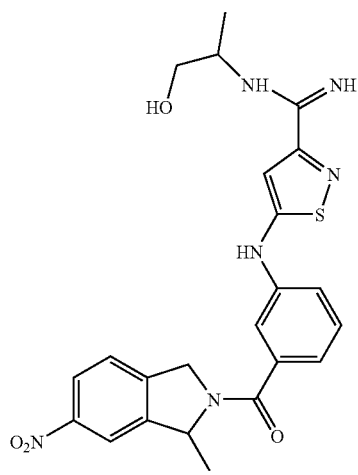 |
| 23. | 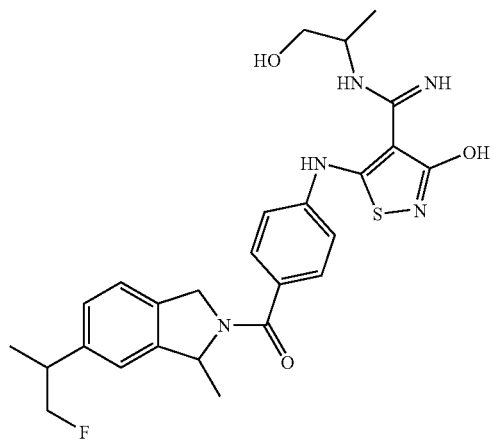 |

-continued

| Cpd # | Structure |
|---|---|
| 24. | 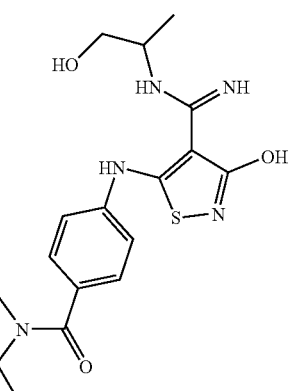 |

In an additional subgeneric embodiment, this invention provides a compound of formula XIIB-1,

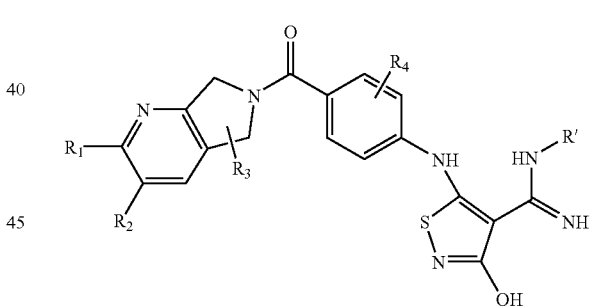

VIIB-1 where $R_1$-R' are defined as for formula A.

In a more specific embodiment, this invention provides a compound of formula XIIB-1, where R' is isopropyl, 2-(2-furyl)ethyl, 2-hydroxyethyl, 2,3-dihydroxy-1-propyl, or 3,4-dihydroxy-2-butyl.

In another more specific embodiment, this invention provides a compound of formula XIIB-1, where $R_1$-$R_4$ are, independently, H, $C_1$-$C_3$ alkyl, or halogen, and R' is —$(CH_2)_n$—B, where n is 1 or 2, and B is pyridyl, piperazinyl, piperazinonyl, piperidinyl, piperidinonyl, morpholyl, furyl, tetrahydrofuryl, or pyrimidyl.

In another subgeneric embodiment, this invention provides a compound of formula XIIB-2 below,

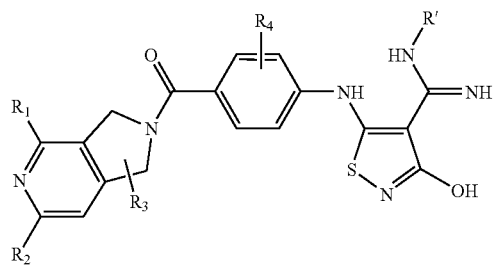

XIIB-2

In a more specific embodiment, this invention provides a compound of formula XIIB-2 where $R_1$-$R_4$ are H and R' is isopropyl, 2-butyl, 2-(2-furyl)ethyl, 2-hydroxyethyl, 2,3-dihydroxy-1-propyl, or 3,4-dihydroxy-2-butyl.

In another more specific embodiment, this invention provides a compound of formula XIIB-2, where $R_1$ is amino, methyl amino, dimethylamino, dimethylaminomethyl, or acetylamino, $R_2$-$R_4$ are H and R' is $C_1$-$C_6$ alkyl, optionally substituted with halogen, $C_1$-$C_3$ alkoxy, or hydroxy.

In another more specific embodiment, this invention provides a compound of formula XIIB-2, where $R_2$ is amino, methyl amino, dimethylamino, dimethylaminomethyl, or acetylamino, $R_1$ and $R_2$-$R_4$ are H, and R' is $C_1$-$C_6$ alkyl, optionally substituted with halogen, $C_1$-$C_3$ alkoxy, or hydroxy.

In another more specific embodiment, this invention provides a compound of formula XIIB-2, where $R_1$ is nitro, cyano, methylcarbamoyl, dimethylcarbamoyl, or aminosulfonyl, $R_2$-$R_4$ are H and R' is $C_1$-$C_6$ alkyl, optionally substituted with halogen, $C_1$-$C_3$ alkoxy, or hydroxy.

Examples of additional embodiments of the aza-substituted type are shown below, along with prophetic examples of each. In the first column, non-carbon ring members of T-Z of formula XII are identified.

| Generic Structure: Formula XII, where | Example |
|---|---|
| X = N<br>XIIB-3 | XIIB-3a |
| X and Z = N<br>XIIB-4 | XIIB-4a |
| X and T = N<br>XIIB-5 | XIIB-5a |

-continued
| Generic Structure: Formula XII, where | Example |
|---|---|
| T = N XIIB-6 | 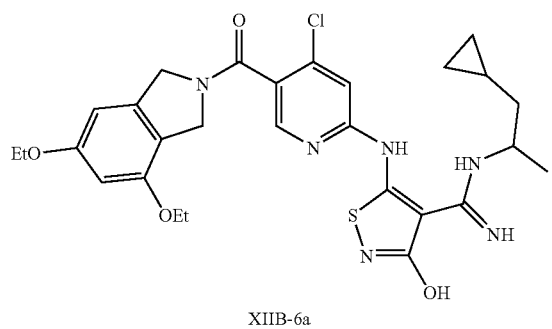<br>XIIB-6a |
| U = N XIIB-7 | 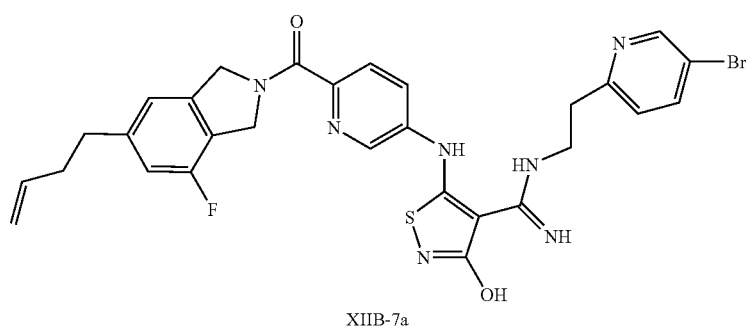<br>XIIB-7a |
| X and U = N XIIB-8 | 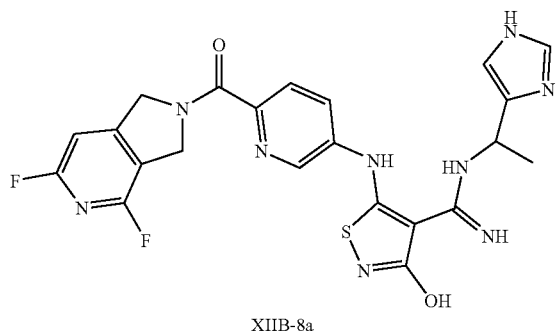<br>XIIB-8a |
| U, X, and Z = N XIIB-9 | 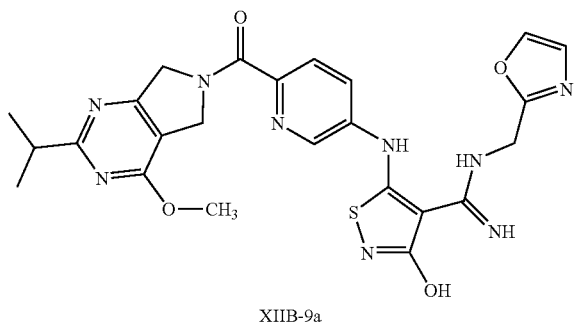<br>XIIB-9a |

| Generic Structure: Formula XII, where | Example |
|---|---|
| U and W = N<br>XIIB-10 | 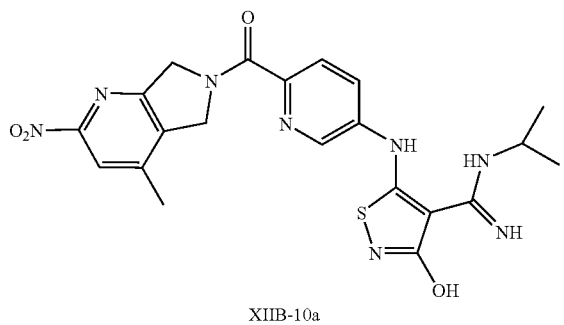<br>XIIB-10a |
| U and Z are N<br>XIIB-11 | 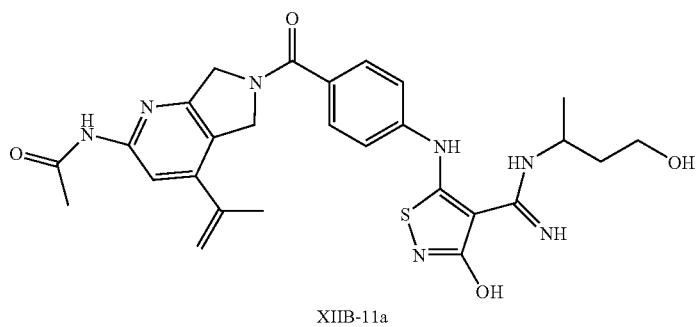<br>XIIB-11a |
| X, V, and T = N<br>XIIB-12 | 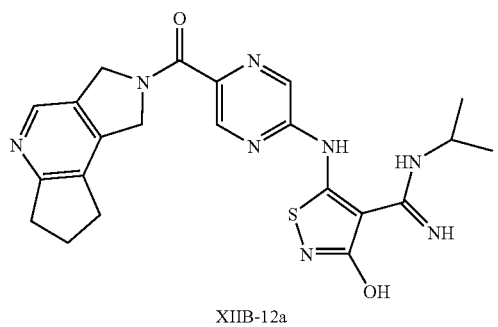<br>XIIB-12a |

In additional more specific embodiments, the invention provides compounds according to any of formulas XIIB-1 to XIIB-12, wherein $R_1$-$R_4$ are all independently halo, halomethyl, methyl, methoxy, ethyl, vinyl, ethynyl, or H, and $R_5$ is —(CH$_2$)$_n$—B, where n is 1 or 2, and B is imidazolyl, cyclopentyl, cyclopenten-3-yl, cyclohexyl, cyclohexen-2-yl, phenyl, pyridyl, piperazinyl, piperazinonyl, piperidinyl, piperidinonyl, morpholyl, furyl, tetrahydrofuryl, or pyrimidyl.

In additional more specific embodiments, the invention contemplates compounds according to any of formulas XIIB-1 to XIIB-12, where $R_1$ is bromo, $R_2$-$R_4$ are all H and $R_5$ is isopropyl, 2-hydroxyethyl, 1-hydroxy-2-propyl, 2,3-dihydroxy-1-propyl, or 3,4-dihydroxy-2-butyl.

In still more specific embodiments, the invention contemplates compounds according to any of formulas XIIB-1 to XIIB-12, where $R_1$-$R_4$ are all H and $R_5$ is isopropyl or 2,3-dihydroxy-1-propyl.

This invention also contemplates other patterns of aza-substitution and poly-aza-substitution not depicted in the examples shown above.

EXPERIMENTAL DETAILS

Synthesis

Compounds of this invention are prepared according to the schemes below.

I. Synthesis of Contemplated Compounds

The choice of synthetic strategy is not critical to the practice of this invention. Suitable approaches include both those in which commercially available or previously synthesized isothiazoles are modified and those involving cyclization of a thiocarbamoyl acetamide to form the isothiazole ring system.

Scheme 1 illustrates a reaction of 2-cyanoacetamide with an isothiocyanate to an intermediate, and subsequent ring closure by oxidation followed by amination by heating the cyano compound with an amine (e.g., isopropylamine, 2-amino-propan-1-ol) to provide the amidine 4. This general strategy can be used for compounds of formulas II-VI.

More specifically, in step 1 of Scheme 1, 2-cyanoacetamide was treated with a strong base (e.g., KOH) and then with a substituted phenyl isothiocyanate 1 in N,N-dimethylformamide (DMF) at a temperature ranging from about −10° C. to 60° C., preferably about 25° C., for a period of about 8 to 24 hours, preferably about 16 hours, to produce compound 2. Then, in step 2 of Scheme 1, compound 2 (in the same reaction vessel as step 1) was treated at about 0° C. with aqueous chloramine solution for about 12 hours, and compound 3 was isolated.

Alternatively, the reaction mixture of step 1 was concentrated and diluted with water, followed by acidification with aqueous hydrochloric acid solution. Filtration and washing with water afforded compound 2. In an organic solvent, preferably ethyl acetate, compound 2 was treated with bromine to provide isothiazole 3. In step 3 of Scheme 1, compound 3 was agitated with an alkylamine (including a hydroxyalkylamine) in ethanol, in a sealed reaction vessel at about 80-120° C., preferably about 100° C., for about 16 to 24 hours, preferably 18 hours, to provide amidine 4 in good yield after chromatography.

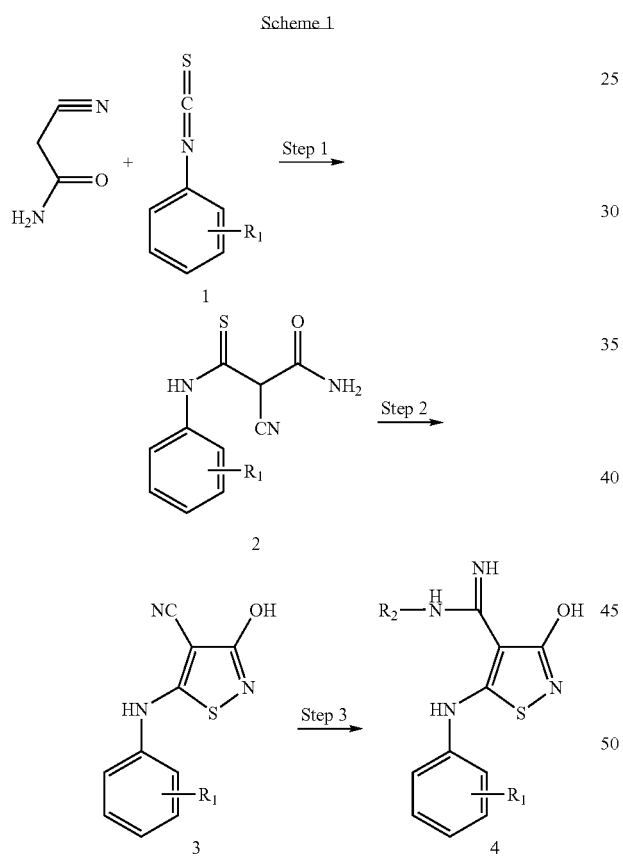

Scheme 1 includes the synthesis of compounds wherein $R_1$ is a phenoxy or phenylthio group. In a variation of Scheme 1, a pyridyl, naphthyl, or quinolyl isothiocyanate may be used in place of the phenyl isothiocyanate that is illustrated. Compounds in which $R_1$ is a benzyl, benzoyl, phenylazido, or phenylacetyl group are prepared using commercially available precursors such as p-nitro benzophenone, p-nitro diphenylmethane, and p-nitro diphenylazide. In a variation of Scheme 1, a pyridyl, naphthyl, or quinolyl isothiocyanate may be used in place of the phenyl isothiocyanate that is illustrated.

Preparation of Isothiazoles Using 4-substituted Anilines

The p-phenoxy phenylisothiocyanates can be synthesized by condensing the appropriately substituted p-fluoronitrobenzene with a phenol or aniline, as shown below.

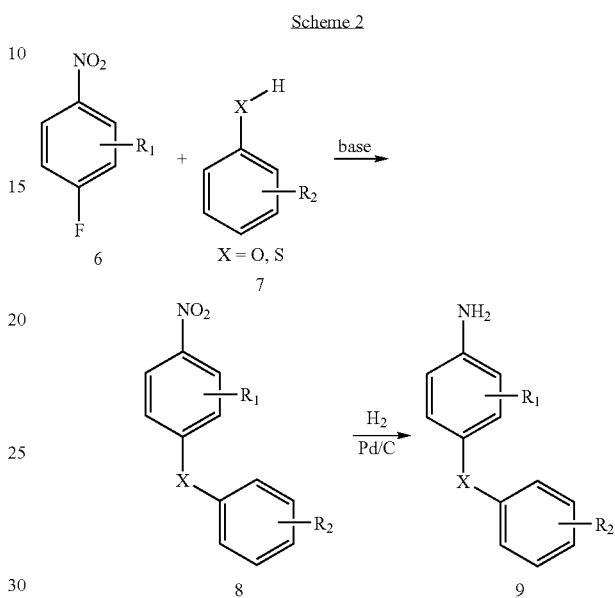

General Procedure for 4-substituted Phenols and Anilines

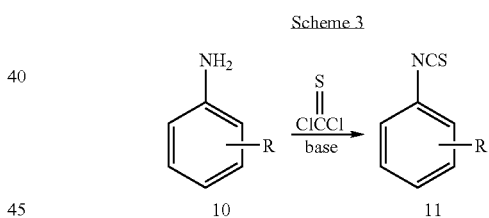

Preparation of Isothiocyanates from Anilines

A mixture comprising a 4-fluoronitrobenzene 6 (0.02 mol), a suitable aniline or phenol 7 (0.022 mol), and potassium carbonate (0.022 mol) in 40 ml of anhydrous DMF was heated overnight at 150° C. with stirring. After cooling to room temperature, the reaction mixture was poured into 500 ml of ice water and stirred for 30 min. The precipitate was collected by filtration, washed with water, and dried in vacuo to give a 4-substituted nitrobenzene 8. The nitrobenzene 8 was dissolved in 100-200 ml of ethanol and stirred for 5-6 hours under hydrogen in the presence of catalyst 10% Pd—C (50-100 mg), at atmospheric pressure and ambient temperature. The catalyst was removed by filtration, and the filtrate was concentrated to dryness to give the crude substituted aniline 9, which was used for the next step without further purification.

Method 1: The appropriate aniline 10 (30 mmol) was added to a biphasic mixture of $CHCl_3$ and saturated aqueous $NaHCO_3$ (1:1, v/v, 247 ml), followed by dropwise addition at room temperature, with stirring, of a solution of thiophosgene (30 mmol) in dichloromethane (20 ml). The mixture was stirred vigorously at room temperature for 1 hour. The bottom layer of the mixture was separated, and the aqueous layer was extracted twice with CHCl$_3$. The combined organic solution was washed with water, dried over MgSO$_4$, and evaporated to give isocyanate 11 as a yellow solid, which was used for the next step without further purification.

Method 2: To a solution of aniline (30 mmol) and DBU (60 mmol) in 60 ml of anhydrous dichloromethane, a solution of thiophosgene (30 mmol) in 20 ml of dry dichloromethane was added dropwise with stirring at room temperature over 30 minutes. The reaction mixture was diluted with 200 ml of chloroform and washed with 1N HCl solution (300 ml×2) and water (300 ml) respectively. The chloroform solution was dried over anhydrous sodium sulfate, and the solvent was evaporated in vacuo. The residue was purified by silica gel column to give pure isothiocyanates.

(3) Preparation of Isothiazoles (see Scheme 1)

3-Hydroxy-5-phenylamino-isothiazol-4-carbonitrile

Method 1: To a cooled suspension of finely ground potassium hydroxide (0.337 g, 6 mmol) in DMF (8 ml) was added cyanoacetamide (0.505 g, 6 mmol) followed by addition of 4-methoxyphenyl isothiocyanate (0.83 ml, 6 mmol). The reaction mixture was stirred at room temperature for 24 hours and treated with aqueous chloramine (30 ml) at 0° C. The mixture was further stirred at room temperature for 12 hours, and evaporated to give a residue, which was partitioned between water and ethyl acetate. The aqueous layer was washed twice with ethyl acetate, then cooled to 0° C. and acidified with 1N HCl solution to about pH-3. The precipitate was filtered and washed with water and dried in vacuo to afford a yellow powder (0.95 g, 73%).

Method 2: Condensation of isothiocyanate with 2-cyanoacetamide: Procedure 1: To a cooled suspension of finely ground potassium hydroxide (0.337 g, 6 mmol) in DMF (8 ml) was added cyanoacetamide (0.505 g, 6 mmol), followed by addition of 4-methoxyphenyl isothiocyanate (0.83 ml, 6 mmol). The reaction mixture was stirred at room temperature for 16 hours and concentrated to give a syrup, which was diluted with water and acidified with 1 N aqueous HCl solution. The suspension was filtered, and the solid was washed with water and dried in vacuo. Procedure 2: To a solution of potassium tert-butoxide (20 mmol) in 20 ml of anhydrous THF was added 2-cyanoacetamide (20 mmol). The mixture was cooled to 5° C. and a solution of isothiocyanates (20 mmol) in 5 ml of dry THF was added dropwise with stirring under argon. After 15 min with stirring at 5° C., the reaction mixture was warmed to room temperature and stirred for another 1 h. The reaction mixture was poured into 1000 ml of ice water and neutralized with 2% HCl solution to pH<7. The solid was filtered and washed with water. After drying in vacuo, the crude product was obtained and it is pure enough for next step (Yield: 72-97%).

Cyclization: The above dried solid was dissolved in ethyl acetate (30 ml), and a solution of bromine (0.31 ml, 6 mmol) in ethyl acetate (25 ml) was added drop wise into the mixture. After 1 hour of stirring at room temperature, the reaction mixture was filtered, and the solid was washed with ethyl acetate and dried in vacuo to afford a yellow powder (0.86 g, 66%).

Preparation of 5-benzimidazole, oxazole, thiazole, and isothiazole carboxamidines

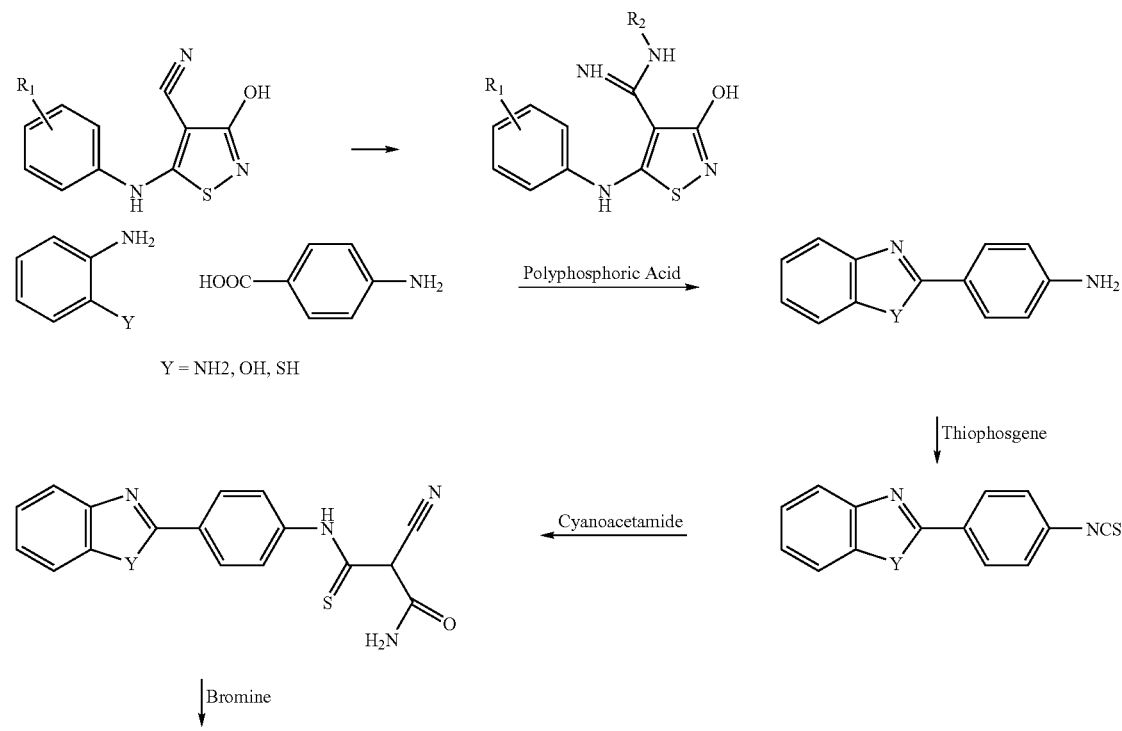

The 2-(4-aminophenyl)benzoxazole, benzothiazole, or benzimidazole was prepared by condensation of the appropriate aniline derivative with p-amino benzoic acid using polyphosphoric acid. The product was converted to the corresponding isothiocyanate with thiophosgene and subsequently condensed with cyanoacetamide to form the thiocarbamoyl cyanoacetamide. Treatment with bromine afforded the cyano hydroxy thiazole, which was converted to carboxamidine by treatment with the appropriate amide, as shown above.

PREPARATION OF EXAMPLES

A typical procedure for synthesis of isothiazole carboxamidines is that employed for synthesis of 3-hydroxy-N-isopropyl-5-(4-phenoxyphenylamino)-isothiazole-4-carboxamidine:

A mixture of 3-hydroxy-4-cyano-5-(4-phenoxyphenylamino)isothiazole (5 g) and isopropylamine (25 ml) in 250 ml of ethanol was placed into a high-pressure reaction equipment and heated to 120° C. with stirring for 9 hours. The reaction mixture was cooled to room temperature, and the solvent was removed under vacuum. The residue was treated with 500 ml of diethyl ether, and the precipitates were filtered and washed with diethyl ether. The filtrates were evaporated to dryness, and the residue was purified by silica gel column chromatography (chloroform/methanol, 60:1) to give 3.51 g (59%) of product as a foam, which was recrystallized from methanol to give yellowish crystals. MS: 368; $^1$H NMR (DMSO-d6): 10.44 (brs, 1/2H, NH, $D_2O$ exchangeable), 9.81 (brs, 1/2H, NH, $D_2O$ exchangeable), 9.51 (brs, 1/2H, NH, $D_2O$ exchangeable), 9.15 (brs, 1/2H, NH, $D_2O$ exchangeable), 8.36 (s, 1H, OH, $D_2O$ exchangeable), 7.87 (brs, 1/2H, NH, $D_2O$ exchangeable), 7.66 (brs, 1/2H, NH, $D_2O$ exchangeable), 7.35 (t, 2H, J=7.5 Hz, ArH), 7.08 (t, 1H, J=7.5 Hz, ArH), 6.96 (m, 6H, ArH), 3.85 (m, 1H, CH), 1.20 (d, 6H, J=6.3 Hz, 2×$CH_3$).

The isothiazole carboxamidines listed in table 2 were synthesized by the procedure above. Most reactions were run using 100-200 mg of starting materials in about 20-30 ml of ethanol at 90° C. for 24-48 hours. In most cases products were purified by silica gel column chromatography. Some compounds were purified by preparative HPLC or TLC.

N-Cyclohexylmethyl-3-hydroxy-5-(3-phenoxy-phenylamino)-isothiazole-4-carboxamidine

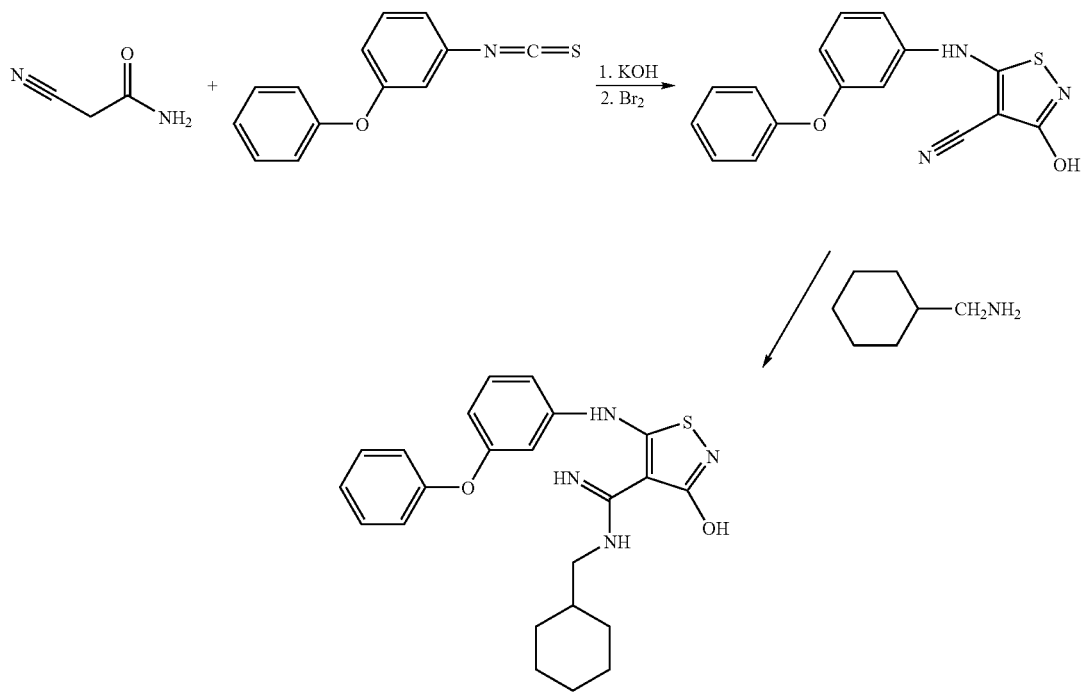

To a suspension of 85% powdered KOH in 20 ml DMF was added 1.74 g of cyanoacetamide at room temperature. The solution was stirred at room temperature for 15 minutes and then cooled in a water bath at room temperature. To this solution 4.7 g of 3-phenoxy-phenyl isothiocyanate was added dropwise. The solution exothermed slightly with the internal temperature rising to 28° C. during the addition. The solution was stirred at room temperature for 16 h, then diluted with 150 ml water and extracted with ethyl acetate to remove small amounts of starting material and by-products. The aqueous layer was isolated and acidified with 1N HCl to pH 1 with vigorous stirring. The resulting tan precipitate was filtered, washed with water, and dried for 16 hours in a vacuum oven to afford 4.66 g of 2-cyano-2-(3-phenoxy-phenylthiocarbamoyl)-acetamide.

The product of the previous step was suspended in 100 ml ethyl acetate and stirred vigorously. A solution of 767 µl Br$_2$ in 25 ml ethyl acetate was added via addition funnel over 30 minutes. After 1.5 h, saturated aqueous NaHCO$_3$ was added, and the resulting biphasic mixture was stirred for 30 minutes. The mixture was filtered and washed with ethyl acetate, followed by water and dried in vacuo to afford 2.75 g (43%) of 3-hydroxy-5-(3-phenoxy-phenylamino)-isothiazole-4-carbonitrile as a tan solid. To a suspension of 190 mg of this material in 10 ml ethyl alcohol in a 40 ml Teflon-lined screw-thread vial was added 500 µl cyclohexyl methylamine and heated to 80° C. After 18 h, the reaction was cooled and the solvent evaporated. The residue was purified by preparative HPLC to afford 26 mg (10%) of N-cyclohexylmethyl-3-hydroxy-5-(3-phenoxy-phenylamino)-isothiazole-4-carboxamidine as a tan solid. $^1$H NMR ((CD$_3$)$_2$SO) δ 0.969 m 2H, 1.161 m 3H, 1.718-1.510 m 6H, 3.109 t 2H J=6.3 Hz, 6.473 s 1H, 6.633 dd 1H J=2.1 and 7.8 Hz, 6.698 dd 1H J=1.2 and 7.8 Hz, 7.014 d 2H J=7.8 Hz, 7.130 t 1H J=7.5 Hz, 7.276 t 1H, J=7.2 Hz, 7.381 t 2H J=8.1 Hz, 7.691 bs 1/2H, 8.416 s 1H, 9.099 bs 1/2H, 9.745 bs 1/2H, 10.566 bs 1/2H. MS m/z. 423 (M+1), 421 (M−1).

Preparation of 5-[4-(2,5-Dichloro-phenoxy)-3-fluoro-phenylamino]-3-hydroxy-N-isopropyl-isothiazole-4-carboxamidine and 5-[4-(2,5-Dichloro-phenoxy)-3-fluoro-phenylamino]-3-hydroxy-N-(2-hydroxy-1-methyl-ethyl)-isothiazole-4-carboxamidine

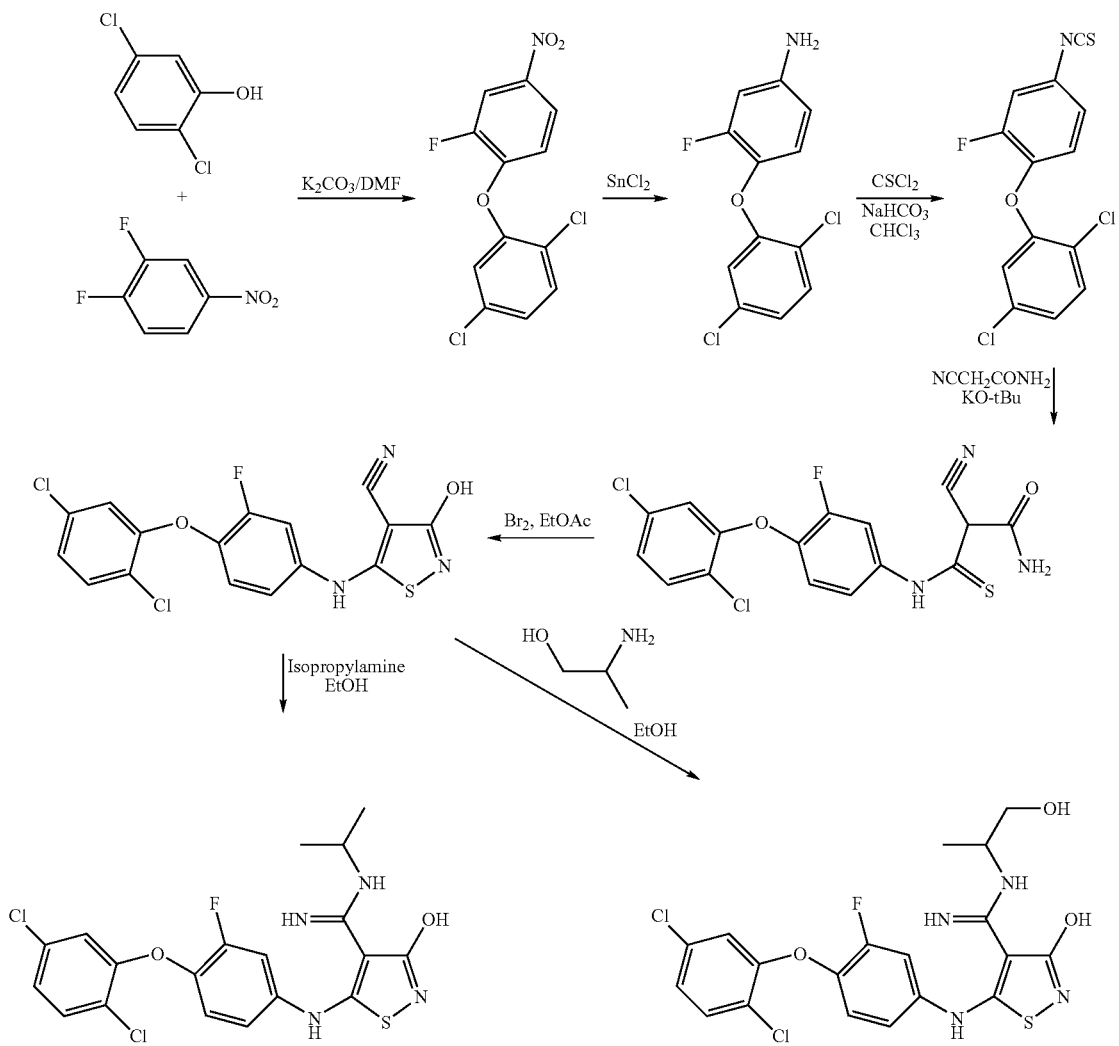

1-(2,5-Dichloro-phenoxy)-2-fluoro-4-nitro-benzene

A mixture of 3,4-difluoronitrobenzene (3.2 g, 0.02 mol), 2,5-dichlorophenol (3.59 g, 0.022 mol), and potassium carbonate (3.0 g, 0.022 mol) in 25 ml of anhydrous DMF was heated to 150° C. with stirring overnight. After cooling to room temperature, the reaction mixture was poured into 500 ml of ice water and stirred for 30 min. The precipitates were collected by filtration, washed with water, and dried in vacuo to give 5.72 g (94.7%) of crude product.

4-(2,5-Dichloro-phenoxy)-3-fluoro-phenylamine

A mixture of 1-(2,5-dichloro-phenoxy)-2-fluoro-4-nitro-benzene (0.5 g, 1.7 mmol) and tin chloride (1.57 g, 8.3 mmol) in 30 ml of anhydrous ethanol was heated to 70° C. under argon and stirred for 4 hours. The solution was allowed to cool and then poured into ice. The solution was made slightly basic (pH 7-8) by addition of saturated aqueous sodium bicarbonate solution, then extracted with ethyl acetate. The organic phase was thoroughly washed with brine and dried treated with anhydrous sodium sulfate. Evaporation of the solvent left a yellow oily product which was used for the next step without further purification.

4-(2,5-Dichloro-phenoxy)-3-fluoro-phenylisothiocyanate 4-(2,5-Dichloro-phenoxy)-3-fluoro-phenylamine (1.36 g, 5 mmol) was dissolved in 150 ml of chloroform and 100 ml of saturated aqueous sodium bicarbonate was added. To this biphasic mixture was added dropwise a solution of thiophosgene (0.39 ml, 5 mmol) in 30 ml of chloroform at room temperature with vigorous stirring. The mixture was stirred vigorously for 1 hour at room temperature. The bottom layer of the mixture was separated, and the aqueous layer was extracted twice with $CHCl_3$. The combined organic solution was washed with water, dried over $Mg_2SO_4$ and evaporated to give 1.53 g (97.4%) of crude product used for next step without further purification.

2-Cyano-2-[4-(2,5-dichloro-phenoxy)-3-fluoro-phenylthiocarbamoyl]-acetamide

To a solution of potassium tert-butoxide (0.6 g, 5.36 mmol) in 10 ml of anhydrous THF was added 2-cyanoacetamide (0.45 g, 5.36 mmol) under argon. The mixture was cooled to 5° C. and added dropwise to a solution of 4-(2,5-dichloro-phenoxy)-3-fluoro-phenylisothiocyanate (1.53 g, 4.87 mmol) in 5 ml of dry THF with stirring under argon. After 15 min of stirring at 5° C., this reaction mixture was warmed to room temperature and stirred for another 2 h. The reaction mixture was poured into 200 ml of ice water with stirring and acidified with 10% HCl. The solid was filtered and washed with water. After drying in vacuo, the crude product (1.6 g, 82.5%) was obtained in sufficient purity for the next step.

5-[4-(2,5-Dichloro-phenoxy)-3-fluoro-phenylamino]-3-hydroxy-isothiazole-4-carbonitrile 2-Cyano-2-[4-(2,5-dichloro-phenoxy)-3-fluoro-phenylthiocarbamoyl]-acetamide (1.6 g, 4 mmol) was dissolved in anhydrous ethyl acetate (60 ml) and a solution of bromine (0.2 ml, 4 mmol) in anhydrous ethyl acetate (10 ml) was added dropwise into the mixture with stirring at room temperature. After addition, the reaction mixture was stirred for another 3 hours. The precipitate was filtered and the solid was washed with ethyl ether and suspended in a saturated sodium bicarbonate with stirring for 10 min. The solid was filtered, then washed with water and dried in vacuo to afford a white powder.

Exemplary Physical Data

5-[4-(2,5-Dichloro-phenoxy)-3-fluoro-phenylamino]-3-hydroxy-N-isopropyl-isothiazole-4-carboxamidine A mixture of 5-[4-(2,5-dichloro-phenoxy)-3-fluoro-phenylamino]-3-hydroxy-isothiazole-4-carbonitrile (0.2 g) and isopropylamine (5 ml) in 20 ml of ethanol was placed into a high-pressure reaction apparatus and heated to 100° C. overnight. The reaction mixture was cooled to room temperature, and the solvent was removed in vacuo. The residue was chromatographed by silica gel column (chloroform/methanol, 40:1) to give the desired product as a light yellow solid. MS: 454; $^1$H NMR (DMSO-$d_6$, 300 MHz): δ 10.28 (brs, 1/2H, NH, $D_2O$ exchangeable), 9.62 (brs, 1H, NH, $D_2O$ exchangeable), 9.31 (brs, 1/2H, NH, $D_2O$ exchangeable), 8.57 (s, 1H, OH, $D_2O$ exchangeable), 7.88 (brs, 1H, NH, $D_2O$ exchangeable), 7.61 (d, 1H, J=8.7 Hz, ArH), 7.22 (dd, 1H, J=2.1, 8.7 Hz, ArH), 7.16 (t, 1H, J=8.7 Hz, ArH), 6.99 (dd, 1H, J=2.1, 12.6 Hz, ArH), 6.88 (d, 1H, J=2.1 Hz, ArH), 6.83 (dd, 1H, J=2.1, 8.7 Hz, ArH), 3.85 (m, 1H, CH), 1.20 (d, 6H, J=6.3 Hz, 2×$CH_3$).

5-[4-(2,5-Dichloro-phenoxy)-3-fluoro-phenylamino]-3-hydroxy-N-(2-hydroxy-1-methyl-ethyl)-isothiazole-4-carboxamidine A mixture of 5-[4-(2,5-dichloro-phenoxy)-3-fluoro-phenylamino]-3-hydroxy-isothiazole-4-carbonitrile (0.2 g) and DL-2-amino-1-propanol (0.7 g) in 20 ml of ethanol was placed in a high-pressure reaction equipment and heated to 100° C. overnight. The reaction mixture was cooled to room temperature and the solvent was removed in vacuo. The residue was chromatographed by silica gel column (chloroform/methanol, 25:1) to give the desired product as a light yellow solid. MS: 470; $^1$H NMR (DMSO-$d_6$, 300 MHz): δ 10.60 (brs, 1/2H, NH, $D_2O$ exchangeable), 9.69 (brs, 1/2H, NH, $D_2O$ exchangeable), 9.22 (brs, 1/2H, NH, $D_2O$ exchangeable), 8.55 (s, 1H, OH, $D_2O$ exchangeable), 7.91 (brs, 1/2H, NH, $D_2O$ exchangeable), 7.70 (brs, 1/2H, NH, $D_2O$ exchangeable), 7.61 (d, 1H, J=8.7 Hz, ArH), 7.22 (dd, 1H, J=2.1, 8.7 Hz, ArH), 7.16 (t, 1H, J=8.7 Hz, ArH), 6.99 (dd, 1H, J=2.1, 12.6 Hz, ArH), 6.88 (d, 1H, J=2.1 Hz, ArH), 6.83 (dd, 1H, J=2.1, 8.7 Hz, ArH), 5.09 (brs, 1H, OH), 3.80 (m, 1H, CH), 3.49 (m, 1H, CH). 3.44 (m, 1H, CH), 1.15 (d, 3H, J=6.3 Hz, $CH_3$).

3-Hydroxy-N-(3-hydroxy-2,2-dimethyl-propyl)-5-(4-phenoxy-phenylamino)-isothiazole-4-carboxamidine $^1$H NMR (DMSO-$d_6$, 300 MHz) δ 10.64 (broad s, 1/2H), 9.81 (broad s, 1/2H), 9.15 (broad s, 1H), 8.38 (broad s, 1H), 7.64 (broad s, 1/2H), 7.40 (apparent d, J=7.2 Hz, 2H), 7.14 (apparent t, J=7.2 Hz, 1H), 7.01 (s, 6H), 4.90 (broad s, 1H), 3.24 (s, 2H), 3.18 (s, 2H), 0.941 (s, 6H). MS (EI) m/z 413 $(M+1)^+$.

3-Hydroxy-N-(4-hydroxy-butyl)-5-(4-phenoxy-phenylamino)-isothiazole-4-carboxamidine $^1$H NMR (DMSO-$d_6$, 300 MHz) δ 11.21 (broad s, 1/2H), 10.59 (broad s, 1/2H), 10.38 (broad s, 1/2H), 9.92 (broad s, 1/2H), 9.15 (s, 1H), 8.66 (broad s, 1/2H), 8.48 (broad s, 1/2H), 8.17 (t, J=8.4 Hz, 2H), 7.89 (t, J=7.2 Hz, 1H), 7.77 (d, J=5.4 Hz, 1H), 7.76 (s, 5H), 5.30 (t, J=4.8 Hz, 1H), 4.23 (q, J=6.0 Hz, 2H), 4.20-4.08 (m, 2H), 2.41-2.28 (m, 4H).

3-Hydroxy-N-(2-hydroxy-ethyl)-5-[4-(pyrimidin-5-yloxy)-phenylamino]-isothiazole-4-carboxamidine $^1$H NMR (DMSO-d$_6$, 300 MHz) δ 11.62 (broad s, 1/2H), 9.86 (broad s, 1/2H), 9.72 (broad s, 1/2H), 9.22 (broad s, 1/2H), 9.01 (s, 1H), 8.62 (s, 2H), 8.44 (s, 1H), 7.91 (broad s, 1/2H), 7.68 (broad s, 1/2H), 7.15 (d, J=8.7 Hz, 2H), 7.05 (t, J=9.0 Hz, 2H), 5.05 (t, J=5.1 Hz, 1H), 3.64 (apparent d, J=5.1 Hz, 2H), 3.38 (apparent t, J=5.7 Hz, 2H).

N-tert-Butyl-3-hydroxy-5-(4-phenoxy-phenylamino)-isothiazole-4-carboxamidine $^1$H NMR (DMSO-d$_6$, 300 MHz) δ 10.93 (broad s, 1/2H), 10.15 (broad s, 1/2H), 9.94 (broad s, 1/2H), 9.48 (broad s, 1/2H), 8.47 (broad s, 1H), 7.41 (t, J=8.1 Hz, 2H), 7.14 (t, J=7.2 Hz, 1H), 7.02 (d, J=5.4 Hz, 2H), 7.01 (s, 5H), 1.45 (s, 9H). MS (EI) m/z 381 (M−1)$^+$.

3-Hydroxy-N-(4-hydroxy-cyclohexyl)-5-(4-phenoxy-phenylamino)-isothiazole-4-carboxamidine $^1$H NMR (DMSO-d$_6$, 300 MHz) δ 10.56 (broad s, 1/2H), 9.83 (broad s, 1/2H), 9.61 (broad s, 1/2H), 9.18 (broad s, 1/2H), 8.41 (broad s, 1H), 7.98 (broad s, 1/2H), 7.73 (broad s, 1/2H), 7.41 (t, J=7.8 Hz, 2H), 7.14 (t, J=7.5 Hz, 1H), 7.01 (d, J=5.4 Hz, 1H), 7.00 (s, 5H), 4.66 (d, J=4.5 Hz, 1H), 3.59-3.53 (m, 2H), 2.00 (broad s, 2H), 1.85 (broad s, 2H), 1.34 (broad s, 4H). MS (EI) m/z 423 (M−1)$^+$.

3-Hydroxy-N-(2-hydroxy-1-methyl-ethyl)-5-(4-phenoxy-phenylamino)-isothiazole-4-carboxamidine MS: 384; $^1$H NMR (DMSO-d6): 10.60 (brs, 1/2H, NH, D$_2$O exchangeable), 9.83 (brs, 1/2H, NH, D$_2$O exchangeable), 9.61 (brs, 1/2H, NH, D$_2$O exchangeable), 9.15 (brs, 1/2H, NH, D$_2$O exchangeable), 8.33 (s, 1H, OH, D$_2$O exchangeable), 7.85 (brs, 1/2H, NH, D$_2$O exchangeable), 7.58 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.06 (t, 1H, J=5.1 Hz, OH, D$_2$O exchangeable), 3.78 (m, 1H, CH), 3.47 (m, 1H, CH), 3.43 (m, 1H, CH), 1.15 (d, 3H, J=6.3 Hz, CH$_3$).

3-Hydroxy-N-[(S)-2-hydroxy-1-methyl-ethyl]-5-(4-phenoxy-phenylamino)-isothiazole-4-carboxamidine MS: 384; $^1$H NMR (DMSO-d6): 10.60 (brs, 1/2H, NH, D$_2$O exchangeable), 9.84 (brs, 1/2H, NH, D$_2$O exchangeable), 9.60 (brs, 1/2H, NH, D$_2$O exchangeable), 9.17 (brs, 1/2H, NH, D$_2$O exchangeable), 8.33 (s, 1H, OH, D$_2$O exchangeable), 7.85 (brs, 1/2H, NH, D$_2$O exchangeable), 7.58 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.06 (t, 1H, J=5.1 Hz, OH, D$_2$O exchangeable), 3.78 (m, 1H, CH), 3.47 (m, 1H, CH), 3.42 (m, 1H, CH), 1.15 (d, 3H, J=6.3 Hz, CH$_3$).

3-Hydroxy-N-[(R)-2-hydroxy-1-methyl-ethyl]-5-(4-phenoxy-phenylamino)-isothiazole-4-carboxamidine MS: 384; $^1$H NMR (DMSO-d6): 10.60 (brs, 1/2H, NH, D$_2$O exchangeable), 9.84 (brs, 1/2H, NH, D$_2$O exchangeable), 9.59 (brs, 1/2H, NH, D$_2$O exchangeable), 9.17 (brs, 1/2H, NH, D$_2$O exchangeable), 8.34 (s, 1H, OH, D$_2$O exchangeable), 7.85 (brs, 1/2H, NH, D$_2$O exchangeable), 7.59 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.06 (t, 1H, J=5.1 Hz, OH, D$_2$O exchangeable), 3.78 (m, 1H, CH), 3.48 (m, 1H, CH), 3.42 (m, 1H, CH), 1.15 (d, 3H, J=6.3 Hz, CH$_3$).

3-Hydroxy-N-(1-hydroxymethyl-propyl)-5-(4-phenoxy-phenylamino)-isothiazole-4-carboxamidine MS: 398; $^1$H NMR (DMSO-d6): 10.61 (brs, 1/2H, NH, D$_2$O exchangeable), 9.83 (brs, 1/2H, NH, D$_2$O exchangeable), 9.62 (brs, 1/2H, NH, D$_2$O exchangeable), 9.15 (brs, 1/2H, NH, D$_2$O exchangeable), 8.34 (s, 1H, OH, D$_2$O exchangeable), 7.83 (brs, 1/2H, NH, D$_2$O exchangeable), 7.56 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.00 (t, 1H, J=5.1 Hz, OH, D$_2$O exchangeable), 3.62 (m, 1H, CHN), 3.47 (m, 2H, CH$_2$O), 1.62 (m, 1H, CHMe), 1.50 (m, 1H, CHMe), 0.90 (t, 3H, J=7.2 Hz, CH$_3$).

3-Hydroxy-N-[(S)-1-hydroxymethyl-propyl]-5-(4-phenoxy-phenylamino)-isothiazole-4-carboxamidine MS: 398; $^1$H NMR (DMSO-d6): 10.59 (brs, 1/2H, NH, D$_2$O exchangeable), 9.82 (brs, 1/2H, NH, D$_2$O exchangeable), 9.61 (brs, 1/2H, NH, D$_2$O exchangeable), 9.16 (brs, 1/2H, NH, D$_2$O exchangeable), 8.33 (s, 1H, OH, D$_2$O exchangeable), 7.83 (brs, 1/2H, NH, D$_2$O exchangeable), 7.56 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.00 (t, 1H, J=5.1 Hz, OH, D$_2$O exchangeable), 3.62 (m, 1H, CHN), 3.47 (m, 2H, CH$_2$O), 1.62 (m, 1H, CHMe), 1.49 (m, 1H, CHMe), 0.90 (t, 3H, J=7.2 Hz, CH$_3$).

3-Hydroxy-N-[(R)-1-hydroxymethyl-propyl]-5-(4-phenoxy-phenylamino)-isothiazole-4-carboxamidine MS: 398; $^1$H NMR (DMSO-d6): 10.59 (brs, 1/2H, NH, D$_2$O exchangeable), 9.83 (brs, 1/2H, NH, D$_2$O exchangeable), 9.60 (brs, 1/2H, NH, D$_2$O exchangeable), 9.15 (brs, 1/2H, NH, D$_2$O exchangeable), 8.33 (s, 1H, OH, D$_2$O exchangeable), 7.83 (brs, 1/2H, NH, D$_2$O exchangeable), 7.58 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.00 (t, 1H, J=5.1 Hz, OH, D$_2$O exchangeable), 3.62 (m, 1H, CHN), 3.47 (m, 2H, CH$_2$O), 1.62 (m, 1H, CHMe), 1.49 (m, 1H, CHMe), 0.90 (t, 3H, J=7.2 Hz, CH$_3$).

3-Hydroxy-N-(1-hydroxymethyl-2-methyl-propyl)-5-(4-phenoxy-phenylamino)-isothiazole-4-carboxamidine MS: 412; $^1$H NMR (DMSO-d6): 10.62 (brs, 1/2H, NH, D$_2$O exchangeable), 9.81 (brs, 1/2H, NH, D$_2$O exchangeable), 9.68 (brs, 1/2H, NH, D$_2$O exchangeable), 9.15 (brs, 1/2H, NH, D$_2$O exchangeable), 8.36 (s, 1H, OH, D$_2$O exchangeable), 7.82 (brs, 1/2H, NH, D$_2$O exchangeable), 7.56 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 4.97 (t, 1H, J=5.1 Hz, OH, D$_2$O exchangeable), 3.58 (m, 1H, CHN), 3.49 (m, 2H, CH$_2$O), 1.96 (m, 1H, CHMe), 1.49 (m, 1H, CHMe), 0.92 (d, 6H, J=6.9 Hz, 2×CH$_3$).

3-Hydroxy-N-(2-hydroxy-propyl)-5-(4-phenoxy-phenylamino)-isothiazole-4-carboxamidine MS: 384; $^1$H NMR (DMSO-d6): 10.62 (brs, 1/2H, NH, D$_2$O exchangeable), 9.82 (brs, 1/2H, NH, D$_2$O exchangeable), 9.67 (brs, 1/2H, NH, D$_2$O exchangeable), 9.13 (brs, 1/2H, NH, D$_2$O exchangeable), 8.31 (s, 1H, OH, D$_2$O exchangeable), 7.82 (brs, 1/2H, NH, D$_2$O exchangeable), 7.56 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.00 (d, 1H, J=4.8 Hz, OH, D$_2$O exchangeable), 3.82 (m, 1H, CH), 3.24 (m, 1H, CH), 3.12 (m, 1H, CH), 1.11 (d, 3H, J=6.0 Hz, CH$_3$).

3-Hydroxy-N-(trans-2-hydroxy-cyclohexyl)-5-(4-phenoxy-phenylamino)-isothiazole-4-carboxamidine MS: 424; $^1$H NMR (DMSO-d6): 10.61 (brs, 1/2H, NH, D$_2$O exchangeable), 9.74 (brs, 1/2H, NH, D$_2$O exchangeable), 9.60 (brs, 1/2H, NH, D$_2$O exchangeable), 9.08 (brs, 1/2H, NH, D$_2$O exchangeable), 8.34 (s, 1H, OH, D$_2$O exchangeable), 7.74 (brs, 1/2H, NH, D$_2$O exchangeable), 7.48 (brs, 1/2H, NH, D$_2$O exchangeable), 7.35 (t, 2H, J=7.5 Hz, ArH), 7.08 (t, 1H, J=7.5 Hz, ArH), 6.95 (m, 6H, ArH), 5.08 (d, 1H, J=4.8 Hz, OH, D$_2$O exchangeable), 3.34 (m, 2H, 2×CH), 1.88 (m, 2H, CH$_2$), 1.63 (m, 2H, CH$_2$), 1.27 (m, 4H, 2×CH$_2$).

3-Hydroxy-N-[(S)-1-hydroxymethyl-3-methyl-butyl]-5-(4-phenoxy-phenylamino)-isothiazole-4-carboxamidine MS: 426; $^1$H NMR (DMSO-d6): 10.49 (brs, 1/2H, NH, D$_2$O exchangeable), 9.81 (brs, 1/2H, NH, D$_2$O exchangeable), 9.50 (brs, 1/2H, NH, D$_2$O exchangeable), 9.15 (brs, 1/2H, NH, D$_2$O exchangeable), 8.34 (s, 1H, OH, D$_2$O exchangeable), 7.85 (brs, 1/2H, NH, D$_2$O exchangeable), 7.57 (brs, 1/2H, NH, D$_2$O exchangeable), 7.35 (t, 2H, J=7.5 Hz, ArH), 7.08 (t, 1H, J=7.5 Hz, ArH), 6.94 (m, 6H, ArH), 4.99 (t, 1H, J=4.8 Hz, OH, D$_2$O exchangeable), 3.76 (m, 1H, CHN), 3.45 (m, 1H, CH$_2$O), 3.40 (m, 1H, CH$_2$O), 1.64 (m, 1H, CHMe$_2$), 1.41 (t, 2H, CH$_2$), 0.90 (d, 3H, J=6.6 Hz, CH$_3$), 0.87 (d, 3H, J=6.6 Hz, CH$_3$).

3-Hydroxy-N-[2-hydroxy-2-(3-hydroxy-phenyl)-ethyl]-5-(4-phenoxy-phenylamino)-isothiazole-4-carboxamidine MS: 462; $^1$H NMR (DMSO-d6): 10.65 (brs, 1/2H, NH, D$_2$O exchangeable), 9.76 (brs, 1/2H, NH, D$_2$O exchangeable), 9.37 (brs, 1/2H, NH, D$_2$O exchangeable), 9.14 (brs, 1/2H, NH, D$_2$O exchangeable), 8.31 (s, 1H, OH, D$_2$O exchangeable), 7.84 (brs, 1/2H, NH, D$_2$O exchangeable), 7.57 (brs, 1/2H, NH, D$_2$O exchangeable), 7.35 (t, 2H, J=7.5 Hz, ArH), 7.08 (m, 2H, J=7.5 Hz, ArH), 6.94 (m, 6H, ArH), 6.85 (m, 2H, ArH), 6.64 (d, 1H, J=7.5 Hz, ArH), 5.76 (brs, 1H, OH, D$_2$O exchangeable), 4.69 (brs, 1H, OH, D$_2$O exchangeable), 4.12 (m, 1H, CH), 3.15 (d, 2H, J=4.2 Hz, CH$_2$).

Similar procedures can be used in the synthesis of N-2-(2-tetrahydrofuryl)ethyl-3-hydroxy-5-[4-(2,5-Dichloro-phenoxy)-3-fluoro-phenylamino]-isothiazole-4-carboxamidine and N-2-(4-methylpiperazinyl)ethyl-3-hydroxy-5-[4-(2,5-dichloro-phenoxy)-3-fluoro-phenylamino]-isothiazole-4-carboxamidine, as shown below.

The scheme below shows alternative syntheses for compounds of this invention in which R' includes a cyclic moiety.

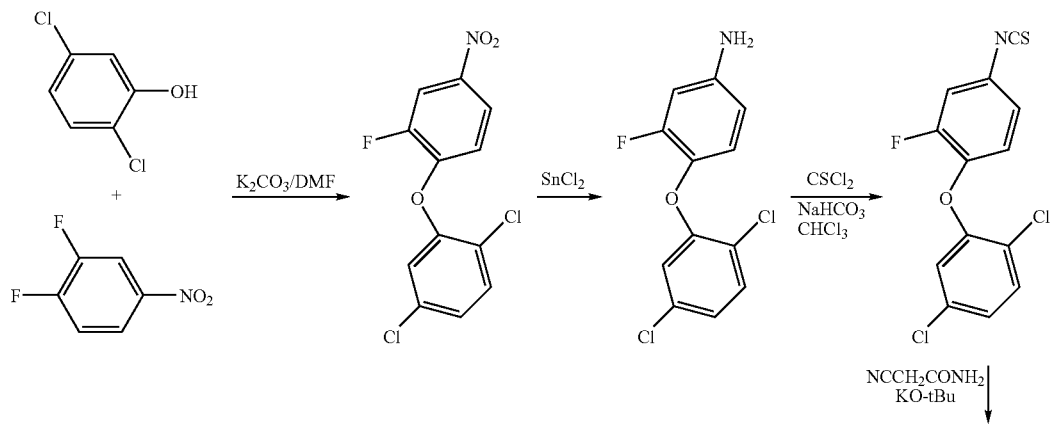

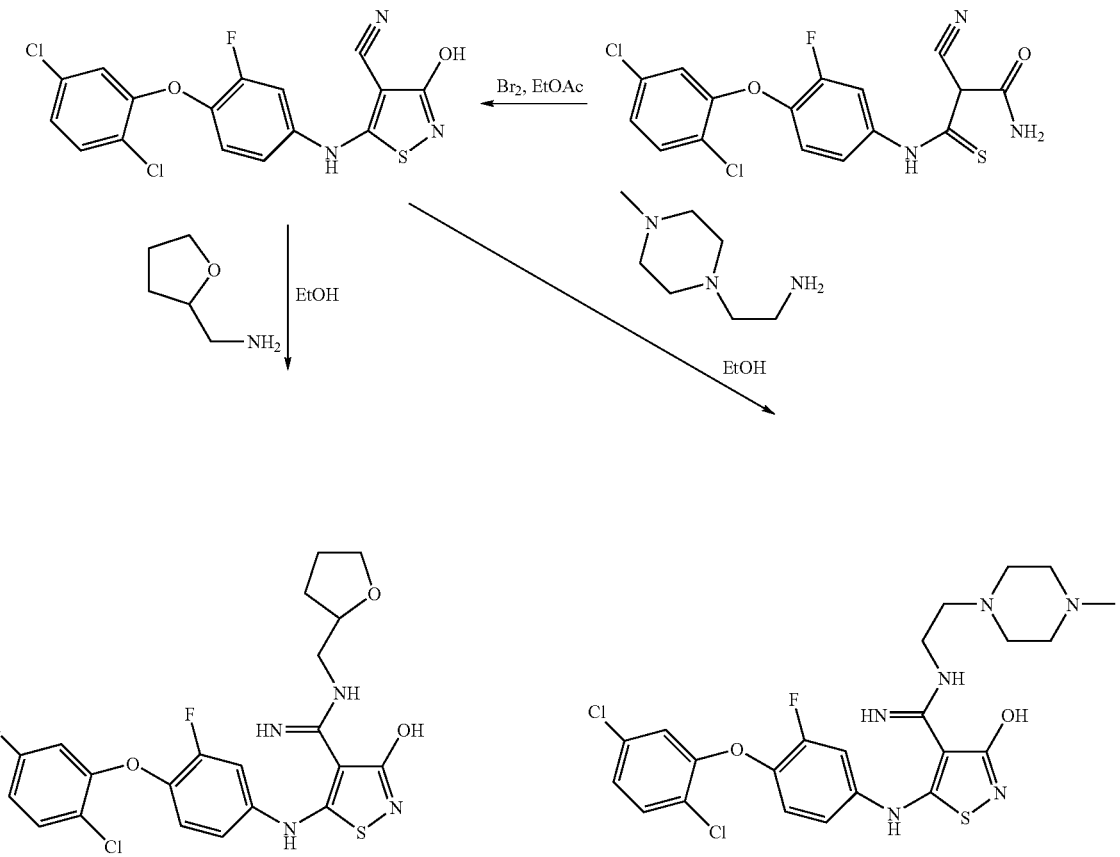
The following synthetic procedure is provided as an example of synthesis scheme for compounds of formula VII.
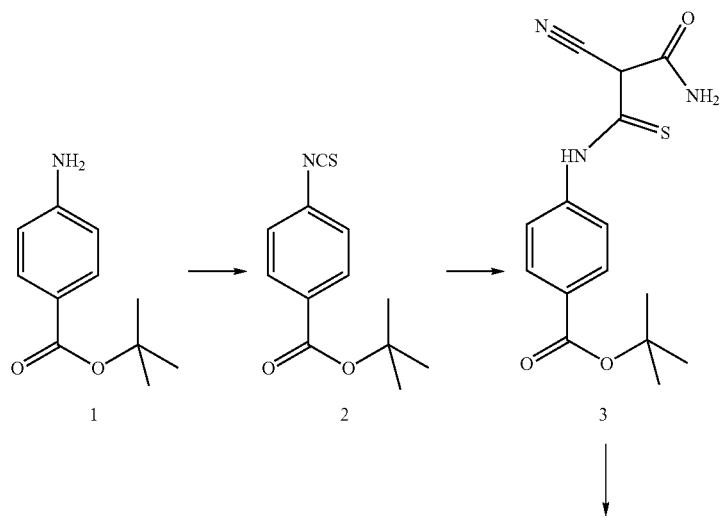

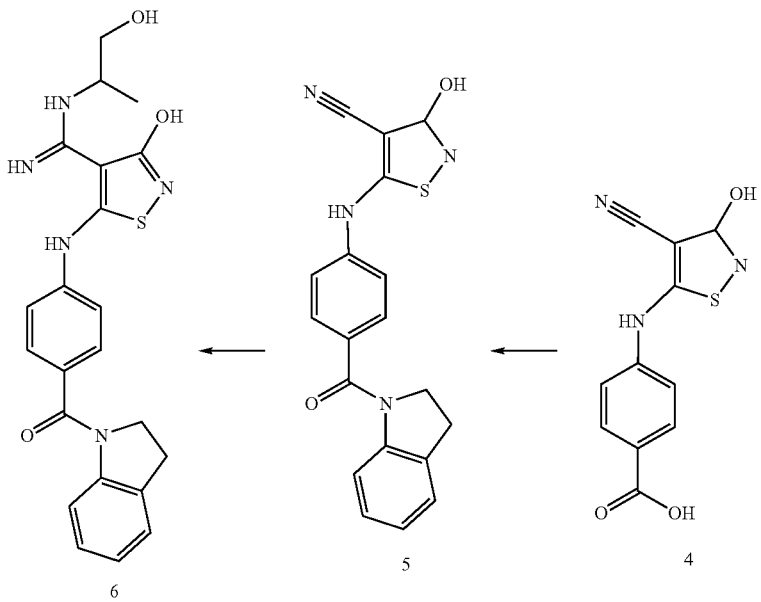

4-Isothiocyanato-benzoic acid t-butyl ester 2: To 4-amino-t-butyl-benzoate 1, (25.0 g., 129.4 mmol) in a stirred biphasic mixture of CHCl$_3$ (250 ml) and saturated NaHCO$_3$ solution (100 ml) in an ice bath, thiophosgene (9.9 ml, 129.4 mmol) was added dropwise. After addition of thiophosgene stirring at room temperature was continued for 90 min. The organic layer was washed with water, dried over anhydrous Na$_2$SO$_4$, and further purified by column chromatography to provide 28.3 g. of 4-isothiocyanato-benzoic acid, t-butyl ester 2.

4-(2-carbamoyl-2-cyano-thioacetylamino)-benzoic acid t-butyl ester 3: To 28.3 g., 120.4 mmol of 4-isothiocyanato-benzoic acid t-butyl ester 2 in DMF (200 ml), KOH (6.74 g., 120.4 mmol) and cyanoacetamide (10.21 g., 120.4 mmol) were added. The reaction mixture was stirred at room temperature for 16 hours, then acidified with 1N HCl. The precipitate obtained was filtered, washed with water, and dried under vacuum, to provide 32.10 g. of 4-(2-carbamoyl-2-cyano-thioacetylamino)-benzoic acid t-butyl ester 3.

4-(4-Cyano-3-hydroxy-isothiazole)-benzoic acid 4: To 4-(2-carbamoyl-2-cyano-thioacetylamino)-benzoic acid t-butyl ester 3 (32.10 gm, 100.36 mmol) in EtOAc (250 ml), Br$_2$ (5.2 ml, 100.36 mmol) was added slowly. The reaction mixture was kept stirring at room temperature for 2 hrs. The precipitate obtained was filtered and washed with saturated NaHCO$_3$ solution and dried under vacuum to provide 31 g. of 4-(4-cyano-3-hydroxy-isothiazole)-benzoic acid 4.

5-[4-(2,3-dihydro-indole-1-carbonyl)-phenylamino]-3-hydroxy-isothiazole-4-carbonitrile 5: To 1.0 g. 4-(4-cyano-3-hydroxy-isothiazole)-benzoic acid 4 (3.82 mmol) in DMF (30 ml) were added DMAP (dimethylaminopyridine)(0.46 gm, 3.82 mmol), EDC (1-ethyl-3,3'-dimethylaminopropyl carbodiimide HCl) (0.732 gm, 3.82 mmol) and indoline (1.28 gm, 3.82 mmol). The reaction mixture was kept stirring at room temperature for 16 h, concentrated to dryness, and purified by column chromatography to provide 1.08 gm of 5-[4-(2,3-Dihydro-indole-1-carbonyl)-phenylamino]-3-hydroxy-isothiazole-4-carbonitrile 5.

5-[4-(2,3-dihydro-indole-3-carbonyl)-phenylamino]-3-hydroxy-N-(2-hydroxy-1-methyl-ethyl)-isothiazole-4-carboxamidine 6: To 5-[4-(2,3-dihydro-indole-1-carbonyl)-phenylamino]-3-hydroxy-isothiazole-4-carbonitrile 5 (0.362 gm, 1 mmol) in 10 ml anhydrous EtOH was added (2-amino-propan-1-ol (0.375 gm, 5 mmol). The reaction mixture was maintained at 80° C. for 16 h. with stirring, then concentrated to dryness and purified by column chromatography to provide 5-[4-(2,3-dihydro-indole-1-carbonyl)-phenylamino]-3-hydroxy-N-(2-hydroxy-1-methyl-ethyl)-isothiazole-4-carboxamidine 6.

A typical synthetic scheme for compounds of formula VIII is shown below.

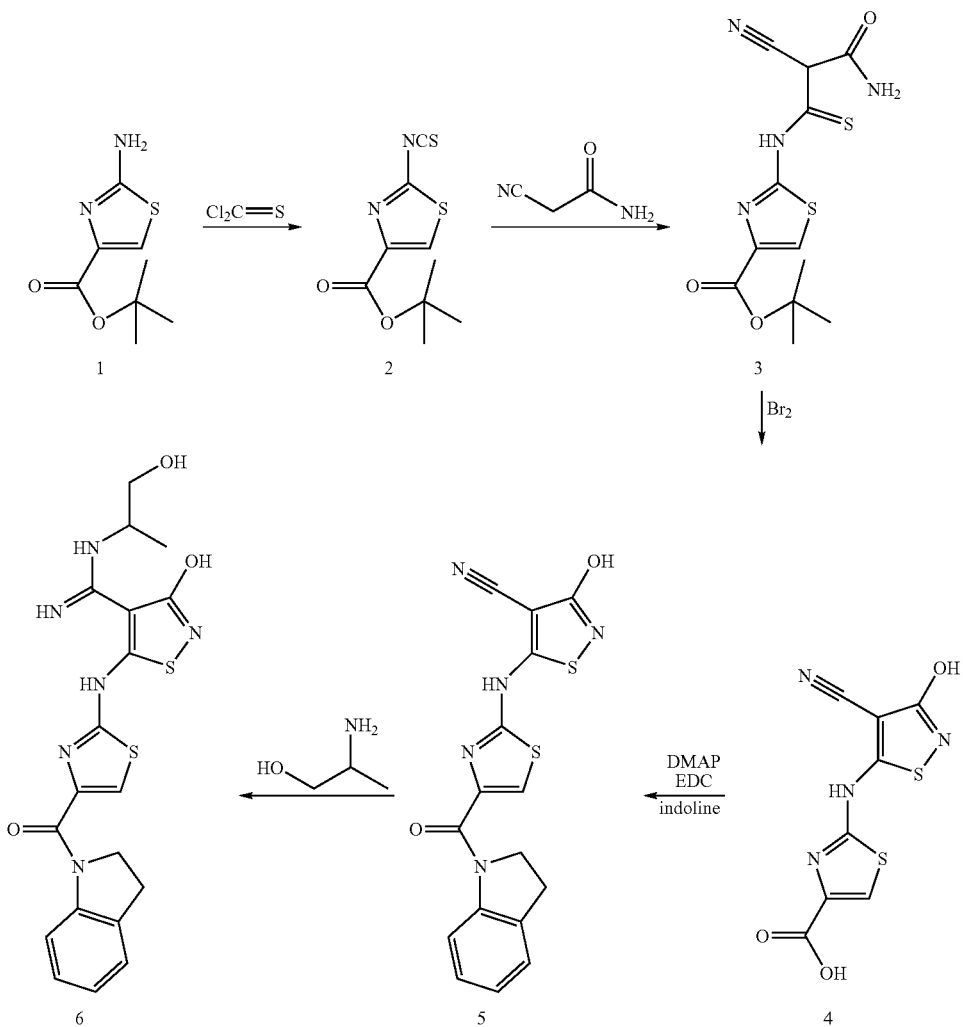

Compounds of formulas IX and X are prepared by standard synthetic procedures that are analogous with those employed for compounds of formulas II-VIII.

A typical synthesis scheme for compounds of formula XI is illustrated by the procedure for a 5-(meta-indolecarbonylaryl amino isothizole amidine):

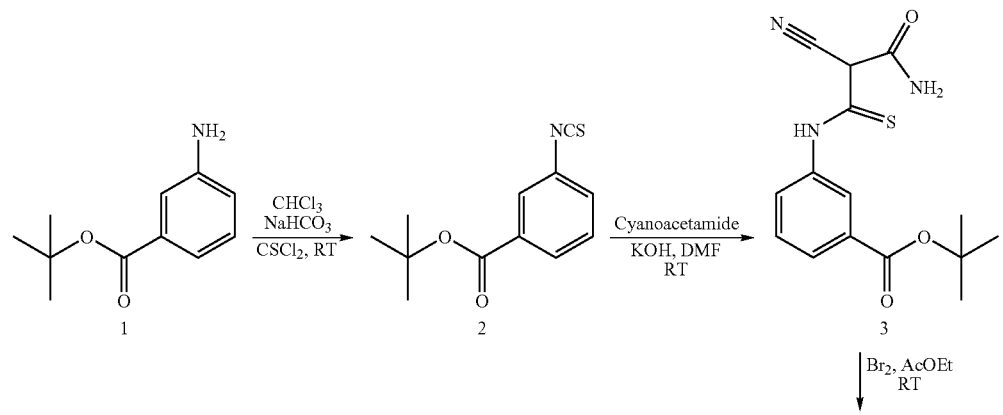

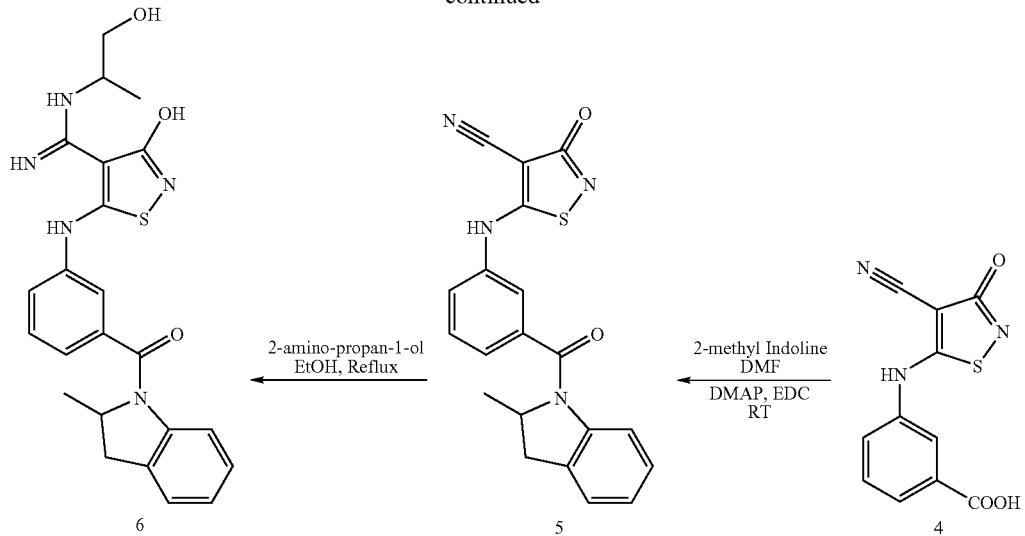
Synthesis scheme for a 5-(meta-dihydroindolecarbonylaryl amino isothiazole amidine):
Example: 5-[4-(2,3-dihydro-indole-1-carbonyl)-phenylamino]-3-hydroxy-N-(2-hydroxy-1-methyl-ethyl)-isothiazole-4-carboxamidine 6.
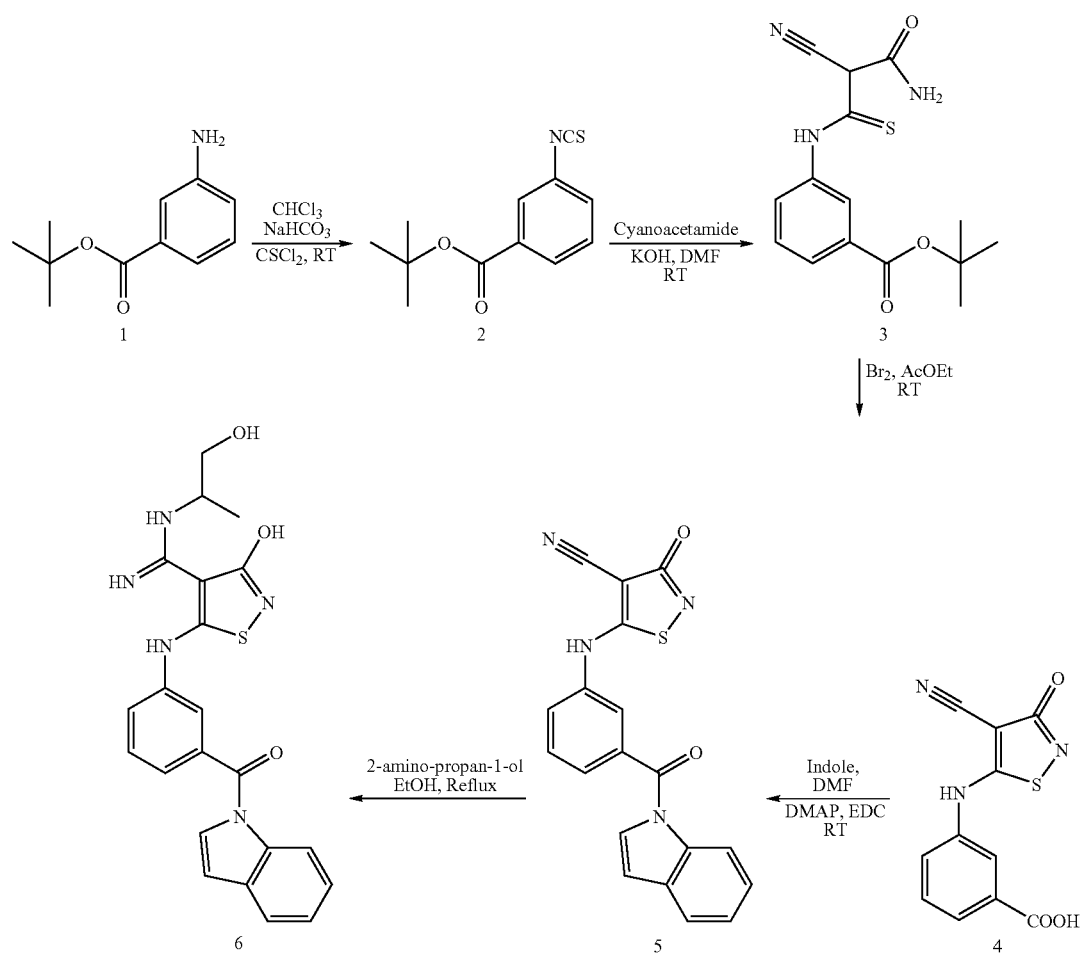

4-isothiocyanato-benzoic acid t-butyl ester 2: t-Butyl-4-aminobenzoate 1, (25.0 gm, 129.4 mmol) was taken into CHCl$_3$ (250 ml) and saturated NaHCO$_3$ (100 ml) in ice bath. To the stirred mixture thiophosgene (9.9 ml, 129.4 mmol) was added dropwise, and stirring continued for another 90 min. at room temperature after addition was complete. The organic layer was washed with water, dried over Na$_2$SO$_4$, and further purified by column chromatography to provide 28.3 gm of 4-isothiocyanato-benzoic acid t-butyl ester 2.

4-(2-carbamoyl-2-cyano-thioacetylamino)-benzoic acid t-butyl ester 3: 4-Isothiocyanato-benzoic acid t-butyl ester 2 (28.3 gm, 120.4 mmol) was taken into DMF (200 ml). To this KOH (6.74 gm, 120.4 mmol) and cyanoacetamide (10.21 gm, 120.4 mmol) were added. The reaction mixture was stirred at room temperature for 16 h. The reaction mixture was acidified with 1N HCl, the precipitate obtained was filtered, washed with water, and dried under vacuum, to provide 32.10 gm of 4-(2-Carbamoyl-2-cyano-thioacetylamino)-benzoic acid t-butyl ester 3.

4-(4-cyano-3-hydroxy-isothiazole)-benzoic acid 4: 4-(2-carbamoyl-2-cyano-thioacetylamino)-benzoic acid t-butyl ester 3 (32.10 gm, 100.36 mmol) was taken into EtOAc (250 ml) and to this Br$_2$ (5.2 ml, 100.36 mmol) was added slowly. Reaction mixture was stirred at room temperature for 2 h. The precipitate obtained was filtered and washed with saturated NaHCO$_3$ and dried under vacuum to provide 31 gm of 4-(4-cyano-3-hydroxy-isothiazole)-benzoic acid 4.

5-[3-(3-(1H-indole-1-carbonyl)phenylamino]-3-hydroxy-isothiazole-4-carbonitrile 5: 4-(4-cyano-3-hydroxy-isothiazole)-benzoic acid 4 (1.0 gm, 3.82 mmol) was taken into DMF (30 ml). To this solution DMAP (0.46 gm, 3.82 mmol), EDC (0.732 gm, 3.82 mmol) and indoline (1.28 gm, 3.82 mmol) were added. The reaction mixture was stirred at room temperature for 16 h., concentrated to dryness, and purified by column chromatography to provide 1.08 gm of 5-[4-(2,3-dihydro-indole-1-carbonyl)-phenylamino]-3-hydroxy-isothiazole-4-carbonitrile 5.

5-[3-(3-(1H-indole-1-carbonyl)phenylamino]-3-hydroxy-N-(1-hydroxypropan-2-yl)isothiazole-4-carboximidamide 6: 5-[3-(3-(1H-indole-1-carbonyl)phenylamino]-3-hydroxy-isothaizole-4-carbonitrile 5: (0.362 gm, 1 mmol) was taken into anhydrous EtOH (10 ml) and to this 2-amino-propan-1-ol (0.375 gm, 5 mmol) was added. The reaction mixture was stirred at 80° C. for 16 h., then concentrated to dryness and purified by column chromatography to provide 5-[4-(2,3-dihydro-indole-1-carbonyl)-phenylamino]-3-hydroxy-N-(2-hydroxy-1-methyl-ethyl)-isothiazole-4-carboxamidine 6.

Biological Data

Selected compounds were used in various assays to evaluate inhibitory activity of the compounds according to the inventive subject matter, and experimental procedures and results are indicated in tables below, where, unless otherwise indicated, "A" denotes inhibitory concentrations of 1 nM-100 nM, "B" denotes inhibitory concentrations of 100 nM-500 nM, and "C" denotes inhibitory concentrations of greater than 500 nM (hydroxy groups in the structures of the table below are denoted as single bonded oxygen as the structures were generated in "hide proton view").

Generation of IC50 Data

Materials and preparation of reagents: Human GST-MEK1 and the constitutively active allele GST-MEK1$^{CA}$ (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Determination of enzymatic activity: Compounds were diluted from dimethylsulfoxide (DMSO) stocks into 1×HMNDE (20 mM HEPES pH 7.2, 1 mM MgCl$_2$, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 µCi [γ$^{33}$P] ATP. The screening assay essentially comprised four additions. Five µl of diluted compound were dispensed to 96-well assay plates. Ten µl of 2.5× enzyme cocktail (MEK1$^{CA}$ and ERK2 only) were then added to each well followed by a pre-incubation for 30 minutes at ambient temperature. Ten µl of 2.5× substrate cocktail (labeled and unlabeled ATP plus MBP) were then added, followed by incubation for 60 minutes at ambient temperature. Finally, 100 µl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 µl of scintillation cocktail were dispensed to each well. A top seal was applied and the plate was counted in the TopCount for two seconds per well.

Generation of EC50 Data

Effects of compounds in the cell were determined by Western blotting for phosphorylated ERK. MDA-MB-231 breast cancer cells were plated in a 48 well plate at 20,000 cells per well and grown in a 37° humidified CO$_2$ incubator. The following day, the growth media (DMEM+10% fetal bovine serum) was removed and replaced with starve media (DMEM+0.1% fetal bovine serum). Cells were incubated in the starve media for sixteen hours and then treated with a range of compound concentrations for thirty minutes. After incubation with compound, cells were stimulated with 100 ng/ml EGF for five minutes. The cells were then lysed and analyzed by Western blot using a monoclonal antibody raised to phosphorylated ERK. The signal was amplified using a secondary antibody conjugated to a near –IR dye and detected on a Licor Odyssey scanner. The intensity of signal was quantitated and this data was used to generate dose response curves and EC50 calculations.

TABLE 1

Biological Activity of Compounds of Formula I

| # | Structure | Avg IC50 |
|---|-----------|----------|
| 1 | (structure) | B |
| 2 | (structure) | B |
| 3 | (structure) | C |
| 4 | (structure) | B |

TABLE 1-continued

Biological Activity of Compounds of Formula I

| # | Structure | Avg IC50 |
|---|-----------|----------|
| 5 | 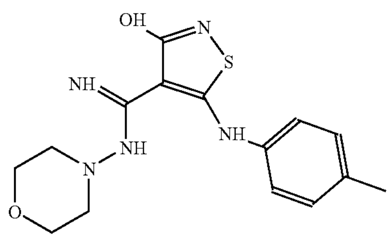 | B |
| 6 | 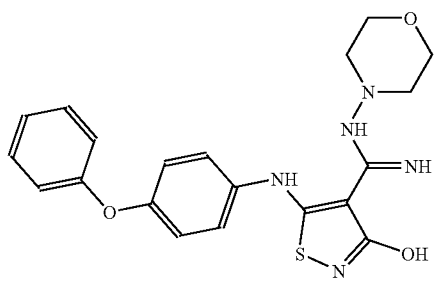 | A |
| 7 | 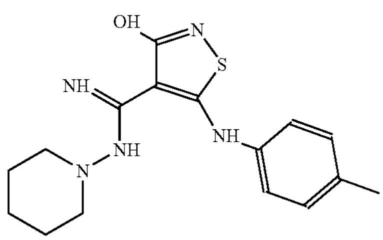 | B |
| 8 | 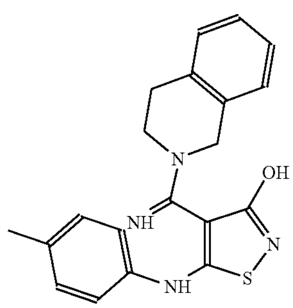 | C |
| 9 | 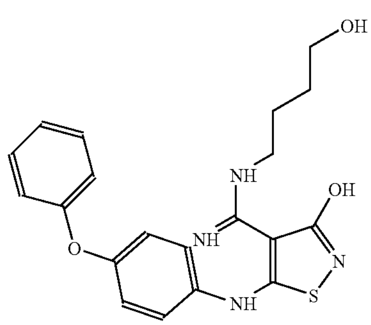 | A |

TABLE 1-continued

Biological Activity of Compounds of Formula I

| # | Structure | Avg IC50 |
|---|---|---|
| 10 | 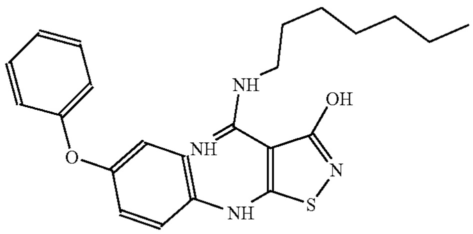 | A |
| 11 | 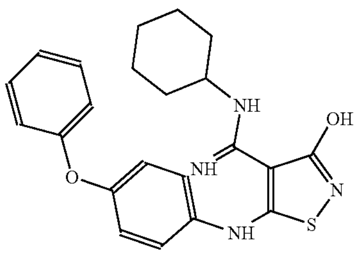 | A |
| 12 | 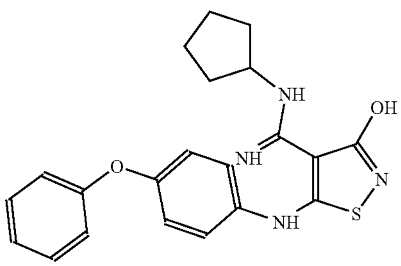 | A |
| 13 | 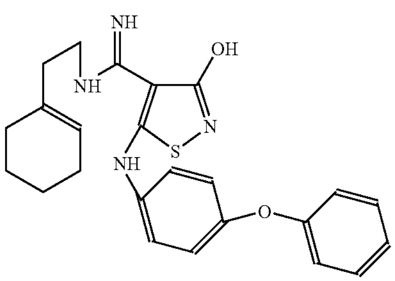 | A |
| 14 | 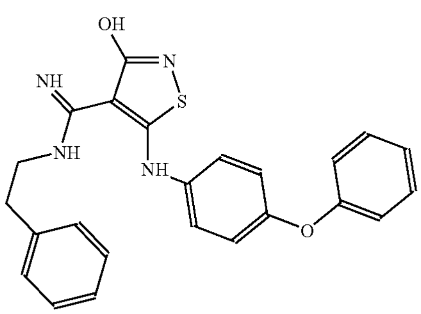 | B |

TABLE 1-continued

Biological Activity of Compounds of Formula I

| # | Structure | Avg IC50 |
|---|-----------|----------|
| 15 | 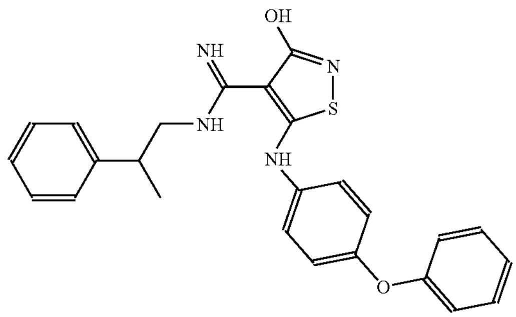 | A |
| 16 | 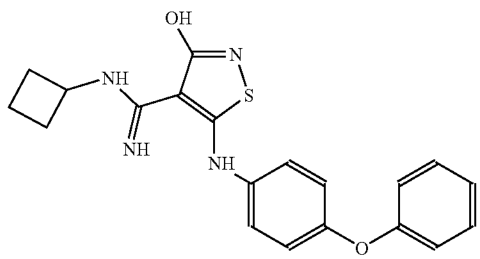 | A |
| 17 | 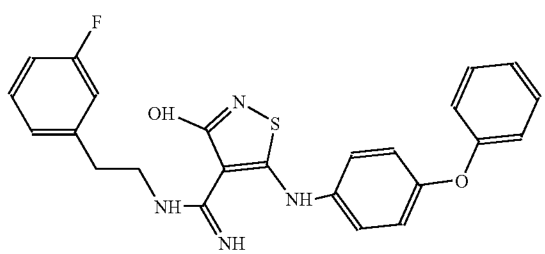 | B |
| 18 | 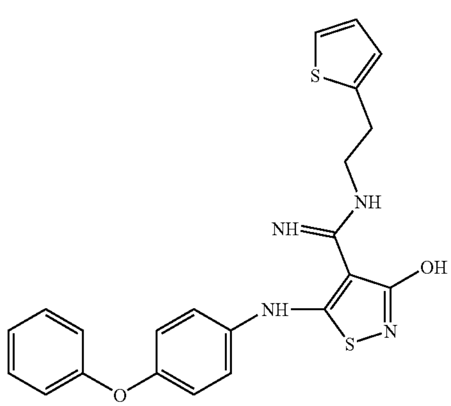 | B |

TABLE 1-continued
Biological Activity of Compounds of Formula I
| # | Structure | Avg IC50 |
|---|-----------|----------|
| 19 | 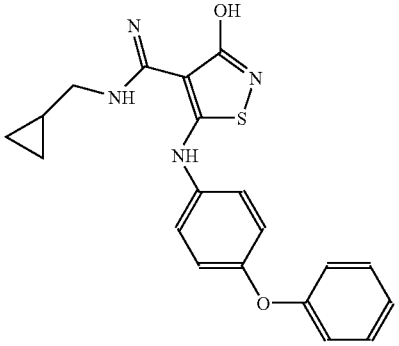 | A |
| 20 | 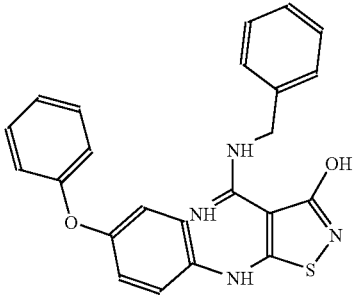 | B |
| 21 | 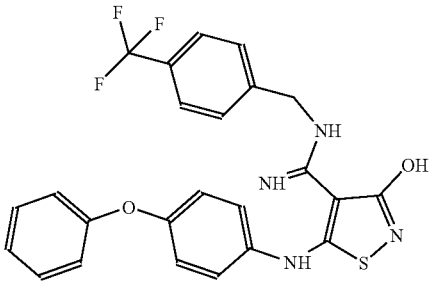 | A |
| 22 | 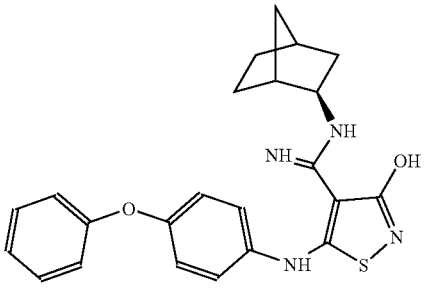 | A |
| 23 | 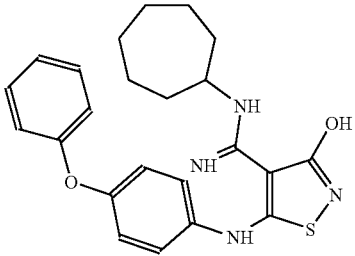 | A |

TABLE 1-continued

Biological Activity of Compounds of Formula I

| # | Structure | Avg IC50 |
|---|---|---|
| 24 | 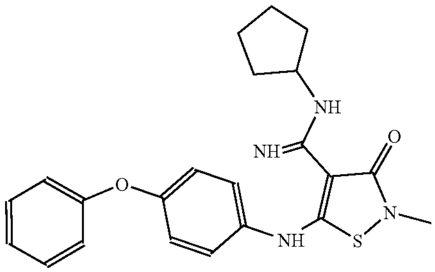 | C |
| 25 | 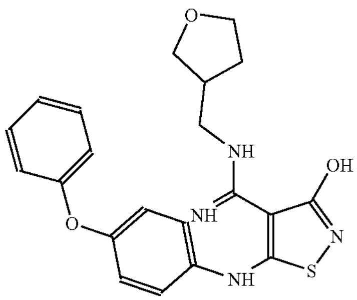 | A |
| 26 | 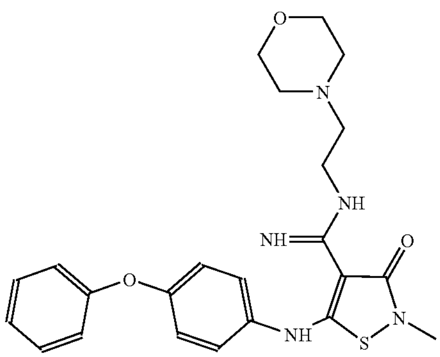 | C |
| 27 | 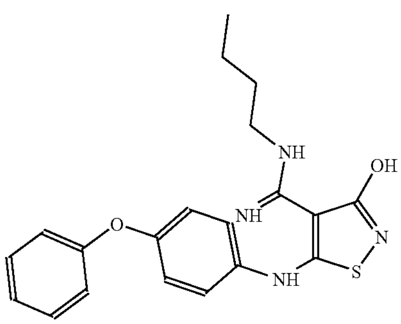 | B |
| 28 | 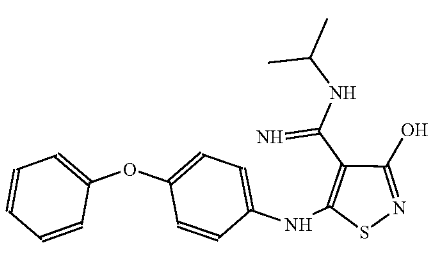 | A |

TABLE 1-continued

Biological Activity of Compounds of Formula I

| # | Structure | Avg IC50 |
|---|-----------|----------|
| 29 | 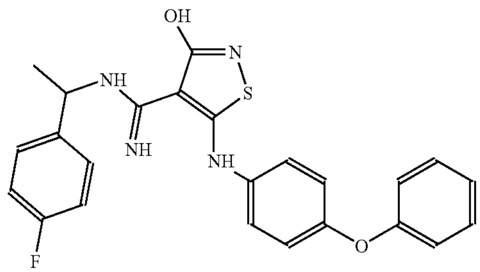 | B |
| 30 | 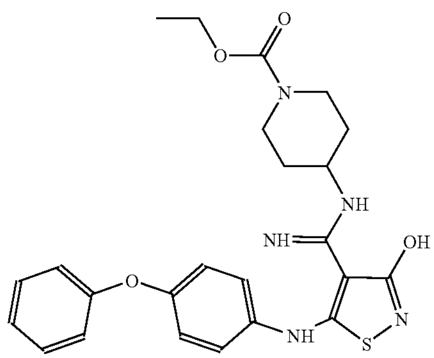 | B |
| 31 | 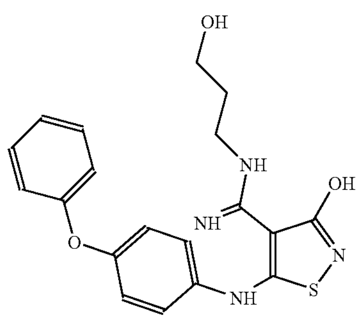 | A |
| 32 | 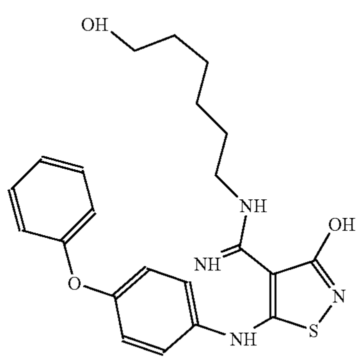 | A |

TABLE 1-continued
Biological Activity of Compounds of Formula I
| # | Structure | Avg IC50 |
|---|-----------|----------|
| 33 | 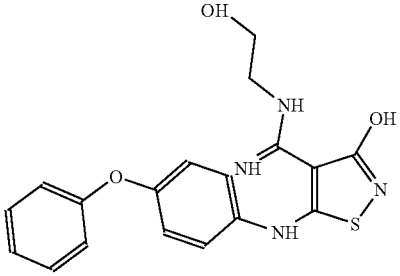 | A |
| 34 | 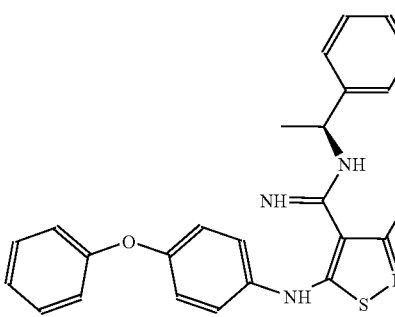 | B |
| 35 | 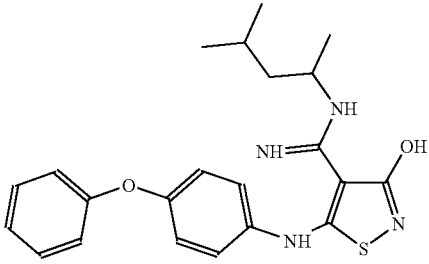 | B |
| 36 | 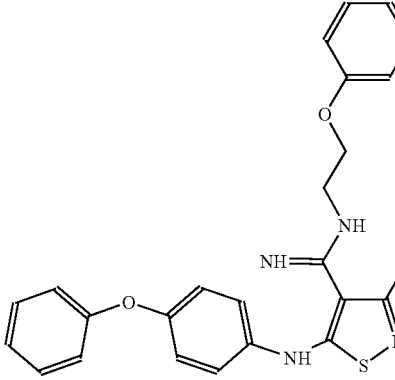 | B |
| 37 | 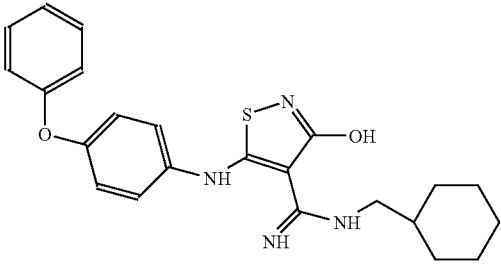 | A |

TABLE 1-continued
Biological Activity of Compounds of Formula I
| # | Structure | Avg IC50 |
|---|-----------|----------|
| 38 | 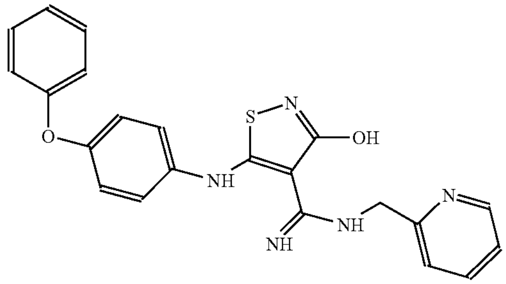 | B |
| 39 | 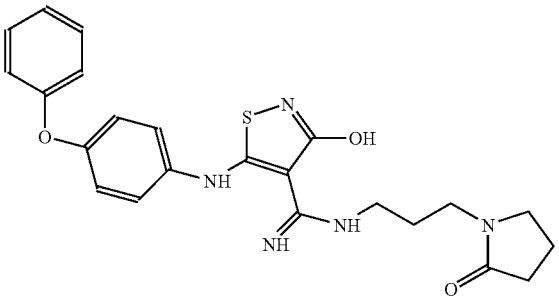 | A |
| 40 | 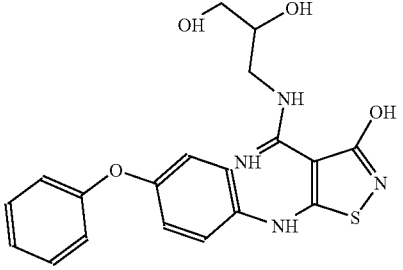 | A |
| 41 | 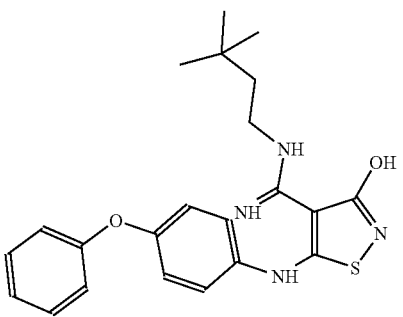 | B |
| 42 | 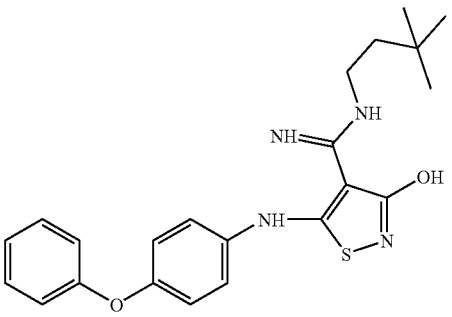 | A |

TABLE 1-continued

Biological Activity of Compounds of Formula I

| # | Structure | Avg IC50 |
|---|-----------|----------|
| 43 | 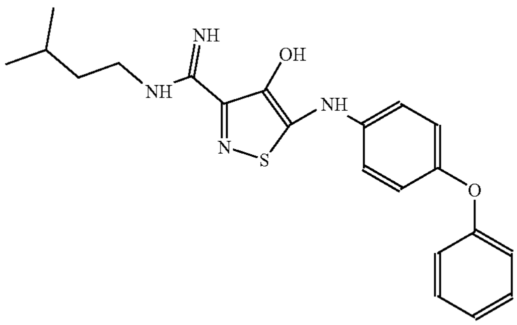 | A |
| 44 | 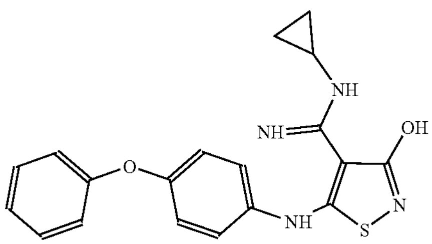 | C |
| 45 | 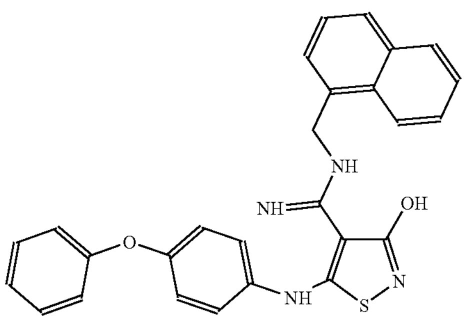 | A |
| 46 | 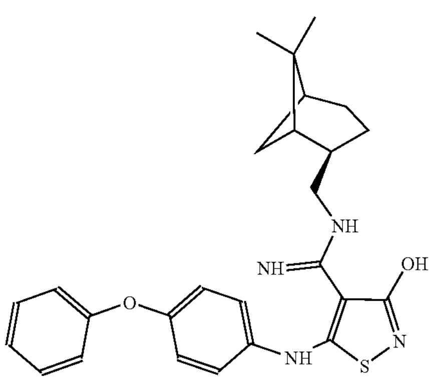 | A |

TABLE 1-continued
Biological Activity of Compounds of Formula I
| # | Structure | Avg IC50 |
|---|-----------|----------|
| 47 | 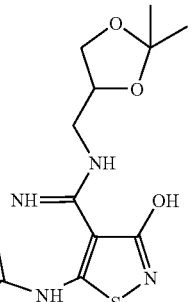 | A |
| 48 | 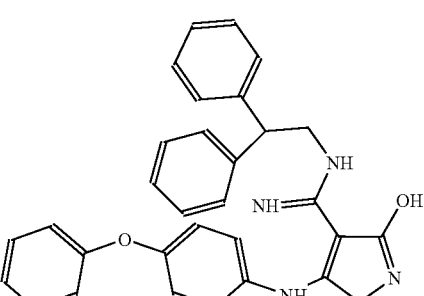 | A |
| 49 | 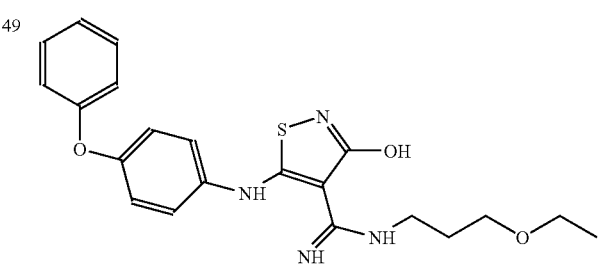 | A |
| 50 | 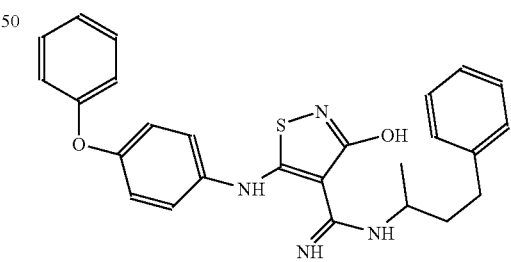 | A |
| 51 | 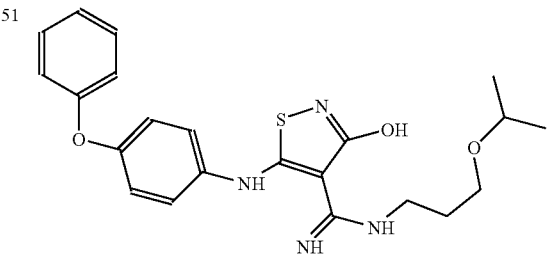 | A |

TABLE 1-continued

Biological Activity of Compounds of Formula I

| # | Structure | Avg IC50 |
|---|---|---|
| 52 | 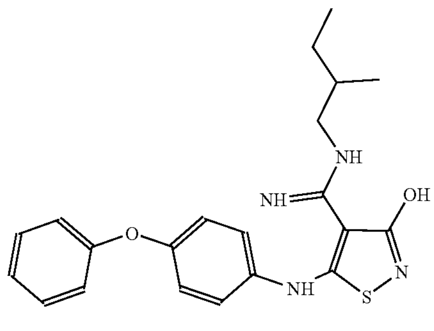 | A |
| 53 | 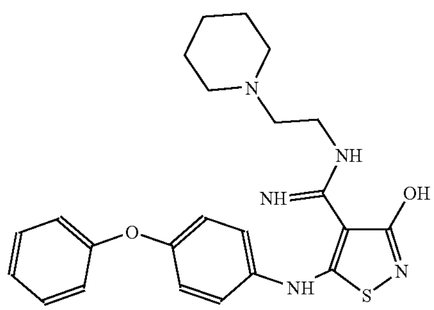 | B |
| 54 | 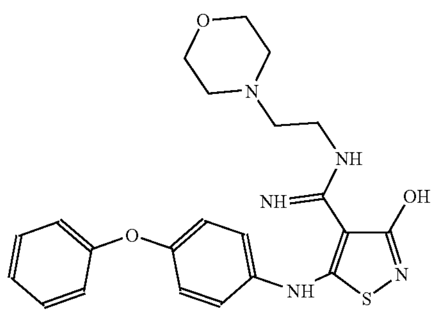 | B |
| 55 | 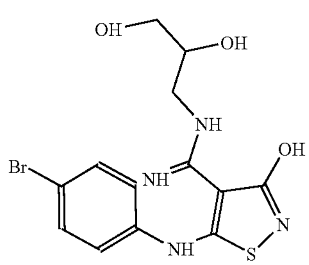 | B |
| 56 | 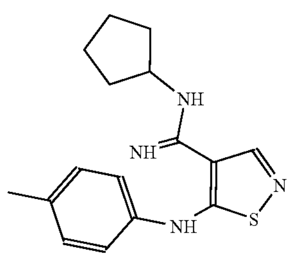 | C |

TABLE 1-continued

Biological Activity of Compounds of Formula I

| # | Structure | Avg IC50 |
|---|-----------|----------|
| 57 | 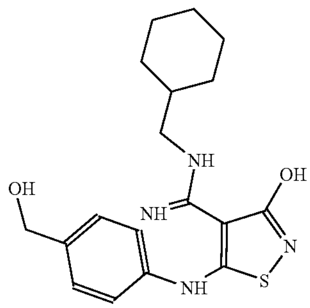 | C |
| 58 | 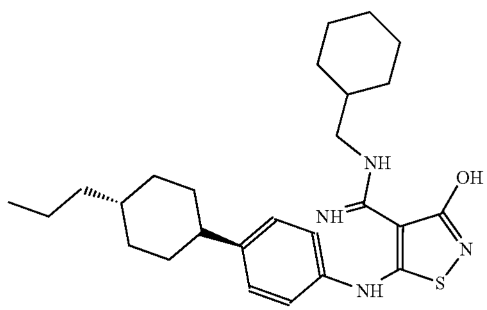 | C |
| 59 | 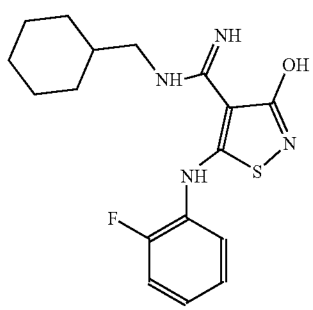 | C |
| 60 | 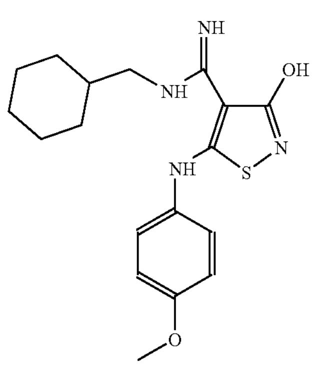 | C |

TABLE 1-continued

Biological Activity of Compounds of Formula I

| # | Structure | Avg IC50 |
|---|---|---|
| 61 | 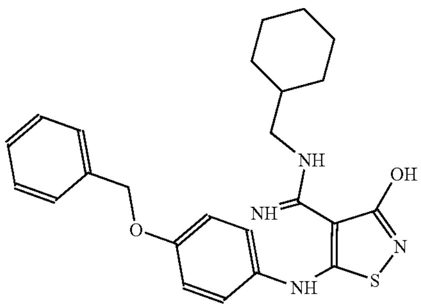 | B |
| 62 | 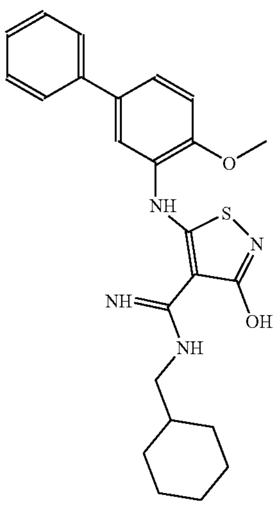 | C |
| 63 | 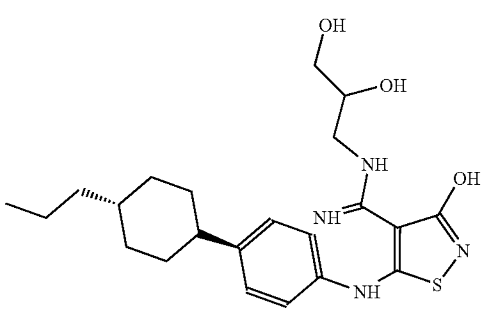 | B |
| 64 | 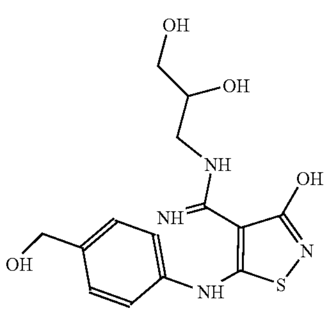 | C |

TABLE 1-continued

Biological Activity of Compounds of Formula I

| # | Structure | Avg IC50 |
|---|-----------|----------|
| 65 | 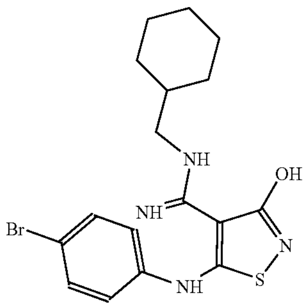 | B |
| 66 | 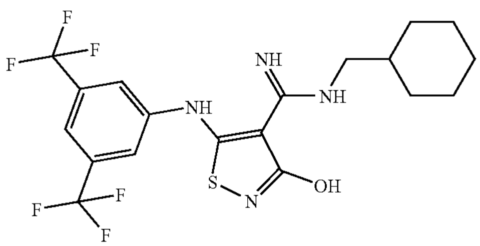 | C |
| 67 | 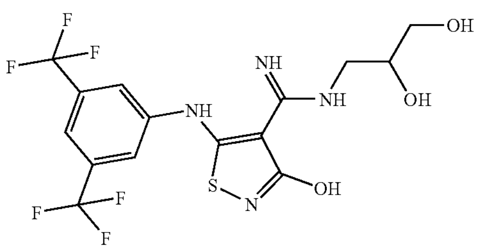 | C |
| 68 | 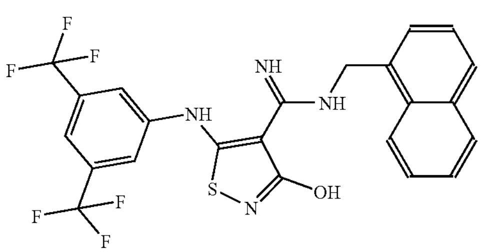 | C |
| 69 | 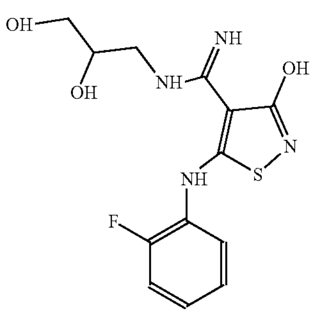 | C |

TABLE 1-continued

Biological Activity of Compounds of Formula I

| # | Structure | Avg IC50 |
|---|-----------|----------|
| 70 | 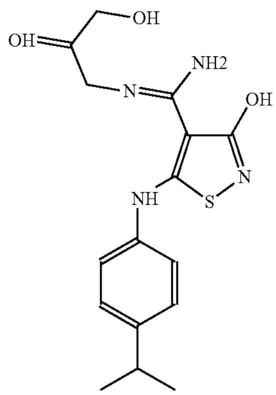 | B |
| 71 | 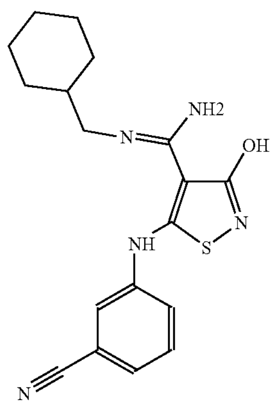 | C |
| 72 | 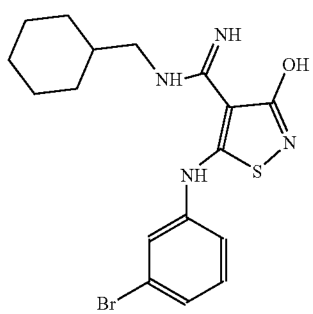 | C |
| 73 | 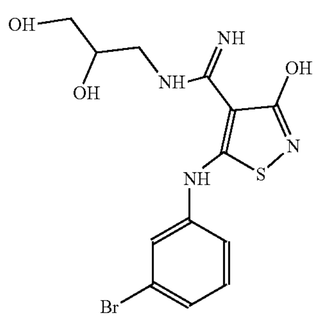 | B |

TABLE 1-continued

Biological Activity of Compounds of Formula I

| # | Structure | Avg IC50 |
|---|-----------|----------|
| 74 | 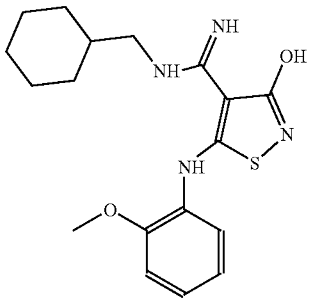 | C |
| 75 | 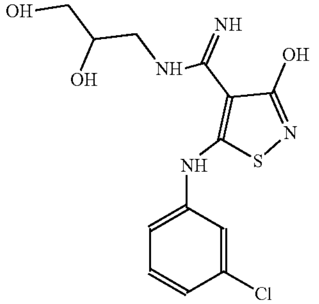 | B |
| 76 | 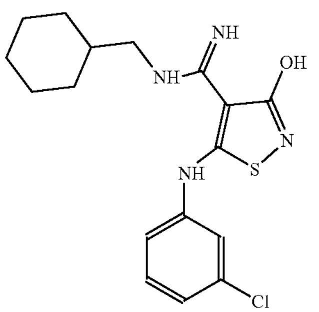 | C |
| 77 | 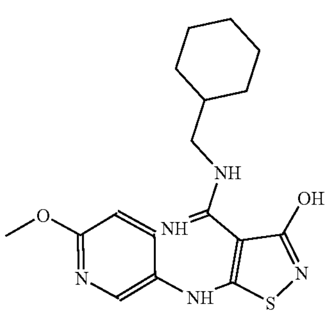 | A |

TABLE 1-continued

Biological Activity of Compounds of Formula I

| # | Structure | Avg IC50 |
|---|-----------|----------|
| 78 | 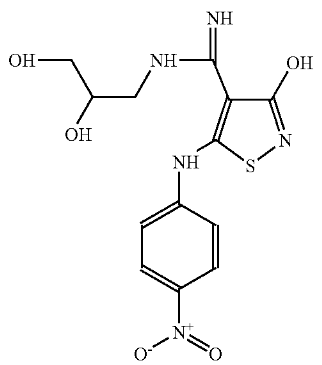 | C |
| 79 | 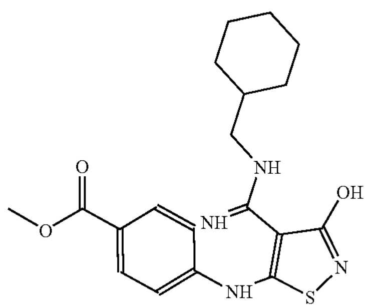 | B |
| 80 | 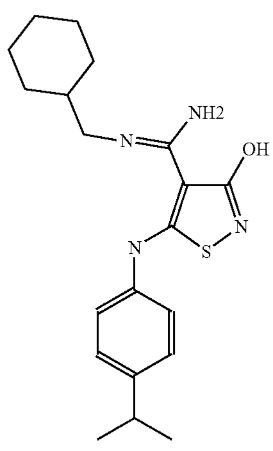 | C |
| 81 | 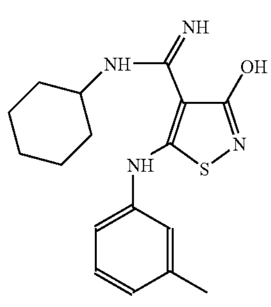 | C |

TABLE 1-continued

Biological Activity of Compounds of Formula I

| # | Structure | Avg IC50 |
|---|-----------|----------|
| 82 | 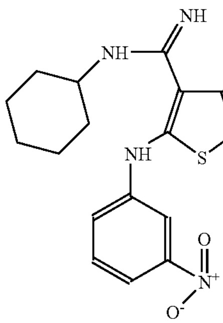 | B |
| 83 | 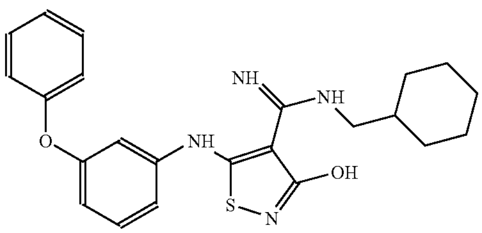 | B |
| 84 | 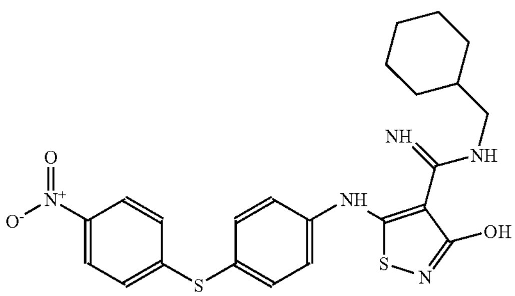 | B |
| 85 | 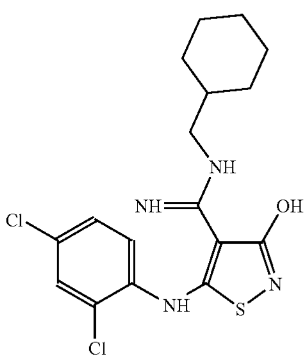 | B |
| 86 | 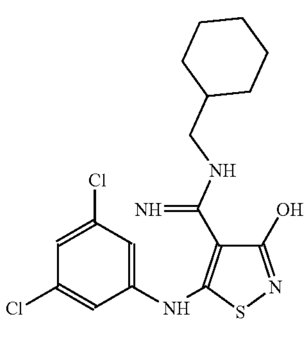 | B |

TABLE 1-continued

Biological Activity of Compounds of Formula I

| # | Structure | Avg IC50 |
|---|-----------|----------|
| 87 | 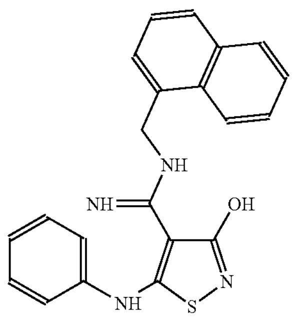 | C |
| 88 | 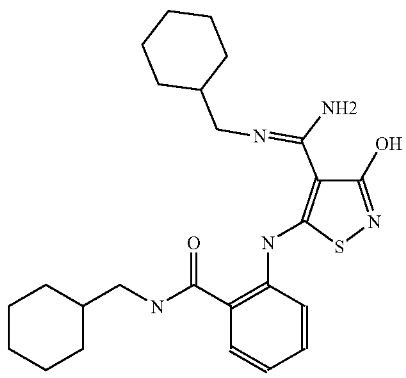 | C |
| 89 | 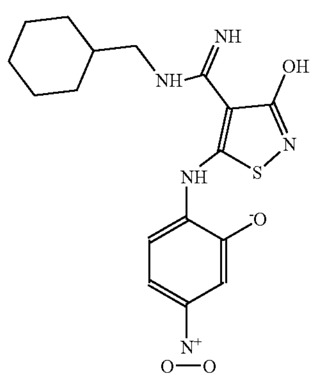 | C |
| 90 | 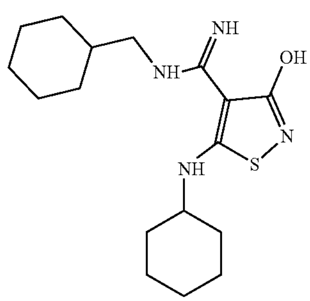 | C |

TABLE 1-continued

Biological Activity of Compounds of Formula I

| # | Structure | Avg IC50 |
|---|-----------|----------|
| 91 | 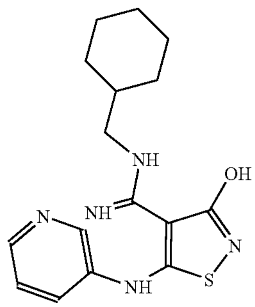 | C |
| 92 | 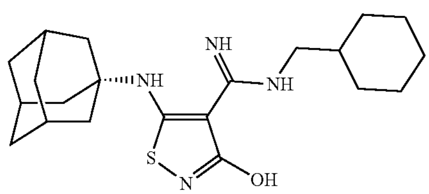 | C |
| 93 | 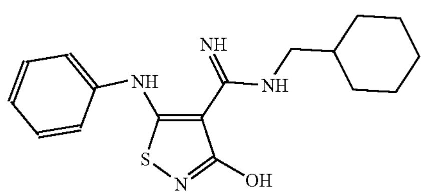 | C |
| 94 | 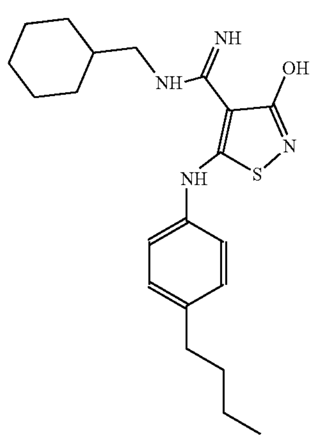 | B |
| 95 | 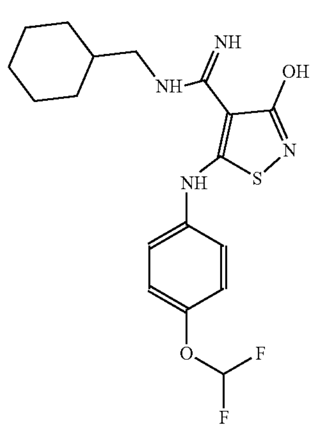 | C |

TABLE 1-continued

Biological Activity of Compounds of Formula I

| # | Structure | Avg IC50 |
|---|-----------|----------|
| 96 | 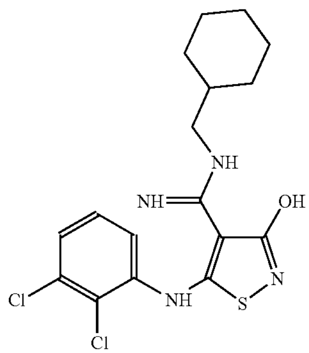 | C |
| 97 | 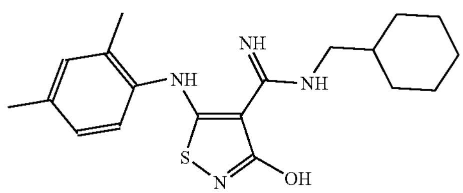 | C |
| 98 | 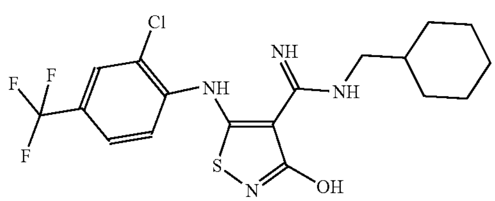 | C |
| 99 | 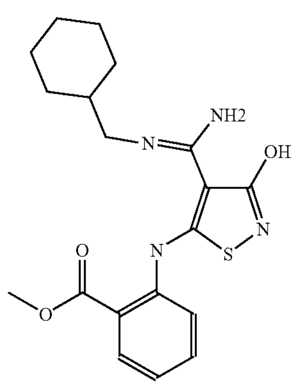 | C |
| 100 | 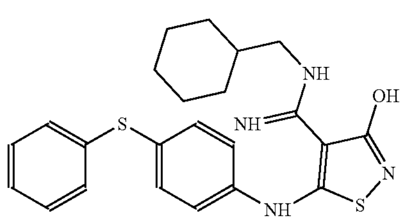 | A |

TABLE 1-continued

Biological Activity of Compounds of Formula I

| # | Structure | Avg IC50 |
|---|-----------|----------|
| 101 | 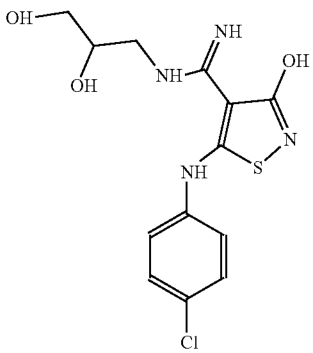 | B |
| 102 | 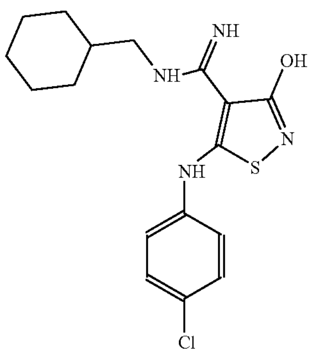 | B |
| 103 | 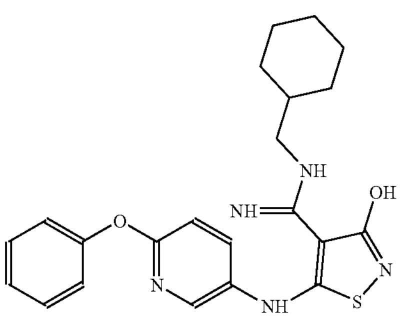 | B |
| 104 | 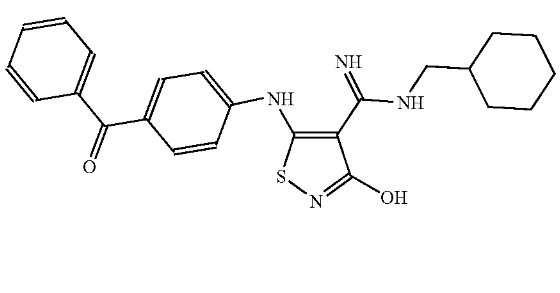 | B |

TABLE 1-continued

Biological Activity of Compounds of Formula I

| # | Structure | Avg IC50 |
|---|-----------|----------|
| 105 | 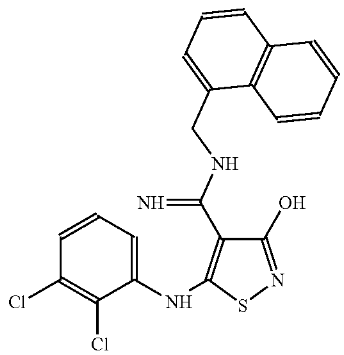 | C |
| 106 | 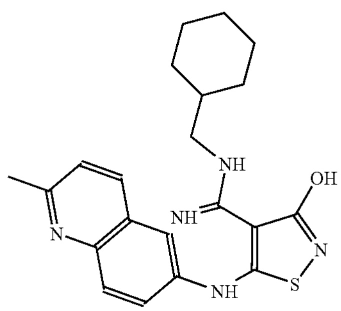 | C |
| 107 | 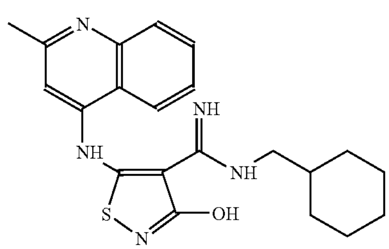 | C |
| 108 | 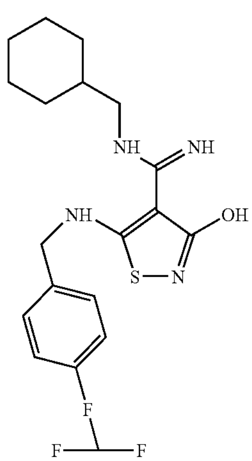 | C |

TABLE 1-continued
Biological Activity of Compounds of Formula I
| # | Structure | Avg IC50 |
|---|-----------|----------|
| 109 | 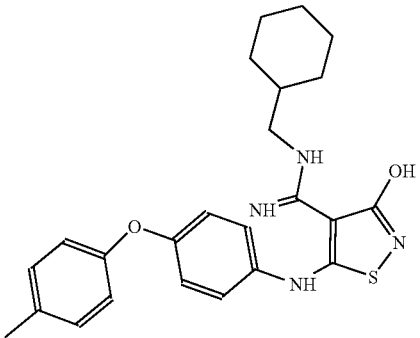 | A |
| 110 | 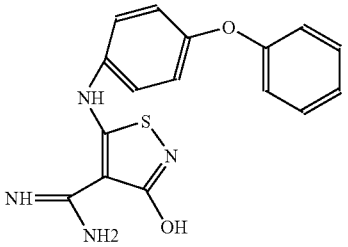 | B |
| 111 | 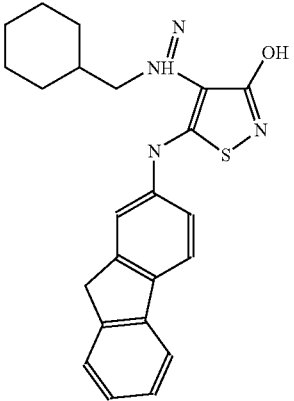 | C |
| 112 | 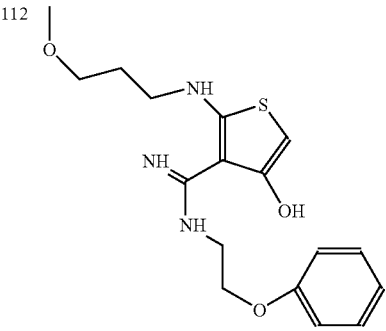 | C |

TABLE 1-continued

Biological Activity of Compounds of Formula I

| # | Structure | Avg IC50 |
|---|---|---|
| 113 | 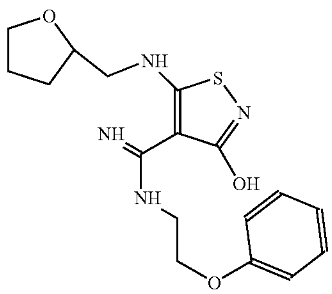 | C |
| 114 | 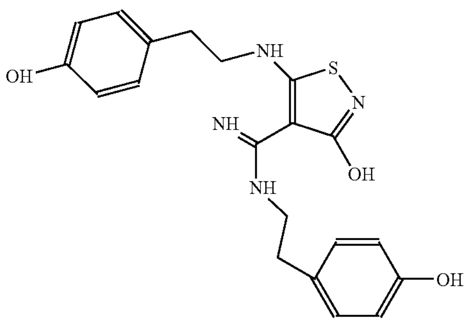 | C |
| 115 | 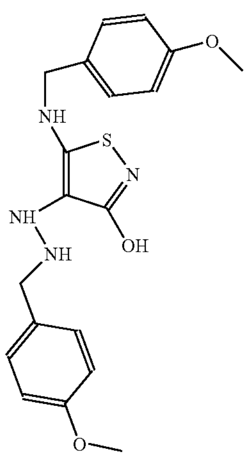 | C |
| 116 | 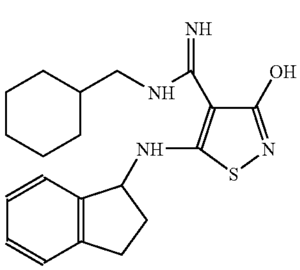 | C |

TABLE 1-continued

Biological Activity of Compounds of Formula I

| # | Structure | Avg IC50 |
|---|-----------|----------|
| 117 | 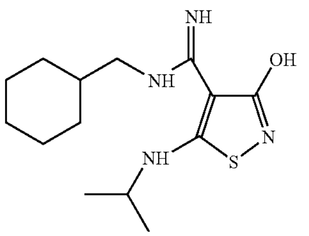 | C |
| 118 | 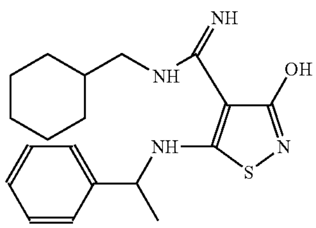 | C |
| 119 | 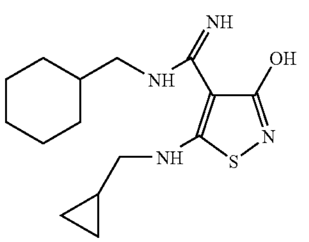 | C |
| 120 | 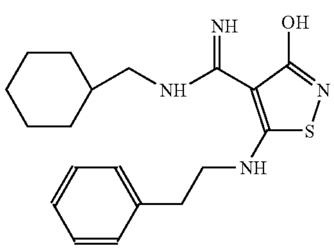 | C |
| 121 | 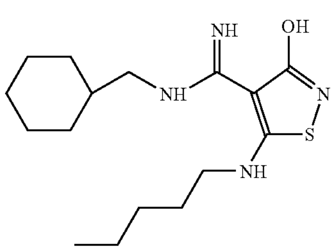 | C |

TABLE 1-continued

Biological Activity of Compounds of Formula I

| # | Structure | Avg IC50 |
|---|---|---|
| 122 | 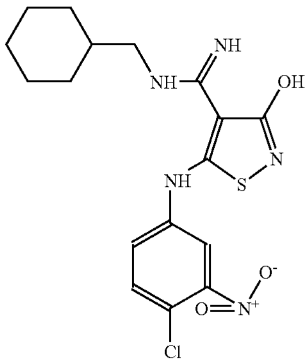 | C |
| 123 | 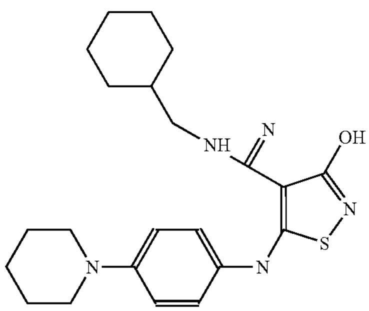 | C |
| 124 | 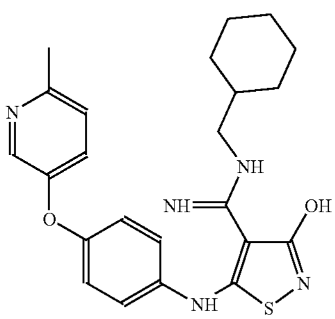 | B |
| 125 | 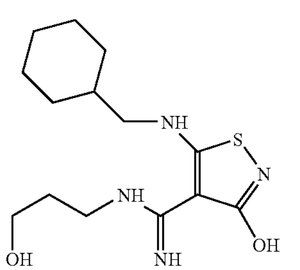 | C |

TABLE 1-continued

Biological Activity of Compounds of Formula I

| # | Structure | Avg IC50 |
|---|-----------|----------|
| 126 | 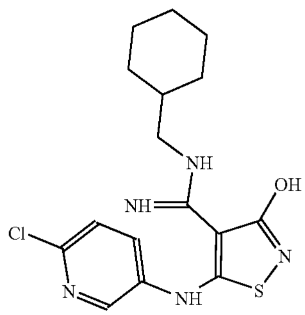 | C |
| 127 | 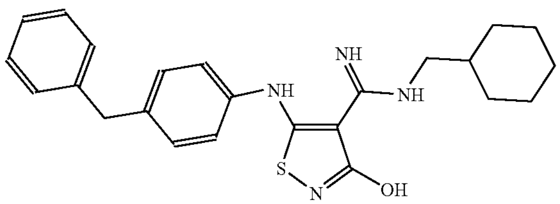 | B |
| 128 | 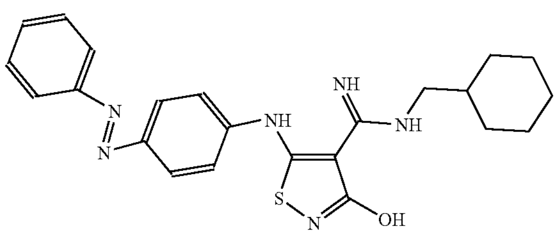 | B |
| 129 | 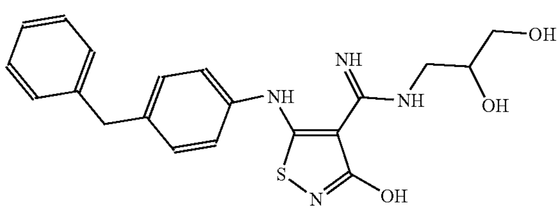 | B |
| 130 | 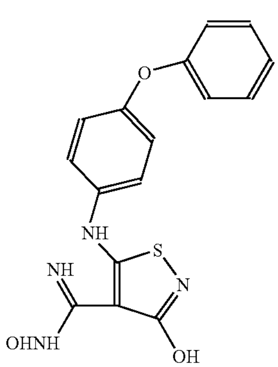 | A |

TABLE 1-continued
Biological Activity of Compounds of Formula I
| # | Structure | Avg IC50 |
|---|---|---|
| 131 | 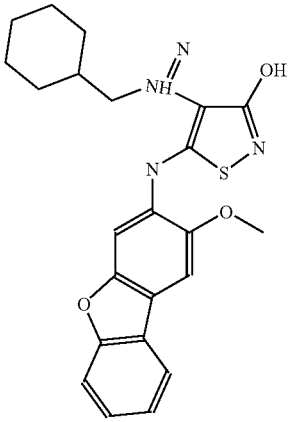 | C |
| 132 | 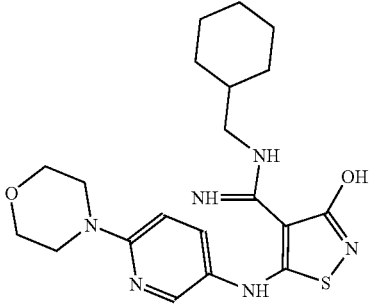 | C |
| 133 | 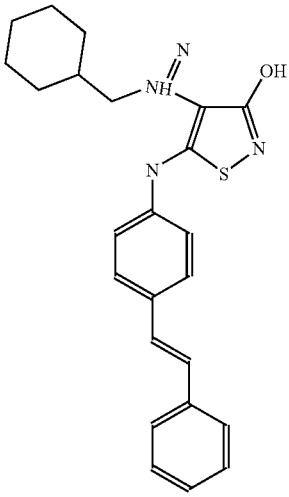 | C |
| 134 | 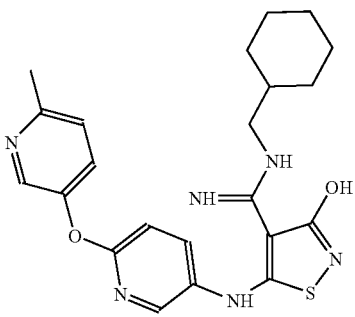 | C |

TABLE 1-continued

Biological Activity of Compounds of Formula I

| # | Structure | Avg IC50 |
|---|---|---|
| 135 | 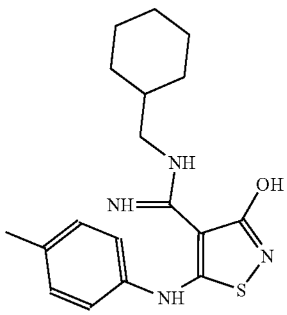 | C |
| 136 | 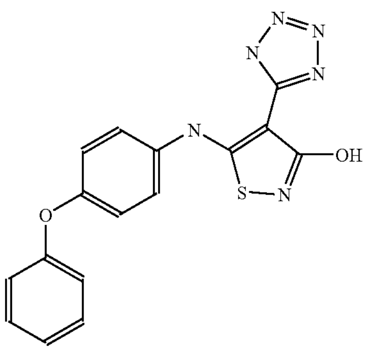 | C |
| 137 | 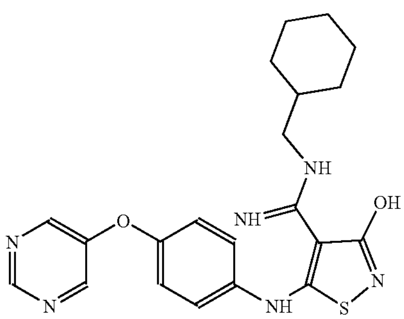 | C |
| 138 | 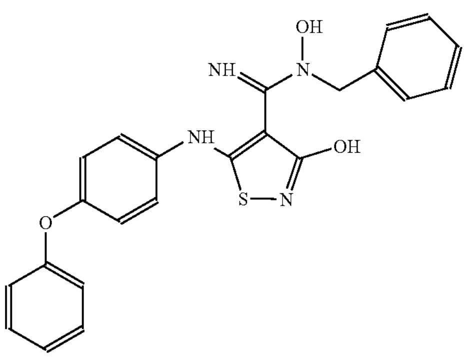 | B |

TABLE 1-continued
Biological Activity of Compounds of Formula I
| # | Structure | Avg IC50 |
|---|-----------|----------|
| 139 | 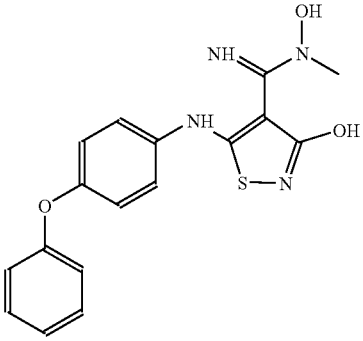 | B |
| 140 | 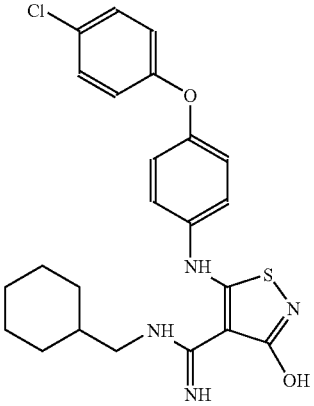 | A |
| 141 | 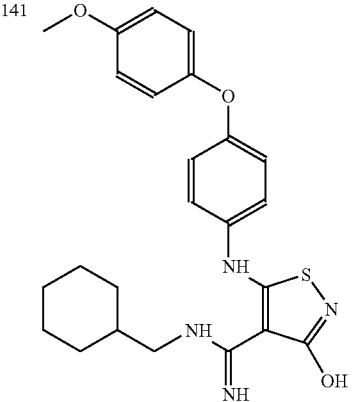 | B |

TABLE 1-continued

Biological Activity of Compounds of Formula I

| # | Structure | Avg IC50 |
|---|-----------|----------|
| 142 | 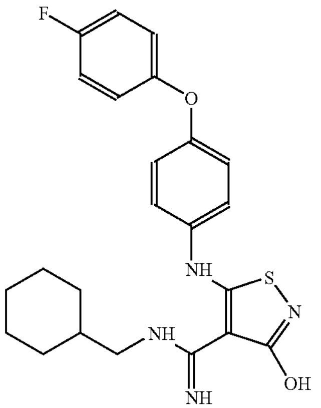 | A |
| 143 | 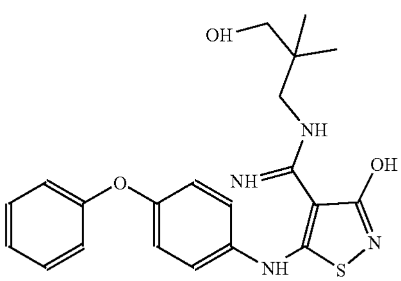 | A |
| 144 | 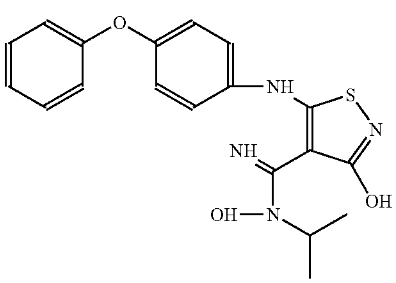 | A |
| 145 | 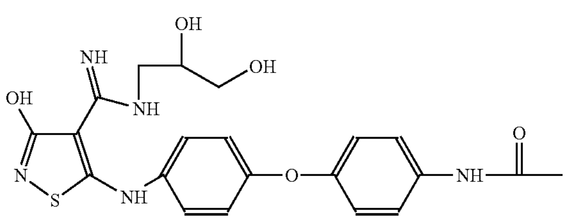 | C |
| 146 | 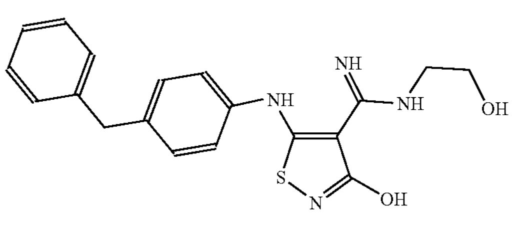 | C |

TABLE 1-continued
Biological Activity of Compounds of Formula I
| # | Structure | Avg IC50 |
|---|---|---|
| 147 | 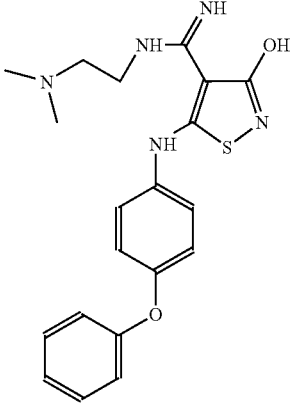 | B |
| 148 | 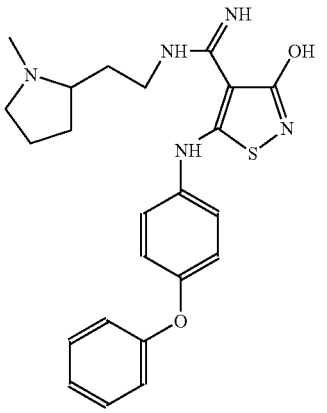 | C |
| 149 | 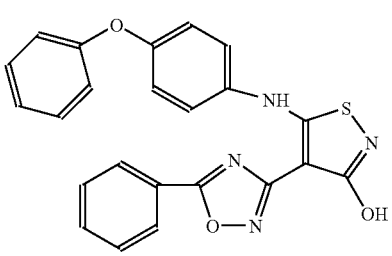 | C |
| 150 | 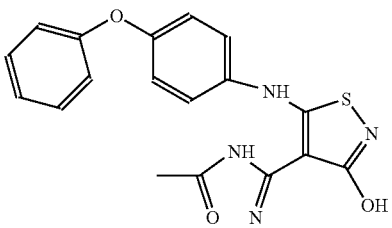 | C |
| 151 | 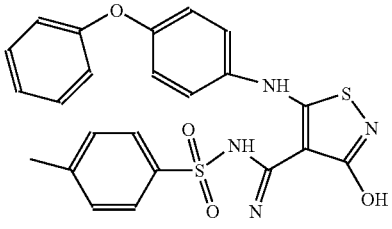 | C |

TABLE 1-continued
Biological Activity of Compounds of Formula I
| # | Structure | Avg IC50 |
|---|-----------|----------|
| 152 | 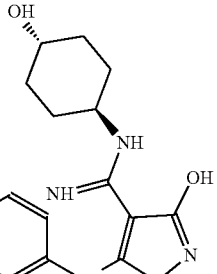 | A |
| 153 | 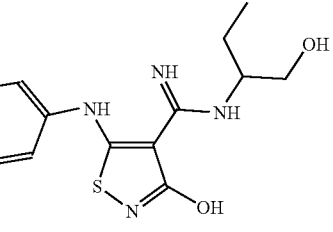 | B |
| 154 | 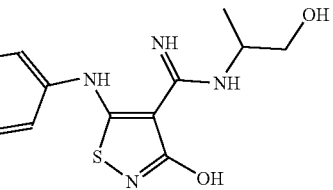 | A |
| 155 | 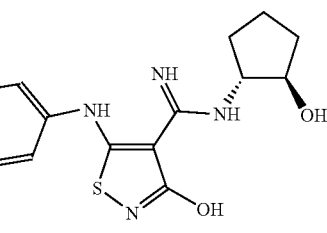 | B |
| 156 | 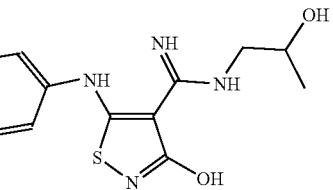 | B |
| 157 | 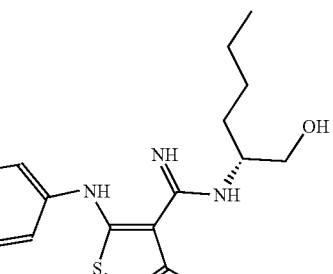 | B |

TABLE 1-continued

Biological Activity of Compounds of Formula I

| # | Structure | Avg IC50 |
|---|-----------|----------|
| 158 | 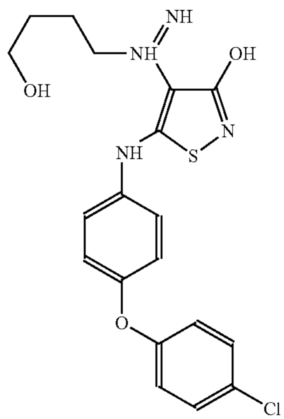 | B |
| 159 | 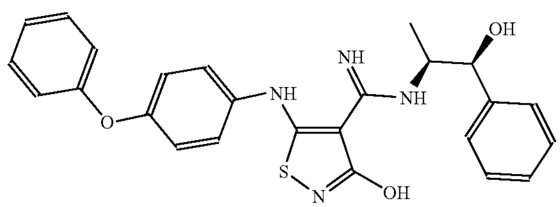 | A |
| 160 | 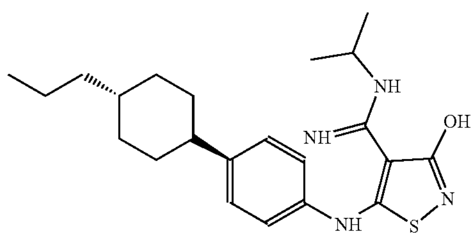 | B |
| 161 | 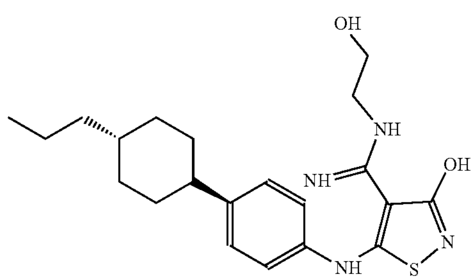 | C |
| 162 | 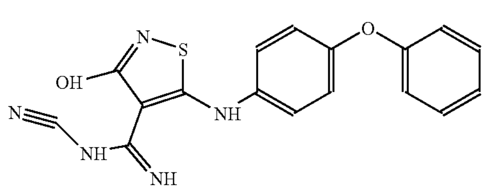 | C |

TABLE 1-continued

Biological Activity of Compounds of Formula I

| # | Structure | Avg IC50 |
|---|-----------|----------|
| 163 | 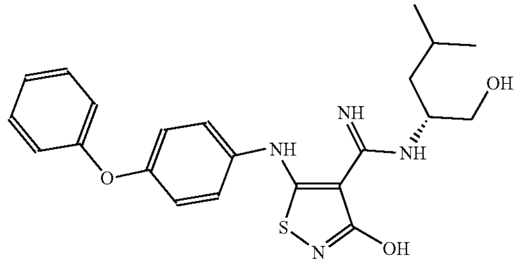 | B |
| 164 | 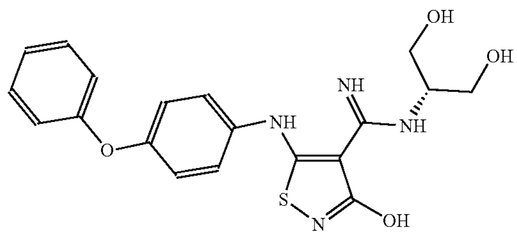 | A |
| 165 | 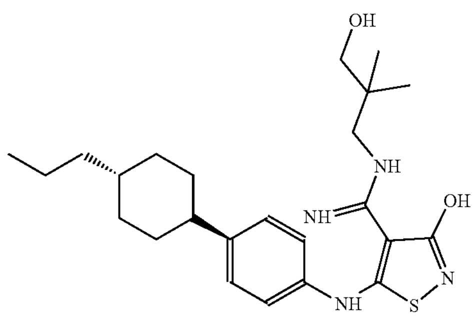 | B |
| 166 | 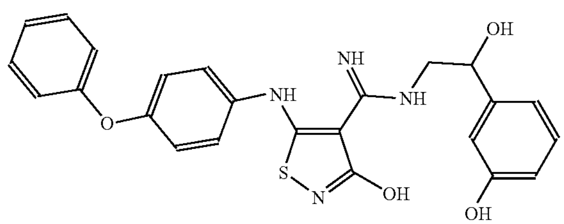 | A |
| 167 | 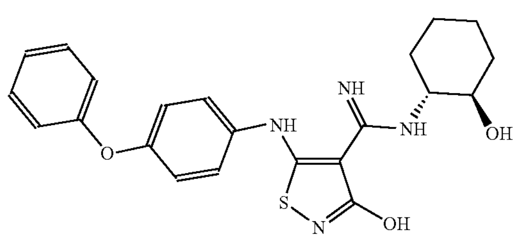 | B |

TABLE 1-continued

Biological Activity of Compounds of Formula I

| # | Structure | Avg IC50 |
|---|---|---|
| 168 | 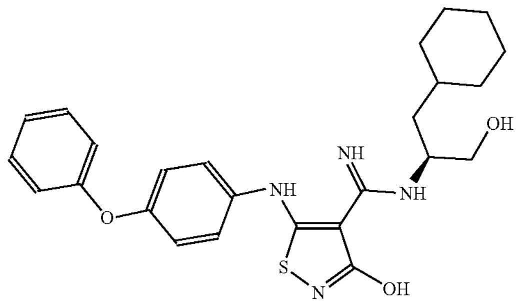 | C |
| 169 | 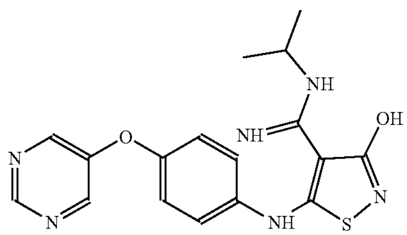 | B |
| 170 | 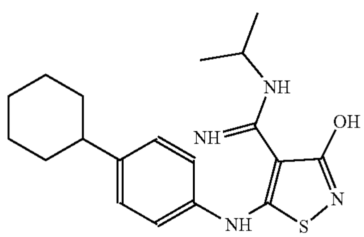 | B |
| 171 | 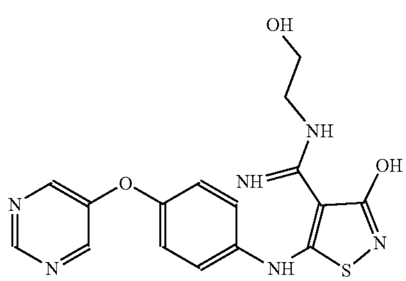 | C |
| 172 | 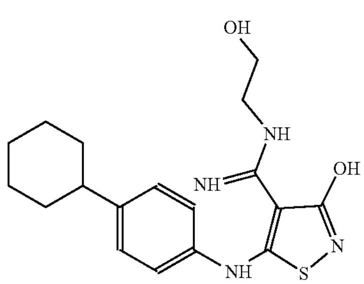 | C |

TABLE 1-continued

Biological Activity of Compounds of Formula I

| # | Structure | Avg IC50 |
|---|-----------|----------|
| 173 | 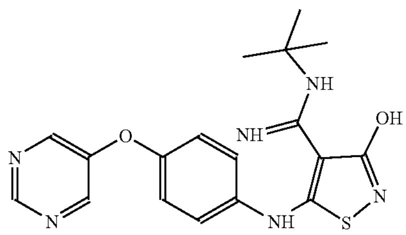 | A |
| 174 | 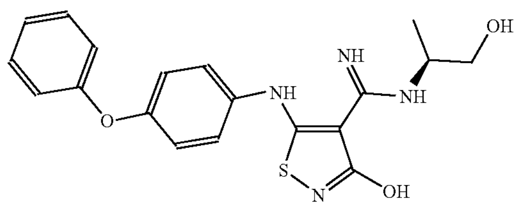 | A |
| 175 | 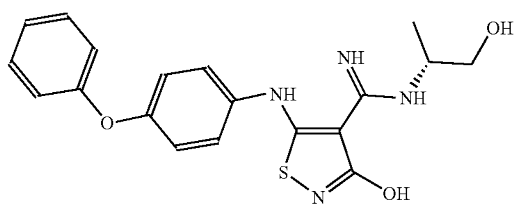 | A |
| 176 | 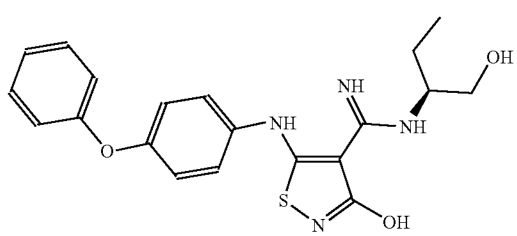 | B |
| 177 | 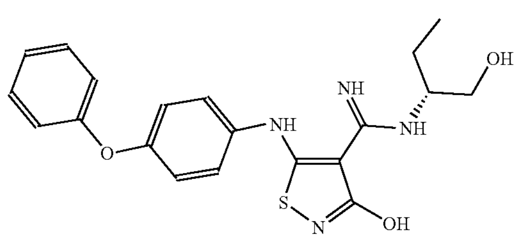 | B |
| 178 | 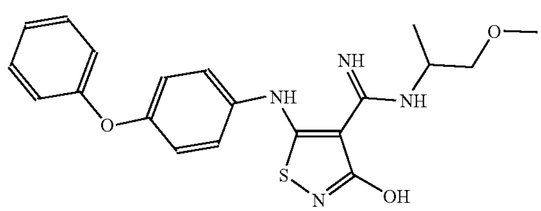 | A |

TABLE 1-continued

Biological Activity of Compounds of Formula I

| # | Structure | Avg IC50 |
|---|-----------|----------|
| 179 | 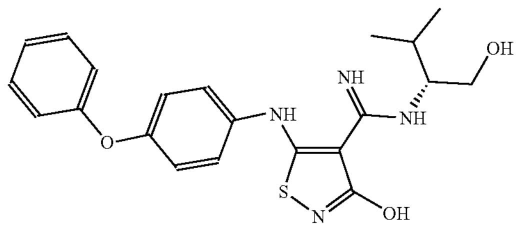 | B |
| 180 | 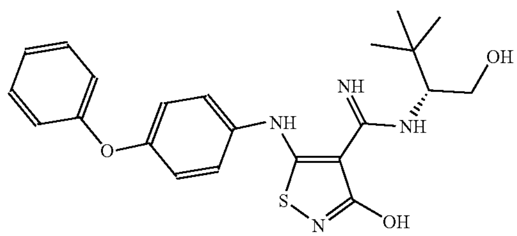 | B |
| 181 | 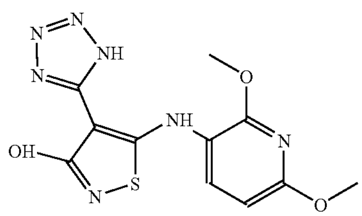 | C |
| 182 | 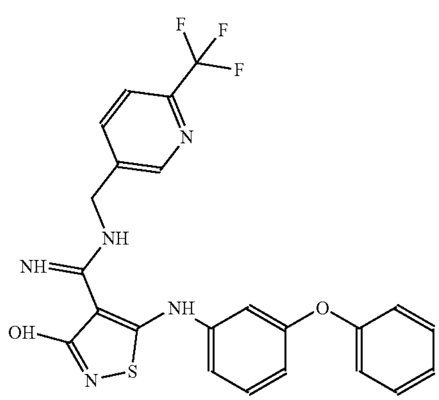 | B |
| 183 | 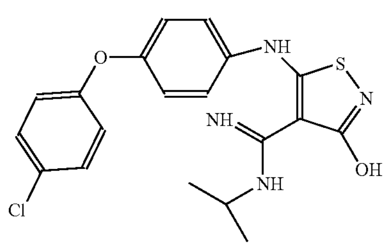 | A |

TABLE 1-continued

Biological Activity of Compounds of Formula I

| # | Structure | Avg IC50 |
|---|-----------|----------|
| 184 | 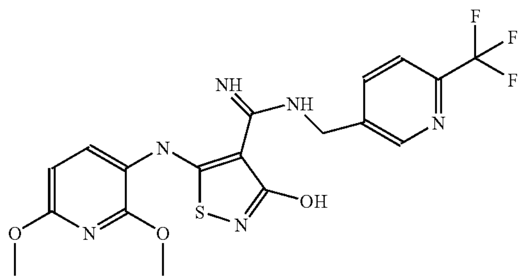 | C |
| 185 | 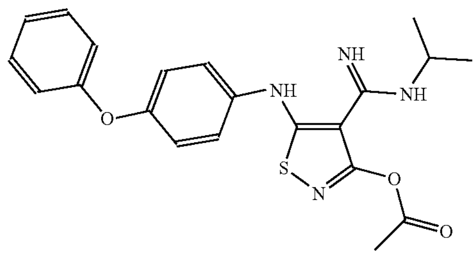 | B |
| 186 | 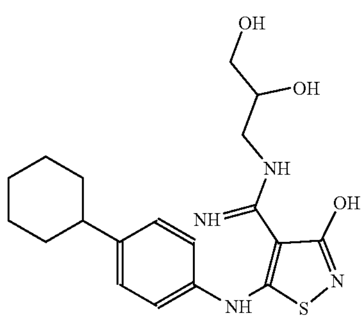 | C |
| 187 | 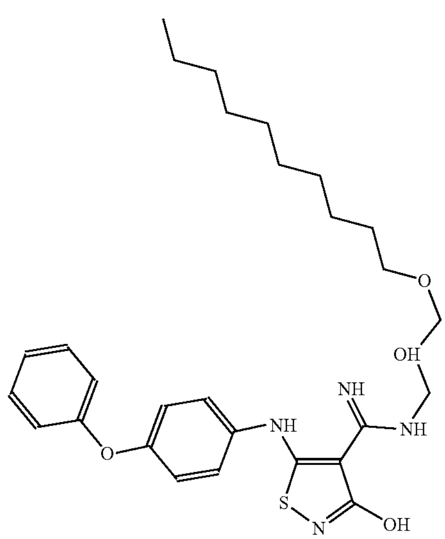 | C |

US 7,429,667 B2

TABLE 1-continued

Biological Activity of Compounds of Formula I

| # | Structure | Avg IC50 |
|---|-----------|----------|
| 188 | (structure) | B |
| 189 | (structure) | B |
| 190 | (structure) | B |
| 191 | (structure) | B |
| 192 | (structure) | B |
| 193 | (structure) | C |

TABLE 1-continued

Biological Activity of Compounds of Formula I

| # | Structure | Avg IC50 |
|---|-----------|----------|
| 194 | 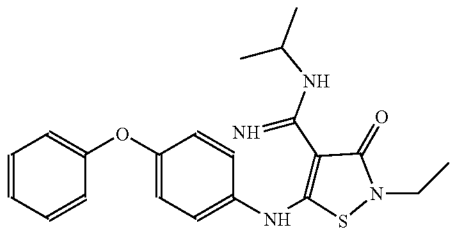 | C |
| 195 | 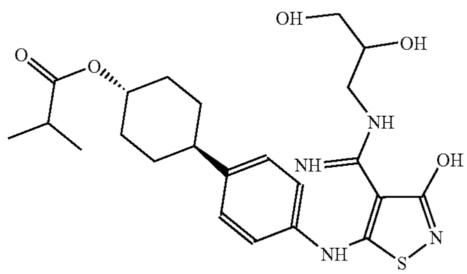 | C |
| 196 | 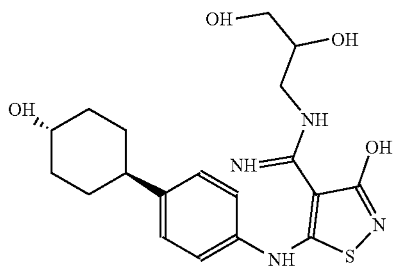 | C |
| 197 | 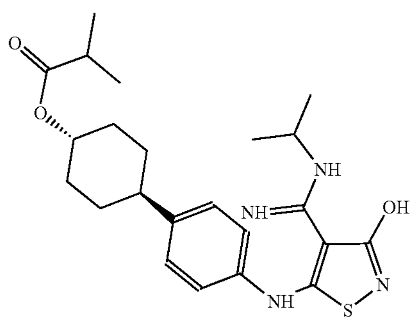 | B |
| 198 | 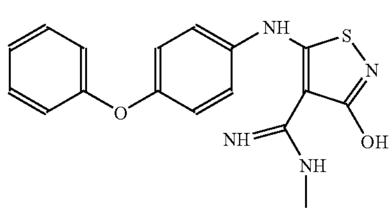 | A |
| 199 | 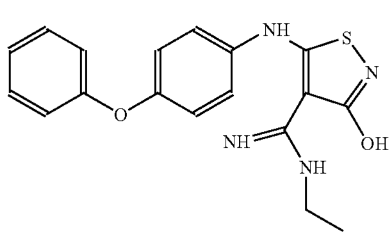 | A |

TABLE 1-continued
Biological Activity of Compounds of Formula I
| # | Structure | Avg IC50 |
|---|-----------|----------|
| 200 | 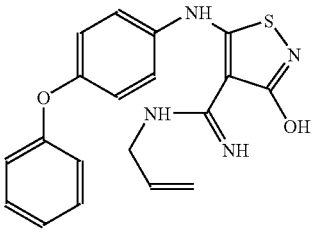 | A |
| 201 | 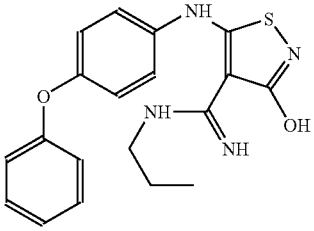 | B |
| 202 | 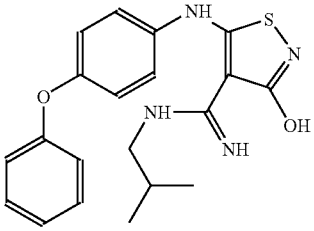 | A |
| 203 | 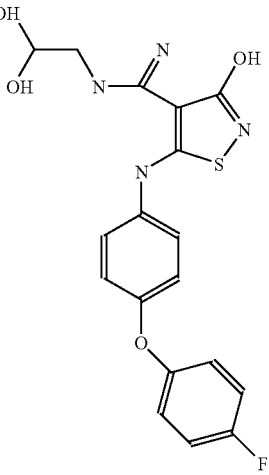 | C |

TABLE 1-continued
Biological Activity of Compounds of Formula I
| # | Structure | Avg IC50 |
|---|-----------|----------|
| 204 | 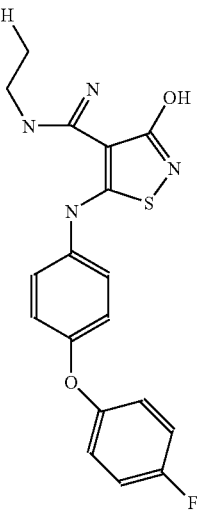 | C |
| 205 | 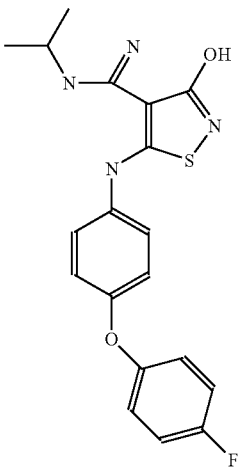 | B |
| 206 | 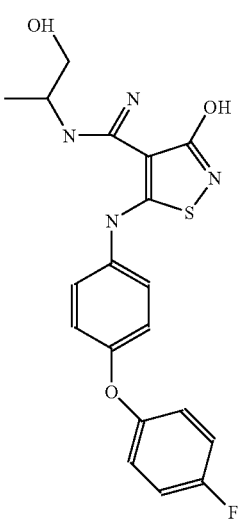 | C |

TABLE 1-continued
Biological Activity of Compounds of Formula I
| # | Structure | Avg IC50 |
|---|-----------|----------|
| 207 | 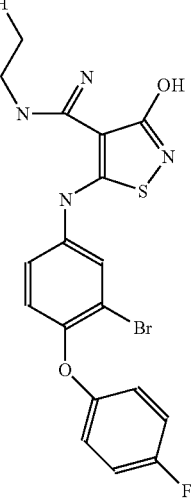 | C |
| 208 | 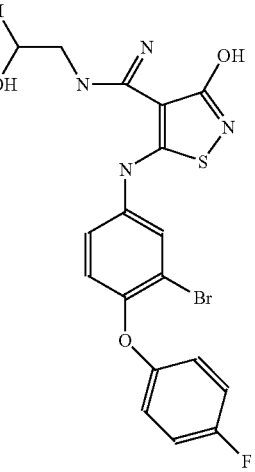 | C |
| 209 | 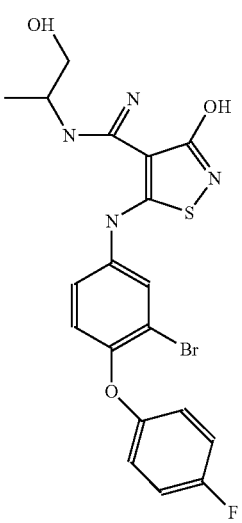 | B |

TABLE 1-continued
Biological Activity of Compounds of Formula I
| # | Structure | Avg IC50 |
|---|-----------|----------|
| 210 | 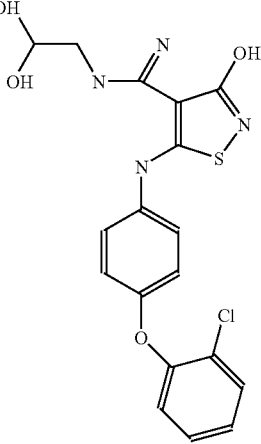 | B |
| 211 | 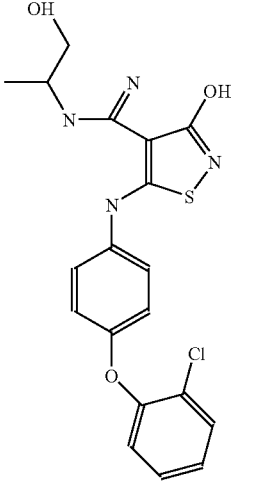 | C |
| 212 | 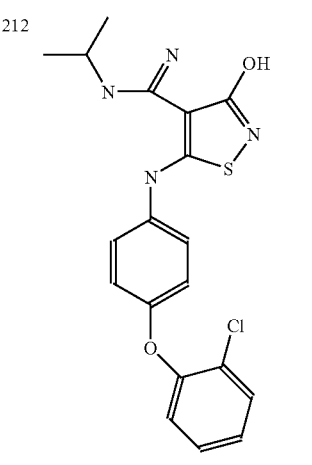 | B |

TABLE 1-continued

Biological Activity of Compounds of Formula I

| # | Structure | Avg IC50 |
|---|-----------|----------|
| 213 | 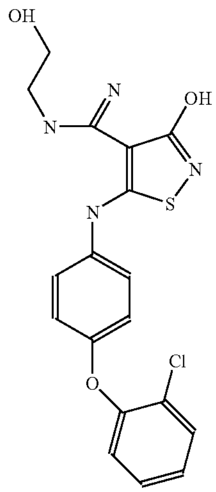 | A |
| 214 | 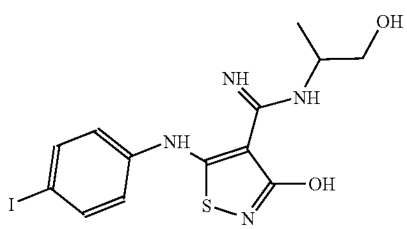 | C |
| 215 | 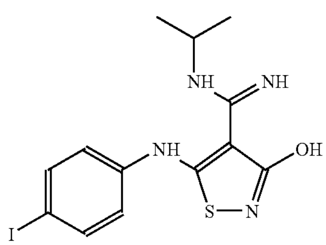 | C |
| 216 | 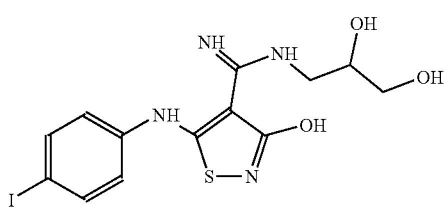 | C |
| 217 | 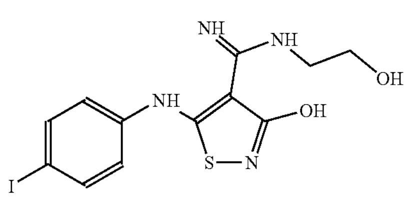 | C |

TABLE 1-continued

Biological Activity of Compounds of Formula I

| # | Structure | Avg IC50 |
|---|-----------|----------|
| 218 | (structure) | A |

"A" denotes inhibitory concentrations of 1 nM-100 nM,
"B" denotes inhibitory concentrations of 100 nM-500 nM, and
"C" denotes inhibitory concentrations of greater than 500 nM.

TABLE 2

Biological Activity of Compounds of Formula I, where Ar¹-A contains an amido or indolo group

| # | Structure | Avg IC50 |
|---|-----------|----------|
| 219 | (structure) | A |
| 220 | (structure) | C |

TABLE 2-continued

Biological Activity of Compounds of Formula I, where Ar¹-A contains an amido or indolo group

| # | Structure | Avg IC50 |
|---|-----------|----------|
| 221 | 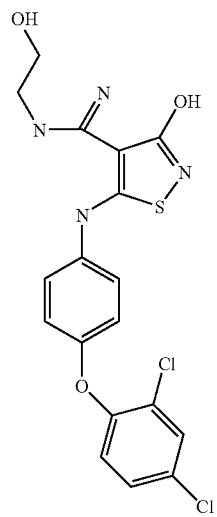 | B |
| 222 | 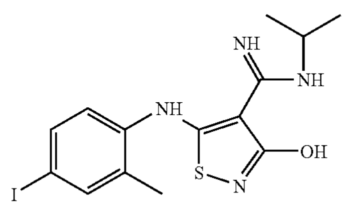 | A |
| 223 | 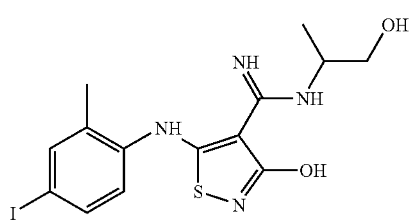 | A |
| 224 | 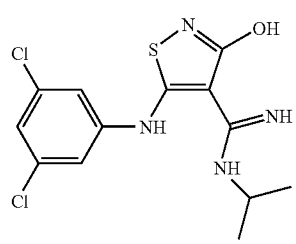 | B |
| 225 | 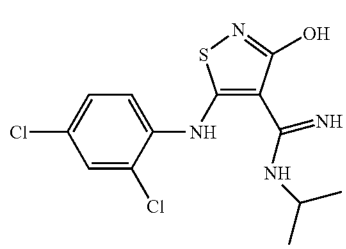 | A |

TABLE 2-continued
Biological Activity of Compounds of Formula I,
where Ar¹-A contains an amido or indolo group
| # | Structure | Avg IC50 |
|---|-----------|----------|
| 226 | 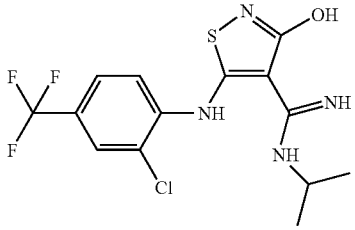 | A |
| 227 | 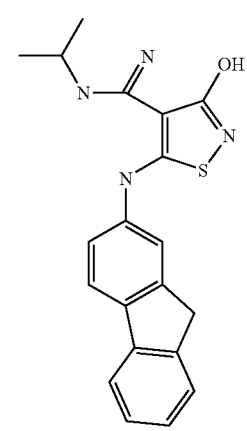 | C |
| 228 | 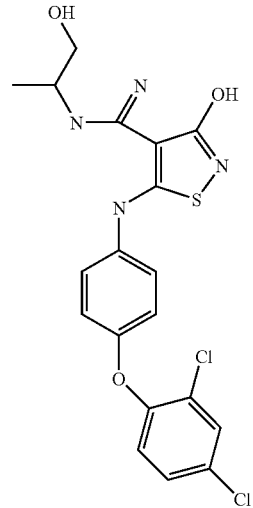 | A |

TABLE 2-continued
Biological Activity of Compounds of Formula I,
where Ar¹-A contains an amido or indolo group
| # | Structure | Avg IC50 |
|---|-----------|----------|
| 229 | 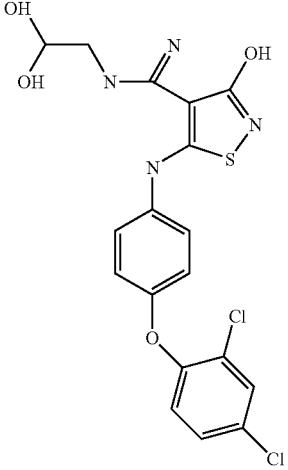 | A |
| 230 | 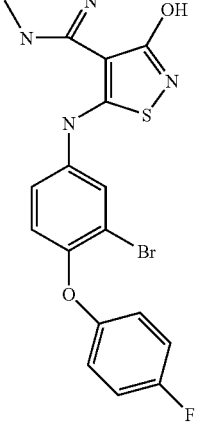 | C |
| 231 | 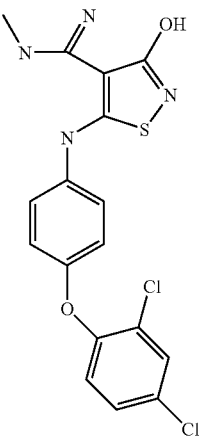 | B |

TABLE 2-continued

Biological Activity of Compounds of Formula I,
where Ar¹-A contains an amido or indolo group

| # | Structure | Avg IC50 |
|---|-----------|----------|
| 232 | 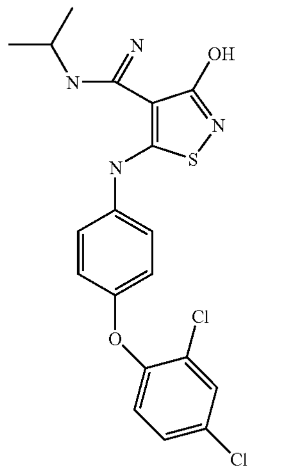 | A |
| 233 | 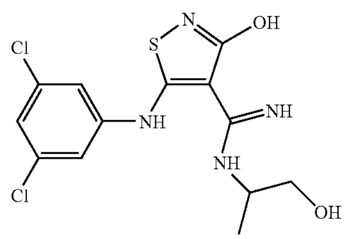 | B |
| 234 | 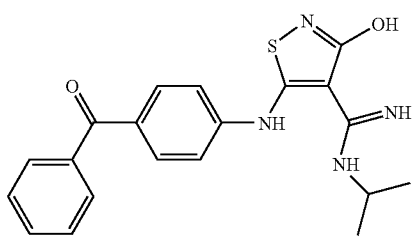 | B |
| 235 | 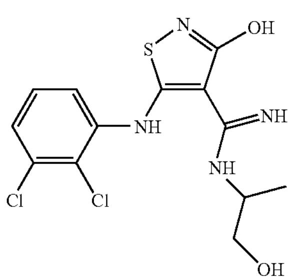 | A |
| 236 | 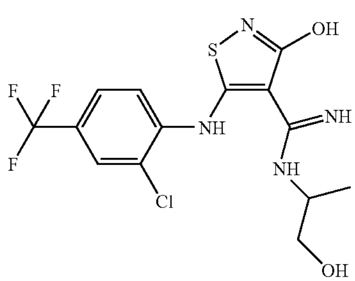 | A |

TABLE 2-continued
Biological Activity of Compounds of Formula I, where Ar¹-A contains an amido or indolo group
| # | Structure | Avg IC50 |
|---|-----------|----------|
| 237 | 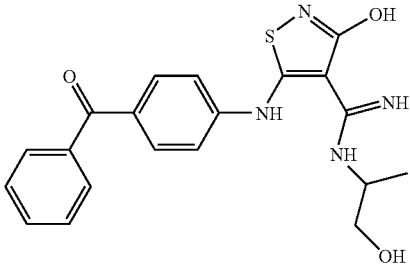 | A |
| 238 | 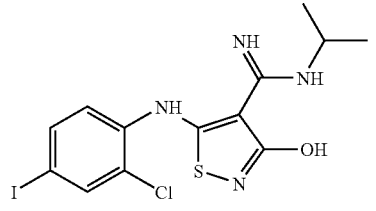 | A |
| 239 | 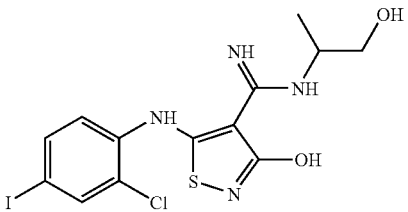 | A |
| 240 | 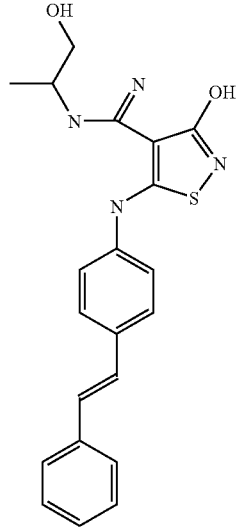 | B |

TABLE 2-continued

Biological Activity of Compounds of Formula I, where Ar¹-A contains an amido or indolo group

| # | Structure | Avg IC50 |
|---|-----------|----------|
| 241 | 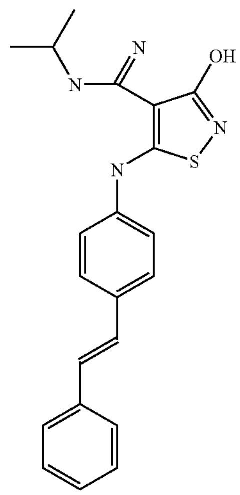 | B |
| 242 | 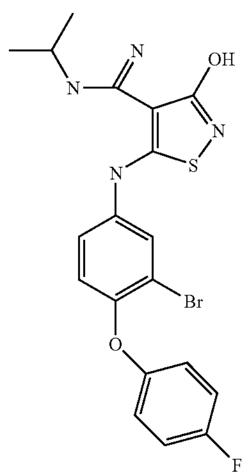 | B |
| 243 | 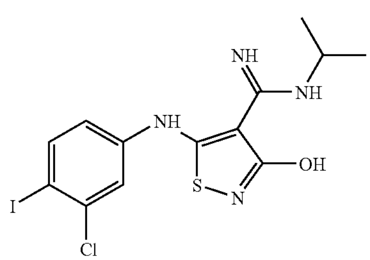 | B |
| 244 | 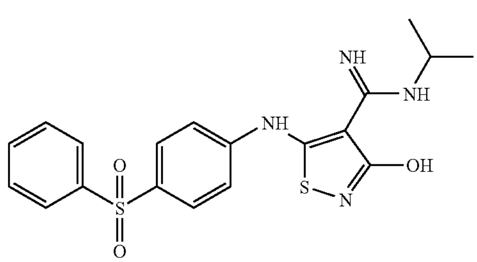 | C |

TABLE 2-continued

Biological Activity of Compounds of Formula I,
where Ar¹-A contains an amido or indolo group

| # | Structure | Avg IC50 |
|---|-----------|----------|
| 245 | 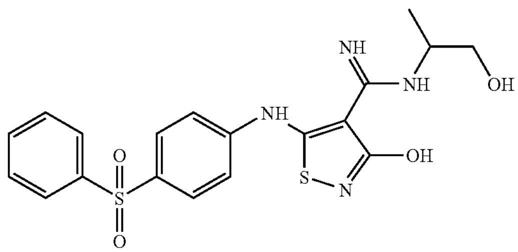 | C |
| 246 | 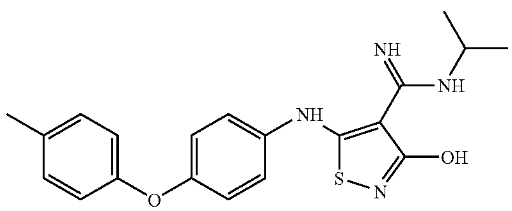 | A |
| 247 | 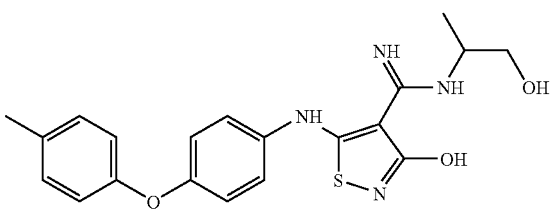 | B |
| 248 | 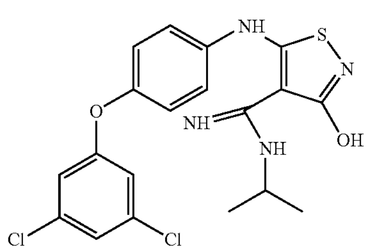 | A |
| 249 | 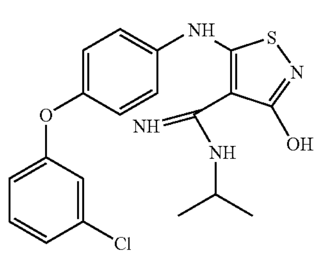 | A |
| 250 | 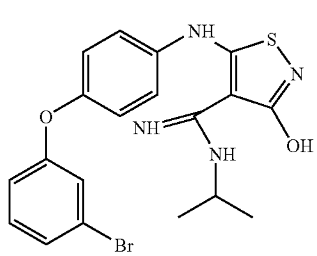 | A |

TABLE 2-continued

Biological Activity of Compounds of Formula I,
where Ar¹-A contains an amido or indolo group

| # | Structure | Avg IC50 |
|---|-----------|----------|
| 251 | 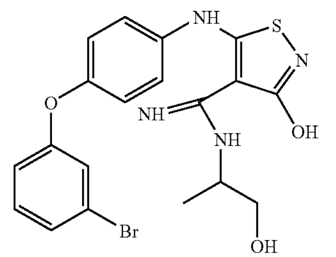 | A |
| 252 | 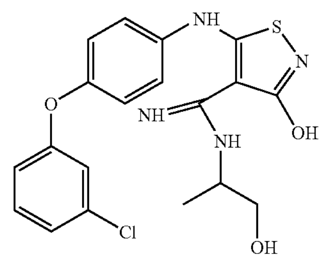 | A |
| 253 | 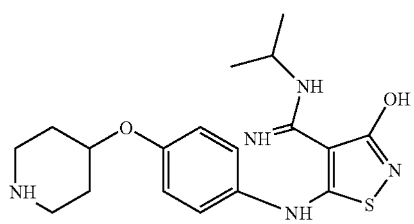 | C |
| 254 | 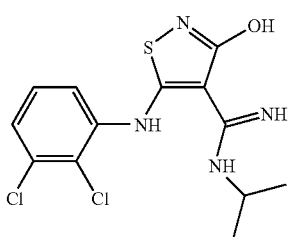 | B |
| 255 | 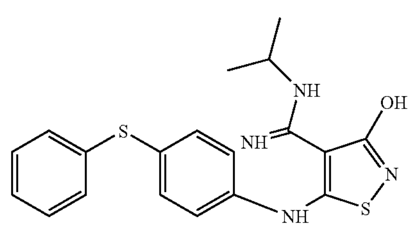 | A |
| 256 | 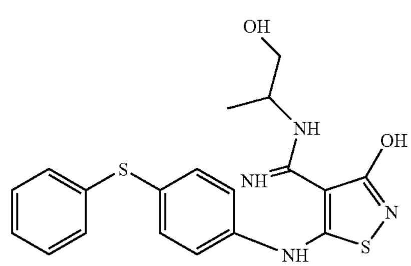 | A |

TABLE 2-continued

Biological Activity of Compounds of Formula I,
where Ar¹-A contains an amido or indolo group

| # | Structure | Avg IC50 |
|---|-----------|----------|
| 257 | 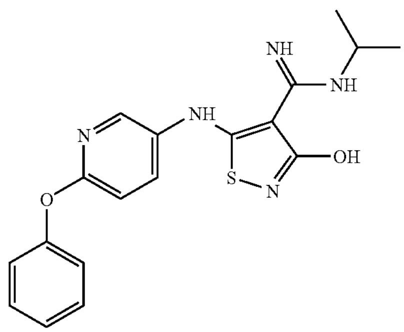 | C |
| 258 | 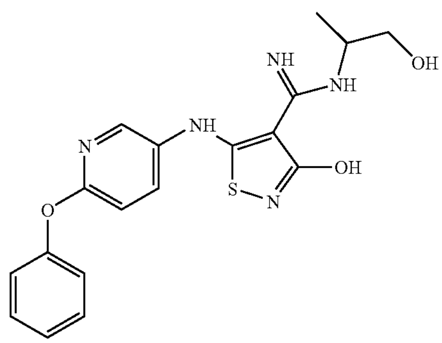 | C |
| 259 | 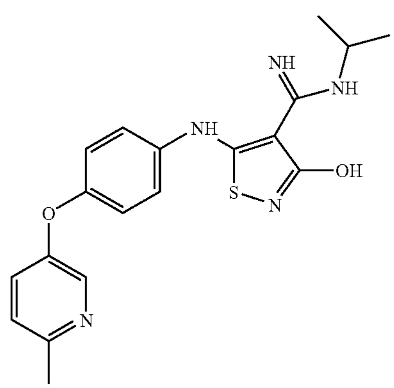 | C |
| 260 | 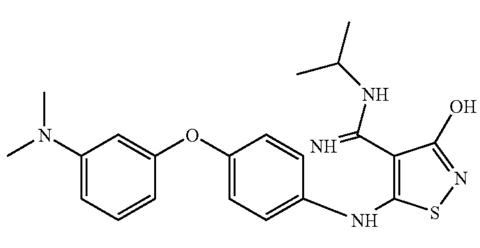 | B |

TABLE 2-continued

Biological Activity of Compounds of Formula I,
where Ar¹-A contains an amido or indolo group

| # | Structure | Avg IC50 |
|---|-----------|----------|
| 261 | 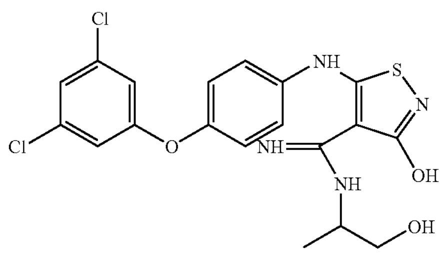 | A |
| 262 | 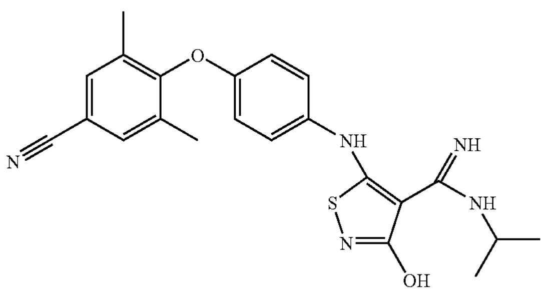 | C |
| 263 | 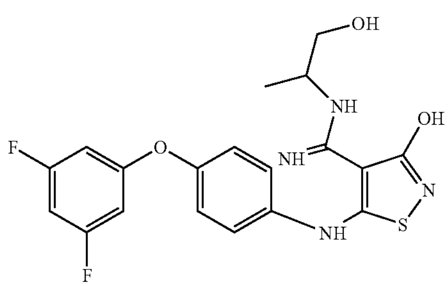 | A |
| 264 | 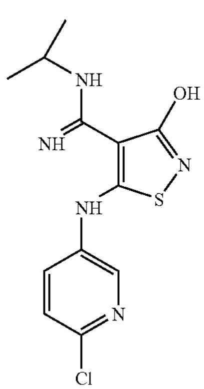 | C |

TABLE 2-continued

Biological Activity of Compounds of Formula I,
where Ar¹-A contains an amido or indolo group

| # | Structure | Avg IC50 |
|---|-----------|----------|
| 265 | 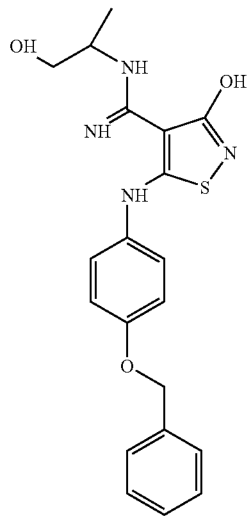 | C |
| 266 | 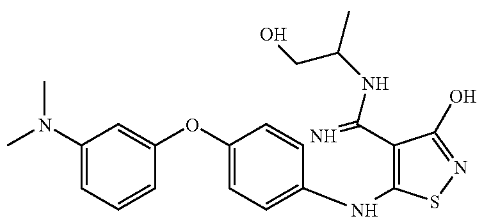 | C |
| 267 | 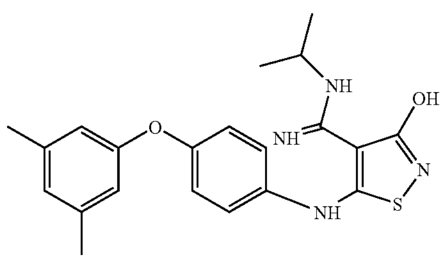 | A |
| 268 | 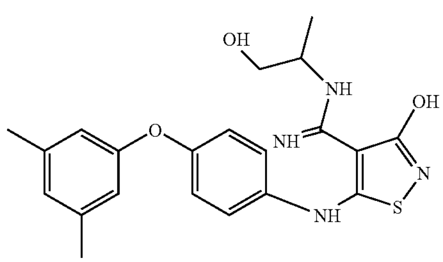 | B |
| 269 | 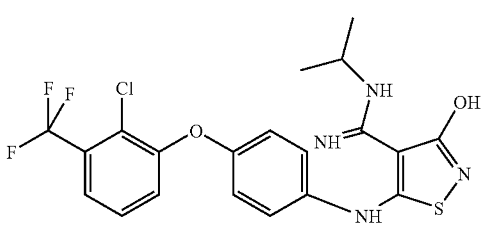 | A |

TABLE 2-continued

Biological Activity of Compounds of Formula I, where Ar¹-A contains an amido or indolo group

| # | Structure | Avg IC50 |
|---|---|---|
| 270 | 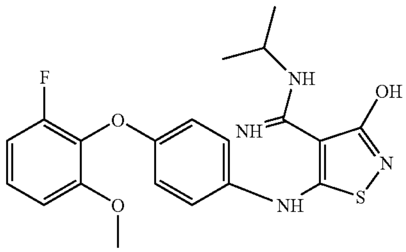 | C |
| 271 | 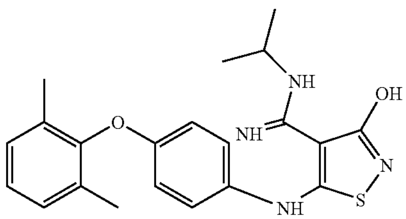 | C |
| 272 | 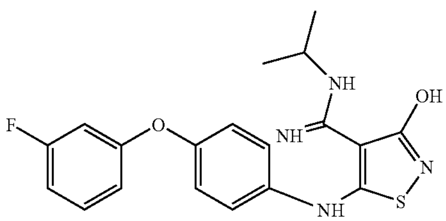 | A |
| 273 | 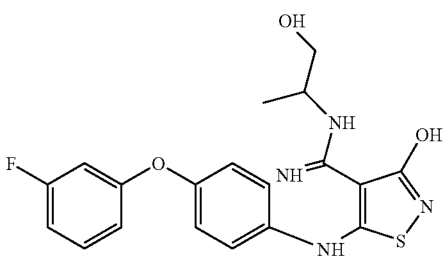 | A |
| 274 | 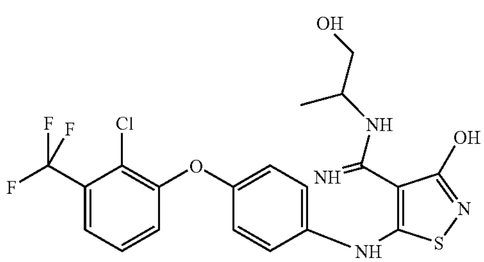 | A |
| 275 | 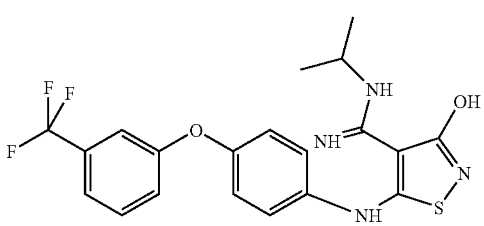 | A |

TABLE 2-continued
Biological Activity of Compounds of Formula I,
where Ar¹-A contains an amido or indolo group
| # | Structure | Avg IC50 |
|---|-----------|----------|
| 276 | 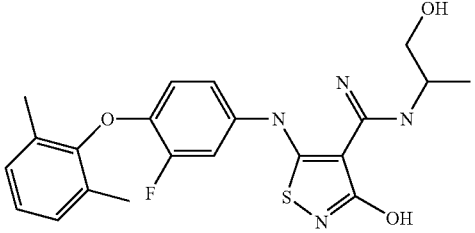 | C |
| 277 | 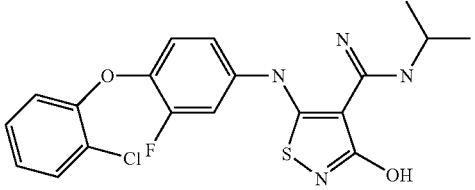 | A |
| 278 | 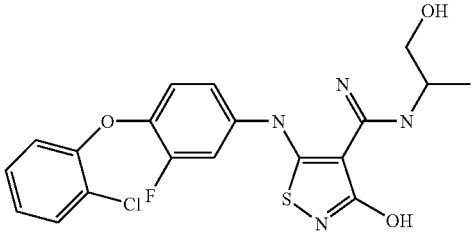 | A |
| 279 | 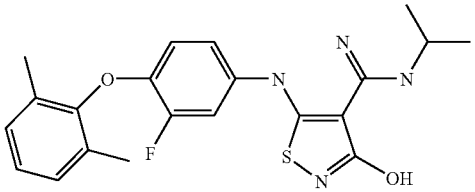 | A |
| 280 | 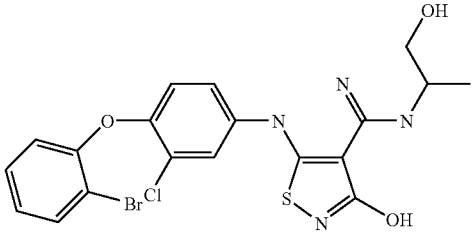 | A |
| 281 | 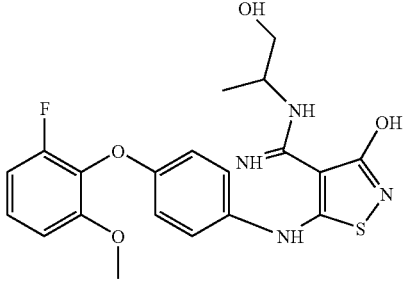 | B |

TABLE 2-continued

Biological Activity of Compounds of Formula I, where Ar¹-A contains an amido or indolo group

| # | Structure | Avg IC50 |
|---|-----------|----------|
| 282 | 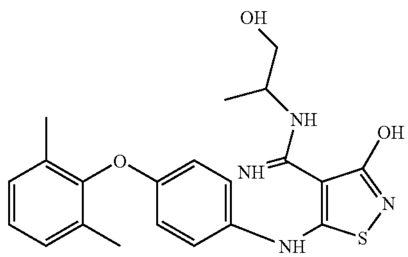 | C |
| 283 | 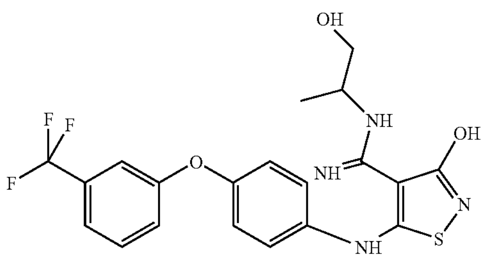 | A |
| 284 | 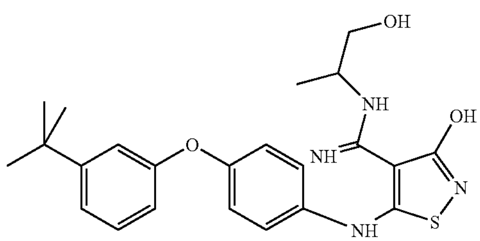 | B |
| 285 | 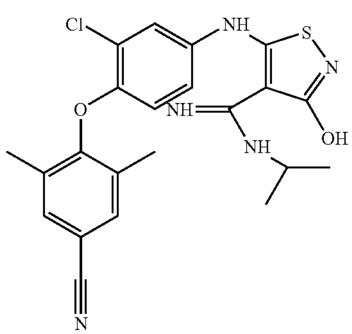 | C |
| 286 | 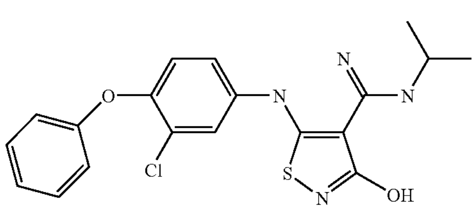 | A |

TABLE 2-continued

Biological Activity of Compounds of Formula I,
where Ar¹-A contains an amido or indolo group

| # | Structure | Avg IC50 |
|---|-----------|----------|
| 287 | 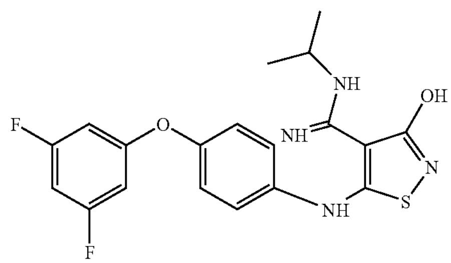 | A |
| 288 | 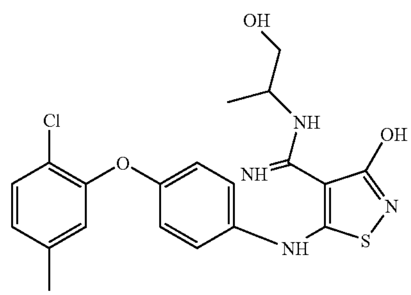 | A |
| 289 | 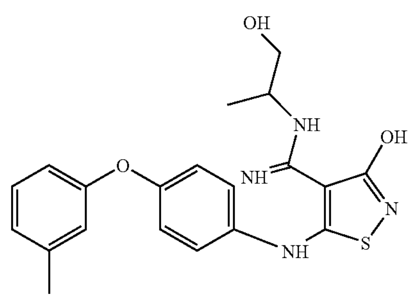 | A |
| 290 | 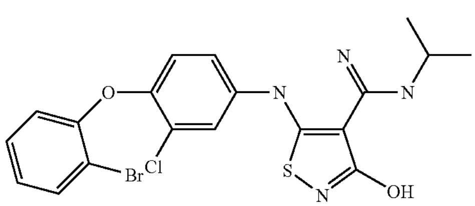 | A |
| 291 | 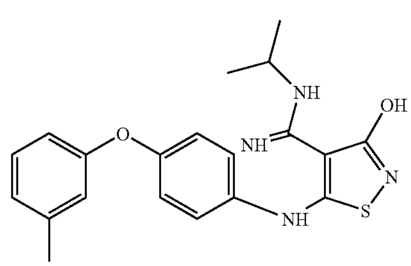 | A |

TABLE 2-continued

Biological Activity of Compounds of Formula I, where Ar¹-A contains an amido or indolo group

| # | Structure | Avg IC50 |
|---|-----------|----------|
| 292 | 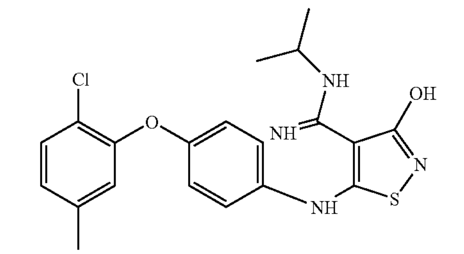 | A |
| 293 | 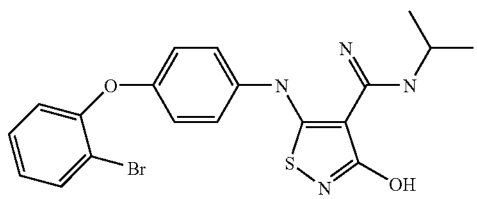 | A |
| 294 | 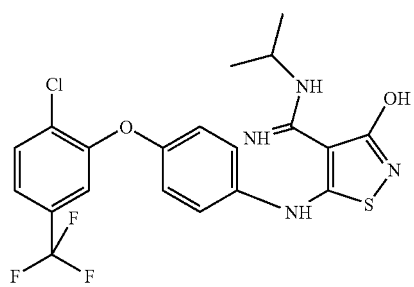 | B |
| 295 | 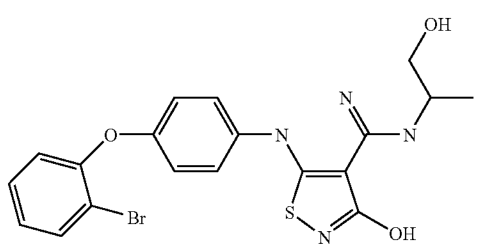 | A |
| 296 | 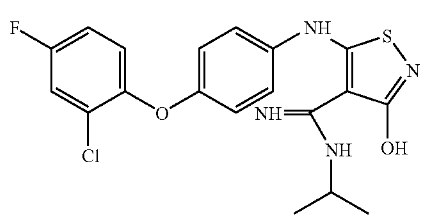 | B |
| 297 | 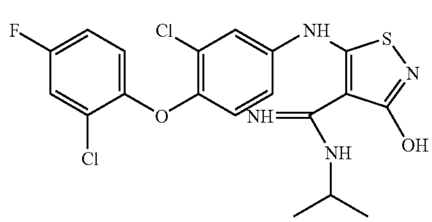 | B |

TABLE 2-continued

Biological Activity of Compounds of Formula I, where Ar¹-A contains an amido or indolo group

| # | Structure | Avg IC50 |
|---|-----------|----------|
| 298 | 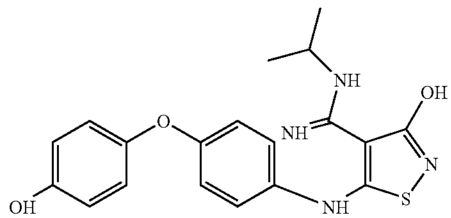 | B |
| 299 | 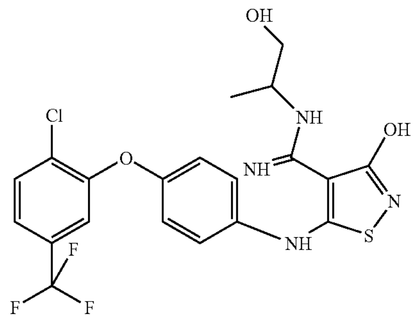 | C |
| 300 | 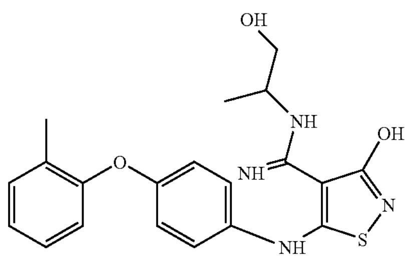 | A |
| 301 | 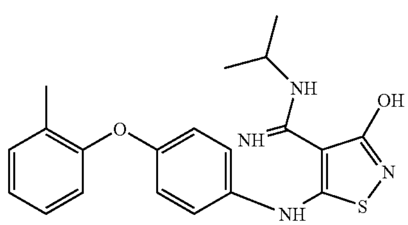 | A |
| 302 | 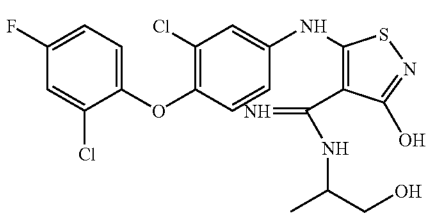 | B |
| 303 | 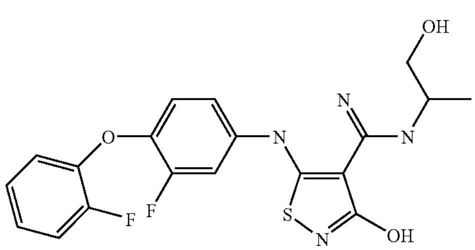 | A |

TABLE 2-continued
Biological Activity of Compounds of Formula I,
where Ar¹-A contains an amido or indolo group
| # | Structure | Avg IC50 |
|---|-----------|----------|
| 304 | 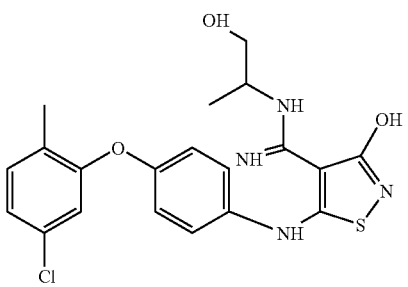 | A |
| 305 | 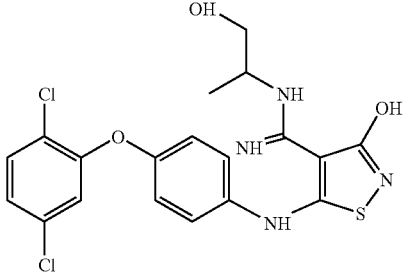 | A |
| 306 | 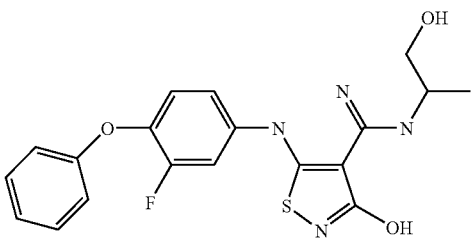 | A |
| 307 | 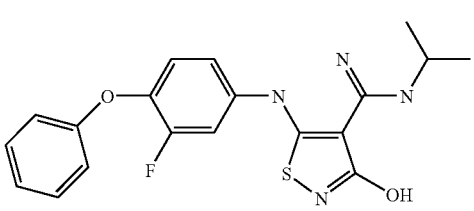 | A |
| 308 | 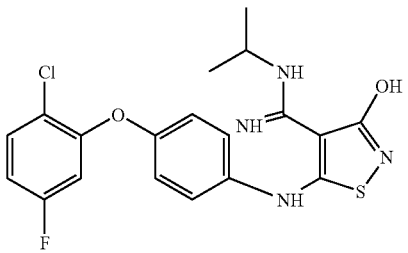 | B |
| 309 | 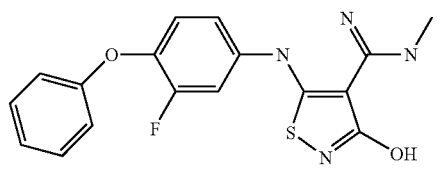 | C |

TABLE 2-continued

Biological Activity of Compounds of Formula I,
where Ar¹-A contains an amido or indolo group

| # | Structure | Avg IC50 |
|---|-----------|----------|
| 310 | | A |
| 311 | | B |
| 312 | | A |
| 313 | | C |
| 314 | | C |

TABLE 2-continued

Biological Activity of Compounds of Formula I,
where Ar¹-A contains an amido or indolo group

| # | Structure | Avg IC50 |
|---|---|---|
| 315 | 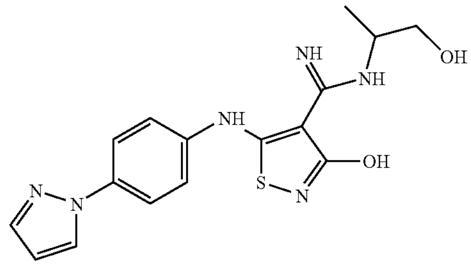 | C |
| 316 | 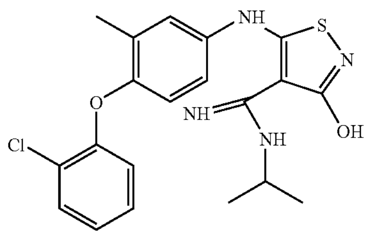 | A |
| 317 | 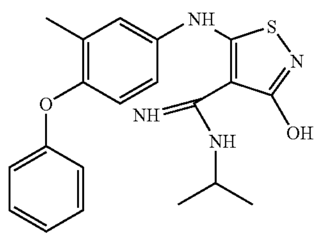 | B |
| 318 | 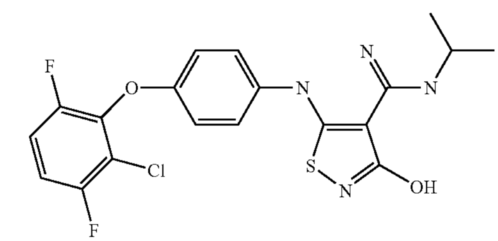 | B |
| 319 | 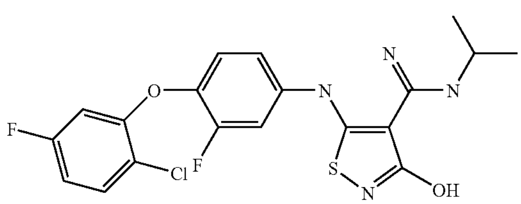 | A |
| 320 | 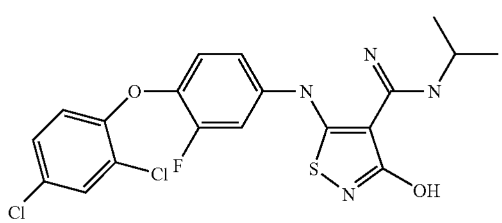 | A |

TABLE 2-continued
Biological Activity of Compounds of Formula I, where Ar¹-A contains an amido or indolo group
| # | Structure | Avg IC50 |
|---|---|---|
| 321 | 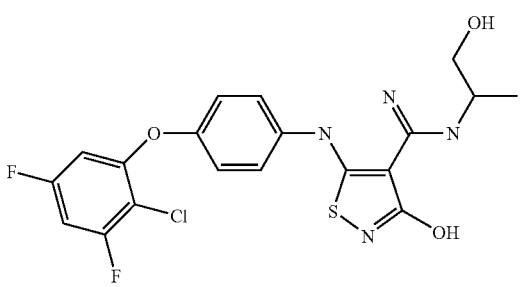 | A |
| 322 | 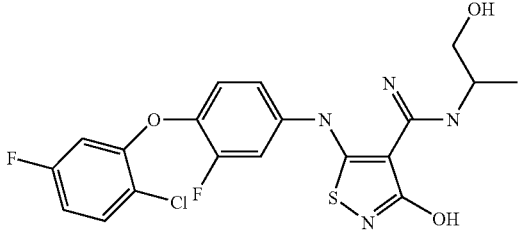 | A |
| 323 | 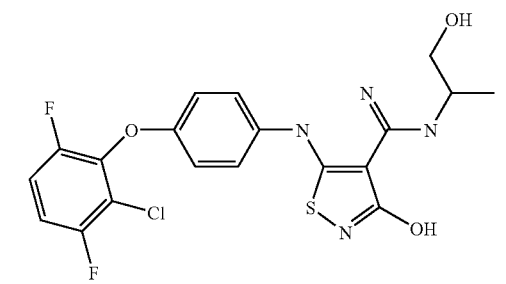 | B |
| 324 | 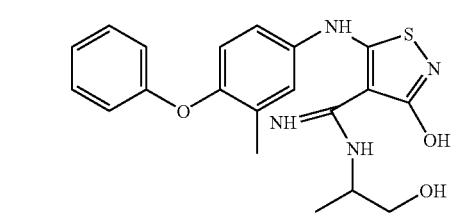 | B |
| 325 | 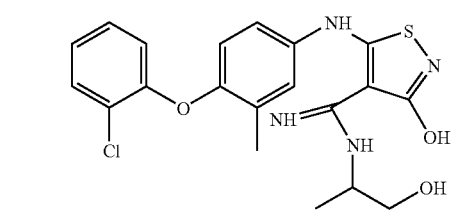 | C |
| 326 | 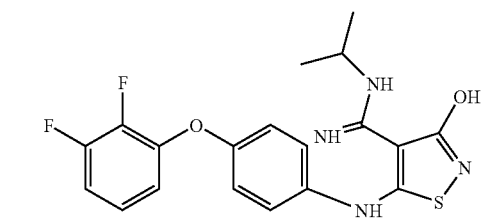 | A |

TABLE 2-continued

Biological Activity of Compounds of Formula I, where Ar¹-A contains an amido or indolo group

| # | Structure | Avg IC50 |
|---|-----------|----------|
| 327 | 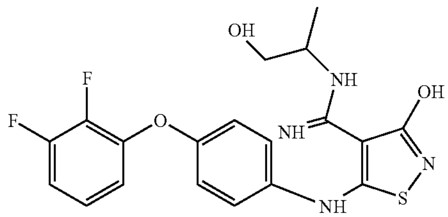 | A |
| 328 | 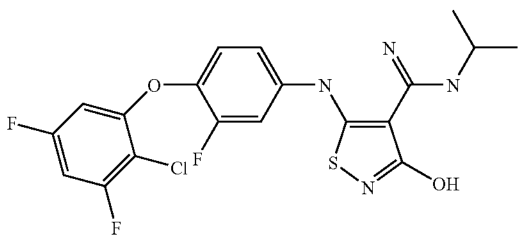 | A |
| 329 | 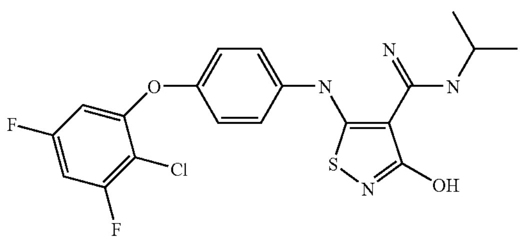 | A |
| 330 | 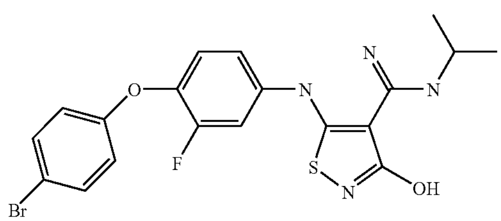 | A |
| 331 | 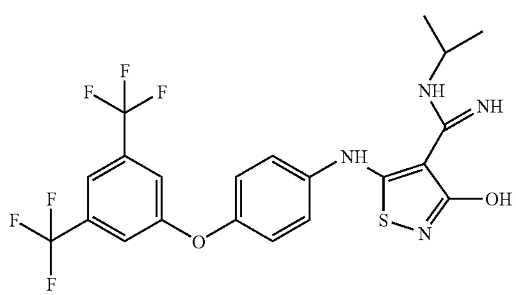 | A |
| 332 | 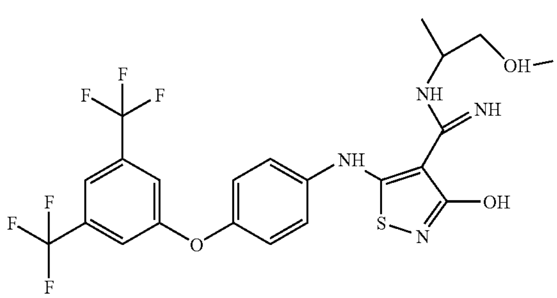 | B |

TABLE 2-continued

Biological Activity of Compounds of Formula I, where Ar¹-A contains an amido or indolo group

| # | Structure | Avg IC50 |
|---|-----------|----------|
| 333 | 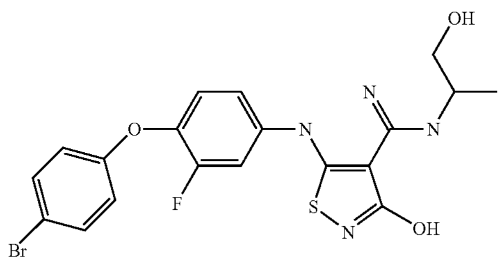 | A |
| 334 | 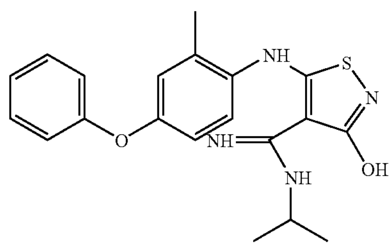 | A |
| 335 | 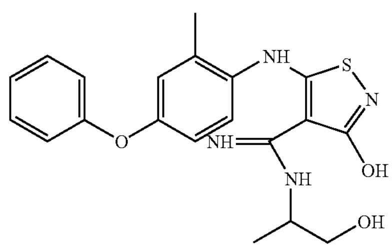 | A |
| 336 | 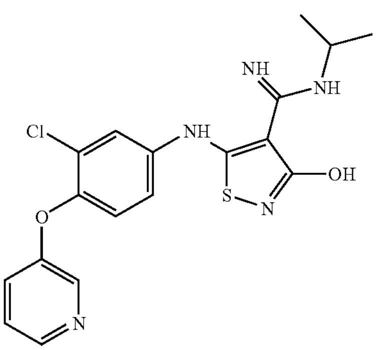 | C |
| 337 | 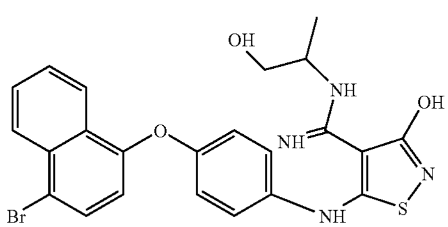 | A |

TABLE 2-continued

Biological Activity of Compounds of Formula I, where Ar¹-A contains an amido or indolo group

| # | Structure | Avg IC50 |
|---|-----------|----------|
| 338 | 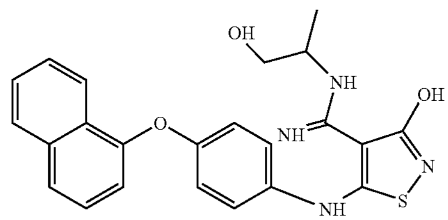 | A |
| 339 | 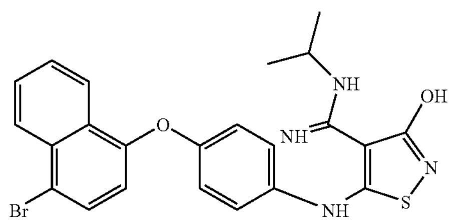 | A |
| 340 | 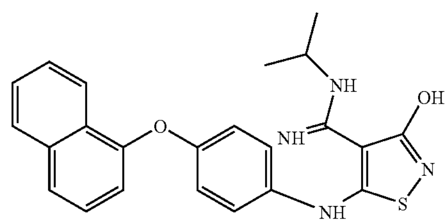 | A |
| 341 | 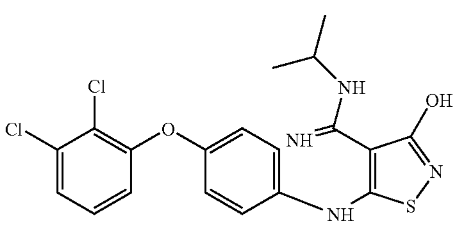 | A |
| 342 | 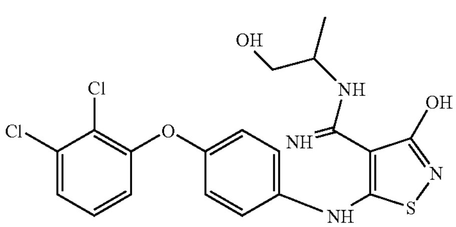 | A |
| 343 | 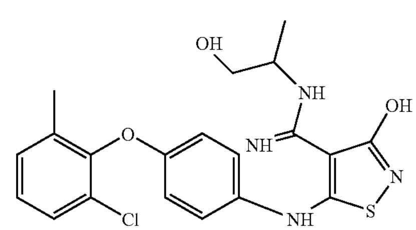 | C |

TABLE 2-continued

Biological Activity of Compounds of Formula I,
where Ar¹-A contains an amido or indolo group

| # | Structure | Avg IC50 |
|---|-----------|----------|
| 344 | 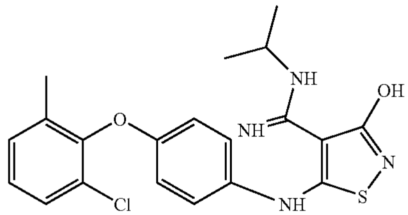 | C |
| 345 | 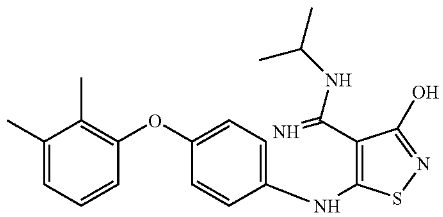 | A |
| 346 | 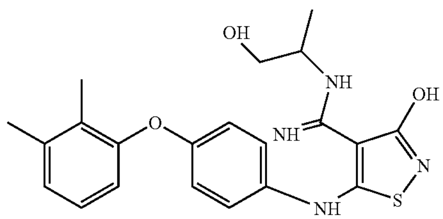 | A |
| 347 | 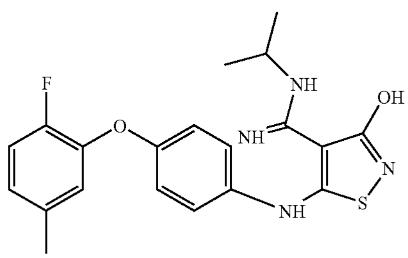 | A |
| 348 | 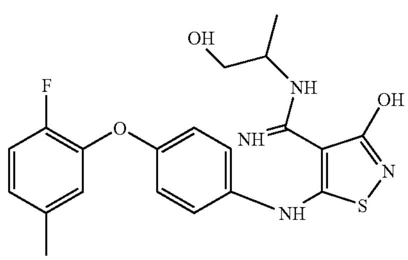 | A |
| 349 | 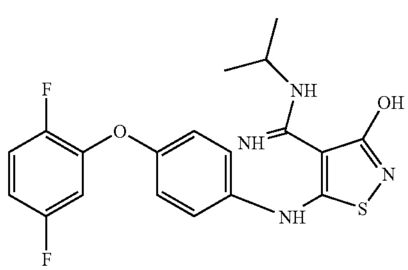 | A |

TABLE 2-continued

Biological Activity of Compounds of Formula I,
where Ar¹-A contains an amido or indolo group

| # | Structure | Avg IC50 |
|---|-----------|----------|
| 350 | 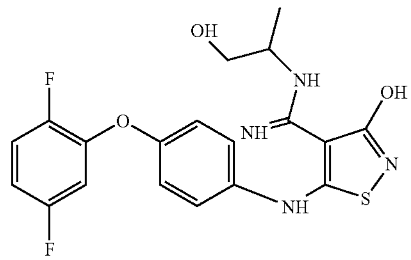 | A |
| 351 | 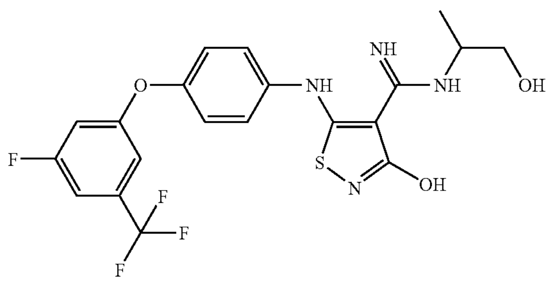 | B |
| 352 | 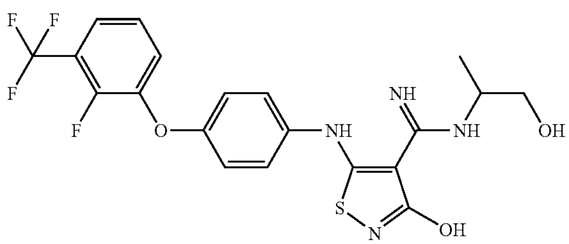 | A |
| 353 | 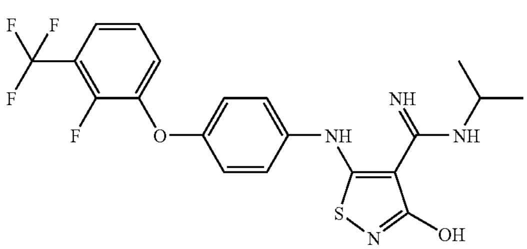 | A |
| 354 | 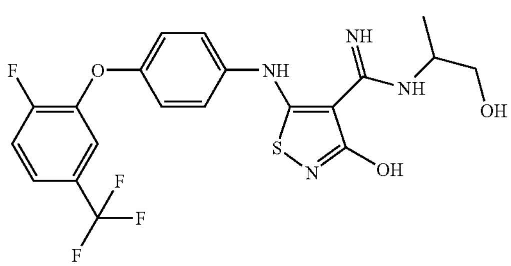 | A |

TABLE 2-continued

Biological Activity of Compounds of Formula I,
where Ar¹-A contains an amido or indolo group

| # | Structure | Avg IC50 |
|---|---|---|
| 355 | 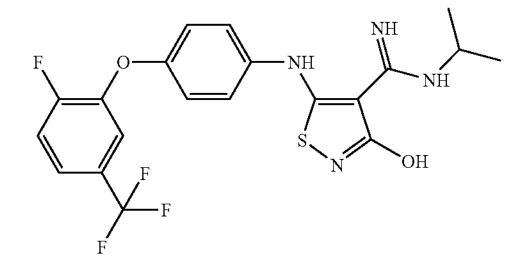 | A |
| 356 | 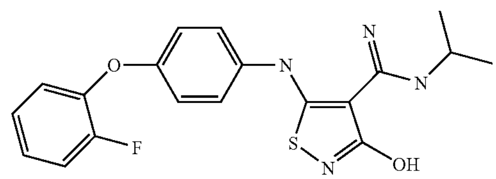 | A |
| 357 | 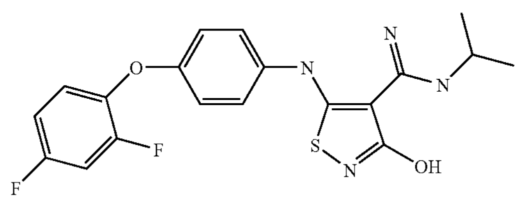 | A |
| 358 | 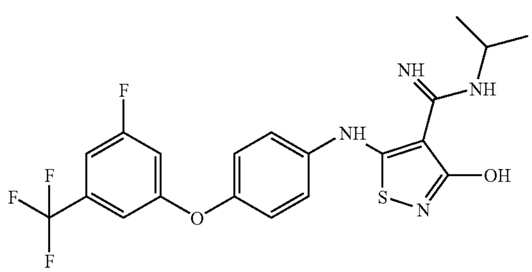 | B |
| 359 | 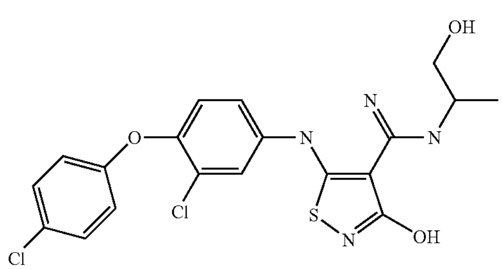 | B |
| 360 | 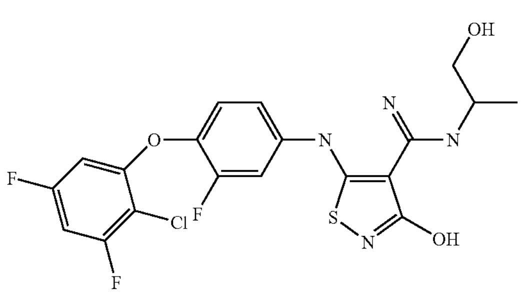 | A |

TABLE 2-continued

Biological Activity of Compounds of Formula I,
where Ar¹-A contains an amido or indolo group

| # | Structure | Avg IC50 |
|---|-----------|----------|
| 361 | 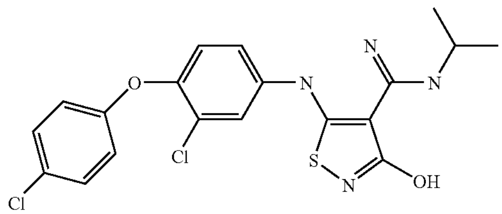 | B |
| 362 | 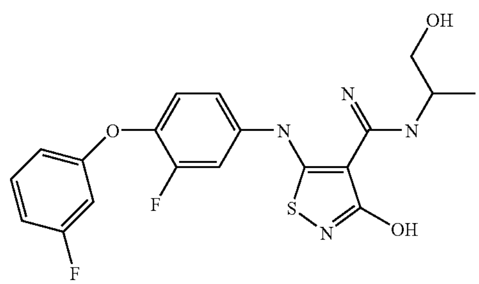 | A |
| 363 | 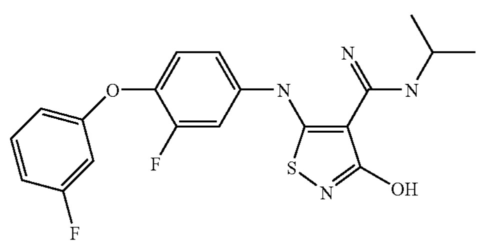 | C |
| 364 | 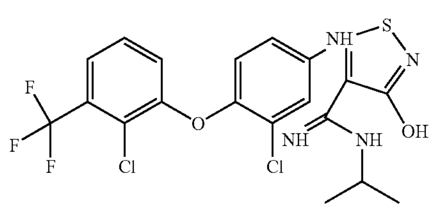 | A |
| 365 | 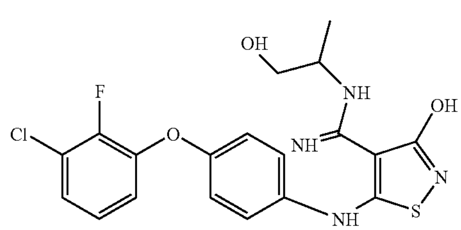 | B |
| 366 | 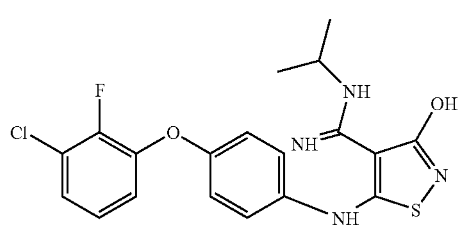 | A |

TABLE 2-continued

Biological Activity of Compounds of Formula I,
where Ar¹-A contains an amido or indolo group

| # | Structure | Avg IC50 |
|---|-----------|----------|
| 367 | 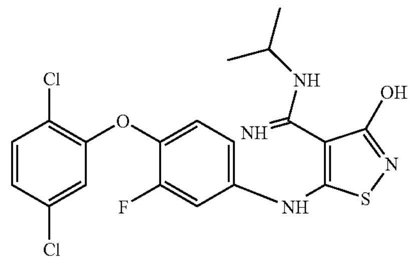 | A |
| 368 | 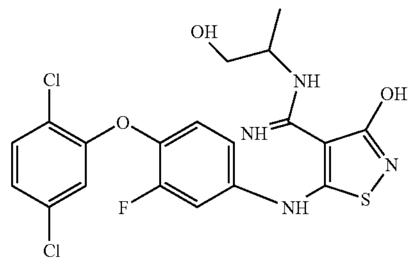 | A |
| 369 | 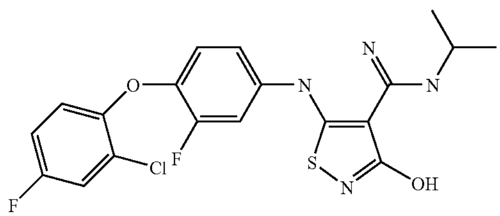 | A |
| 370 | 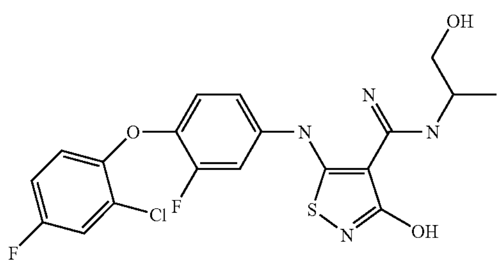 | A |
| 371 | 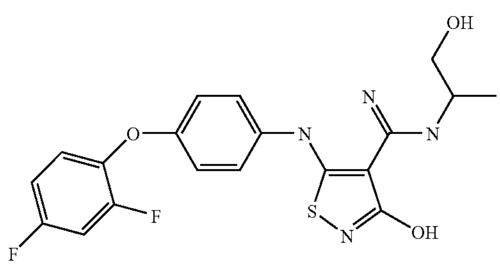 | B |
| 372 | 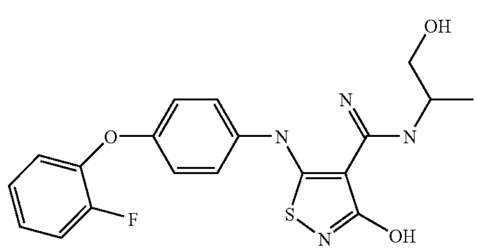 | B |

TABLE 2-continued

Biological Activity of Compounds of Formula I,
where Ar¹-A contains an amido or indolo group

| # | Structure | Avg IC50 |
|---|-----------|----------|
| 373 | 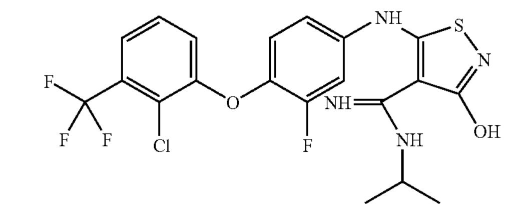 | A |
| 374 | 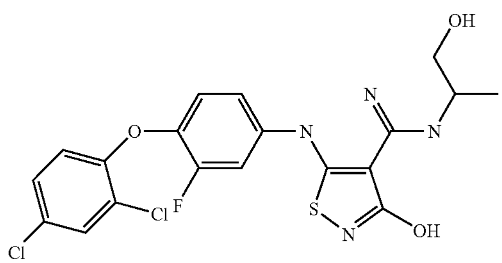 | A |
| 375 | 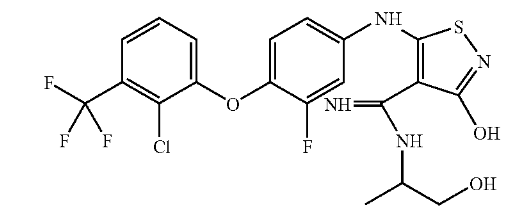 | A |
| 376 | 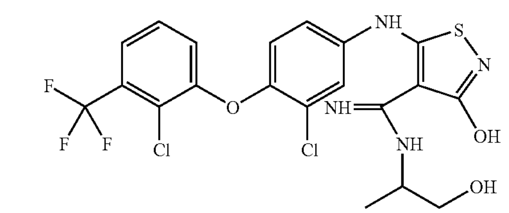 | A |
| 377 | 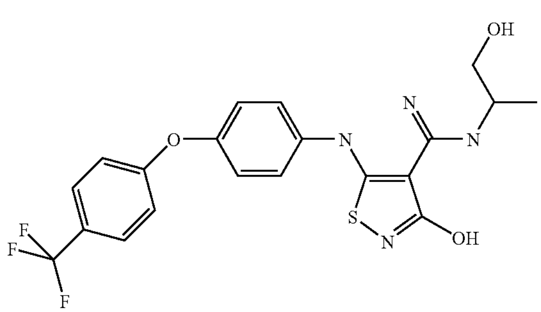 | C |
| 378 | 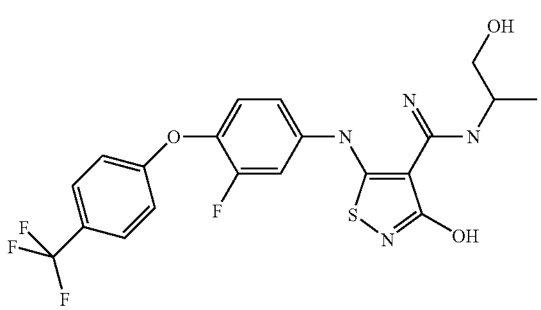 | B |

TABLE 2-continued

Biological Activity of Compounds of Formula I,
where Ar¹-A contains an amido or indolo group

| # | Structure | Avg IC50 |
|---|-----------|----------|
| 379 | 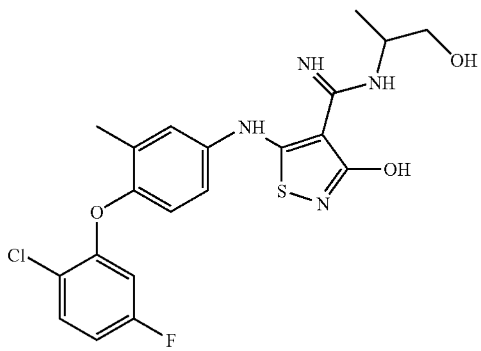 | B |
| 380 | 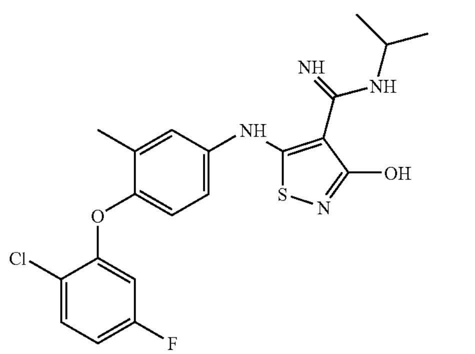 | B |
| 381 | 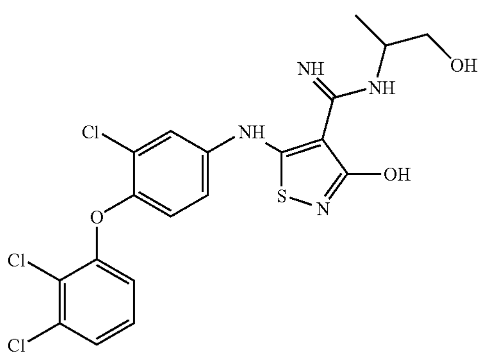 | A |
| 382 | 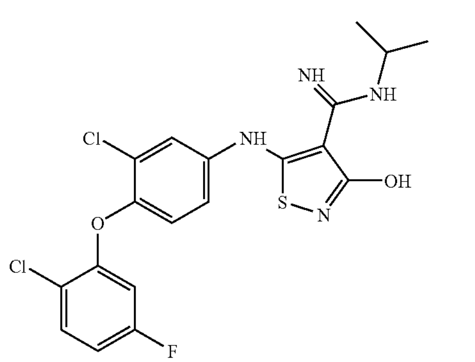 | A |

TABLE 2-continued

Biological Activity of Compounds of Formula I, where Ar¹-A contains an amido or indolo group

| # | Structure | Avg IC50 |
|---|---|---|
| 383 | | A |
| 384 | | B |
| 385 | | A |
| 386 | | C |
| 387 | | B |

TABLE 2-continued

Biological Activity of Compounds of Formula I, where Ar¹-A contains an amido or indolo group

| # | Structure | Avg IC50 |
|---|-----------|----------|
| 388 | 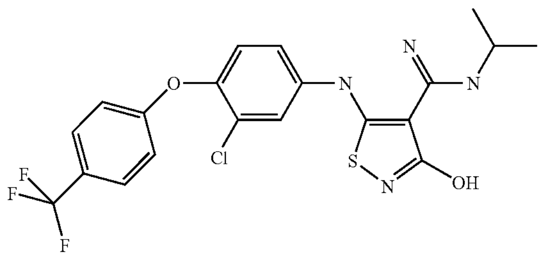 | B |
| 389 | 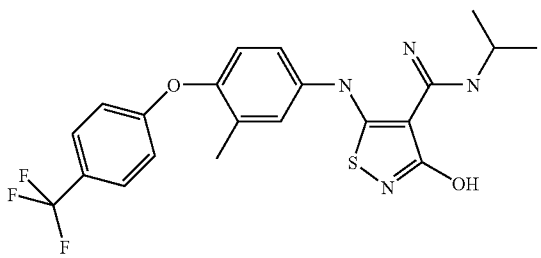 | C |
| 390 | 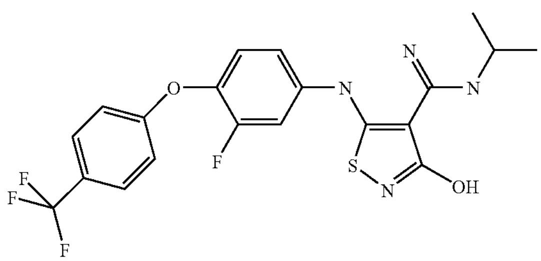 | B |
| 391 | 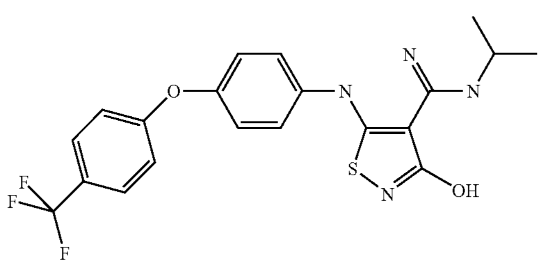 | B |
| 392 | 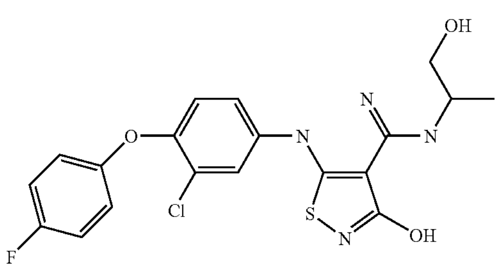 | B |

TABLE 2-continued

Biological Activity of Compounds of Formula I, where Ar¹-A contains an amido or indolo group

| # | Structure | Avg IC50 |
|---|-----------|----------|
| 393 | 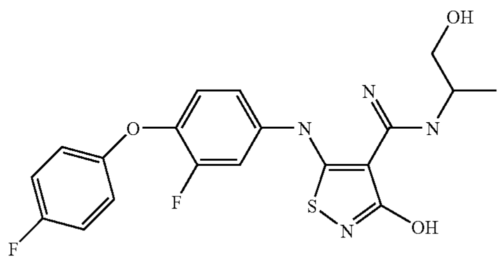 | A |
| 394 | 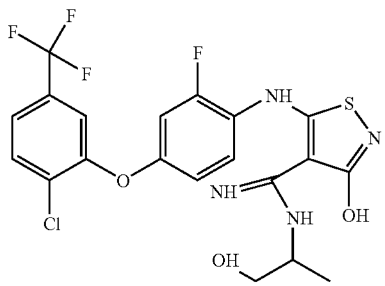 | A |
| 395 | 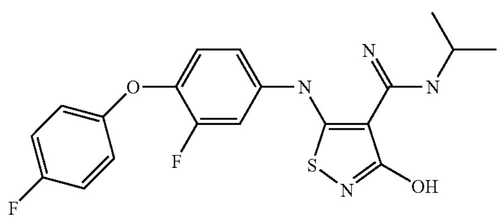 | B |
| 396 | 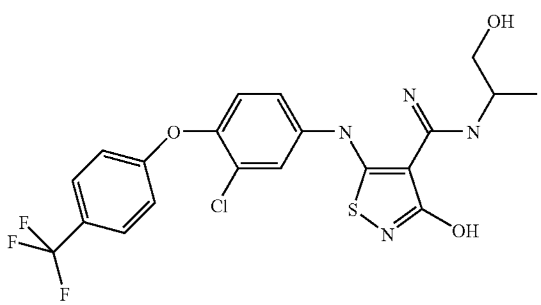 | B |
| 397 | 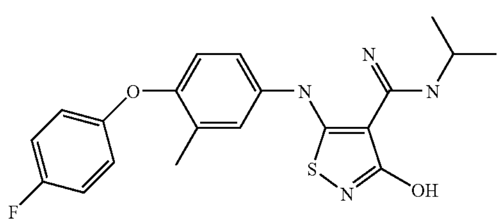 | C |
| 398 | 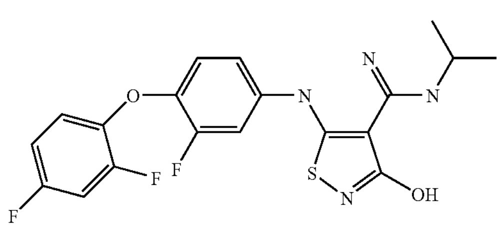 | B |

TABLE 2-continued

Biological Activity of Compounds of Formula I,
where Ar¹-A contains an amido or indolo group

| # | Structure | Avg IC50 |
|---|-----------|----------|
| 399 | 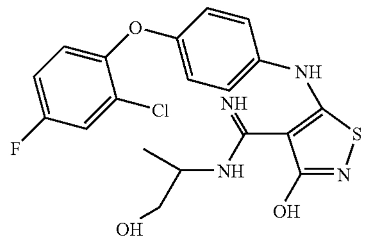 | B |
| 400 | 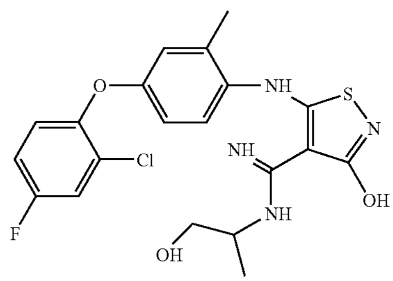 | B |
| 401 | 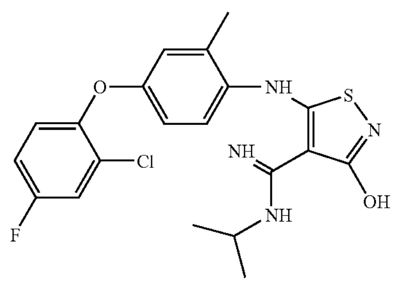 | A |
| 402 | 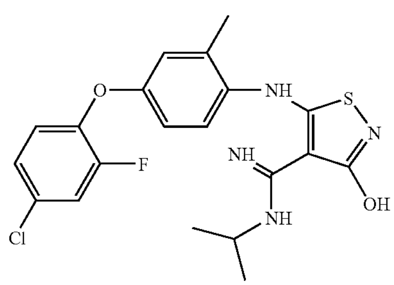 | A |
| 403 | 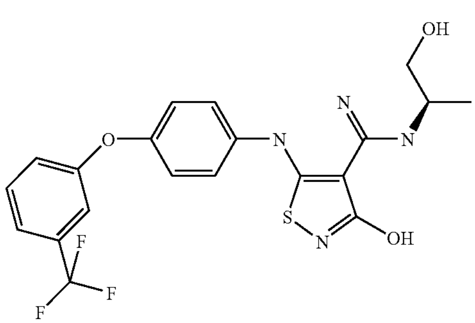 | B |

TABLE 2-continued

Biological Activity of Compounds of Formula I,
where Ar¹-A contains an amido or indolo group

| # | Structure | Avg IC50 |
|---|-----------|----------|
| 404 | 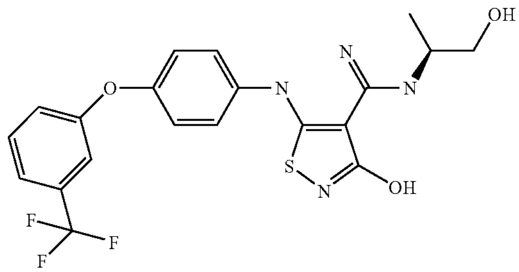 | A |
| 405 | 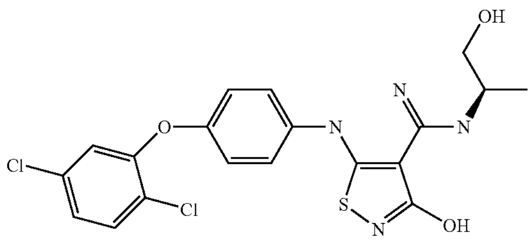 | A |
| 406 | 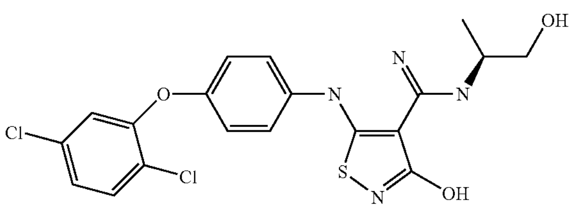 | A |
| 407 | 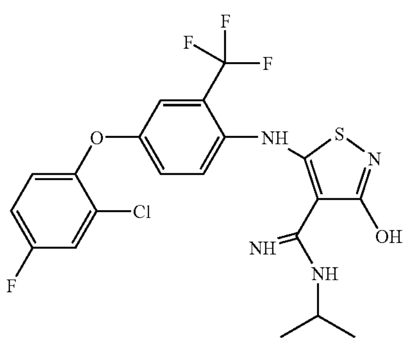 | A |
| 408 | 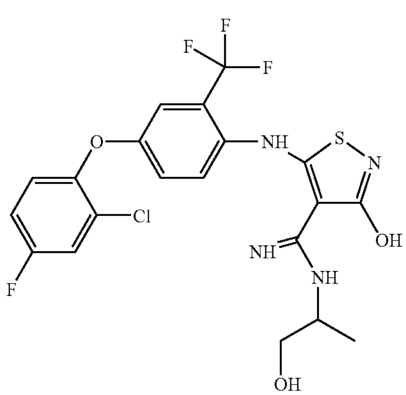 | A |

TABLE 2-continued

Biological Activity of Compounds of Formula I,
where Ar¹-A contains an amido or indolo group

| # | Structure | Avg IC50 |
|---|-----------|----------|
| 409 | | A |
| 410 | | A |
| 411 | | B |
| 412 | | A |
| 413 | | B |

TABLE 2-continued

Biological Activity of Compounds of Formula I,
where Ar¹-A contains an amido or indolo group

| # | Structure | Avg IC50 |
|---|-----------|----------|
| 414 | 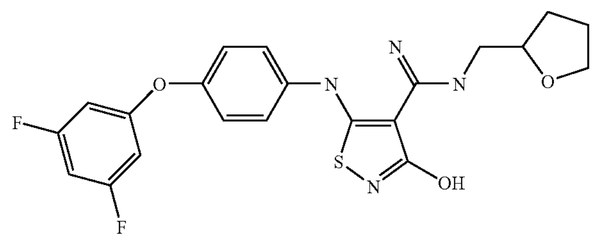 | A |
| 415 | 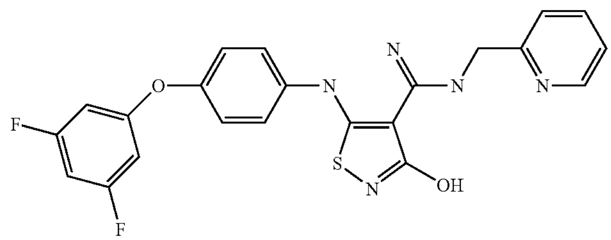 | A |
| 416 | 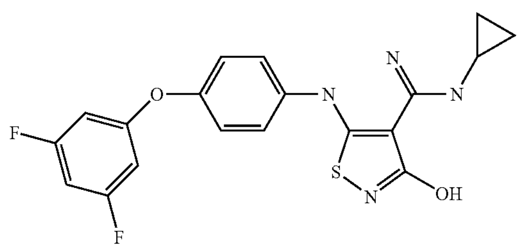 | B |
| 417 | 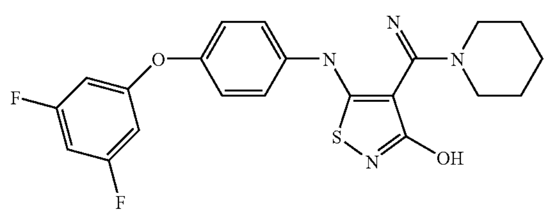 | C |
| 418 | 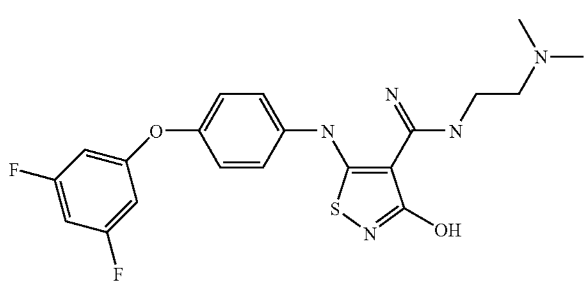 | B |
| 419 | 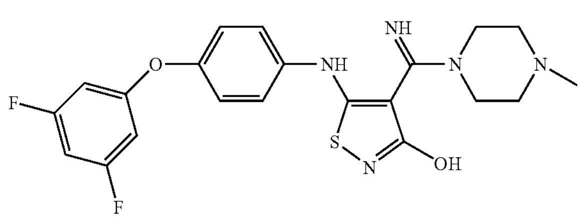 | C |

TABLE 2-continued

Biological Activity of Compounds of Formula I, where Ar¹-A contains an amido or indolo group

| # | Structure | Avg IC50 |
|---|-----------|----------|
| 420 | 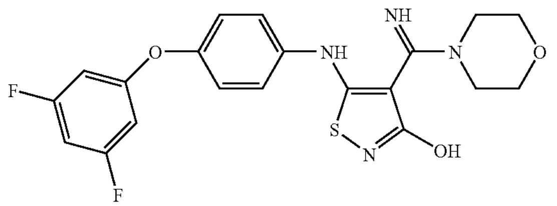 | C |
| 421 | 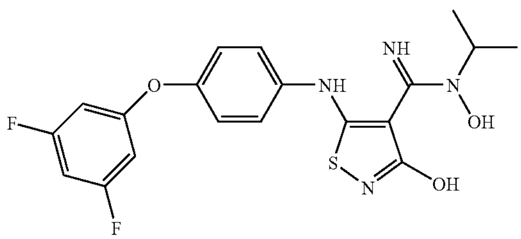 | A |
| 422 | 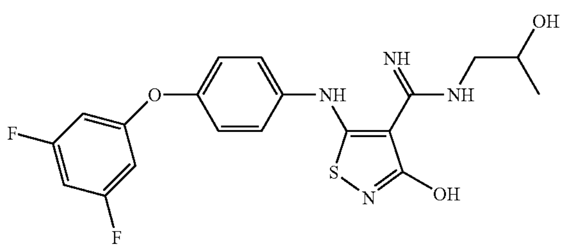 | A |
| 423 | 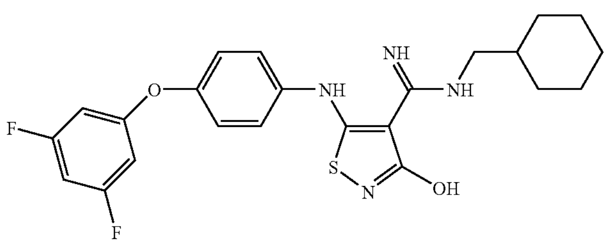 | A |
| 424 | 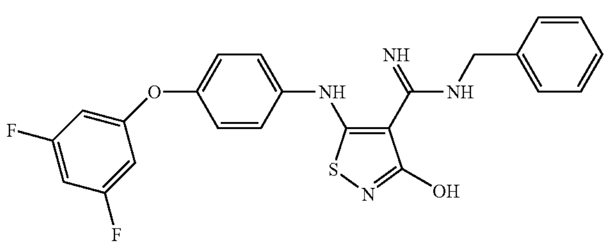 | A |
| 425 | 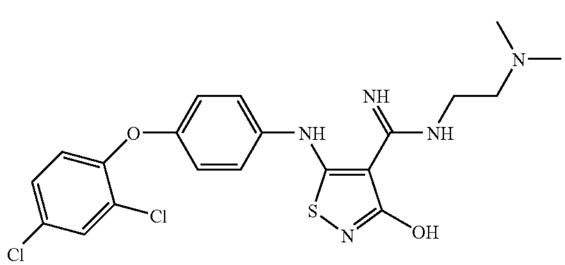 | B |

TABLE 2-continued

Biological Activity of Compounds of Formula I,
where Ar¹-A contains an amido or indolo group

| # | Structure | Avg IC50 |
|---|-----------|----------|
| 426 | 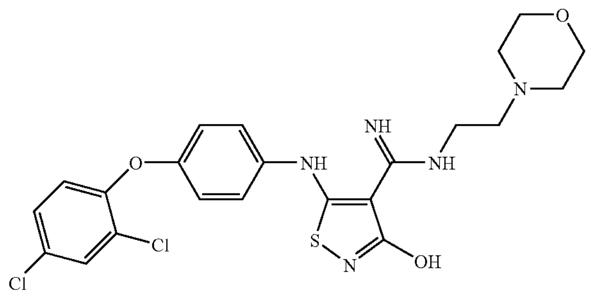 | A |
| 427 | 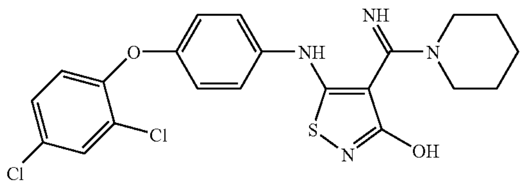 | C |
| 428 | 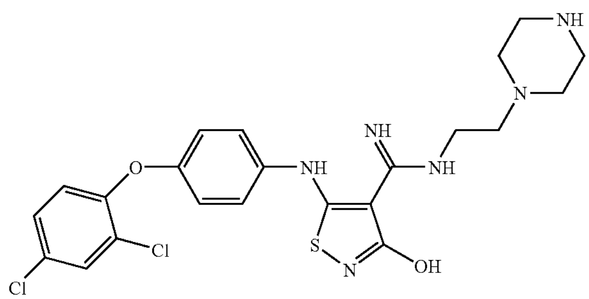 | B |
| 429 | 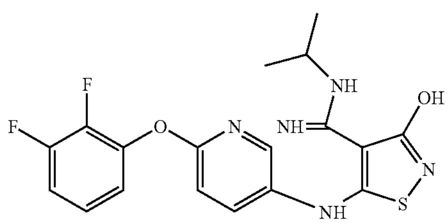 | B |
| 430 | 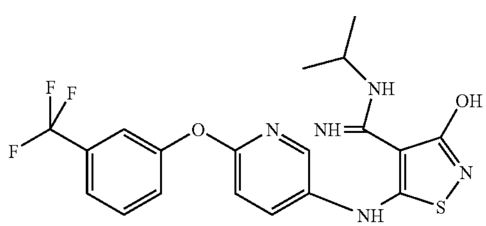 | B |
| 431 | 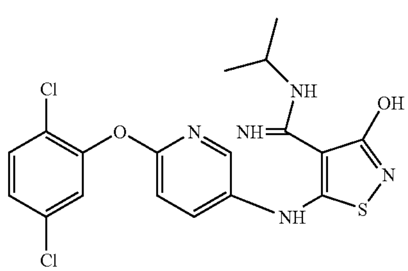 | A |

TABLE 2-continued

Biological Activity of Compounds of Formula I, where Ar¹-A contains an amido or indolo group

| # | Structure | Avg IC50 |
|---|-----------|----------|
| 432 | 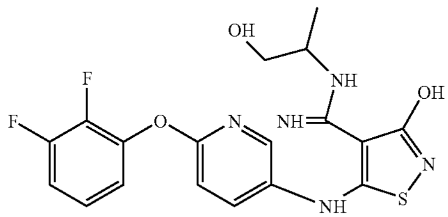 | B |
| 433 | 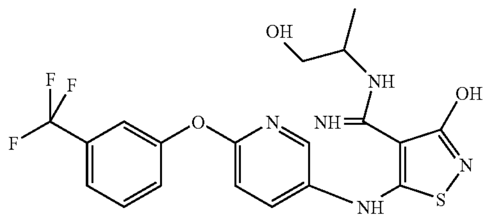 | A |
| 434 | 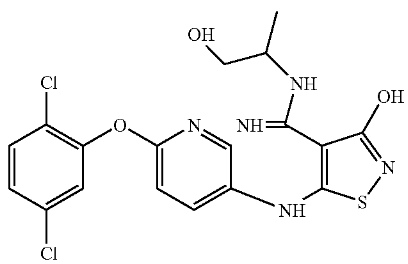 | A |
| 435 | 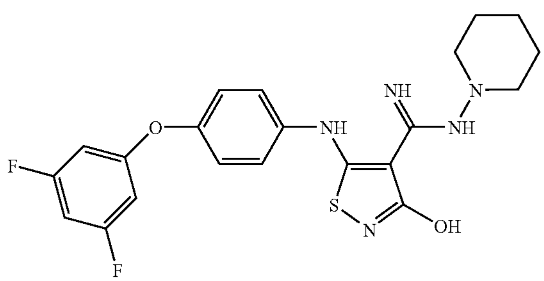 | A |
| 436 | 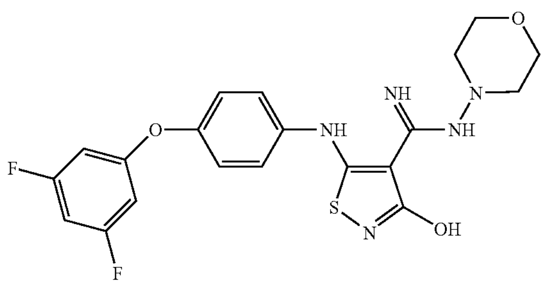 | B |
| 437 | 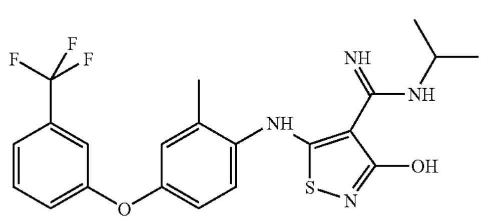 | A |

TABLE 2-continued

Biological Activity of Compounds of Formula I, where Ar¹-A contains an amido or indolo group

| # | Structure | Avg IC50 |
|---|-----------|----------|
| 438 | 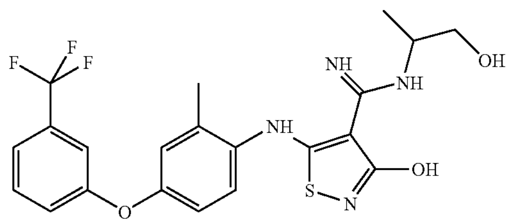 | A |
| 439 | 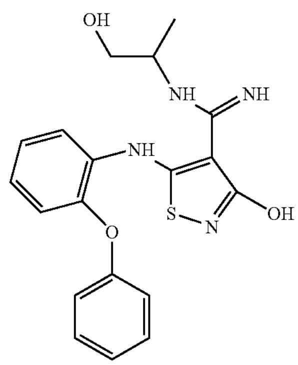 | C |
| 440 | 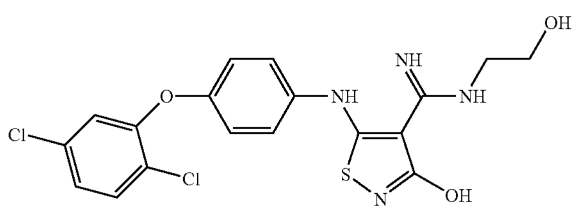 | A |
| 441 | 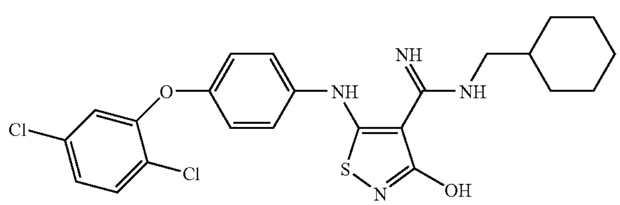 | A |
| 442 | 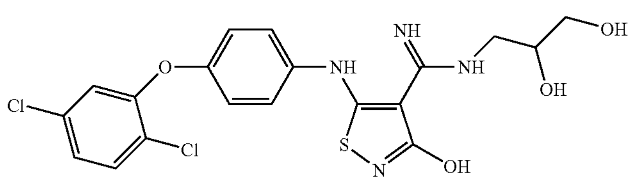 | A |
| 443 | 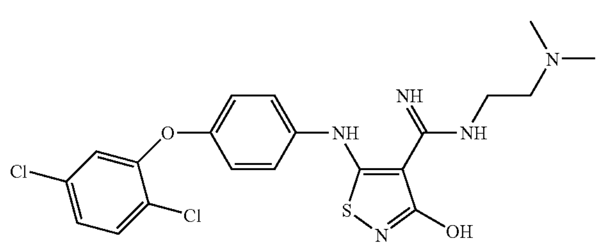 | A |

TABLE 2-continued

Biological Activity of Compounds of Formula I,
where Ar¹-A contains an amido or indolo group

| # | Structure | Avg IC50 |
|---|---|---|
| 444 | 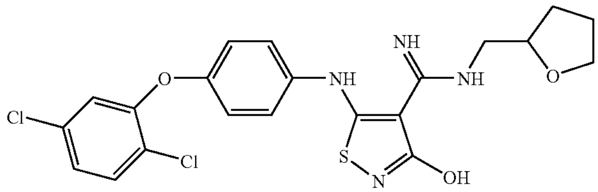 | A |
| 445 | 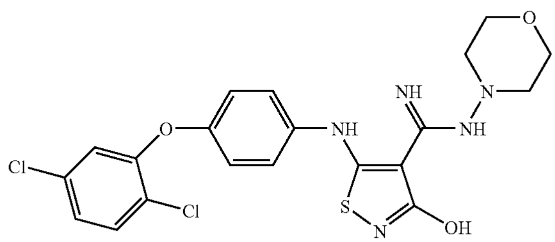 | A |
| 446 | 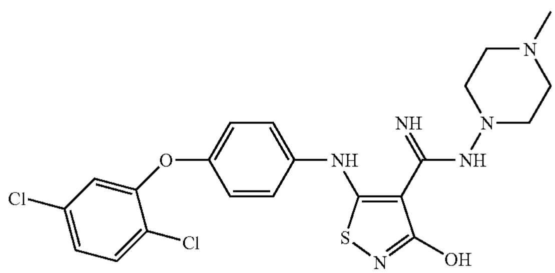 | A |
| 447 | 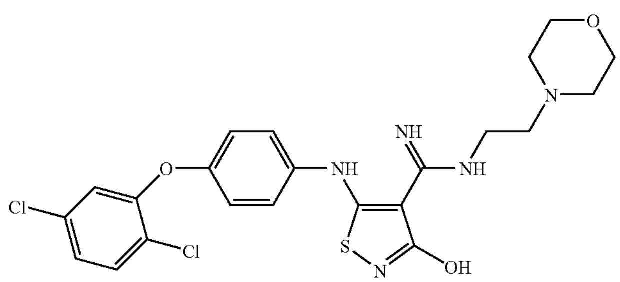 | A |
| 448 | 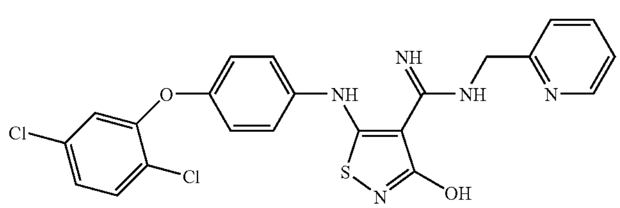 | A |
| 449 | 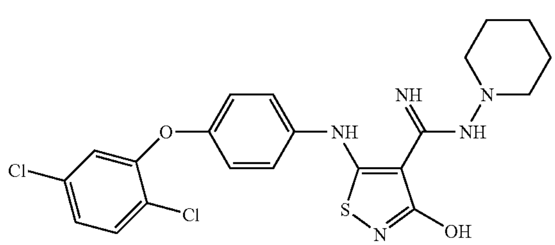 | A |

TABLE 2-continued

Biological Activity of Compounds of Formula I,
where Ar¹-A contains an amido or indolo group

| # | Structure | Avg IC50 |
|---|---|---|
| 450 | 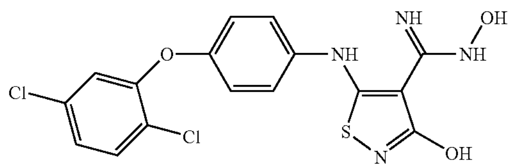 | A |
| 451 | 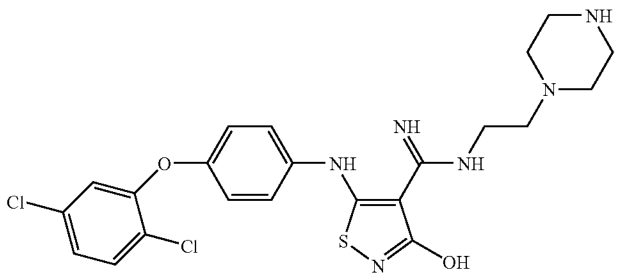 | A |
| 452 | 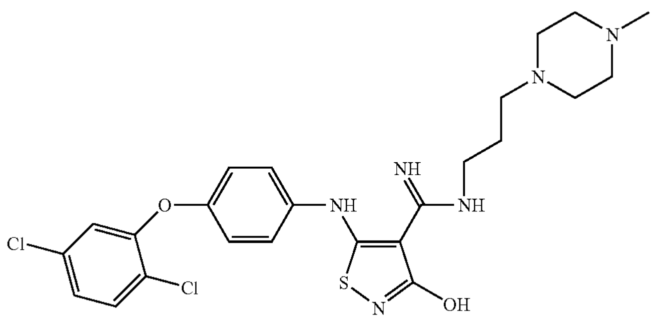 | A |
| 453 | 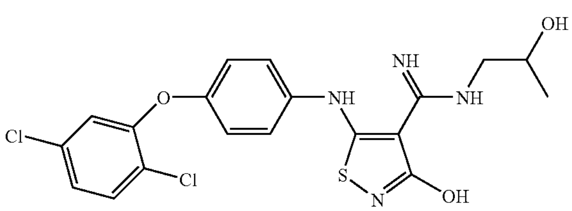 | A |
| 454 | 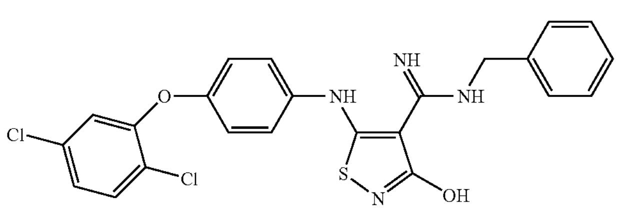 | A |
| 455 | 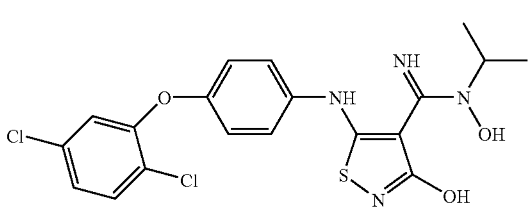 | A |

TABLE 2-continued

Biological Activity of Compounds of Formula I,
where Ar¹-A contains an amido or indolo group

| # | Structure | Avg IC50 |
|---|-----------|----------|
| 456 | 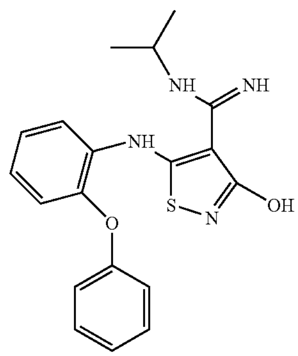 | B |
| 457 | 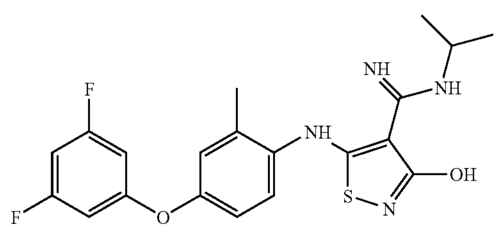 | A |
| 458 | 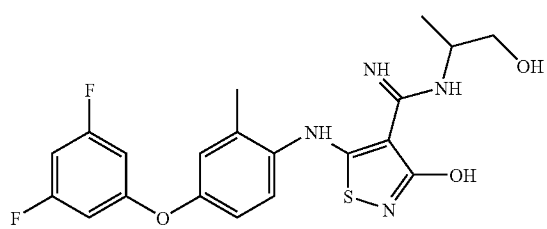 | A |
| 459 | 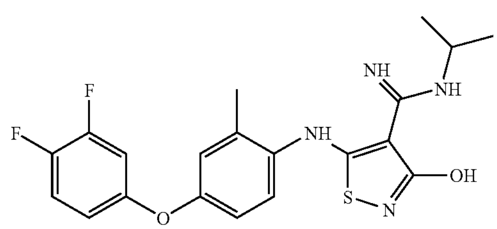 | A |
| 460 | 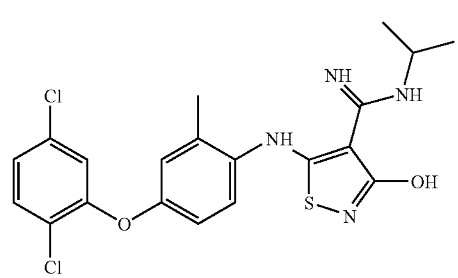 | A |

TABLE 2-continued
Biological Activity of Compounds of Formula I, where Ar¹-A contains an amido or indolo group
| # | Structure | Avg IC50 |
|---|---|---|
| 461 | 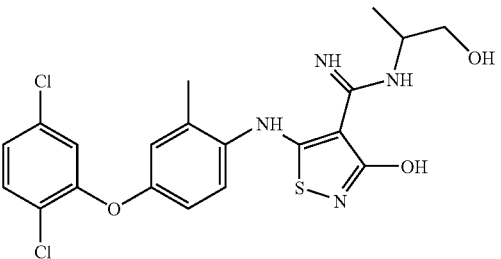 | A |
| 462 | 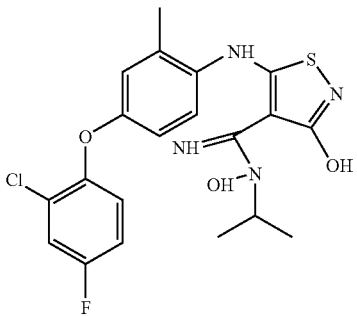 | B |
| 463 | 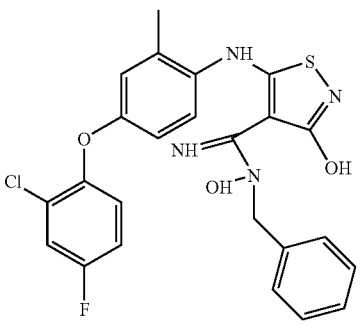 | A |
| 464 | 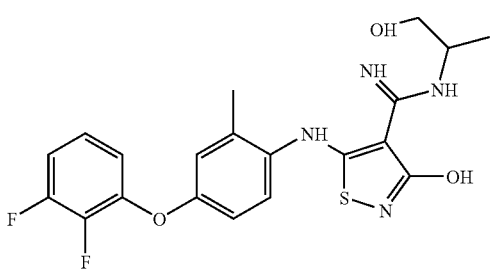 | A |
| 465 | 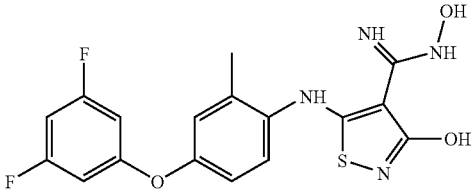 | B |

TABLE 2-continued

Biological Activity of Compounds of Formula I, where Ar¹-A contains an amido or indolo group

| # | Structure | Avg IC50 |
|---|-----------|----------|
| 466 | 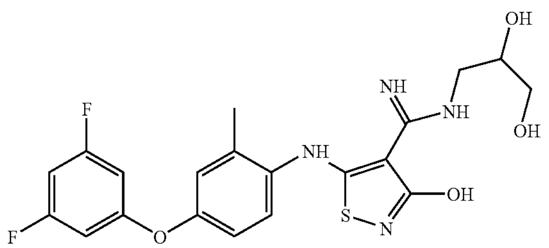 | A |
| 467 | 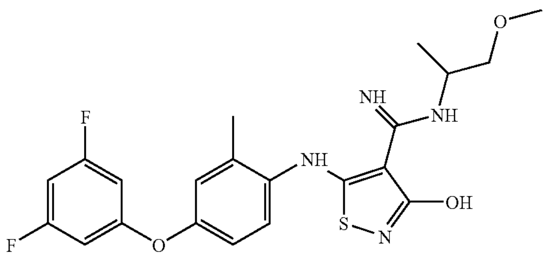 | A |
| 468 | 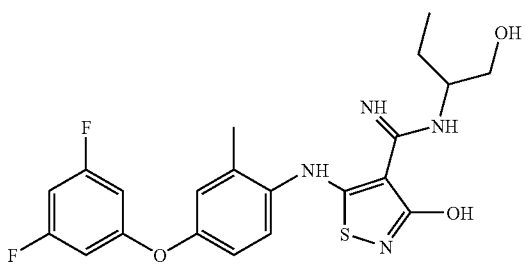 | A |
| 469 | 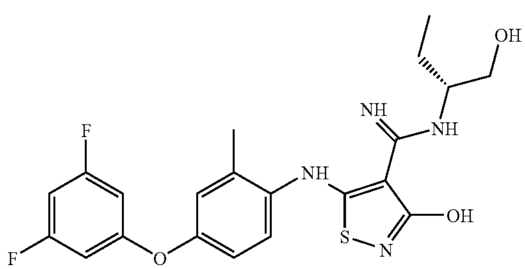 | A |
| 470 | 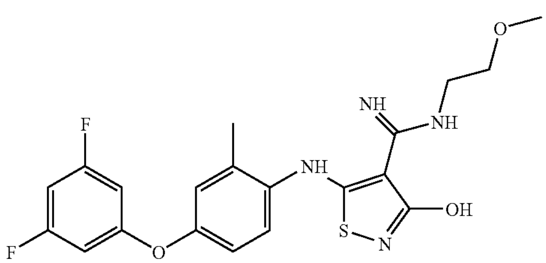 | A |
| 471 | 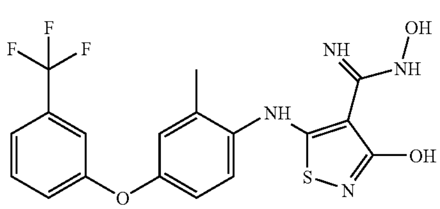 | C |

TABLE 2-continued

Biological Activity of Compounds of Formula I,
where Ar¹-A contains an amido or indolo group

| # | Structure | Avg IC50 |
|---|---|---|
| 472 | 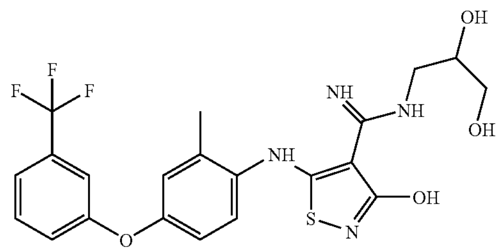 | A |
| 473 | 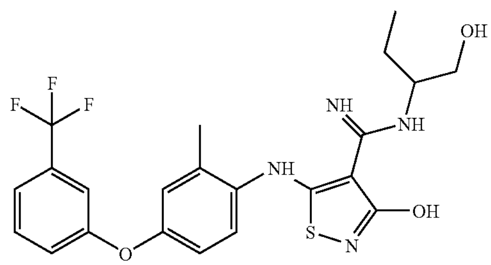 | A |
| 474 | 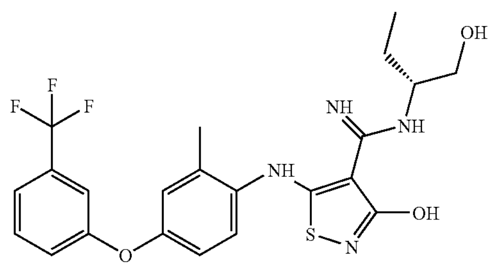 | A |
| 475 | 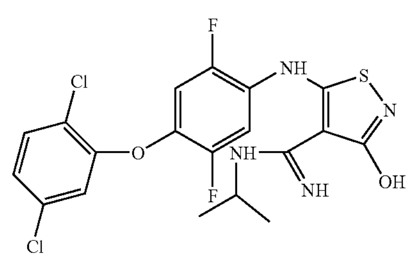 | A |
| 476 | 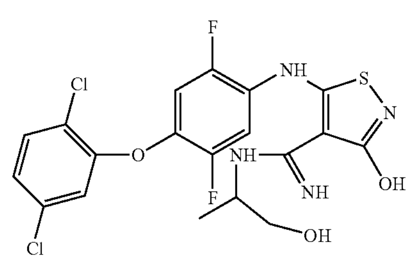 | A |

TABLE 2-continued

Biological Activity of Compounds of Formula I,
where Ar¹-A contains an amido or indolo group

| # | Structure | Avg IC50 |
|---|-----------|----------|
| 477 | 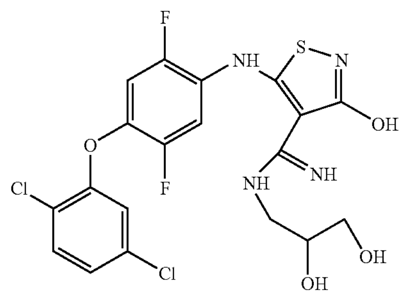 | A |
| 478 | 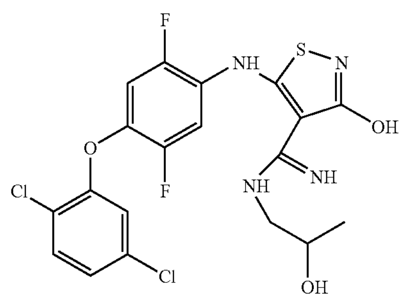 | A |
| 479 | 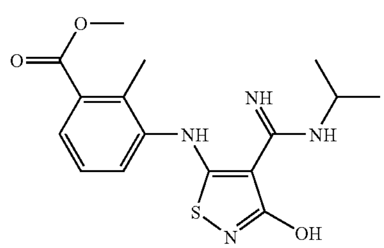 | C |
| 480 | 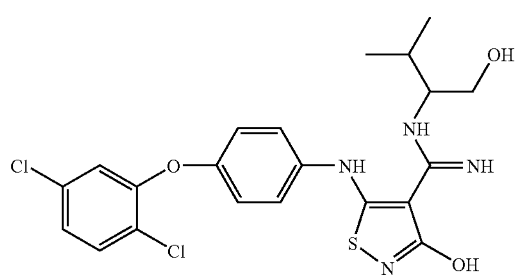 | A |
| 481 | 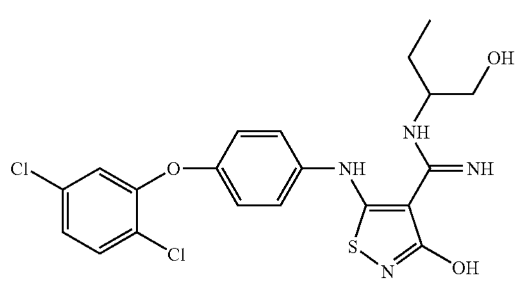 | A |

TABLE 2-continued

Biological Activity of Compounds of Formula I,
where Ar¹-A contains an amido or indolo group

| # | Structure | Avg IC50 |
|---|-----------|----------|
| 482 | 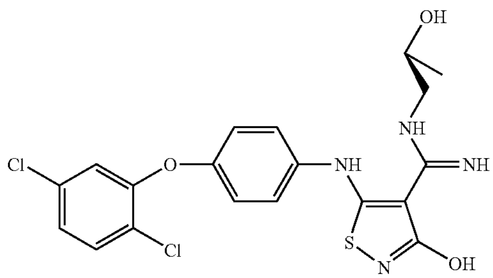 | A |
| 483 | 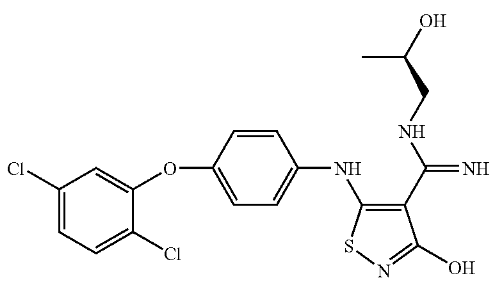 | A |
| 484 | 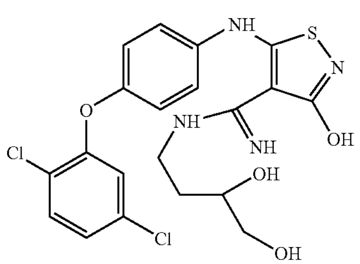 | A |
| 485 | 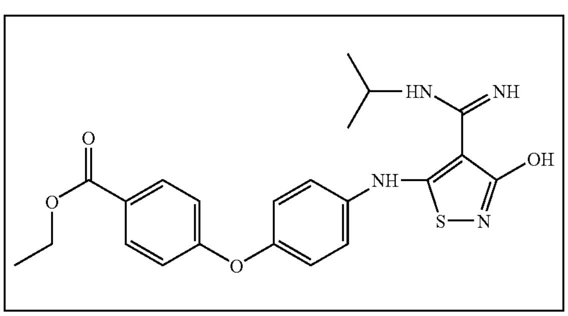 | B |

TABLE 2-continued

Biological Activity of Compounds of Formula I,
where Ar¹-A contains an amido or indolo group

| # | Structure | Avg IC50 |
|---|-----------|----------|
| 486 | 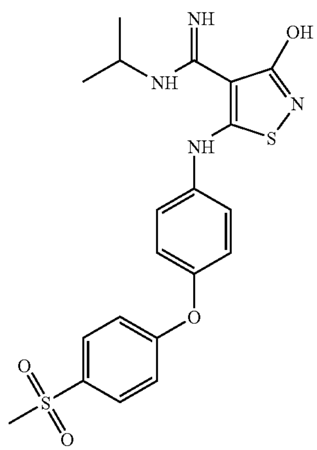 | C |
| 487 | 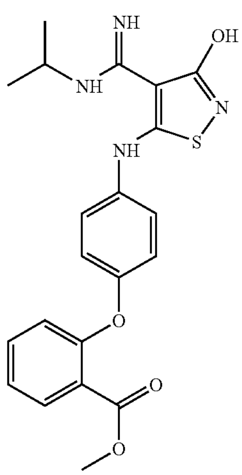 | A |
| 488 | 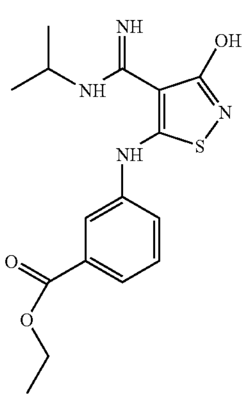 | C |

TABLE 2-continued
Biological Activity of Compounds of Formula I,
where Ar¹-A contains an amido or indolo group
| # | Structure | Avg IC50 |
|---|-----------|----------|
| 489 | 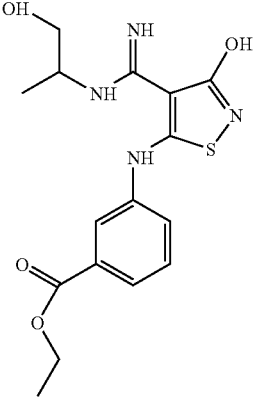 | C |
| 490 | 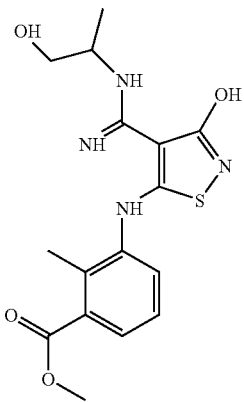 | B |
| 491 | 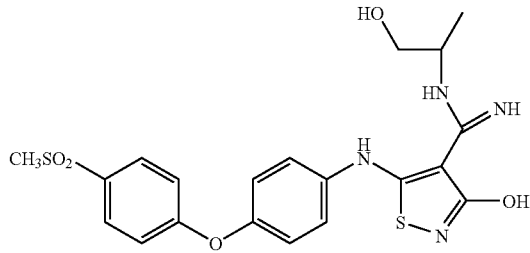 | C |
| 492 | 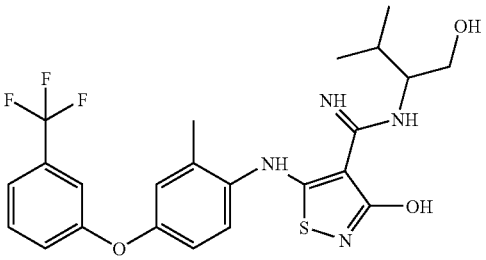 | B |

TABLE 2-continued
Biological Activity of Compounds of Formula I,
where Ar¹-A contains an amido or indolo group
| # | Structure | Avg IC50 |
|---|-----------|----------|
| 493 | 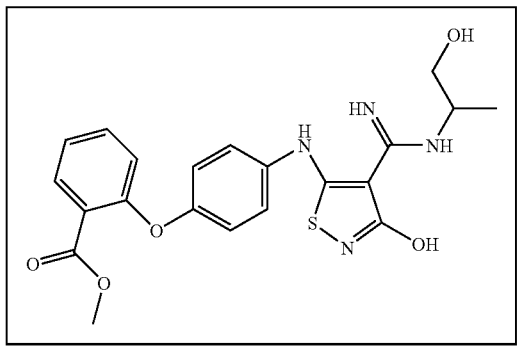 | A |
| 494 | 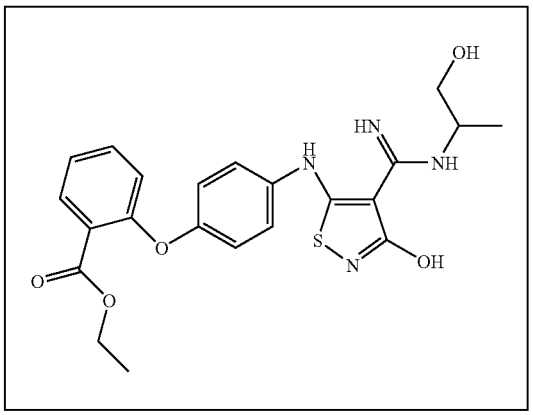 | A |
| 495 | 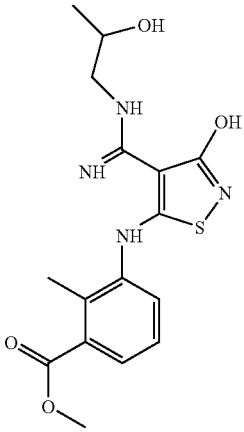 | C |

TABLE 2-continued

Biological Activity of Compounds of Formula I,
where Ar¹-A contains an amido or indolo group

| # | Structure | Avg IC50 |
|---|-----------|----------|
| 496 | | C |
| 497 | | A |
| 498 | | B |

TABLE 2-continued
Biological Activity of Compounds of Formula I,
where Ar¹-A contains an amido or indolo group
| # | Structure | Avg IC50 |
|---|---|---|
| 499 | 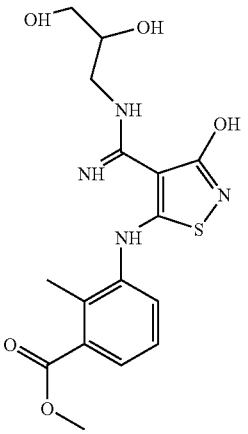 | B |
| 500 | 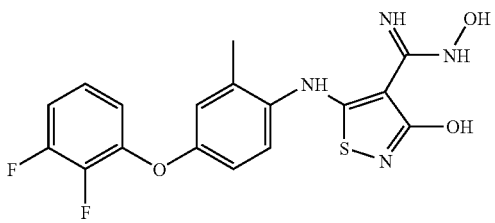 | A |
| 501 | 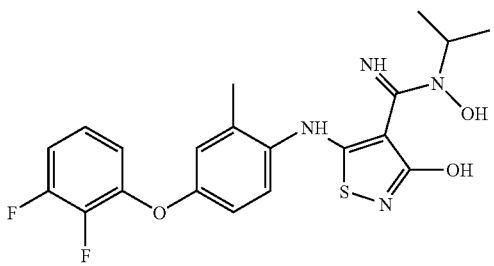 | B |
| 502 | 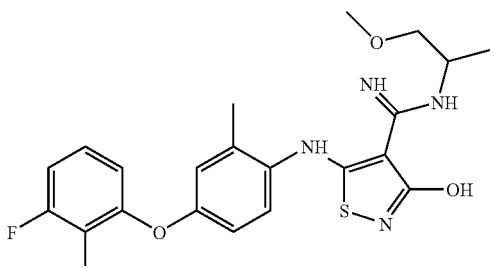 | A |
| 503 | 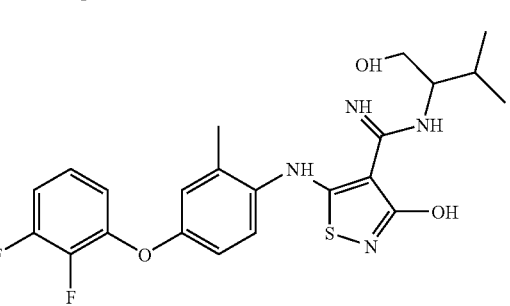 | B |

TABLE 2-continued

Biological Activity of Compounds of Formula I, where Ar¹-A contains an amido or indolo group

| # | Structure | Avg IC50 |
|---|-----------|----------|
| 504 | 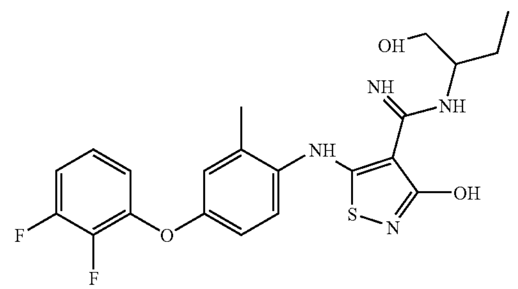 | B |
| 505 | 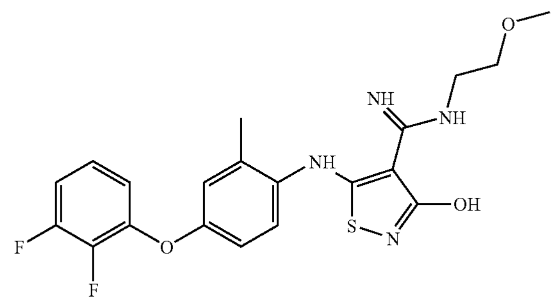 | A |
| 506 | 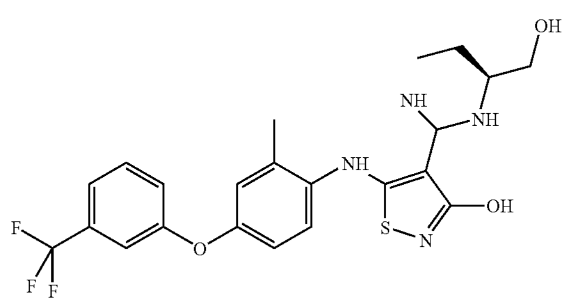 | B |
| 507 | 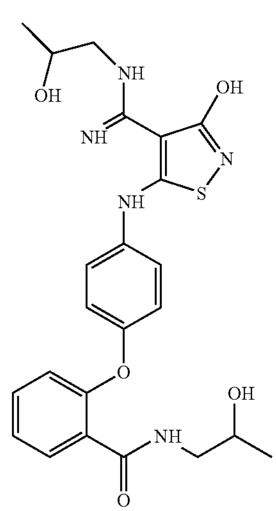 | C |

TABLE 2-continued

Biological Activity of Compounds of Formula I, where Ar¹-A contains an amido or indolo group

| # | Structure | Avg IC50 |
|---|---|---|
| 508 | 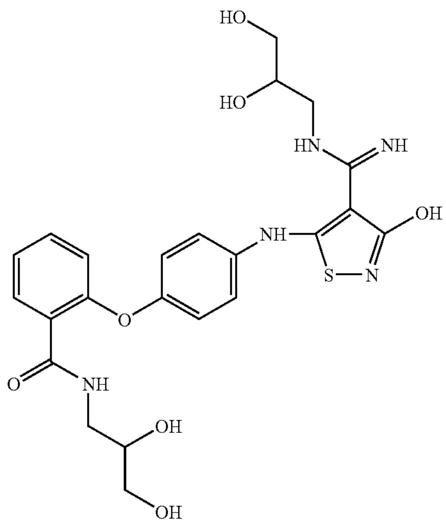 | C |
| 509 | 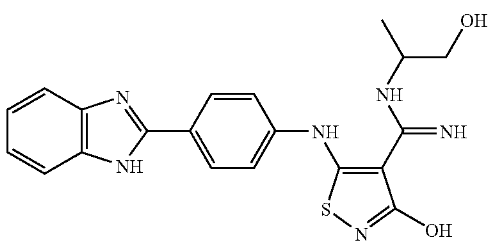 | C |
| 510 | 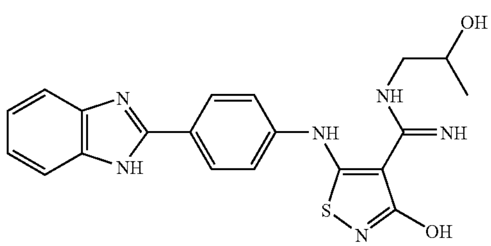 | C |
| 511 | 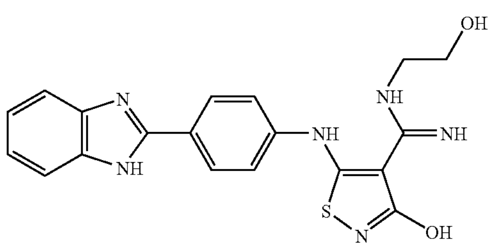 | C |
| 512 | 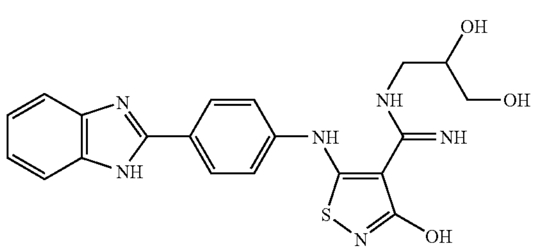 | C |

A" denotes inhibitory concentrations of 1 mM-200 nM, "B" denotes inhibitory concentrations of 200 nM-1000 nM, and "C" denotes inhibitory concentrations of greater than 100 nM.

Examples of compounds of the present invention are provided in the following table.

TABLE 3

| COMPOUND | IC 50 |
|---|---|
| E-1 | C |
| E-2 | C |
| E-4 | C |
| E-5 | C |
| E-6 | C |

TABLE 3-continued

| COMPOUND | IC 50 |
|---|---|
| E-7 | C |
| E-8 | B |
| E-9 | B |
| E-10 | A |
| E-11 | A |
| E-12 | B |

TABLE 3-continued
| COMPOUND | IC 50 |
|---|---|
| E-13 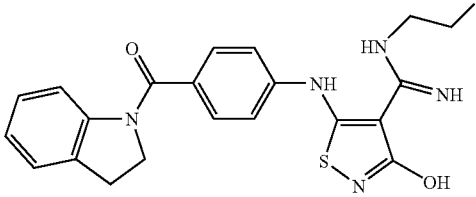 | C |
| E-14 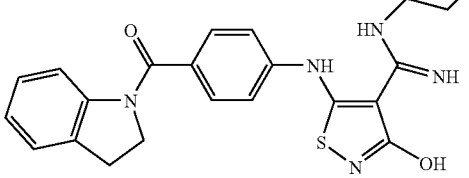 | C |
| E-15 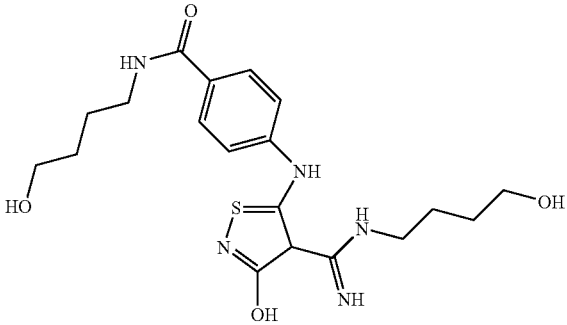 | C |
| E-16 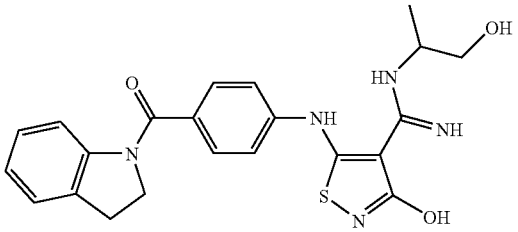 | A |
| E-17 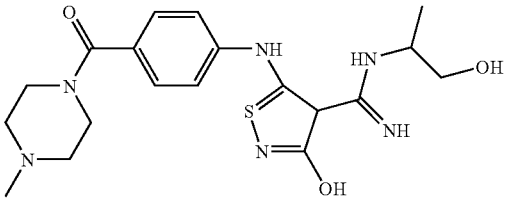 | C |
| E-18 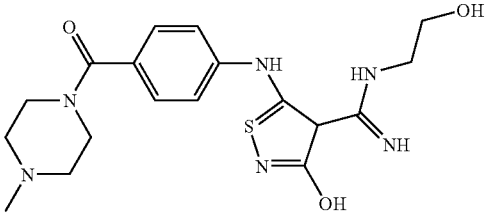 | C |

TABLE 3-continued

| COMPOUND | | IC 50 |
|---|---|---|
| E-19 | (structure) | C |
| E-20 | (structure) | A |
| E-21 | (structure) | B |
| E-22 | (structure) | C |

Biological Activity of Compounds of Formula X—Activity of Benzamides

In the following table IC50's of several benzamides are compared. Here, "A" denotes inhibitory concentrations of 1 nM-100 nM, "B" denotes inhibitory concentrations of 100 nM-500 nM, and "C" denotes inhibitory concentrations of greater than 500 nM.

TABLE 4

| COMPOUND | | IC 50 |
|---|---|---|
| | (structure) | B |
| | (structure) | A |

TABLE 4-continued

| COMPOUND | | IC 50 |
|---|---|---|
| | (structure) | C |
| | (structure) | A |

Biological Activity of Compounds of Formula I, where R' is $(CH_2)_{1\ or\ 2}$-G, where G is a Five- or Six-membered Ring or a 9- to 14-member Fused Ring System The following table shows the effects of substitution in R'. "A" denotes inhibitory concentrations of 1 nM-100 nM, "B" denotes inhibitory concentrations of 100 nM-500 nM, and "C" denotes inhibitory concentrations of greater than 500 nM.

| Compound | IC50 | EC50 |
|---|---|---|
| [structure] | A | A |
| [structure] | A | A |
| [structure] | A | A |
| [structure] | B | B |
| [structure] | B | B |

-continued
| Compound | IC50 | EC50 |
|---|---|---|
| 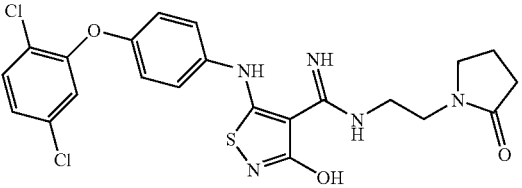 | A | B |
| 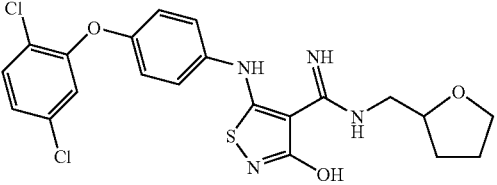 | A | A |
| 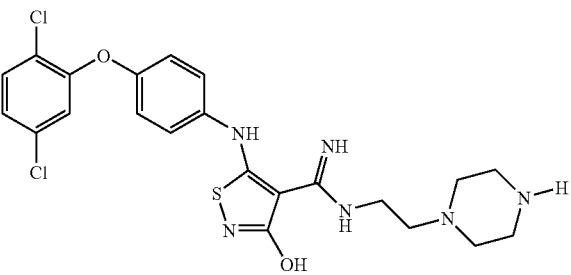 | A | A |
| 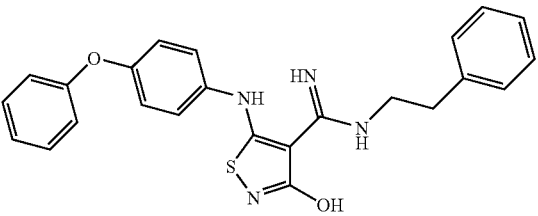 | B | B |
| 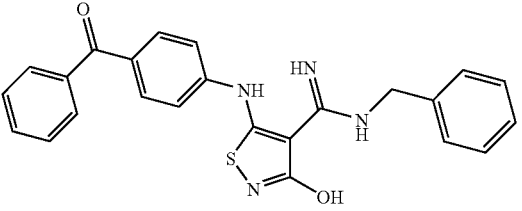 | B | |
| 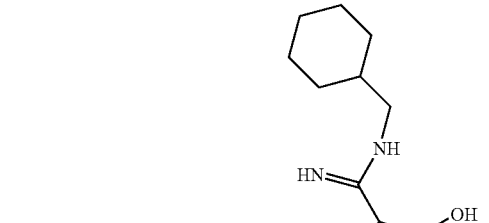 | A | |

-continued
| Compound | IC50 | EC50 |
|---|---|---|
| 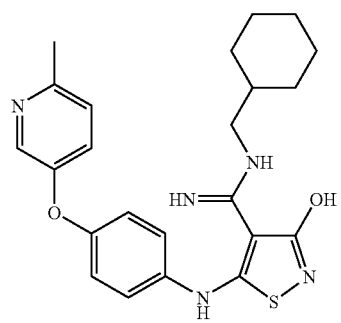 | B | |
| 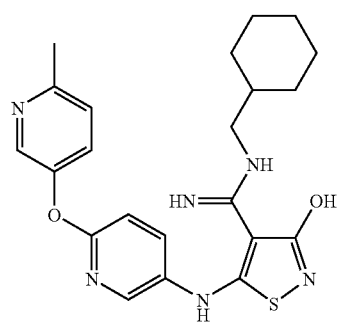 | C | |
| 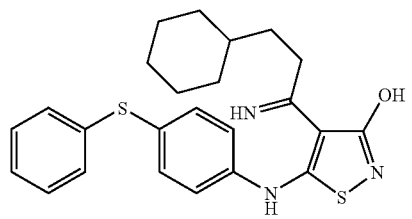 | A | |
| 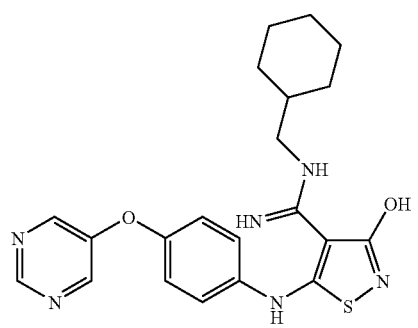 | C | |
| 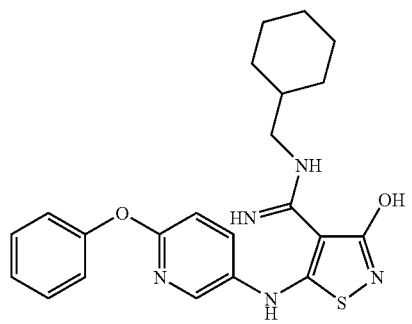 | B | |

-continued

| Compound | IC50 | EC50 |
|---|---|---|

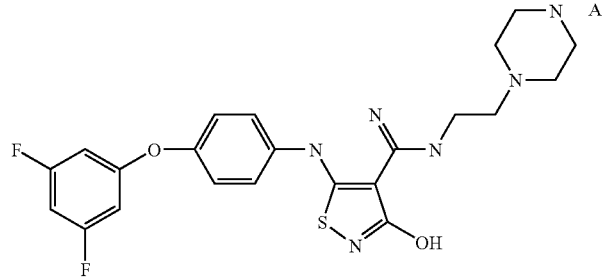  A

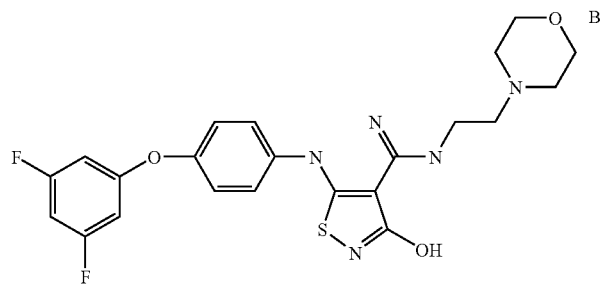  B

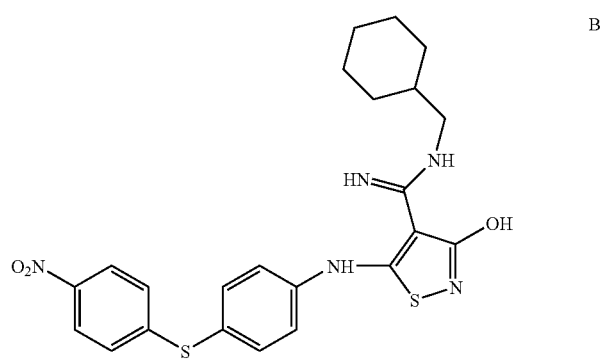  B

What is claimed is:

1. A compound of formula I

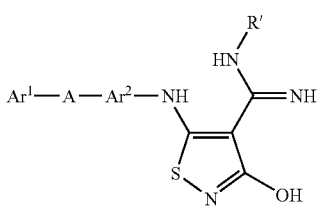   I where Ar¹ is phenyl, pyridyl, pyrimidyl, pyridazinyl, or triazinyl, in which all ring carbon atoms are optionally substituted with substituents $R_1$, $R_2$, and $R_3$, which are selected independently from hydrogen; halogen; hydroxy; nitro; cyano; $C_1$-$C_4$ alkyl, optionally substituted with one to three fluorine atoms; $CH_3O$; 2-methoxy ethenyl; $(CH_3)_2N$; $CH_3OC(O)$; $CH_3CH_2OC(O)$; $NR_7R_8$, —$C(O)NR_7R_8$; or —$S(O)_2NR_7R_8$, where $R_7$ and $R_8$ are, independently, H, $CH_3$, or $CH_3CH_2$; and $R_1$ may also be 2-C(O)K, where K is selected from:

—OJ, where J is isopropyl, cyclopropyl, cyclopentyl, dimethylamino, or methoxyethyl;

—NHJ' where J' is methyl, ethyl, isopropyl, cyclopropyl, dimethylaminomethyl, or 3-methyl-2-yl-butanoic acid methyl ester; and —$N(CH_3)_2$; or 4-methylpiperzin-1-yl;

or $R_1$ and $R_2$ are attached to adjacent carbons and, together with the ring atoms to which they are attached, form an additional, fused, five- or six-membered ring, optionally containing one heteroatom, which ring may be aromatic or aliphatic;

A is O, S, $CH_2$, $N_2$, CO, NHCO, $COCH_2$, or $CH_2CO$;

or Ar¹-A is

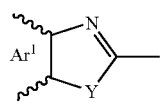

where the five-membered ring is fused to Ar¹ and Y is NH, S, or O;

or Ar$^1$-A is

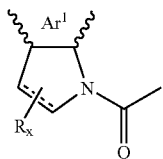

where the dotted line represents an optional double bond, the five-membered ring is fused to Ar$^1$, and R$_x$ is selected from substituents listed above for R$_3$;

or Ar$^1$-A is

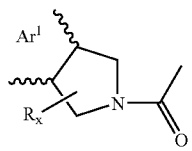

where the five-membered ring is fused to Ar$^1$, and R$_x$ is selected from substituents listed above for R$_3$;

Ar$^2$ is phenyl, pyridyl, pyrimidyl, pyridazinyl, or triazinyl, where ring carbon atoms are optionally substituted with substituents R$_4$-R$_6$ which are selected independently from H, F, Cl, Br, CH$_3$, or CF$_3$;

or Ar$^2$—NH— is

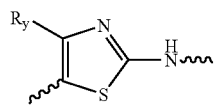

where R$_y$ is selected from substituents listed above for R$_3$;

and R' is OH; O—C$_1$-C$_6$ alkyl; C$_1$-C$_6$ alkyl, said C$_1$-C$_6$ alkyl groups optionally substituted with one to three groups selected independently from hydroxy, halogen, C$_1$-C$_3$ alkoxy, and phenyl; —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or R' is (CH$_2$)$_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and C$_1$-C$_4$ alkyl, wherein said C$_1$-C$_4$ alkyl group is optionally substituted with one to three halogen atoms; and wherein each ring optionally contains one or more double bonds;

or R' is —CH(CH$_2$OH)CH$_2$D, where D is selected from imidazolyl, indolyl, carboxamido, phenyl, cyclohexyl, —CH$_2$SCH$_3$, and adamantin-1-yl.

2. The compound of claim 1 shown in formula II

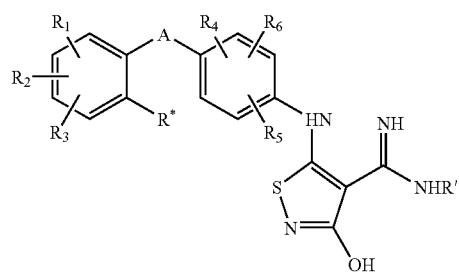

where substituents R$_1$-R$_6$ and R' are as defined for formula I and R* is H, except when R$_1$ and R$_2$ are both F, and when R$_1$ and R$_2$ are both F, R* is either H or Cl.

3. The compound of claim 2 shown in formula III

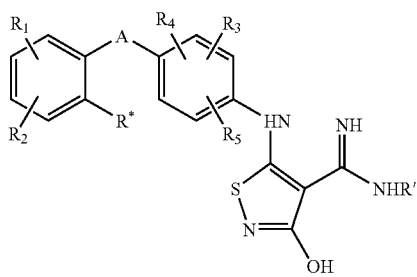

wherein A is —O—, —CH$_2$—, —N$_2$—, —CH$_2$C(O)—, —S—, or —C(O)—;

R$_1$, R$_2$, and R$_3$ are, independently, hydrogen; halogen; hydroxy; nitro; cyano; C$_1$-C$_4$ alkyl, optionally substituted with one to three fluorine atoms; CH$_3$O; 2-methoxy ethenyl; (CH$_3$)$_2$N; CH$_3$OC(O); CH$_3$CH$_2$OC(O); NR$_7$R$_8$, —C(O)NR$_7$R$_8$; or —S(O)$_2$NR$_7$R$_8$, where R$_7$ and R$_8$ are, independently, H, CH$_3$, or CH$_3$CH$_2$; or R$_1$ and R$_2$ are attached to adjacent carbons and, together with the ring atoms to which they are attached, form an additional, fused, five- or six-membered ring, optionally containing one heteroatom, which ring may be aromatic or aliphatic;

R$_4$-R$_6$ are, independently, H, F, Cl, Br, CH$_3$, or CF$_3$;

R* is H, except when R$_1$ and R$_2$ are both F; when R$_1$ and R$_2$ are both F, R* is either H or Cl;

R' is OH; O—C$_1$-C$_6$ alkyl; C$_1$-C$_6$ alkyl, said C$_1$-C$_6$ alkyl groups optionally substituted with one to three groups selected independently from hydroxy, halogen, C$_1$-C$_3$ alkoxy, and phenyl; —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl;

or R' is (CH$_2$)$_n$-G, where n is 1 or 2 and G is a five- or six-membered ring or a 9-14-membered fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

4. The compound of claim 1 shown in formula IV

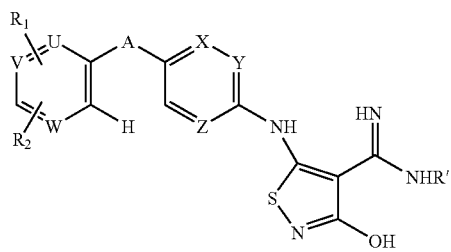

IV wherein U, V, W, X, Y, and Z are, independently CH or N, provided that U, V, W, X, Y, and Z are not all CH; A is —O—, —CH$_2$—, —N$_2$—, —NHC(O)—, —S—, or —C(O)—;

$R_1$ and $R_2$ are, independently, hydrogen; halogen; hydroxy; cyano; CH$_3$, optionally substituted with 1-3 fluorine atoms; CH$_3$O; (CH$_3$)$_2$N; CH$_3$OC(O); 2-methoxy ethenyl; and CH$_3$CH$_2$OC(O);

and R' is OH; OC$_1$-C$_6$ alkyl; C$_1$-C$_6$ alkyl, optionally substituted with one to three groups selected independently from hydroxy, halogen, C$_1$-C$_3$ alkoxy, and phenyl; —CH$_2$B or —CH$_2$CH$_2$B, where B is selected from C$_{3-7}$ cycloalkyl, C$_7$-C$_9$ bicycloalkyl, pyridyl, piperazinyl, piperidinyl, N-morpholyl, tetrahydrofuryl, and naphthyl; C$_3$-C$_7$ cycloalkyl; C$_7$-C$_9$ bicycloalkyl, where all cycloalkyl, bicycloalkyl, pyridyl, piperazinyl, piperidinyl, N-morpholyl, tetrahydrofuryl, and naphthyl groups are optionally substituted with one to three groups selected independently from hydroxy, halogen, and methyl.

5. The compound of claim 4 shown in formula V

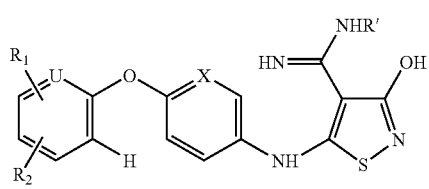

V wherein $Q_1$ and $Q_2$ are, independently CH or N, provided that $Q_1$ and $Q_2$ are not both CH; $R_1$ and $R_2$ are, independently, hydrogen; halogen; hydroxy; cyano; CH$_3$, optionally substituted with 1-3 fluorine atoms; CH$_3$O; (CH$_3$)$_2$N; CH$_3$OC(O); 2-methoxy ethenyl; and CH$_3$CH$_2$OC(O); and R' is selected from C$_1$-C$_6$ alkyl, optionally substituted with 1-3 hydroxyl groups; cyclopropyl; —CH$_2$B; and —CH$_2$CH$_2$B, where B is selected from C$_{3-6}$ cycloalkyl, phenyl, pyridyl, piperzin-1-yl, piperidin-1-yl, N-morpholyl, tetrahydrofuryl, and naphthyl.

6. The compound of claim 1 shown in formula VI

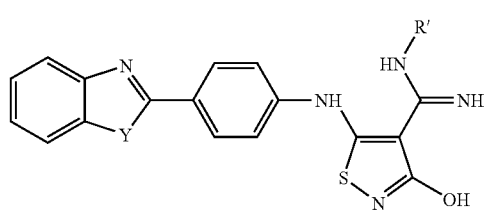

VI where Y is —NH—, —S— or —O—, and R' is selected from 1-hydroxy-isopropyl, 2-hydroxy-n-propyl, 2-hydroxy-ethyl, and 2,3,-dihydroxy-n-propyl.

7. The compound of claim 1 shown in Formula VII

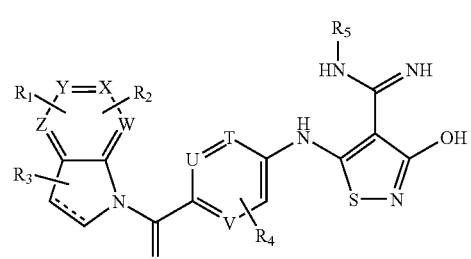

VII where the dashed bond represents an optional double bond, and where symbols T-Z represent N, CH, or CR$_{1, 2, or 4}$; provided that at most two of W, X, Y, and Z are N and at most 2 of T, U, and V are N; where R$_1$-R$_4$ are, independently, hydrogen; halogen; hydroxy; nitro; cyano; C$_1$-C$_6$ alkyl; O—C$_1$-C$_6$ alkyl; C$_2$-C$_6$ alkenyl; C$_2$-C$_6$ alkynyl; C$_1$-C$_6$ cycloalkyl; 2-methoxy ethenyl; CH$_3$OC(O); CH$_3$CH$_2$OC(O); C$_1$-C$_5$ alkyl-C(O)—; C$_1$-C$_5$ alkyl-C(O)O—; —NR$_6$R$_7$, —CH$_2$NR$_6$R$_7$, —NH—C(O)—R$_6$, —C(O)NR$_8$R$_9$; CH$_3$S(O)$_2$—, or —S(O)$_2$NR$_8$R$_9$, where R$_6$-R$_9$ are, independently, H or C$_1$-C$_4$ alkyl; or any of the pairs R$_1$ and R$_2$, R$_6$ and R$_7$, or R$_8$ and R$_9$ are attached to adjacent carbons and, together with the ring atoms to which they are attached, form an additional, fused, five- or six-membered ring, optionally containing one or two heteroatoms selected from O, N, and S, which ring may be aromatic or aliphatic; wherein all alkyl, alkenyl, and cycloalkyl groups and all rings are optionally substituted with 1-3 halogen atoms, and all rings are also optionally substituted with 1-3 C$_1$-C$_3$ alkyl groups or trifluoromethyl groups; R$_5$ is OH; O—C$_1$-C$_6$ alkyl; C$_1$-C$_6$ alkyl, said C$_1$-C$_6$ alkyl groups optionally substituted with one to three groups selected independently from hydroxy, halogen, C$_1$-C$_3$ alkoxy, and phenyl; or R$_5$ is —(CH$_2$)$_n$—B where n is 1 or 2 and B is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and C$_1$-C$_4$ alkyl, wherein said C$_1$-C$_4$ alkyl group is optionally substituted with one to three halogen atoms; and wherein each ring optionally contains one or more double bonds.

8. The compound of claim 1 shown in Formula VIII below, where the dashed bond represents an optional double bond,

VIII

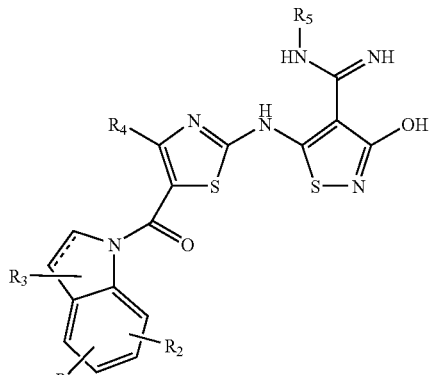

where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$; $CH_3CH_2OC(O)$; $C_1$-$C_5$ alkyl-C(O)—; $C_1$-$C_5$ alkyl-C(O)O—; —$NR_6R_7$—$CH_2NR_6R_7$, —NH—C(O)—$R_6$, —C(O)$NR_8R_9$; $CH_3S(O)_2$—, or —S(O)$_2NR_8R_9$, where $R_6$-$R_9$ are, independently, H or $C_1$-$C_4$ alkyl; or any of the pairs $R_1$ and $R_2$, $R_6$ and $R_7$, or $R_8$ and $R_9$ are attached to adjacent carbons and, together with the ring atoms to which they are attached, form an additional, fused, five- or six-membered ring, optionally containing one or two heteroatoms selected from O, N, and S, which ring may be aromatic or aliphatic; wherein all alkyl, alkenyl, and cycloalkyl groups and all rings are optionally substituted with 1-3 halogen atoms; $R_5$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_5$ is —(CH$_2$)$_n$—B where n is 1 or 2 and B is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

9. The compound of claim 1 shown in formula IX, where the dashed bond represents an optional double bond, where $R_1$-$R_5$ are defined as for formula A, and where symbols W-Z represent N, CH, or $CR_{1\ or\ 2}$, provided that at least one of W-Z is N.

IX

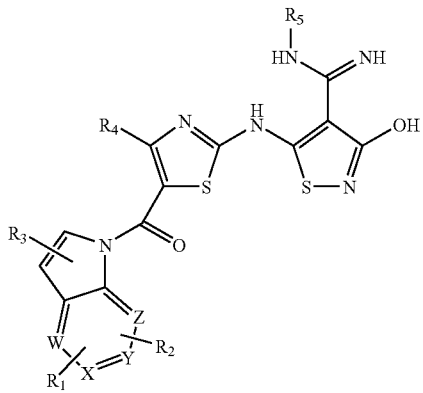

10. The compound of claim 1 shown in formula X

X

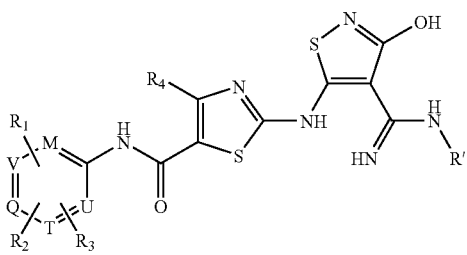

where M, Q, T, U, and V represent N, CH, or $CR_{1,\ 2,\ or\ 3}$, provided that no two nitrogen atoms are adjacent, where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$; $CH_3CH_2OC(O)$; $C_1$-$C_5$ alkyl-C(O)—; $C_1$-$C_5$ alkyl-C(O)O—; —$NR(R_7$, —$CH_2NR_6R_7$, —NH—C(O)—$R_6$, —C(O)$NR_8R_9$; $CH_3S(O)_2$—, or —S(O)$_2NR_8R_9$, where $R_6$-$R_9$ are, independently, H or $C_1$-$C_4$ alkyl; or any of the pairs $R_1$ and $R_2$, $R_6$ and $R_7$, or $R_8$ and $R_9$, together with the ring atoms to which they are attached, form an additional, five- or six-membered ring, optionally containing one or two heteroatoms selected from O, N, and S, which ring may be aromatic or aliphatic, and which ring is fused in the case of $R_1$ and $R_2$; and where $R_1$ may also be isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, tolyl, or phenyl, wherein all alkyl, alkenyl, and cycloalkyl groups and all rings are optionally substituted with 1-3 halogen atoms, $C_1$-$C_3$ alkyl groups, or trifluoromethyl groups; $R_5$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_5$ is —(CH$_2$)$_n$-G where n is 1 or 2 and G is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

11. The compound of claim 1 shown in formula XI

XI

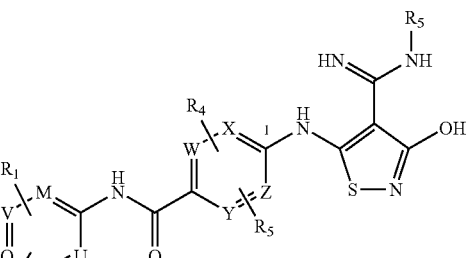

where M, Q, T, U, V, W, X, Y, and Z represent N, CH, or $CR_{1,\ 2,\ 3,\ or\ 4}$, where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$; $CH_3CH_2OC(O)$; $C_1$-$C_5$ alkyl-C(O)—; $C_1$-$C_5$ alkyl-C(O)O—; —$NR_7$, —$CH_2NR_6R_7$, —NH—C(O)—$R_6$, —C(O)$NR_8R_9$;

$CH_3S(O)_2$—, or —$S(O)_2NR_8R_9$, where $R_6$-$R_9$ are, independently, H or $C_1$-$C_4$ alkyl; or any of the pairs $R_1$ and $R_2$; $R_6$ and $R_7$, or $R_8$ and $R_9$ are attached to adjacent carbons and, together with the ring atoms to which they are attached, form an additional, fused, five- or six-membered ring, optionally containing one or two heteroatoms selected from O, N, and S, which ring may be aromatic or aliphatic; and where $R_1$ may also be isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, tolyl, or phenyl, wherein all alkyl, alkenyl, and cycloalkyl groups and all rings are optionally substituted with 1-3 halogen atoms, $C_1$-$C_3$ alkyl groups, or trifluoromethyl groups; $R_5$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_5$ is —$(CH_2)_n$-G where n is 1 or 2 and G is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

12. The compound of claim 11, where M, Q, T, U, V, W, X, Y, and Z are all CH or $CR_{1, 2, 3, or 4}$.

13. The compound of claim 1 shown in formula XII

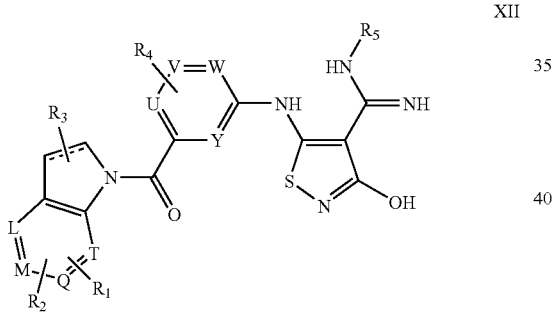

where the dashed bond represents an optional double bond, and where symbols L, T, U, V, and W-Z represent N, CH, or $CR_{1, 2, or 4}$, provided that no two nitrogen atoms are adjacent, where $R_1$-$R_4$ are, independently, hydrogen; halogen; hydroxy; nitro; cyano; $C_1$-$C_6$ alkyl; O—$C_1$-$C_6$ alkyl; $C_2$-$C_6$ alkenyl; $C_2$-$C_6$ alkynyl; $C_1$-$C_6$ cycloalkyl; 2-methoxy ethenyl; $CH_3OC(O)$;

$CH_3CH_2OC(O)$; $C_1$-$C_5$ alkyl-C(O)—; $C_1$-$C_5$ alkyl-C(O)O—; —$NR_6R_7$—$CH_2NR_6R_7$—NH—C(O)—$R_6$, —$C(O)NR_8R_9$; $CH_3S(O)_2$—, or —$S(O)_2NR_8R_9$, where $R_6$-$R_9$ are, independently, H or $C_1$-$C_4$ alkyl; or any of the pairs $R_1$ and $R_2$, $R_6$ and $R_7$, or $R_8$ and $R_9$, together with the ring atoms to which they are attached, form an additional, five- or six-membered ring, optionally containing one or two heteroatoms selected from O, N, and S, which ring may be aromatic or aliphatic, and which ring is fused in the case of $R_1$ and $R_2$; and where $R_1$ may also be isothiazolyl, isoxazolyl, oxazolyl, oxazolinyl, oxazolidinyl, thiazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, tolyl, or phenyl, wherein all alkyl, alkenyl, and cycloalkyl groups and all rings are optionally substituted with 1-3 halogen atoms, $C_1$-$C_3$ alkyl groups, or trifluoromethyl groups; $R_5$ is OH; O—$C_1$-$C_6$ alkyl; $C_1$-$C_6$ alkyl, said $C_1$-$C_6$ alkyl groups optionally substituted with one to three groups selected independently from hydroxy, halogen, $C_1$-$C_3$ alkoxy, and phenyl; or $R_5$ is —$(CH_2)_n$-G, where n is 1 or 2 and G is a five- or six-membered ring or a 9- to 14-member fused ring system, wherein each ring optionally contains 1-3 heteroatoms selected independently from O, N, and S; wherein each ring is optionally substituted with 1-3 groups selected independently from the following: halogen, hydroxy, cyano, oxo, and $C_1$-$C_4$ alkyl, wherein said $C_1$-$C_4$ alkyl group is optionally substituted with one to three halogen atoms; and wherein each ring optionally contains one or more double bonds.

\* \* \* \* \*